US009758550B2

(12) United States Patent
Saito et al.

(10) Patent No.: US 9,758,550 B2
(45) Date of Patent: Sep. 12, 2017

(54) COBALAMIN ACQUISITION PROTEIN AND USE THEREOF

(71) Applicant: Woods Hole Oceanographic Institution, Woods Hole, MA (US)

(72) Inventors: Makoto Saito, Falmouth, MA (US); Erin M. Bertrand, San Diego, CA (US)

(73) Assignee: Woods Hole Oceanographic Institution, Woods Hole, MA (US)

( * ) Notice: Subject to any disclaimer, the term of this patent is extended or adjusted under 35 U.S.C. 154(b) by 0 days.

(21) Appl. No.: 14/958,321

(22) Filed: Dec. 3, 2015

(65) Prior Publication Data

US 2016/0279192 A1  Sep. 29, 2016

Related U.S. Application Data

(62) Division of application No. 13/874,437, filed on Apr. 30, 2013, now Pat. No. 9,234,012.

(60) Provisional application No. 61/640,261, filed on Apr. 30, 2012.

(51) Int. Cl.
| *C07K 14/405* | (2006.01) |
| *C07K 14/00* | (2006.01) |
| *G01N 33/82* | (2006.01) |
| *C07K 14/435* | (2006.01) |
| *A61K 38/16* | (2006.01) |
| *A61K 38/00* | (2006.01) |

(52) U.S. Cl.
CPC .............. *C07K 14/00* (2013.01); *A61K 38/16* (2013.01); *C07K 14/405* (2013.01); *C07K 14/43504* (2013.01); *G01N 33/82* (2013.01); *A61K 38/00* (2013.01)

(58) Field of Classification Search
CPC .................................................. C07K 14/405
See application file for complete search history.

(56) References Cited

U.S. PATENT DOCUMENTS

| 5,770,435 A | 6/1998 | Donnelly et al. |
| 5,869,301 A | 2/1999 | Nghiem et al. |
| 6,743,610 B2 | 6/2004 | Donnelly et al. |
| 9,234,012 B2 | 1/2016 | Saito et al. |
| 2009/0304679 A1 | 12/2009 | Weidanz |
| 2011/0237831 A1 | 9/2011 | Fruchey et al. |
| 2011/0245515 A1 | 10/2011 | Fruchey et al. |
| 2011/0262975 A1 | 10/2011 | Berry et al. |
| 2011/0269219 A1 | 11/2011 | Holland et al. |

FOREIGN PATENT DOCUMENTS

| WO | WO-2007/136762 A2 | 11/2007 |
| WO | WO-2007/139925 A2 | 12/2007 |
| WO | WO-2009/022236 A2 | 2/2009 |
| WO | WO-2011/123268 A1 | 10/2011 |

OTHER PUBLICATIONS

Allen et al., (2008), "Whole-cell Response of the Pennate Diatom *Phaeodactylum tricornutum* to Iron Starvation," *PNAS*, 105(30):10438-10443.
Apt et al., (2002) 'In vivo Characterization of Diatom Multipartite Plastid Targeting Signals,' *J. Cell Sci.*, 115(Pt 21):4061-4069.
Archambault et al., (1997), An Essential Component of a C-Terminal Domain Phosphatase that Interacts with Transcription Factor IIF in *Saccharomyces cerevisiae*, *Proc. Natl. Acad. Sci. USA*, 94(26):14300-14305.
Armbrust et al., (2004), "The Genome of the Diatom *Thalassiosira pseudonana*: Ecology, Evolution, and Metabolism," *Science*, 306(5693):79-86.
Azam and Malfatti, (2007) "Microbial Structuring of Marine Ecosystems," *Nat. Rev. Microbiol.*, 5(10):782-791.
Banerjee and Matthews, (1990) "Cobalamin-Dependent Methionine Synthase," *FASEB*, 4(5):1449-1459.
Bertrand et al., (2007) "Vitamin B12 and Iron Co-Limitation of Phytoplankton Growth in the Ross Sea," *Limnol. Oceanogr.*, 52(3):1079-1093.
Bertrand et al., (2011) "Vitamin $B_{12}$ Biosynthesis Gene Diversity in the Ross Sea: the Identification of a New Group of Putative Polar $B_{12}$-Biosynthesizers," *Environ. Microbiol.*, 13(5):1285-1298.
Bertrand et al., (2012), "Inflluence of Cobalamin Scarcity on Diatom Molecular Physiology and Identification of a Cobalamin Acquisition Protein," *Proc. Natl. Acad. Sci .USA*, 109(26):E1762-1771.
Bertrand et al., (2012), "PNAS Plus: Influence of Cobalamin Scarcity on Diatom Molecular Physiology and Identification of a Covlamin Acquisition Protein," *Proc. Natl. Acad. Sci .USA*, 109(26):E1762-1771.
Bian et al., (2012) "Genome Sequences of Six *Pseudoalteromanas* Strains Isolated from Arctic Sea Ice," *J. Bacteriol.*, 194(4):908-909.
Bowler et al., (2008), "The Phaeodactylum Genome Reveals the Evolutionary History of Diatom Genomes," *Nature*, 456(7219):239-244 and Supplementary Information (46 pages).
Boyd et al., (2007) "Mesoscale Iron Enrichment Experiments 1993-2005: Synthesis and Future Directions," *Science*, 315(5812):612-618.
Cadieux et al., (2002) "Identification of the Periplasmic Cobalamin-Binding Protein BtuF of *Escherichia coli*," *J. Bacteriol.*, 184(3): 706-717.
Chan et al., (2007) "Covalent Attachment of Proteins to Solid Supports and Surfaces via Sortase-Mediated Ligation," *PLoS One*, 2(11):e1164 (5 pages).
Chatterjee et al., (2008) "Reconstitution of ThiC in Thiamine Pyrimidine Biosynthesis Expands the Radical SAM Superfamily," *Nat. Chem. Biol.*, 4(12):758-765.
Cowey, (1956) "A Preliminary Investigation of the Variaton of Vitamin $B_{12}$ in Oceanic and Coastal Waters," *J. Mar. Biol. Ass. UK*, 35(3):609-620.
Croft et al., (2005) "Algae Acquire Vitamin $B_{12}$ Through a Symbiotic Relationship With Bacteria," *Nature*, 438(7064):90-93.

(Continued)

*Primary Examiner* — Karen Cochrane Carlson
(74) *Attorney, Agent, or Firm* — Goodwin Procter LLP

(57) ABSTRACT

The present invention relates to a cobalamin acquisition protein, compositions containing the cobalamin acquisition protein, and the use of such compositions.

10 Claims, 24 Drawing Sheets

(56) References Cited

OTHER PUBLICATIONS

Croft et al., (2006) "Algae Need Their Vitamins," *Eukaryot. Cell*, 5(8):1175-1183.
Dev et al., (1984) "Regulation of Synthesis of Serine Hydroxymethyltransferase in Chemostat Cultures of *E. coli*," *J. Biol. Chem.*, 259(13):8394-8401.
Dobson et al., (2002) "Identification of the Gene Responsible for the cblB Complementation Group of Vitamin $B_{12}$-Dependent Methylalonic Aciduria," *Hum. Mol. Genet.*, 11(26):3361-3369.
Drennan et al., (1994) "Cobalamin-dependent Methionine Synthase: the Structure of a Methylcobalamin-Binding Fragment and Implications for Other $B_{12}$-Dependent Enzymes," *Curr. Opin. Struct. Biol.*, 4(6):919-929.
Droop, (1957) "Vitamin B12 in Marine Ecology," *Nature*, 180(4594):1041-1042.
Droop, (2007) "Vitamins, Phytoplankton and Bacteria: Symbiosis or Scavenging?," *J. Plankton Res.*, 29(2):107-113.
Essich et al., (1990) "Chromosomal Transformation in the Cyanobacterium *Agmenellum quadruplicatum*," *J. Bacteriol.*, 172(4):1916-1922.
Falciatore et al., (1999) "Transformation of Nonselectable Reporter Genes in Marine Diatoms," *Mar. Biotechnol.*, 1(3):239-251.
Falkowski et al., (2004) "The Evolution of Modern Eukaryotic Phytoplankton," *Science*, 305(2004):354-360.
Formosa et al., (1991), "Using Protein Affinity Chromatography to Probe Structure of Protein Machines," *Methods Enzymol.*, 208:24-45.
Frigaard et al., (2004) "Gene Inactivation in the Cyanobacterium *Synechococcus* sp. PCC 7002 and the Green Sulfur Bacterium *Chlorobium tepidum* Using in vitro-Made DNA Constructs and Natural Transformation," *Methods Mol. Biol.*, 274:325-340.
Gobler et al., (2007) "Effect of B-Vitamins and Inorganic Nutrients on Algal Bloom Dynamics in a Coastal Ecosystem," *Aquat. Microb. Ecol.*, 49(2):181-194.
Gonzalez et al., (1992) "Comparison of Cobalamin-Independent and Cobalamin-Dependent Methionine Synthases from *E. coli*: Two Solutions to the Same Chemical Problem," *Biochemistry*, 31(26):6045-6056.
Gottlieb et al., (1965) "Rapid Charcoal Assay for Intrinsic Factor (IF), Gastric Juice Unsaturated $B_{12}$-Binding Capacity, Antibody to IF, and Serum Unsaturated $B_{12}$-Binding Capacity," *Blood*, 25(6):875-884.
Goulding et al., (1997) "Cobalamin-Dependent Methionine Synthase is a Modular Protein with Distinct Regions for Homocysteine, Methyltetrahydrofolate, Cobalamin and Adenosylmethionine," *Biochemistry*, 36(26):8082-8091.
Helliwell et al., (2011) "Insights into the Evolution of Vitamin $B_{12}$ Auxotrophy from Sequenced Algal Genomes," *Mol. Biol. Evol.*, 28(10):2921-2933.
Herbig et al., (2002) "Cytoplasmic Serine Hydroxymethyltransferase Mediates Competition Between Folate-dependent Deoxyribonucleotide and S-adenosylmethionine Biosyntheses," *J. Biol. Chem.*, 277(41):38381-38389.
International Search Report for PCT/US2013/038953, mailed Sep. 24, 2013 (6 pages).
Invitrogen Corp, Carlsbad, CA (2010), "CloneMiner™ cDNA Library Construct Kit—High-quality cDNA Libraries without the Use of Restriction Enzyme Cloning Techniques," Catalog No. 18249-029, (95 pages).
Karl, (2002) "Nutrient Dynamics in the Deep Blue Sea," *Trends Microbiol.*, 10(9):410-418.
Koch et al., (2011) "The Effect of Vitamin $B_{12}$ on Phytoplankton Growth and Community Structure in the Gulf of Alaska," *Limnol. Oceanog.*, 56(3):1023-1034.
Kustka et al., (2007), "Sequence Analysis and Transcriptional Regulation of Iron Acquisition Genes in Two Marine Diatoms," *J. Phycol.*, 43(4):715-729.
Lovelock, (1983) "Gaia as Seen Through the Atmosphere," *Biomineralization and Biological Metal Accumulation*, P. Westbroek and E. W. deJong (eds.), D. Reidel Publishing Company, Dordrecht, NL (Publ), 1:15-25.
Lu et al., (2008) "Simultaneous Determination of Four Water-Soluble Vitamins in Fortified Infant Foods by Ultra-Performance Liquid Chromatography, Coupled with Triple Quadruple Mass Spectrometry," *J. Chrom. Sci.*, 46(3):225-232.
Menzel and Spaeth, (1962) "Occurrence of Vitamin $B_{12}$ in the Sargasso Sea," *Limnol. Oceanogr.*, 7(2):151-154.
Moore et al., (2004) "Upper Ocean Ecosystem Dynamics and Iron Cycling in a Global Three-Dimensional Model," *Global Biogeochem. Cy.*, 18(4):GB4028 (21 pages).
Nelson et al., (1995) "Production and Dissolution of Biogenic Silica in the Oceans: Revised Global Estimates, Comparison with Regional Data and Relationship to Biogenic Sedimentation," *Global Biogeochem. Cy.*, 9(3):359-372.
Panzeca et al., (2006) "B Vitamins as Regulators of Phytoplankton Dynamics," *Eos Trans. AGU*, 87(52):593-596.
Price et al., (1988/1989) "Preparation and Chemistry of the Artificial Algal Culture Medium Aquil," *Biol. Oceanogr.*, 6(5-6):443-461.
Price et al., (2004), "Identification of a SulP-type Bicarbonate Transporter in Marine Cyanobacteria," *Proc Natl. Acad. Sci. USA*, 101(52):18228-18233.
Rodionov et al., (2003) "Comparative Genomics of the Vitamin $B_{12}$ Metabolism and Regulation in Prokaryotes," *J. Biol. Chem.*, 278(42):41148-41159.
Saito et al., (2011), "Iron Conservation by Reduction of Metalloenzyme Inventories in the Marine Diazotroph *Crocosphaera watsonii*," *PNAS*, 108(6):2184-2189.
Scott and Weir, (1981) "The Methyl Folate Trap: A Physiological Response in Man to Prevent Methyl Group Deficiency in Kwashiorkor (Methionine Deficiency) and an Explanation for Folic-Acid-Induced Exacerbation of Subacute Combined Degeneration in Pernicious Anaemia," *Lancet*, 2(8242):337-340.
Seckbach and Chela-Flores, (2013) "Frontiers of Extremophilic Microorganisms: From Life on the Edge to Astrobiology," *Eur. Space Agency Spec. Rep.*, ESA SP 496, 1:255-260.
Selhub et al., (1993) "Vitamin Status and Intake as Primary Determinants of Homocysteinemia in an Elderly Population," *JAMA*, 270(2):2693-2698.
Selhub, (2002) "Folate, Vitamin $B_{12}$ and Vitamin $B_6$ and One Carbon Metabolism," *J. Nutr. Health Aging*, 6(1):39-42.
Siaut et al., (2007) "Molecular Toolbox for Studying Diatom Biology in *Phaeodactylum tricomutum*," *Gene*, 406(1-2):23-35.
Snell et al., (2000) "The Genetic Organization and Protein Crystallographic Structure of Human Serine Hydroxomethyltransferase," *Adv. Enzyme Regul.*, 40:353-403.
Sopta et al., (1985) "Isolation of Three Proteins that Bind to Mammalian RNA Polymerase II," *J. Biol. Chem.*, 260(18):10353-10360.
Stefels, (2000) "Physiological Aspects of the Production and Conversion of DMSP in Marine Algae and Higher Plants," *J. Sea Res.*, 43(2000):183-197.
Stevens et al., (1973) "The Production of Hydrogen Peroxide by Green Algae: A Survey," *J. Phycol.*, 9(4):427-430.
Sunda et al., (2002) "An Antioxidant Function for DMSP and DMS in Marine Algae," *Nature*, 418(6895):317-320.
Swift and Taylor, (1974) "Growth of Vitamin $B_{12}$-Limited Cultures: *Thalassiosira pseudonana*, *Monochrysis lutheri*, and *Isochrysis galbana*," *J. Phycol.*, 10(4):385-391.
Written Opinion for International Application No. PCT/US2013/038953, mailed Sep. 24, 2013, (5 pages).

FIGURE 7A
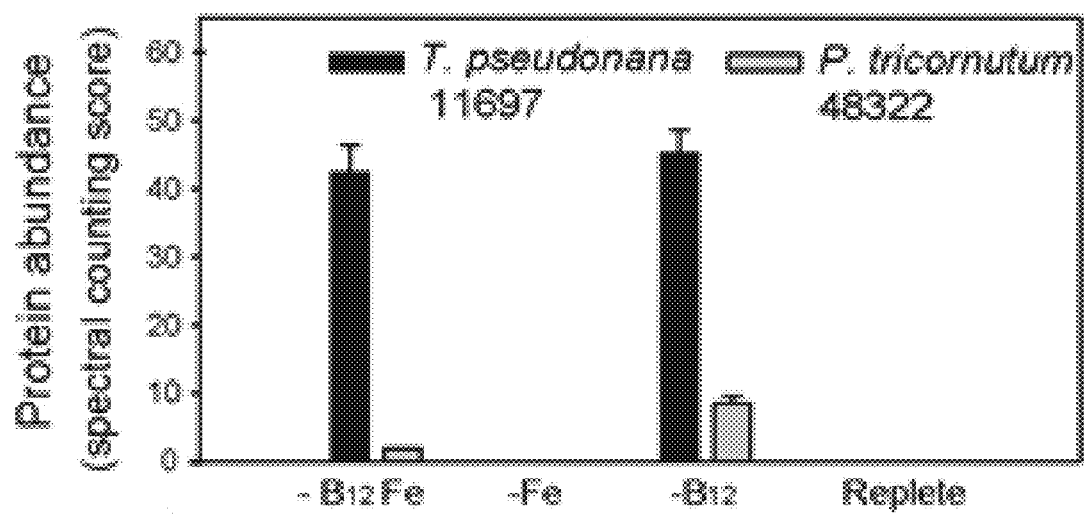
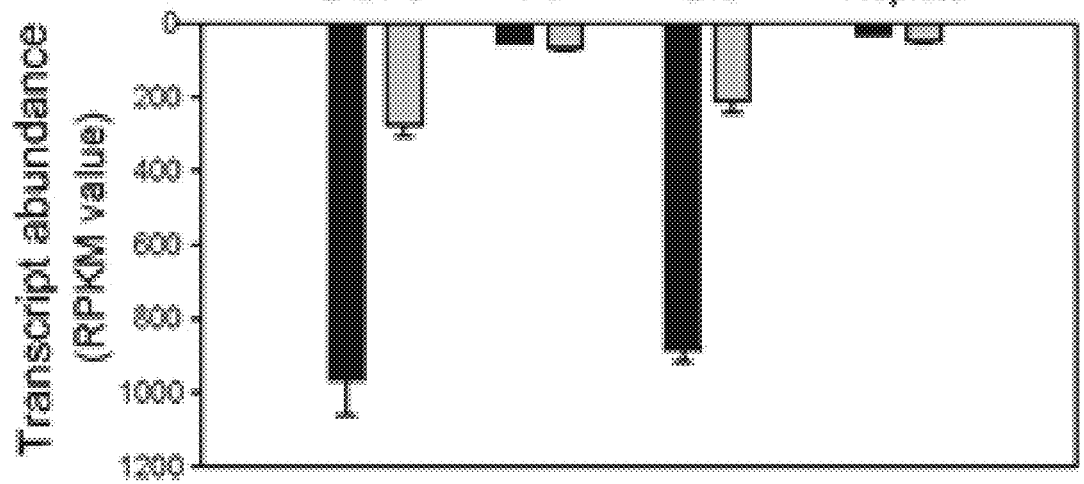
FIGURE 7B

FIGURE 9C

Fragmentation tables for CBA1 peptides (figure content not transcribable)

FIGURE 9D

Detection of CBA1 peptides in *P. tricornutum* samples

| Sample | FFSVFFNK | FFSLFFNK |
|---|---|---|
| Low B.12Fe | 3 | 0 |
| Low B12 | 3 | 3 |
| Low Fe | 0 | 0 |
| Replete | 0 | 0 |

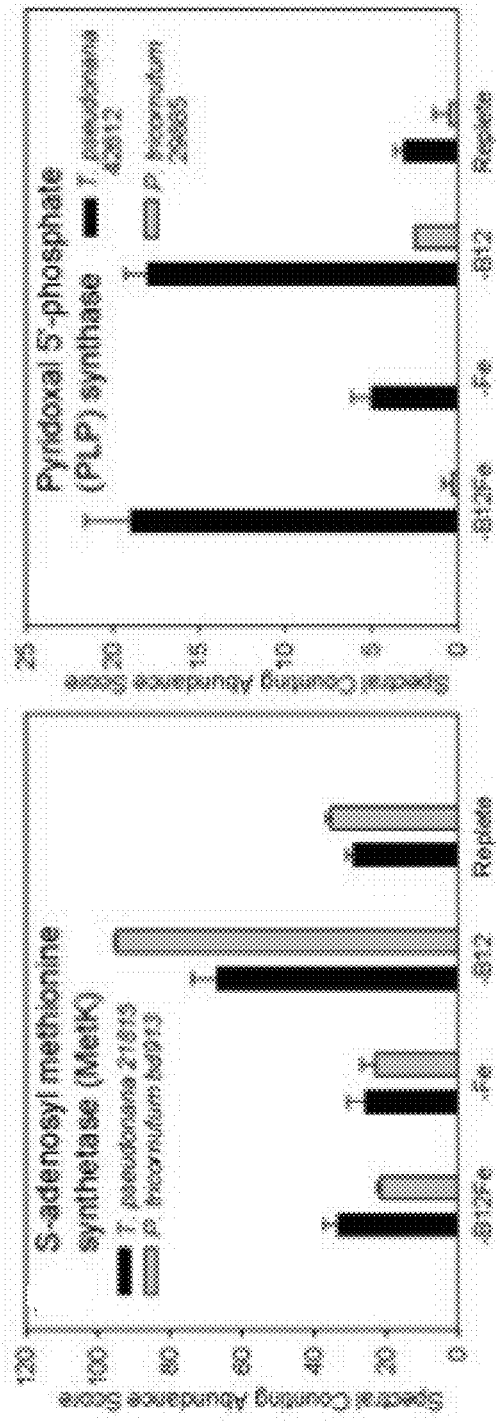
FIGURE 12B
FIGURE 12C
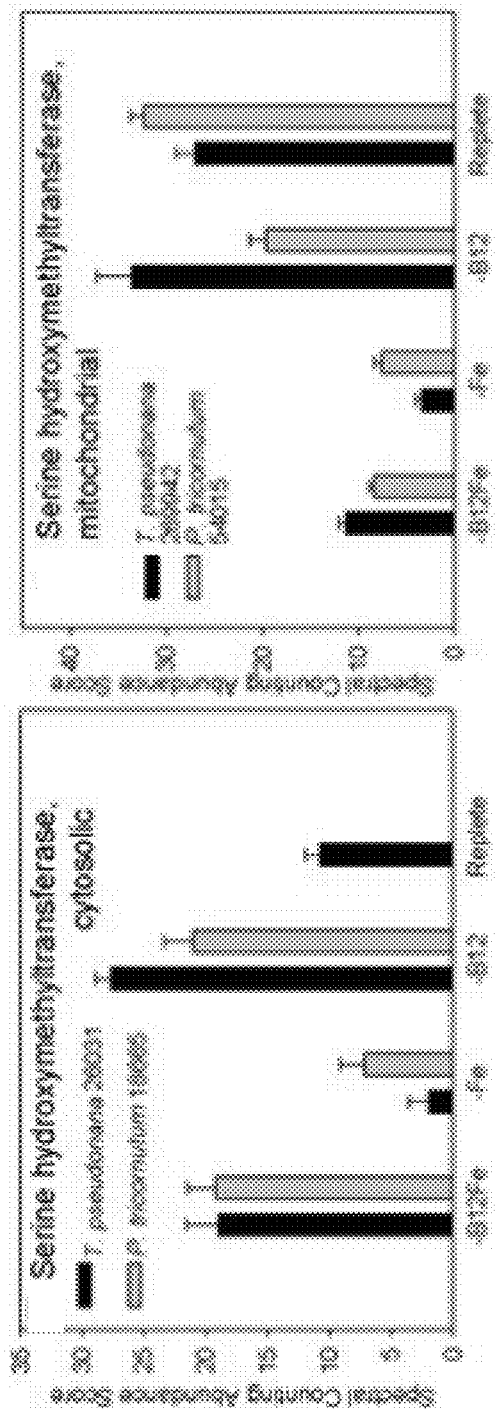
FIGURE 12D
FIGURE 12E

```
                        SEQUENCE LISTING

<160> NUMBER OF SEQ ID NOS: 53

<210> SEQ ID NO 1
<211> LENGTH: 1302
<212> TYPE: DNA
<213> ORGANISM: Phaeodactylum tricornutum

<400> SEQUENCE: 1
gacgaacctc cggcttgcct gacatcgact gcggacctttt cggtggatat cttcaccgac      60
aaggtagaac cgctcttctc ccaaggatgg aatgtgactt accataacac ctacaagatt     120
gccaacaatc tcttcgacaa cacgacctac ctcctctacc agtgtggtag cacgcctccg     180
gccgatgtcg tcgacaacgg caacttcaac gccgtcctcg agattcccct gtccaacgtg     240
ggtctctcgc aaacgccgca cattggcttt atggagcaac tcgaactcgt cgacgaaatt     300
gcggcctttt tgaccgacac ggactttatt tcgtcgcctt gcttcttgga cgagatcgcc     360
gccggtaacg tcctcacact ggtggaaccc agtgaagggg tagacgcacc cgccactggc     420
aacactgcac tcagtgctgg cacggtagcc tttgtagcgt ccttcaccca agtcccctttt    480 gacaatacgg tcaacatcca agagtacagc gaactcacca acgtggccgt ctttgaatgg     540
gtcaagttct tttccgtctt cttcaacaag gagcacaccg ccaaccaagt cgtcgaggcc     600
gcggaatcgc gctttgattg cgtcgcgcaa acgccggag ccgtccaggc cgacaatatg      660
ccggtcaaac ccgtcgtctt gtgggcctac tacagtgatt tctgtggcgg atgggatgtc     720
gccgaatgcc ccaactacta ctgcgaattc gccaacgcgt gcggggccga aattattagc     780
agtaccgaag gcaacaccac cgtctgcggt gcaccctaca tgaccacgga agaattggtg     840
gaactcggaa aggatgccga tcactggatc tatccgtcca gtaactggga tacggcatcg     900
gaaaccttcg gcgagcagct tcagaacatg aaggccgtgc aggaccaaca agtcttcgat     960
taccaggcat ccggagaaaa tgcttggttt gagcagcgct atgcggaata ctacaacgtc    1020
ttggccgact tttgtgccgt tgttggtacc acccagccct tgaccggtcg ttcctggttc    1080
cgcaacgtat ttaccgaacc cgtcggtagt ctccctgatt gctcgcccac tcagtcggcc    1140
aacattttgg acgatgtcca catttgcttc cttcccacga ccggcggtgc tgcggctggt    1200
ggtggcagtg gtagtggcgg tagcagcgcc aaggcgatcg cggtcgggac cgctgcgctg    1260
gcggcgggac tactcagtct tatacacgta ttgttgttct aa                       1302

<210> SEQ ID NO 2
<211> LENGTH: 433
<212> TYPE: PRT
<213> ORGANISM: Phaeodactylum tricornutum

<400> SEQUENCE: 2

Asp Glu Pro Pro Ala Cys Leu Thr Ser Thr Ala Asp Leu Ser Val Asp
1               5                   10                  15

Ile Phe Thr Asp Lys Val Glu Pro Leu Phe Ser Gln Gly Trp Asn Val
            20                  25                  30

Thr Tyr His Asn Thr Tyr Lys Ile Ala Asn Asn Leu Phe Asp Asn Thr
        35                  40                  45
```

```
Thr Tyr Leu Leu Tyr Gln Cys Gly Ser Thr Pro Pro Ala Asp Val Val
         50                  55                  60

Asp Asn Gly Asn Phe Asn Ala Val Leu Glu Ile Pro Leu Ser Asn Val
 65                  70                  75                  80

Gly Leu Ser Gln Thr Pro His Ile Gly Phe Met Glu Gln Leu Glu Leu
                 85                  90                  95

Val Asp Glu Ile Ala Ala Phe Leu Thr Asp Thr Asp Phe Ile Ser Ser
                100                 105                 110

Pro Cys Phe Leu Asp Glu Ile Ala Ala Gly Asn Val Leu Thr Leu Val
             115                 120                 125

Glu Pro Ser Glu Gly Val Asp Ala Pro Ala Thr Gly Asn Thr Ala Leu
130                 135                 140

Ser Ala Gly Thr Val Ala Phe Val Ala Ser Phe Thr Gln Val Pro Phe
145                 150                 155                 160

Asp Asn Thr Val Asn Ile Gln Glu Tyr Ser Glu Leu Thr Asn Val Ala
                165                 170                 175

Val Phe Glu Trp Val Lys Phe Ser Val Phe Phe Asn Lys Glu His
                180                 185                 190

Thr Ala Asn Gln Val Val Glu Ala Ala Glu Ser Arg Phe Asp Cys Val
                195                 200                 205

Ala Gln Asn Ala Gly Ala Val Gln Ala Asp Asn Met Pro Val Lys Pro
        210                 215                 220

Val Val Leu Trp Ala Tyr Tyr Ser Asp Phe Cys Gly Gly Trp Asp Val
225                 230                 235                 240

Ala Glu Cys Pro Asn Tyr Tyr Cys Glu Phe Ala Asn Ala Cys Gly Ala
                245                 250                 255

Glu Ile Ile Ser Ser Thr Glu Gly Asn Thr Thr Val Cys Gly Ala Pro
            260                 265                 270

Tyr Met Thr Thr Glu Glu Leu Val Glu Leu Gly Lys Asp Ala Asp His
        275                 280                 285

Trp Ile Tyr Pro Ser Ser Asn Trp Asp Thr Ala Ser Glu Thr Phe Gly
        290                 295                 300

Glu Gln Leu Gln Asn Met Lys Ala Val Gln Asp Gln Val Phe Asp
305                 310                 315                 320

Tyr Gln Ala Ser Gly Glu Asn Ala Trp Phe Glu Gln Arg Tyr Ala Glu
                325                 330                 335

Tyr Tyr Asn Val Leu Ala Asp Phe Cys Ala Val Val Gly Thr Thr Gln
                340                 345                 350

Pro Leu Thr Gly Arg Ser Trp Phe Arg Asn Val Phe Thr Glu Pro Val
            355                 360                 365

Gly Ser Leu Pro Asp Cys Ser Pro Thr Gln Ser Ala Asn Ile Leu Asp
370                 375                 380

Asp Val His Ile Cys Phe Leu Pro Thr Thr Gly Gly Ala Ala Gly
385                 390                 395                 400

Gly Gly Ser Gly Ser Gly Gly Ser Ala Lys Ala Ile Ala Val Gly
                405                 410                 415

Thr Ala Ala Leu Ala Ala Gly Leu Leu Ser Leu Ile His Val Leu Leu
                420                 425                 430

Phe

<210> SEQ ID NO 3
<211> LENGTH: 1302
<212> TYPE: DNA
<213> ORGANISM: Phaeodactylum tricornutum
```

<400> SEQUENCE: 3

```
gacgaacctc cggcttgcct gacatcgact gcggaccttt cggtggatat cttcaccgac      60
aaggtagaac cgctcttctc ccaaggatgg aatgtgactt accacaacac ctacaagatt     120
gccaacaatc tcttcgacaa cacgacctac ctcctctacc agtgtggtag cacgcctccg     180
gccgatgtcg tcgacaacgg caacttcaac gccgtcctcg agattcccct gtccaacgtg     240
ggtctctcgc aaacgccgca cattggcttt atggagcaac tcgaactcgt cgacgaaatc     300
gcggcctttt tgaccgacac ggactttatt tcgtcgcctt gcttcttgga cgagatcgcc     360
gccggcaacg tcctcacact ggtggaaccc agtgaagggg tagacgcacc cgccactggc     420
aacactgcac tcagtgctgg cacggtagcc tttgtagcgt ccttcaccca gtcccctt t     480
gacaatacgg tcaacatcca agagtacagc gaactcacca acgtggccgt ctttgaatgg     540
gtcaagttct tttccctctt cttcaacaag gagcacaccg ccaaccaagt cgtcgaggcc     600
gcggaatcgc gctttgattg cgtcgcgcaa aacgccggag ccgtccaggc cgacaatatg     660
ccggtccaac ccgtcgtctt gtgggcctac tacagtgatt tctgtggcgg atgggatgtc     720
gccgaatgcc ccaactacta ctgcgaattc gccaacgcgt gcggggccga aattattagc     780
agtaccgaag caacaccac cgtctgtggc gcaccctaca tgaccacgga gaattggtg     840
gaactcggaa aggatgccga tcactggatc tacccgtcca ataactggga tacggcatcg     900
gaaaccttcg gcgagcagct tcagaacatg aaggccgtgc aggaccaaca agtcttcgat     960
taccaggcat ccggagaaaa tgcttggttt gagcagcgct atgcggaata ctacaacgtc    1020
ttggccgact tttgtgccgt tgttggtacc acccagcccct tgaccggtcg ttcctggttc    1080
cgcaacgtat ttaccgaacc cgtcggtagt ctcccctgatt gctcgcccac tcagtcggcc    1140
aacatttt gg acgatgtcca catttgcttc cttcccacga ccggcggtgc tgcggctggt    1200
ggtggcagtg gtagtggcgg tagcagcgcc aaggcgatcg cggtcgggac cgctgcgctg    1260
gcggcgggac tactcagtct tatacacgta ttgttgttct aa                        1302
```

<210> SEQ ID NO 4
<211> LENGTH: 433
<212> TYPE: PRT
<213> ORGANISM: Phaeodactylum tricornutum

<400> SEQUENCE: 4

```
Asp Glu Pro Pro Ala Cys Leu Thr Ser Thr Ala Asp Leu Ser Val Asp
1               5                   10                  15

Ile Phe Thr Asp Lys Val Glu Pro Leu Phe Ser Gln Gly Trp Asn Val
            20                  25                  30

Thr Tyr His Asn Thr Tyr Lys Ile Ala Asn Asn Leu Phe Asp Asn Thr
        35                  40                  45

Thr Tyr Leu Leu Tyr Gln Cys Gly Ser Thr Pro Ala Asp Val Val
    50                  55                  60

Asp Asn Gly Asn Phe Asn Ala Val Leu Glu Ile Pro Leu Ser Asn Val
65                  70                  75                  80

Gly Leu Ser Gln Thr Pro His Ile Gly Phe Met Glu Gln Leu Glu Leu
                85                  90                  95

Val Asp Glu Ile Ala Ala Phe Leu Thr Asp Thr Asp Phe Ile Ser Ser
            100                 105                 110

Pro Cys Phe Leu Asp Glu Ile Ala Ala Gly Asn Val Leu Thr Leu Val
        115                 120                 125
```

Glu Pro Ser Glu Gly Val Asp Ala Pro Ala Thr Gly Asn Thr Ala Leu
130                 135                 140

Ser Ala Gly Thr Val Ala Phe Val Ala Ser Phe Thr Gln Val Pro Phe
145                 150                 155                 160

Asp Asn Thr Val Asn Ile Gln Glu Tyr Ser Glu Leu Thr Asn Val Ala
            165                 170                 175

Val Phe Glu Trp Val Lys Phe Ser Leu Phe Phe Asn Lys Glu His
        180                 185                 190

Thr Ala Asn Gln Val Val Glu Ala Glu Ser Arg Phe Asp Cys Val
        195                 200                 205

Ala Gln Asn Ala Gly Ala Val Gln Ala Asp Asn Met Pro Val Gln Pro
210                 215                 220

Val Val Leu Trp Ala Tyr Tyr Ser Asp Phe Cys Gly Gly Trp Asp Val
225                 230                 235                 240

Ala Glu Cys Pro Asn Tyr Tyr Cys Glu Phe Ala Asn Ala Cys Gly Ala
            245                 250                 255

Glu Ile Ile Ser Ser Thr Glu Gly Asn Thr Thr Val Cys Gly Ala Pro
            260                 265                 270

Tyr Met Thr Thr Glu Glu Leu Val Glu Leu Gly Lys Asp Ala Asp His
        275                 280                 285

Trp Ile Tyr Pro Ser Asn Asn Trp Asp Thr Ala Ser Glu Thr Phe Gly
290                 295                 300

Glu Gln Leu Gln Asn Met Lys Ala Val Gln Asp Gln Val Phe Asp
305                 310                 315                 320

Tyr Gln Ala Ser Gly Glu Asn Ala Trp Phe Glu Gln Arg Tyr Ala Glu
            325                 330                 335

Tyr Tyr Asn Val Leu Ala Asp Phe Cys Ala Val Val Gly Thr Thr Gln
            340                 345                 350

Pro Leu Thr Gly Arg Ser Trp Phe Arg Asn Val Phe Thr Glu Pro Val
        355                 360                 365

Gly Ser Leu Pro Asp Cys Ser Pro Thr Gln Ser Ala Asn Ile Leu Asp
370                 375                 380

Asp Val His Ile Cys Phe Leu Pro Thr Thr Gly Gly Ala Ala Gly
385                 390                 395                 400

Gly Gly Ser Gly Ser Gly Gly Ser Ser Ala Lys Ala Ile Ala Val Gly
            405                 410                 415

Thr Ala Ala Leu Ala Ala Gly Leu Leu Ser Leu Ile His Val Leu Leu
            420                 425                 430

Phe

<210> SEQ ID NO 5
<211> LENGTH: 1611
<212> TYPE: DNA
<213> ORGANISM: Thassiosira pseudonana

<400> SEQUENCE: 5
gagtacaccc ctccaaccac aaactacgac cgatgcctca ccgccgacga agcagccgac    60
atcaccaccg ccctctccaa cggtgtcgag gttgatctct cccctgagaa ggtatccagc   120
gatcaatccg tttactggga gattgactat cgttccacct acaagatcct caagaataca   180
caagatacag tcaacaccac ctaccttttg taccaatgtg gtctccccga acctactccc   240
gagacacacc ctgaactcga aggaatcaca tttgatagcg tctttagtgt ccctcacact   300
ggaggactgc ttgttactgc tactactcag atcccaaaca tcgagatact taaccgtcgt   360

-continued

```
agtcaagttg ttgcgtttgc agtatctgag aacttggttt ccagtccttg tttgtctcag    420
cagatcatcc ctgccgggaa agaagatggg agtatcacct tcttgccatt gtataatgat    480
acagtgattg aggactacgt aacggaacac cctgacactt tagtgttggg tggagcgtgg    540
gataccgatc tcaagatgaa gaacaaggtc atcatctcgg acgtgggtga gtcgcccgaa    600
gaggcactgg accaaaatcg tgatgtgaac gaagccatct ttgaatggtt ggaagtgtat    660
gggtctttgt ttaacgagga gggattggcg ggaggagttc ccgtggtact ttgggcatac    720
cacaaccagg actttgaagg aaacgacgtt ggatgggacg ttggtgaatg tcccaactac    780
tactgcacct atgccaagca ttgccatgtt gagatgttga actctacgga aggaagtatt    840
gattattggg gatatcctcg catgacggat gaggagtttt tggagtttgg aaagaatgcc    900
gatgtatggg tttacccctc ttctgattgg aacagggtat caacccaaaa gatgttctac    960
ctcagtcagt tcaaggctgt tcaggatgag aaggtctatg actaccagat gagtggagag   1020
agtgcttggt ttgagcagcg tcttgccgag tacgatactg tcctccttga cctctgtcac   1080
atcgttgatc gtgccgtatc caccgaccca ccccacattc gtaagtggtt tcgcaacgtc   1140
tacaccgaag gagtaggaac gttgggaatg tgtgaagacc ctgaagagcc atacacctct   1200
cgtgctactg agtgtgtaag gcttgatgat gttgttggcg gtggtgatgt tgagggggga   1260
ggtgatactg ctactgaagt tcccgctgct tcttctggaa gtcgtttggc cgttgtgttg   1320
ggagctgtct ctatcttgtc cgtggttgcg aatgaggtgt ttaccagcgc ccgagagctt   1380
agcttcacga agaaatgtc catcgatgat gtagcgaatg ttctgagcga ctgcagagtt   1440
atctttggga tacacggagc tggacatatg aatgccttgt ttgcaagacc tgatgttgcc   1500
gtcattgaaa tcattggaaa agatccttct tatcacagct ctgatgaaga tcagaaagga   1560
tatcctgcat actttcggaa tataaacatg ttgcttggac agtactatca a            1611
```

<210> SEQ ID NO 6
<211> LENGTH: 581
<212> TYPE: PRT
<213> ORGANISM: Thassiosira pseudonana

<400> SEQUENCE: 6

```
Glu Tyr Thr Pro Pro Thr Thr Asn Tyr Asp Arg Cys Leu Thr Ala Asp
1               5                   10                  15

Glu Ala Ala Asp Ile Thr Thr Ala Leu Ser Asn Gly Val Glu Val Asp
            20                  25                  30

Leu Phe Pro Glu Lys Val Ser Ser Asp Gln Ser Val Tyr Trp Glu Ile
        35                  40                  45

Asp Tyr Arg Ser Thr Tyr Lys Ile Leu Lys Asn Thr Gln Asp Thr Val
    50                  55                  60

Asn Thr Thr Tyr Leu Leu Tyr Gln Cys Gly Leu Pro Glu Pro Thr Pro
65                  70                  75                  80

Glu Thr His Pro Glu Leu Glu Gly Ile Thr Phe Asp Ser Val Phe Ser
                85                  90                  95

Val Pro His Thr Gly Gly Leu Leu Val Thr Ala Thr Gln Ile Pro
            100                 105                 110

Asn Ile Glu Ile Leu Asn Arg Arg Ser Gln Val Ala Phe Ala Val
        115                 120                 125

Ser Glu Asn Leu Val Ser Ser Pro Cys Leu Ser Gln Gln Ile Ile Pro
    130                 135                 140

Ala Gly Lys Glu Asp Gly Ser Ile Thr Phe Leu Pro Leu Tyr Asn Asp
145                 150                 155                 160
```

```
Thr Val Ile Glu Asp Tyr Val Thr Glu His Pro Asp Thr Leu Val Leu
                165                 170                 175

Gly Gly Ala Trp Asp Thr Asp Leu Lys Met Lys Asn Lys Val Ile Ile
            180                 185                 190

Ser Asp Val Gly Glu Ser Pro Glu Ala Leu Asp Gln Asn Arg Asp
        195                 200                 205

Val Asn Glu Ala Ile Phe Glu Trp Leu Glu Val Tyr Gly Ser Leu Phe
    210                 215                 220

Asn Glu Glu Gly Leu Ala Gly Gly Val Pro Val Leu Trp Ala Tyr
225                 230                 235                 240

His Asn Gln Asp Phe Glu Gly Asn Asp Val Gly Trp Asp Val Gly Glu
                245                 250                 255

Cys Pro Asn Tyr Tyr Cys Thr Tyr Ala Lys His Cys His Val Glu Met
                260                 265                 270

Leu Asn Ser Thr Glu Gly Ser Ile Asp Tyr Trp Gly Tyr Pro Arg Met
                275                 280                 285

Thr Asp Glu Glu Phe Leu Glu Phe Gly Lys Asn Ala Asp Val Trp Val
            290                 295                 300

Tyr Pro Ser Ser Asp Trp Asn Arg Val Ser Thr Gln Lys Met Phe Tyr
305                 310                 315                 320

Leu Ser Gln Phe Lys Ala Val Gln Asp Glu Lys Val Tyr Asp Tyr Gln
                325                 330                 335

Met Ser Gly Glu Ser Ala Trp Phe Glu Gln Arg Leu Ala Glu Tyr Asp
                340                 345                 350

Thr Val Leu Leu Asp Leu Cys His Ile Val Asp Arg Ala Val Ser Thr
            355                 360                 365

Asp Pro Pro His Ile Arg Lys Trp Phe Arg Asn Val Tyr Thr Glu Gly
    370                 375                 380

Val Gly Thr Leu Gly Met Cys Glu Asp Pro Glu Glu Pro Tyr Thr Ser
385                 390                 395                 400

Arg Ala Thr Glu Cys Val Arg Leu Asp Asp Val Val Gly Gly Gly Asp
                405                 410                 415

Val Glu Gly Gly Gly Asp Thr Ala Thr Glu Val Pro Ala Ala Ser Ser
            420                 425                 430

Gly Ser Arg Leu Ala Val Val Leu Gly Ala Val Ser Ile Leu Ser Val
    435                 440                 445

Val Ala Asn Glu Val Phe Thr Ser Ala Arg Glu Leu Ser Phe Thr Lys
450                 455                 460

Glu Met Ser Ile Asp Asp Val Ala Asn Val Leu Ser Asp Cys Arg Val
465                 470                 475                 480

Ile Phe Gly Ile His Gly Ala Gly His Met Asn Ala Leu Phe Ala Arg
                485                 490                 495

Pro Asp Val Ala Val Ile Glu Ile Ile Gly Lys Asp Pro Ser Tyr His
            500                 505                 510

Ser Ser Asp Glu Asp Gln Lys Gly Tyr Pro Ala Tyr Phe Arg Asn Ile
    515                 520                 525

Asn Met Leu Leu Gly Gln Tyr Tyr Gln Ser Ile Ala Gly Asp Ser Thr
530                 535                 540

Arg Gly Met Tyr Asp Asp Gly Tyr Val Ile Asp Leu Glu Glu Ala Arg
545                 550                 555                 560

Glu Ala Leu Val Arg Ala Arg His His Ser Thr Ser Trp Ile Glu Glu
                565                 570                 575
```

His Gly His Trp Arg
        580

<210> SEQ ID NO 7
<211> LENGTH: 1545
<212> TYPE: DNA
<213> ORGANISM: Fragilariopsis cylindrus

<400> SEQUENCE: 7

```
caacaagaga cagtgattgg agtgaataat ctcatcaatg gtgcttgtgc cgtggactat      60
gatccgaatg ataatgtgga ttactttcct atcaagtatc ggaaaccaag catcgaatcg     120
tacggcaaca ttgatatttt cggtaacaag tttgtaccac acgaatcgac tgactttta     180
aacatcgaat atcacgacaa ctacaaaatt gttacaaact ctcaccaaca accaccgaaa     240
acatacctgt tgtatcaatg tggtaccgaa attcctgaca tcgtcactaa tggagacttt     300
gcatttgact tagtcgtatc ggttcctcat caggggggat tggcactcac acaaactcca     360
caaatcccat atatcgaatt actaggattg cgggaagagg tgattgccta cgtaggtgat     420
ccacagtatg tgacaagtcc ctgtatgagt tacatgatga cgggcgccgg agatgatgat     480
caaatccaag tcgtctatga tagcaacatt accataatgg aaggactcac cgatacattt     540
cgcaccgagc atcctaatac tatcatggtg agtggtccca ccaacaatgt tgtgggggat     600
cgagttattg tggcatcggc cacacaagaa aggaccaatg ttgcaacttt tgattggatt     660
gcttttatg catcattcta taacttggaa ggtgaatcta atcgtatctc gacattgatg     720
caggagagct atgattgcat cagcgacgtt tccactaaca ttgtgaaaca gcaacggaac     780
ctggaaaacg taggagaaga gtaccacacc cccaccatct ttgggccaa tttttttcacc     840
tatgatgatt tgggatggag tgttggcgac tgtcccacgt gggatgcaaa tttctattgt     900
gaatacgccg cccattgtga cgcaaccatc ctatcacgac cggaaggtgt tggcttcaac     960
cgaacgtacg gaggatcacc aactgtgtat tggtatatta gcgacgaaga agcgttagag    1020
atgggcaaga atgccgatat tttatttac accggaggtg attgggactc ggtgtataaa    1080
tcacacagtt cgatgctgga tcaattccaa gccgttcaaa acaaacaagt atttgataca    1140
ttgggacagg gaccatcggc atggctcgaa caacggtatg cggaatacaa tacagtagga    1200
ttggacttgt gtgacatcgt tggtcattca tcaatggcga cagtaaatgg tggtaataac    1260
gcgaatcgtt ggtttcgaaa tgtgtatacc gaacctattg gtgcattgcc ggtgtgtgat    1320
gtagcaggag gtgaaatcag ccaaccctat gttcccccaa aagtgaactg tgtccaacca    1380
ccagaggaag gtgtaaaaat tgtgaacaga ccaaaagaaa tctcatcacc atcccaagag    1440
caagtagaag atggtgattc ggctgcttcc gggttttgta attacttctc ctactcgaac    1500
ttaatgttgg tatcgtttgc tggtatggtt gtttctcaaa tgtag                   1545
```

<210> SEQ ID NO 8
<211> LENGTH: 514
<212> TYPE: PRT
<213> ORGANISM: Fragilariopsis cylindrus

<400> SEQUENCE: 8

Gln Gln Glu Thr Val Ile Gly Val Asn Asn Leu Ile Asn Gly Ala Cys
1               5                   10                  15

Ala Val Asp Tyr Asp Pro Asn Asp Asn Val Asp Tyr Phe Pro Ile Lys
            20                  25                  30

Tyr Arg Lys Pro Ser Ile Glu Ser Tyr Gly Asn Ile Asp Ile Phe Gly
        35                  40                  45

```
Asn Lys Phe Val Pro His Glu Ser Thr Asp Phe Leu Asn Ile Glu Tyr
 50                  55                  60

His Asp Asn Tyr Lys Ile Val Thr Asn Ser His Gln Gln Pro Pro Lys
 65                  70                  75                  80

Thr Tyr Leu Leu Tyr Gln Cys Gly Thr Glu Ile Pro Asp Ile Val Thr
                     85                  90                  95

Asn Gly Asp Phe Ala Phe Asp Leu Val Val Ser Val Pro His Gln Gly
                100                 105                 110

Gly Leu Ala Leu Thr Gln Thr Pro Gln Ile Pro Tyr Ile Glu Leu Leu
            115                 120                 125

Gly Leu Arg Glu Glu Val Ile Ala Tyr Val Gly Asp Pro Gln Tyr Val
            130                 135                 140

Thr Ser Pro Cys Met Ser Tyr Met Met Thr Gly Ala Gly Asp Asp Asp
145                 150                 155                 160

Gln Ile Gln Val Val Tyr Asp Ser Asn Ile Thr Ile Met Glu Gly Leu
                165                 170                 175

Thr Asp Thr Phe Arg Thr Glu His Pro Asn Thr Ile Met Val Ser Gly
                180                 185                 190

Pro Thr Asn Asn Val Val Gly Asp Arg Val Ile Val Ala Ser Ala Thr
            195                 200                 205

Gln Glu Arg Thr Asn Val Ala Thr Phe Asp Trp Ile Ala Phe Tyr Ala
            210                 215                 220

Ser Phe Tyr Asn Leu Glu Gly Glu Ser Asn Arg Ile Ser Thr Leu Met
225                 230                 235                 240

Gln Glu Ser Tyr Asp Cys Ile Ser Asp Val Ser Thr Asn Ile Val Lys
                245                 250                 255

Gln Gln Arg Asn Leu Glu Asn Val Gly Glu Glu Tyr His Thr Pro Thr
            260                 265                 270

Ile Phe Trp Ala Asn Phe Phe Thr Tyr Asp Asp Leu Gly Trp Ser Val
            275                 280                 285

Gly Asp Cys Pro Thr Trp Asp Ala Asn Phe Tyr Cys Glu Tyr Ala Ala
290                 295                 300

His Cys Asp Ala Thr Ile Leu Ser Arg Pro Glu Gly Val Gly Phe Asn
305                 310                 315                 320

Arg Thr Tyr Gly Gly Ser Pro Thr Val Tyr Trp Tyr Ile Ser Asp Glu
                325                 330                 335

Glu Ala Leu Glu Met Gly Lys Asn Ala Asp Ile Phe Ile Tyr Thr Gly
            340                 345                 350

Gly Asp Trp Asp Ser Val Tyr Lys Ser His Ser Ser Met Leu Asp Gln
            355                 360                 365

Phe Gln Ala Val Gln Asn Lys Gln Val Phe Asp Thr Leu Gly Gln Gly
            370                 375                 380

Pro Ser Ala Trp Leu Glu Gln Arg Tyr Ala Glu Tyr Asn Thr Val Gly
385                 390                 395                 400

Leu Asp Leu Cys Asp Ile Val Gly His Ser Ser Met Ala Thr Val Asn
                405                 410                 415

Gly Gly Asn Asn Ala Asn Arg Trp Phe Arg Asn Val Tyr Thr Glu Pro
            420                 425                 430

Ile Gly Ala Leu Pro Val Cys Asp Val Ala Gly Gly Glu Ile Ser Gln
            435                 440                 445

Pro Tyr Val Pro Pro Lys Val Asn Cys Val Gln Pro Pro Glu Glu Gly
450                 455                 460
```

Val Lys Ile Val Asn Arg Pro Lys Glu Ile Ser Ser Pro Ser Gln Glu
465                 470                 475                 480

Gln Val Glu Asp Gly Asp Ser Ala Ala Ser Gly Phe Cys Asn Tyr Phe
            485                 490                 495

Ser Tyr Ser Asn Leu Met Leu Val Ser Phe Ala Gly Met Val Val Ser
        500                 505                 510

Gln Met

<210> SEQ ID NO 9
<211> LENGTH: 1332
<212> TYPE: DNA
<213> ORGANISM: Fragilariopsis cylindrus

<400> SEQUENCE: 9
caggacatca acgtaggcgg aacaactcaa gatgaaggtt ctatcttggt ggaaaatctc      60
gtcgatcgat gcgtaatcga ctatgatccg gacgttgatt actttcctgt gaagtatcaa     120
aaaccatcga tttcttccta tggtgacatt gatatcttcg gagagaaatt tgaaccacac     180
aatacaaccg attttttaga aatcacatac ttcaaaacat acaagatcgt tacgaacaaa     240
catcaagatc caccagtcag ttacttactg taccaatgtg gtacggaaaa accacaagat     300
gtgatcgatg atcccgataa caagtttgat ttagttttac caattcctca tcaaggaggt     360
cttgcgttga ctcaaacccc acaaatcccg taccctgaaa tgttaggatt acgtggagaa     420
attattggat taattggaaa cccgtcgtac gtgacaagtc cttgtctcag ctccttgtta     480
gatgatggat cagtcgaagt tgtatatgat tccaattcta ctatacaaag agagcttatt     540
gatgattaca ttgaacgtaa tccaaatgtt attatcttta gtggaccaac gaacaacgtt     600
gttggtgatc gtgtcatggt tgtttctgct actcaagaac gaacaaatgt tgctacattt     660
gattggatgg cattttgggc ggccttatac aacctagagg gagaagcatc aagaattaca     720
agtgaaatgc aagcatcgta tgattgttca agtgataatg ccaaggctgt tgctgcacaa     780
caacgtgaac ttgttcccga agaaaaacaa ccagtaattc tatgggcaaa ttacttcacc     840
tatcaaaatc ttggctggtc cgttgccgag tgccccactt gggactcggc atactattgt     900
gagtacgcag cgcattgtga tgcgaccatc ttatctcgtc ctgaaggagc tggttataac     960
aagacatatg gcggttcgcc aacagtttac tggtatttga cactctggg a cagggtcca    1020
tcagcatgga atgaacaacg gtatgctgaa atgacgttg ttggattaga catgtgtgat    1080
attgttggac gttccagtac gacaggtgtt cagcacgaac gtcgttggtt ccgtaatgta    1140
ttcactgaac caatcggttc cttagaaacg tgcaacgttc ccgatgaaat ctttcaaccg    1200
tacgtaccac caggaacaga atgcgattca gcaggagaag aagatactac ctcggagtcg    1260
tcttctgcac cggaaaaatc atctttgtta gcattttatc ttgctatggt tgcatttgtt    1320
ttggtcgtct aa                                                       1332

<210> SEQ ID NO 10
<211> LENGTH: 443
<212> TYPE: PRT
<213> ORGANISM: Fragilariopsis cylindrus

<400> SEQUENCE: 10

Gln Asp Ile Asn Val Gly Gly Thr Thr Gln Asp Glu Gly Ser Ile Leu
1               5                   10                  15

Val Glu Asn Leu Val Asp Arg Cys Val Ile Asp Tyr Asp Pro Asp Val
            20                  25                  30

-continued

```
Asp Tyr Phe Pro Val Lys Tyr Gln Lys Pro Ser Ile Ser Ser Tyr Gly
         35                  40                  45
Asp Ile Asp Ile Phe Gly Glu Lys Phe Glu Pro His Asn Thr Thr Asp
 50                  55                  60
Phe Leu Glu Ile Thr Tyr Phe Lys Thr Tyr Lys Ile Val Thr Asn Lys
65                   70                  75                  80
His Gln Asp Pro Pro Val Ser Tyr Leu Leu Tyr Gln Cys Gly Thr Glu
                     85                  90                  95
Lys Pro Gln Asp Val Ile Asp Asp Pro Asp Asn Lys Phe Asp Leu Val
                100                 105                 110
Leu Pro Ile Pro His Gln Gly Gly Leu Ala Leu Thr Gln Thr Pro Gln
                115                 120                 125
Ile Pro Tyr Pro Glu Met Leu Gly Leu Arg Gly Glu Ile Ile Gly Leu
                130                 135                 140
Ile Gly Asn Pro Ser Tyr Val Thr Ser Pro Cys Leu Ser Ser Leu Leu
145                 150                 155                 160
Asp Asp Gly Ser Val Glu Val Val Tyr Asp Ser Asn Ser Thr Ile Gln
                165                 170                 175
Arg Glu Leu Ile Asp Asp Tyr Ile Glu Arg Asn Pro Asn Val Ile Ile
                180                 185                 190
Phe Ser Gly Pro Thr Asn Asn Val Val Gly Asp Arg Val Met Val Val
                195                 200                 205
Ser Ala Thr Gln Glu Arg Thr Asn Val Ala Thr Phe Asp Trp Met Ala
                210                 215                 220
Phe Trp Ala Ala Leu Tyr Asn Leu Glu Gly Glu Ala Ser Arg Ile Thr
225                 230                 235                 240
Ser Glu Met Gln Ala Ser Tyr Asp Cys Ser Ser Asp Asn Ala Lys Ala
                245                 250                 255
Val Ala Ala Gln Gln Arg Glu Leu Val Pro Glu Glu Lys Gln Pro Val
                260                 265                 270
Ile Leu Trp Ala Asn Tyr Phe Thr Tyr Gln Asn Leu Gly Trp Ser Val
                275                 280                 285
Ala Glu Cys Pro Thr Trp Asp Ser Ala Tyr Tyr Cys Glu Tyr Ala Ala
                290                 295                 300
His Cys Asp Ala Thr Ile Leu Ser Arg Pro Glu Gly Ala Gly Tyr Asn
305                 310                 315                 320
Lys Thr Tyr Gly Gly Ser Pro Thr Val Tyr Trp Tyr Leu Ile His Ser
                325                 330                 335
Gly Gln Gly Pro Ser Ala Trp Asn Glu Gln Arg Tyr Ala Glu Tyr Asp
                340                 345                 350
Val Val Gly Leu Asp Met Cys Asp Ile Val Gly Arg Ser Ser Thr Thr
                355                 360                 365
Gly Val Gln His Glu Arg Arg Trp Phe Arg Asn Val Phe Thr Glu Pro
                370                 375                 380
Ile Gly Ser Leu Glu Thr Cys Asn Val Pro Asp Glu Ile Phe Gln Pro
385                 390                 395                 400
Tyr Val Pro Pro Gly Thr Glu Cys Asp Ser Ala Gly Glu Glu Asp Thr
                405                 410                 415
Thr Ser Glu Ser Ser Ala Pro Glu Lys Ser Ser Leu Leu Ala Phe
                420                 425                 430
Tyr Leu Ala Met Val Ala Phe Val Leu Val Val
                435                 440
```

```
<210> SEQ ID NO 11
<211> LENGTH: 7
<212> TYPE: PRT
<213> ORGANISM: Unknown
<220> FEATURE:
<223> OTHER INFORMATION: Description of Unknown: Cobalamin acquisition
      protein

<400> SEQUENCE: 11

Tyr Leu Leu Tyr Gln Cys Gly
1               5

<210> SEQ ID NO 12
<211> LENGTH: 10
<212> TYPE: PRT
<213> ORGANISM: Unknown
<220> FEATURE:
<223> OTHER INFORMATION: Description of Unknown: Cobalamin acquisition
      protein

<400> SEQUENCE: 12

Asn Thr Thr Tyr Leu Leu Tyr Gln Cys Gly
1               5                   10

<210> SEQ ID NO 13
<211> LENGTH: 7
<212> TYPE: PRT
<213> ORGANISM: Unknown
<220> FEATURE:
<223> OTHER INFORMATION: Description of Unknown: Cobalamin acquisition
      protein

<400> SEQUENCE: 13

Glu Cys Pro Asn Tyr Tyr Cys
1               5

<210> SEQ ID NO 14
<211> LENGTH: 7
<212> TYPE: PRT
<213> ORGANISM: Unknown
<220> FEATURE:
<223> OTHER INFORMATION: Description of Unknown: Cobalamin acquisition
      protein

<400> SEQUENCE: 14

Pro Val Val Leu Trp Ala Tyr
1               5

<210> SEQ ID NO 15
<211> LENGTH: 6
<212> TYPE: PRT
<213> ORGANISM: Unknown
<220> FEATURE:
<223> OTHER INFORMATION: Description of Unknown: Cobalamin acquisition
      protein

<400> SEQUENCE: 15

Ala Trp Phe Glu Gln Arg
1               5

<210> SEQ ID NO 16
<211> LENGTH: 5
<212> TYPE: PRT
<213> ORGANISM: Unknown
<220> FEATURE:
<223> OTHER INFORMATION: Description of Unknown: Cobalamin acquisition
      protein

<400> SEQUENCE: 16
```

```
Trp Phe Arg Asn Val
1               5

<210> SEQ ID NO 17
<211> LENGTH: 18
<212> TYPE: PRT
<213> ORGANISM: Thassiosira pseudonana

<400> SEQUENCE: 17

Val Ile Ile Ser Asp Val Gly Glu Ser Pro Glu Glu Ala Leu Asp Gln
1               5                   10                  15

Asn Arg

<210> SEQ ID NO 18
<211> LENGTH: 8
<212> TYPE: PRT
<213> ORGANISM: Phaeodactylum tricornutum

<400> SEQUENCE: 18

Phe Phe Ser Val Phe Phe Asn Lys
1               5

<210> SEQ ID NO 19
<211> LENGTH: 14
<212> TYPE: PRT
<213> ORGANISM: Phaeodactylum tricornutum

<400> SEQUENCE: 19

Glu His Thr Ala Asn Gln Val Val Glu Ala Ala Glu Ser Arg
1               5                   10

<210> SEQ ID NO 20
<211> LENGTH: 601
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (1)..(16)
<223> OTHER INFORMATION: May or may not be present
<220> FEATURE:
<221> NAME/KEY: MOD_RES
<222> LOCATION: (17)..(17)
<223> OTHER INFORMATION: Asp or Glu
<220> FEATURE:
<221> NAME/KEY: MOD_RES
<222> LOCATION: (18)..(18)
<223> OTHER INFORMATION: Glu or Ala
<220> FEATURE:
<221> NAME/KEY: MOD_RES
<222> LOCATION: (19)..(19)
<223> OTHER INFORMATION: Pro or Ala
<220> FEATURE:
<221> NAME/KEY: MOD_RES
<222> LOCATION: (20)..(20)
<223> OTHER INFORMATION: Pro or Asp
<220> FEATURE:
<221> NAME/KEY: MOD_RES
<222> LOCATION: (21)..(21)
<223> OTHER INFORMATION: Ala or Ile
<220> FEATURE:
<221> NAME/KEY: MOD_RES
<222> LOCATION: (22)..(22)
<223> OTHER INFORMATION: Cys or Thr
<220> FEATURE:
<221> NAME/KEY: MOD_RES
<222> LOCATION: (23)..(23)
<223> OTHER INFORMATION: Leu or Thr
```

```
-continued

<220> FEATURE:
<221> NAME/KEY: MOD_RES
<222> LOCATION: (24)..(24)
<223> OTHER INFORMATION: Thr or Ala
<220> FEATURE:
<221> NAME/KEY: MOD_RES
<222> LOCATION: (25)..(25)
<223> OTHER INFORMATION: Ser or Leu
<220> FEATURE:
<221> NAME/KEY: MOD_RES
<222> LOCATION: (26)..(26)
<223> OTHER INFORMATION: Thr or Ser
<220> FEATURE:
<221> NAME/KEY: MOD_RES
<222> LOCATION: (27)..(27)
<223> OTHER INFORMATION: Ala or Asn
<220> FEATURE:
<221> NAME/KEY: MOD_RES
<222> LOCATION: (28)..(28)
<223> OTHER INFORMATION: Asp or Gly
<220> FEATURE:
<221> NAME/KEY: MOD_RES
<222> LOCATION: (29)..(29)
<223> OTHER INFORMATION: Leu or Val
<220> FEATURE:
<221> NAME/KEY: MOD_RES
<222> LOCATION: (30)..(30)
<223> OTHER INFORMATION: Ser or Glu
<220> FEATURE:
<221> NAME/KEY: MOD_RES
<222> LOCATION: (33)..(33)
<223> OTHER INFORMATION: Ile or Leu
<220> FEATURE:
<221> NAME/KEY: MOD_RES
<222> LOCATION: (35)..(35)
<223> OTHER INFORMATION: Thr or Pro
<220> FEATURE:
<221> NAME/KEY: MOD_RES
<222> LOCATION: (36)..(36)
<223> OTHER INFORMATION: Asp or Glu
<220> FEATURE:
<221> NAME/KEY: MOD_RES
<222> LOCATION: (39)..(39)
<223> OTHER INFORMATION: Glu or Ser
<220> FEATURE:
<221> NAME/KEY: MOD_RES
<222> LOCATION: (40)..(40)
<223> OTHER INFORMATION: Pro or Ser
<220> FEATURE:
<221> NAME/KEY: MOD_RES
<222> LOCATION: (41)..(41)
<223> OTHER INFORMATION: Leu or Asp
<220> FEATURE:
<221> NAME/KEY: MOD_RES
<222> LOCATION: (42)..(42)
<223> OTHER INFORMATION: Phe or Gln
<220> FEATURE:
<221> NAME/KEY: MOD_RES
<222> LOCATION: (44)..(44)
<223> OTHER INFORMATION: Gln or Val
<220> FEATURE:
<221> NAME/KEY: MOD_RES
<222> LOCATION: (45)..(45)
<223> OTHER INFORMATION: Gly or Tyr
<220> FEATURE:
<221> NAME/KEY: MOD_RES
<222> LOCATION: (47)..(47)
<223> OTHER INFORMATION: Asn or Glu
<220> FEATURE:
<221> NAME/KEY: MOD_RES
<222> LOCATION: (48)..(48)
<223> OTHER INFORMATION: Val or Ile
<220> FEATURE:
<221> NAME/KEY: MOD_RES
<222> LOCATION: (49)..(49)
<223> OTHER INFORMATION: Thr or Asp
<220> FEATURE:
<221> NAME/KEY: MOD_RES
<222> LOCATION: (51)..(51)
```

```
<223> OTHER INFORMATION: His or Arg
<220> FEATURE:
<221> NAME/KEY: MOD_RES
<222> LOCATION: (52)..(52)
<223> OTHER INFORMATION: Asn or Ser
<220> FEATURE:
<221> NAME/KEY: MOD_RES
<222> LOCATION: (57)..(57)
<223> OTHER INFORMATION: Ala or Leu
<220> FEATURE:
<221> NAME/KEY: MOD_RES
<222> LOCATION: (58)..(58)
<223> OTHER INFORMATION: Asn or Lys
<220> FEATURE:
<221> NAME/KEY: MOD_RES
<222> LOCATION: (60)..(60)
<223> OTHER INFORMATION: Leu or Thr
<220> FEATURE:
<221> NAME/KEY: MOD_RES
<222> LOCATION: (61)..(61)
<223> OTHER INFORMATION: Phe or Gln
<220> FEATURE:
<221> NAME/KEY: MOD_RES
<222> LOCATION: (63)..(64)
<223> OTHER INFORMATION: May or may not be present
<220> FEATURE:
<221> NAME/KEY: MOD_RES
<222> LOCATION: (75)..(75)
<223> OTHER INFORMATION: Ser or Leu
<220> FEATURE:
<221> NAME/KEY: MOD_RES
<222> LOCATION: (76)..(76)
<223> OTHER INFORMATION: Thr or Pro
<220> FEATURE:
<221> NAME/KEY: MOD_RES
<222> LOCATION: (77)..(77)
<223> OTHER INFORMATION: Pro or Glu
<220> FEATURE:
<221> NAME/KEY: MOD_RES
<222> LOCATION: (79)..(79)
<223> OTHER INFORMATION: Ala or Thr
<220> FEATURE:
<221> NAME/KEY: MOD_RES
<222> LOCATION: (80)..(80)
<223> OTHER INFORMATION: Asp or Pro
<220> FEATURE:
<221> NAME/KEY: MOD_RES
<222> LOCATION: (81)..(81)
<223> OTHER INFORMATION: Val or Glu
<220> FEATURE:
<221> NAME/KEY: MOD_RES
<222> LOCATION: (82)..(82)
<223> OTHER INFORMATION: Val or Thr
<220> FEATURE:
<221> NAME/KEY: MOD_RES
<222> LOCATION: (83)..(83)
<223> OTHER INFORMATION: Asp or His
<220> FEATURE:
<221> NAME/KEY: MOD_RES
<222> LOCATION: (84)..(87)
<223> OTHER INFORMATION: May or may not be present
<220> FEATURE:
<221> NAME/KEY: MOD_RES
<222> LOCATION: (88)..(88)
<223> OTHER INFORMATION: Asn or Gly
<220> FEATURE:
<221> NAME/KEY: MOD_RES
<222> LOCATION: (89)..(89)
<223> OTHER INFORMATION: Gly or Ile
<220> FEATURE:
<221> NAME/KEY: MOD_RES
<222> LOCATION: (90)..(90)
<223> OTHER INFORMATION: Asn or Thr
<220> FEATURE:
<221> NAME/KEY: MOD_RES
<222> LOCATION: (92)..(92)
<223> OTHER INFORMATION: Asn or Asp
<220> FEATURE:
<221> NAME/KEY: MOD_RES
```

```
<222> LOCATION: (93)..(93)
<223> OTHER INFORMATION: Ala or Ser
<220> FEATURE:
<221> NAME/KEY: MOD_RES
<222> LOCATION: (95)..(95)
<223> OTHER INFORMATION: Leu or Phe
<220> FEATURE:
<221> NAME/KEY: MOD_RES
<222> LOCATION: (96)..(96)
<223> OTHER INFORMATION: Glu or Ser
<220> FEATURE:
<221> NAME/KEY: MOD_RES
<222> LOCATION: (97)..(97)
<223> OTHER INFORMATION: Ile or Val
<220> FEATURE:
<221> NAME/KEY: MOD_RES
<222> LOCATION: (99)..(99)
<223> OTHER INFORMATION: Leu or His
<220> FEATURE:
<221> NAME/KEY: MOD_RES
<222> LOCATION: (100)..(100)
<223> OTHER INFORMATION: Ser or Thr
<220> FEATURE:
<221> NAME/KEY: MOD_RES
<222> LOCATION: (101)..(101)
<223> OTHER INFORMATION: Asn or Gly
<220> FEATURE:
<221> NAME/KEY: MOD_RES
<222> LOCATION: (102)..(102)
<223> OTHER INFORMATION: May or may not be present
<220> FEATURE:
<221> NAME/KEY: MOD_RES
<222> LOCATION: (103)..(103)
<223> OTHER INFORMATION: Val or Leu
<220> FEATURE:
<221> NAME/KEY: MOD_RES
<222> LOCATION: (104)..(104)
<223> OTHER INFORMATION: Gly or Leu
<220> FEATURE:
<221> NAME/KEY: MOD_RES
<222> LOCATION: (105)..(105)
<223> OTHER INFORMATION: Leu or Val
<220> FEATURE:
<221> NAME/KEY: MOD_RES
<222> LOCATION: (106)..(106)
<223> OTHER INFORMATION: Ser or Thr
<220> FEATURE:
<221> NAME/KEY: MOD_RES
<222> LOCATION: (107)..(107)
<223> OTHER INFORMATION: Gln or Ala
<220> FEATURE:
<221> NAME/KEY: MOD_RES
<222> LOCATION: (109)..(109)
<223> OTHER INFORMATION: Pro or Thr
<220> FEATURE:
<221> NAME/KEY: MOD_RES
<222> LOCATION: (110)..(110)
<223> OTHER INFORMATION: His or Gln
<220> FEATURE:
<221> NAME/KEY: MOD_RES
<222> LOCATION: (112)..(112)
<223> OTHER INFORMATION: Gly or Pro
<220> FEATURE:
<221> NAME/KEY: MOD_RES
<222> LOCATION: (113)..(113)
<223> OTHER INFORMATION: Phe or Asn
<220> FEATURE:
<221> NAME/KEY: MOD_RES
<222> LOCATION: (114)..(114)
<223> OTHER INFORMATION: Met or Ile
<220> FEATURE:
<221> NAME/KEY: MOD_RES
<222> LOCATION: (116)..(116)
<223> OTHER INFORMATION: Gln or Ile
<220> FEATURE:
<221> NAME/KEY: MOD_RES
<222> LOCATION: (118)..(118)
<223> OTHER INFORMATION: Glu or Asn
<220> FEATURE:
```

-continued

```
<221> NAME/KEY: MOD_RES
<222> LOCATION: (119)..(119)
<223> OTHER INFORMATION: Leu or Arg
<220> FEATURE:
<221> NAME/KEY: MOD_RES
<222> LOCATION: (120)..(120)
<223> OTHER INFORMATION: Val or Arg
<220> FEATURE:
<221> NAME/KEY: MOD_RES
<222> LOCATION: (121)..(121)
<223> OTHER INFORMATION: Asp or Ser
<220> FEATURE:
<221> NAME/KEY: MOD_RES
<222> LOCATION: (122)..(122)
<223> OTHER INFORMATION: Glu or Gln
<220> FEATURE:
<221> NAME/KEY: MOD_RES
<222> LOCATION: (123)..(123)
<223> OTHER INFORMATION: Ile or Val
<220> FEATURE:
<221> NAME/KEY: MOD_RES
<222> LOCATION: (124)..(124)
<223> OTHER INFORMATION: Ala or Val
<220> FEATURE:
<221> NAME/KEY: MOD_RES
<222> LOCATION: (127)..(127)
<223> OTHER INFORMATION: Leu or Ala
<220> FEATURE:
<221> NAME/KEY: MOD_RES
<222> LOCATION: (128)..(128)
<223> OTHER INFORMATION: Thr or Val
<220> FEATURE:
<221> NAME/KEY: MOD_RES
<222> LOCATION: (129)..(129)
<223> OTHER INFORMATION: Asp or Ser
<220> FEATURE:
<221> NAME/KEY: MOD_RES
<222> LOCATION: (130)..(130)
<223> OTHER INFORMATION: Thr or Glu
<220> FEATURE:
<221> NAME/KEY: MOD_RES
<222> LOCATION: (131)..(131)
<223> OTHER INFORMATION: Asp or Asn
<220> FEATURE:
<221> NAME/KEY: MOD_RES
<222> LOCATION: (132)..(132)
<223> OTHER INFORMATION: Phe or Leu
<220> FEATURE:
<221> NAME/KEY: MOD_RES
<222> LOCATION: (133)..(133)
<223> OTHER INFORMATION: Ile or Val
<220> FEATURE:
<221> NAME/KEY: MOD_RES
<222> LOCATION: (138)..(138)
<223> OTHER INFORMATION: Phe or Leu
<220> FEATURE:
<221> NAME/KEY: MOD_RES
<222> LOCATION: (139)..(139)
<223> OTHER INFORMATION: Leu or Ser
<220> FEATURE:
<221> NAME/KEY: MOD_RES
<222> LOCATION: (140)..(140)
<223> OTHER INFORMATION: Asp or Gln
<220> FEATURE:
<221> NAME/KEY: MOD_RES
<222> LOCATION: (141)..(141)
<223> OTHER INFORMATION: Glu or Gln
<220> FEATURE:
<221> NAME/KEY: MOD_RES
<222> LOCATION: (143)..(143)
<223> OTHER INFORMATION: Ala or Ile
<220> FEATURE:
<221> NAME/KEY: MOD_RES
<222> LOCATION: (144)..(144)
<223> OTHER INFORMATION: Ala or Pro
<220> FEATURE:
<221> NAME/KEY: MOD_RES
<222> LOCATION: (145)..(164)
<223> OTHER INFORMATION: May or may not be present
```

```
<220> FEATURE:
<221> NAME/KEY: MOD_RES
<222> LOCATION: (165)..(165)
<223> OTHER INFORMATION: Thr or Ala
<220> FEATURE:
<221> NAME/KEY: MOD_RES
<222> LOCATION: (166)..(166)
<223> OTHER INFORMATION: Ala or Gly
<220> FEATURE:
<221> NAME/KEY: MOD_RES
<222> LOCATION: (167)..(167)
<223> OTHER INFORMATION: Leu or Lys
<220> FEATURE:
<221> NAME/KEY: MOD_RES
<222> LOCATION: (168)..(168)
<223> OTHER INFORMATION: Ser or Glu
<220> FEATURE:
<221> NAME/KEY: MOD_RES
<222> LOCATION: (169)..(169)
<223> OTHER INFORMATION: Ala or Asp
<220> FEATURE:
<221> NAME/KEY: MOD_RES
<222> LOCATION: (171)..(171)
<223> OTHER INFORMATION: Thr or Ser
<220> FEATURE:
<221> NAME/KEY: MOD_RES
<222> LOCATION: (172)..(172)
<223> OTHER INFORMATION: Val or Ile
<220> FEATURE:
<221> NAME/KEY: MOD_RES
<222> LOCATION: (173)..(173)
<223> OTHER INFORMATION: Ala or Thr
<220> FEATURE:
<221> NAME/KEY: MOD_RES
<222> LOCATION: (175)..(175)
<223> OTHER INFORMATION: Val or Leu
<220> FEATURE:
<221> NAME/KEY: MOD_RES
<222> LOCATION: (176)..(176)
<223> OTHER INFORMATION: Ala or Pro
<220> FEATURE:
<221> NAME/KEY: MOD_RES
<222> LOCATION: (177)..(177)
<223> OTHER INFORMATION: Ser or Leu
<220> FEATURE:
<221> NAME/KEY: MOD_RES
<222> LOCATION: (178)..(178)
<223> OTHER INFORMATION: Phe or Tyr
<220> FEATURE:
<221> NAME/KEY: MOD_RES
<222> LOCATION: (179)..(179)
<223> OTHER INFORMATION: Thr or Asn
<220> FEATURE:
<221> NAME/KEY: MOD_RES
<222> LOCATION: (180)..(180)
<223> OTHER INFORMATION: Gln or Asp
<220> FEATURE:
<221> NAME/KEY: MOD_RES
<222> LOCATION: (181)..(181)
<223> OTHER INFORMATION: Val or Thr
<220> FEATURE:
<221> NAME/KEY: MOD_RES
<222> LOCATION: (182)..(182)
<223> OTHER INFORMATION: Pro or Val
<220> FEATURE:
<221> NAME/KEY: MOD_RES
<222> LOCATION: (183)..(183)
<223> OTHER INFORMATION: Phe or Ile
<220> FEATURE:
<221> NAME/KEY: MOD_RES
<222> LOCATION: (184)..(184)
<223> OTHER INFORMATION: Asp or Glu
<220> FEATURE:
<221> NAME/KEY: MOD_RES
<222> LOCATION: (185)..(185)
<223> OTHER INFORMATION: Asn or Asp
<220> FEATURE:
<221> NAME/KEY: MOD_RES
<222> LOCATION: (186)..(186)
```

```
<223> OTHER INFORMATION: Thr or Tyr
<220> FEATURE:
<221> NAME/KEY: MOD_RES
<222> LOCATION: (188)..(188)
<223> OTHER INFORMATION: Asn or Thr
<220> FEATURE:
<221> NAME/KEY: MOD_RES
<222> LOCATION: (189)..(189)
<223> OTHER INFORMATION: Ile or Glu
<220> FEATURE:
<221> NAME/KEY: MOD_RES
<222> LOCATION: (190)..(190)
<223> OTHER INFORMATION: Gln or His
<220> FEATURE:
<221> NAME/KEY: MOD_RES
<222> LOCATION: (191)..(191)
<223> OTHER INFORMATION: Glu or Pro
<220> FEATURE:
<221> NAME/KEY: MOD_RES
<222> LOCATION: (192)..(192)
<223> OTHER INFORMATION: Tyr or Asp
<220> FEATURE:
<221> NAME/KEY: MOD_RES
<222> LOCATION: (193)..(193)
<223> OTHER INFORMATION: Ser or Thr
<220> FEATURE:
<221> NAME/KEY: MOD_RES
<222> LOCATION: (194)..(194)
<223> OTHER INFORMATION: Glu or Leu
<220> FEATURE:
<221> NAME/KEY: MOD_RES
<222> LOCATION: (195)..(195)
<223> OTHER INFORMATION: Leu or Val
<220> FEATURE:
<221> NAME/KEY: MOD_RES
<222> LOCATION: (196)..(196)
<223> OTHER INFORMATION: Thr or Leu
<220> FEATURE:
<221> NAME/KEY: MOD_RES
<222> LOCATION: (197)..(197)
<223> OTHER INFORMATION: Asn or Gly
<220> FEATURE:
<221> NAME/KEY: MOD_RES
<222> LOCATION: (198)..(203)
<223> OTHER INFORMATION: May or may not be present
<220> FEATURE:
<221> NAME/KEY: MOD_RES
<222> LOCATION: (204)..(204)
<223> OTHER INFORMATION: Val or Leu
<220> FEATURE:
<221> NAME/KEY: MOD_RES
<222> LOCATION: (205)..(205)
<223> OTHER INFORMATION: Ala or Lys
<220> FEATURE:
<221> NAME/KEY: MOD_RES
<222> LOCATION: (206)..(206)
<223> OTHER INFORMATION: Val or Met
<220> FEATURE:
<221> NAME/KEY: MOD_RES
<222> LOCATION: (207)..(207)
<223> OTHER INFORMATION: Phe or Lys
<220> FEATURE:
<221> NAME/KEY: MOD_RES
<222> LOCATION: (208)..(208)
<223> OTHER INFORMATION: Glu or Asn
<220> FEATURE:
<221> NAME/KEY: MOD_RES
<222> LOCATION: (209)..(209)
<223> OTHER INFORMATION: Trp or Lys
<220> FEATURE:
<221> NAME/KEY: MOD_RES
<222> LOCATION: (211)..(211)
<223> OTHER INFORMATION: Lys or Ile
<220> FEATURE:
<221> NAME/KEY: MOD_RES
<222> LOCATION: (212)..(212)
<223> OTHER INFORMATION: Phe or Ile
<220> FEATURE:
<221> NAME/KEY: MOD_RES
```

```
<222> LOCATION: (213)..(213)
<223> OTHER INFORMATION: Phe or Ser
<220> FEATURE:
<221> NAME/KEY: MOD_RES
<222> LOCATION: (214)..(214)
<223> OTHER INFORMATION: Ser or Asp
<220> FEATURE:
<221> NAME/KEY: MOD_RES
<222> LOCATION: (216)..(216)
<223> OTHER INFORMATION: Phe or Gly
<220> FEATURE:
<221> NAME/KEY: MOD_RES
<222> LOCATION: (217)..(217)
<223> OTHER INFORMATION: Phe or Glu
<220> FEATURE:
<221> NAME/KEY: MOD_RES
<222> LOCATION: (218)..(218)
<223> OTHER INFORMATION: Asn or Ser
<220> FEATURE:
<221> NAME/KEY: MOD_RES
<222> LOCATION: (219)..(219)
<223> OTHER INFORMATION: Lys or Pro
<220> FEATURE:
<221> NAME/KEY: MOD_RES
<222> LOCATION: (221)..(221)
<223> OTHER INFORMATION: His or Glu
<220> FEATURE:
<221> NAME/KEY: MOD_RES
<222> LOCATION: (222)..(222)
<223> OTHER INFORMATION: Thr or Ala
<220> FEATURE:
<221> NAME/KEY: MOD_RES
<222> LOCATION: (223)..(223)
<223> OTHER INFORMATION: Ala or Leu
<220> FEATURE:
<221> NAME/KEY: MOD_RES
<222> LOCATION: (224)..(224)
<223> OTHER INFORMATION: Asn or Asp
<220> FEATURE:
<221> NAME/KEY: MOD_RES
<222> LOCATION: (226)..(226)
<223> OTHER INFORMATION: Val or Asn
<220> FEATURE:
<221> NAME/KEY: MOD_RES
<222> LOCATION: (227)..(227)
<223> OTHER INFORMATION: Val or Arg
<220> FEATURE:
<221> NAME/KEY: MOD_RES
<222> LOCATION: (228)..(228)
<223> OTHER INFORMATION: Glu or Asp
<220> FEATURE:
<221> NAME/KEY: MOD_RES
<222> LOCATION: (229)..(229)
<223> OTHER INFORMATION: Ala or Val
<220> FEATURE:
<221> NAME/KEY: MOD_RES
<222> LOCATION: (230)..(230)
<223> OTHER INFORMATION: Ala or Asn
<220> FEATURE:
<221> NAME/KEY: MOD_RES
<222> LOCATION: (232)..(232)
<223> OTHER INFORMATION: Ser or Ala
<220> FEATURE:
<221> NAME/KEY: MOD_RES
<222> LOCATION: (233)..(233)
<223> OTHER INFORMATION: Arg or Ile
<220> FEATURE:
<221> NAME/KEY: MOD_RES
<222> LOCATION: (235)..(235)
<223> OTHER INFORMATION: Asp or Glu
<220> FEATURE:
<221> NAME/KEY: MOD_RES
<222> LOCATION: (236)..(236)
<223> OTHER INFORMATION: Cys or Trp
<220> FEATURE:
<221> NAME/KEY: MOD_RES
<222> LOCATION: (237)..(237)
<223> OTHER INFORMATION: Val or Leu
<220> FEATURE:
```

-continued

```
<221> NAME/KEY: MOD_RES
<222> LOCATION: (238)..(238)
<223> OTHER INFORMATION: Ala or Glu
<220> FEATURE:
<221> NAME/KEY: MOD_RES
<222> LOCATION: (239)..(239)
<223> OTHER INFORMATION: Gln or Val
<220> FEATURE:
<221> NAME/KEY: MOD_RES
<222> LOCATION: (240)..(240)
<223> OTHER INFORMATION: Asn or Tyr
<220> FEATURE:
<221> NAME/KEY: MOD_RES
<222> LOCATION: (241)..(241)
<223> OTHER INFORMATION: Ala or Gly
<220> FEATURE:
<221> NAME/KEY: MOD_RES
<222> LOCATION: (242)..(242)
<223> OTHER INFORMATION: Gly or Ser
<220> FEATURE:
<221> NAME/KEY: MOD_RES
<222> LOCATION: (243)..(243)
<223> OTHER INFORMATION: Ala or Leu
<220> FEATURE:
<221> NAME/KEY: MOD_RES
<222> LOCATION: (244)..(244)
<223> OTHER INFORMATION: Val or Phe
<220> FEATURE:
<221> NAME/KEY: MOD_RES
<222> LOCATION: (245)..(245)
<223> OTHER INFORMATION: Gln or Asn
<220> FEATURE:
<221> NAME/KEY: MOD_RES
<222> LOCATION: (246)..(246)
<223> OTHER INFORMATION: Ala or Glu
<220> FEATURE:
<221> NAME/KEY: MOD_RES
<222> LOCATION: (247)..(247)
<223> OTHER INFORMATION: Asp or Glu
<220> FEATURE:
<221> NAME/KEY: MOD_RES
<222> LOCATION: (248)..(248)
<223> OTHER INFORMATION: Asn or Gly
<220> FEATURE:
<221> NAME/KEY: MOD_RES
<222> LOCATION: (249)..(249)
<223> OTHER INFORMATION: Met or Leu
<220> FEATURE:
<221> NAME/KEY: MOD_RES
<222> LOCATION: (250)..(250)
<223> OTHER INFORMATION: Pro or Ala
<220> FEATURE:
<221> NAME/KEY: MOD_RES
<222> LOCATION: (251)..(251)
<223> OTHER INFORMATION: May or may not be present
<220> FEATURE:
<221> NAME/KEY: MOD_RES
<222> LOCATION: (252)..(252)
<223> OTHER INFORMATION: Val or Gly
<220> FEATURE:
<221> NAME/KEY: MOD_RES
<222> LOCATION: (253)..(253)
<223> OTHER INFORMATION: Lys or Val
<220> FEATURE:
<221> NAME/KEY: MOD_RES
<222> LOCATION: (261)..(261)
<223> OTHER INFORMATION: Tyr or His
<220> FEATURE:
<221> NAME/KEY: MOD_RES
<222> LOCATION: (262)..(262)
<223> OTHER INFORMATION: May or may not be present
<220> FEATURE:
<221> NAME/KEY: MOD_RES
<222> LOCATION: (263)..(263)
<223> OTHER INFORMATION: Ser or Gln
<220> FEATURE:
<221> NAME/KEY: MOD_RES
<222> LOCATION: (266)..(266)
<223> OTHER INFORMATION: Cys or Glu
```

```
<220> FEATURE:
<221> NAME/KEY: MOD_RES
<222> LOCATION: (268)..(270)
<223> OTHER INFORMATION: May or may not be present
<220> FEATURE:
<221> NAME/KEY: MOD_RES
<222> LOCATION: (275)..(275)
<223> OTHER INFORMATION: Ala or Gly
<220> FEATURE:
<221> NAME/KEY: MOD_RES
<222> LOCATION: (283)..(283)
<223> OTHER INFORMATION: Glu or Thr
<220> FEATURE:
<221> NAME/KEY: MOD_RES
<222> LOCATION: (284)..(284)
<223> OTHER INFORMATION: Phe or Tyr
<220> FEATURE:
<221> NAME/KEY: MOD_RES
<222> LOCATION: (286)..(286)
<223> OTHER INFORMATION: Asn or Lys
<220> FEATURE:
<221> NAME/KEY: MOD_RES
<222> LOCATION: (287)..(287)
<223> OTHER INFORMATION: Ala or His
<220> FEATURE:
<221> NAME/KEY: MOD_RES
<222> LOCATION: (289)..(289)
<223> OTHER INFORMATION: Gly or His
<220> FEATURE:
<221> NAME/KEY: MOD_RES
<222> LOCATION: (290)..(290)
<223> OTHER INFORMATION: Ala or Val
<220> FEATURE:
<221> NAME/KEY: MOD_RES
<222> LOCATION: (292)..(292)
<223> OTHER INFORMATION: Ile or Met
<220> FEATURE:
<221> NAME/KEY: MOD_RES
<222> LOCATION: (293)..(293)
<223> OTHER INFORMATION: Ile or Leu
<220> FEATURE:
<221> NAME/KEY: MOD_RES
<222> LOCATION: (294)..(294)
<223> OTHER INFORMATION: Ser or Asn
<220> FEATURE:
<221> NAME/KEY: MOD_RES
<222> LOCATION: (299)..(299)
<223> OTHER INFORMATION: Asn or Ser
<220> FEATURE:
<221> NAME/KEY: MOD_RES
<222> LOCATION: (300)..(300)
<223> OTHER INFORMATION: Thr or Ile
<220> FEATURE:
<221> NAME/KEY: MOD_RES
<222> LOCATION: (301)..(301)
<223> OTHER INFORMATION: Thr or Asp
<220> FEATURE:
<221> NAME/KEY: MOD_RES
<222> LOCATION: (302)..(302)
<223> OTHER INFORMATION: Val or Tyr
<220> FEATURE:
<221> NAME/KEY: MOD_RES
<222> LOCATION: (303)..(303)
<223> OTHER INFORMATION: Cys or Trp
<220> FEATURE:
<221> NAME/KEY: MOD_RES
<222> LOCATION: (305)..(305)
<223> OTHER INFORMATION: Ala or Tyr
<220> FEATURE:
<221> NAME/KEY: MOD_RES
<222> LOCATION: (307)..(307)
<223> OTHER INFORMATION: Tyr or Arg
<220> FEATURE:
<221> NAME/KEY: MOD_RES
<222> LOCATION: (310)..(310)
<223> OTHER INFORMATION: Thr or Asp
<220> FEATURE:
<221> NAME/KEY: MOD_RES
<222> LOCATION: (313)..(313)
```

```
<223> OTHER INFORMATION: Leu or Phe
<220> FEATURE:
<221> NAME/KEY: MOD_RES
<222> LOCATION: (314)..(314)
<223> OTHER INFORMATION: Val or Leu
<220> FEATURE:
<221> NAME/KEY: MOD_RES
<222> LOCATION: (316)..(316)
<223> OTHER INFORMATION: Leu or Phe
<220> FEATURE:
<221> NAME/KEY: MOD_RES
<222> LOCATION: (319)..(319)
<223> OTHER INFORMATION: Asp or Asn
<220> FEATURE:
<221> NAME/KEY: MOD_RES
<222> LOCATION: (322)..(322)
<223> OTHER INFORMATION: His or Val
<220> FEATURE:
<221> NAME/KEY: MOD_RES
<222> LOCATION: (324)..(324)
<223> OTHER INFORMATION: Ile or Val
<220> FEATURE:
<221> NAME/KEY: MOD_RES
<222> LOCATION: (329)..(329)
<223> OTHER INFORMATION: Asn or Asp
<220> FEATURE:
<221> NAME/KEY: MOD_RES
<222> LOCATION: (331)..(331)
<223> OTHER INFORMATION: Asp or Asn
<220> FEATURE:
<221> NAME/KEY: MOD_RES
<222> LOCATION: (332)..(332)
<223> OTHER INFORMATION: Thr or Arg
<220> FEATURE:
<221> NAME/KEY: MOD_RES
<222> LOCATION: (333)..(333)
<223> OTHER INFORMATION: Ala or Val
<220> FEATURE:
<221> NAME/KEY: MOD_RES
<222> LOCATION: (335)..(335)
<223> OTHER INFORMATION: Glu or Thr
<220> FEATURE:
<221> NAME/KEY: MOD_RES
<222> LOCATION: (336)..(336)
<223> OTHER INFORMATION: Thr or Gln
<220> FEATURE:
<221> NAME/KEY: MOD_RES
<222> LOCATION: (337)..(337)
<223> OTHER INFORMATION: Phe or Lys
<220> FEATURE:
<221> NAME/KEY: MOD_RES
<222> LOCATION: (338)..(338)
<223> OTHER INFORMATION: Gly or Met
<220> FEATURE:
<221> NAME/KEY: MOD_RES
<222> LOCATION: (339)..(339)
<223> OTHER INFORMATION: Glu or Phe
<220> FEATURE:
<221> NAME/KEY: MOD_RES
<222> LOCATION: (340)..(340)
<223> OTHER INFORMATION: Gln or Tyr
<220> FEATURE:
<221> NAME/KEY: MOD_RES
<222> LOCATION: (342)..(342)
<223> OTHER INFORMATION: Gln or Ser
<220> FEATURE:
<221> NAME/KEY: MOD_RES
<222> LOCATION: (343)..(343)
<223> OTHER INFORMATION: Asn or Gln
<220> FEATURE:
<221> NAME/KEY: MOD_RES
<222> LOCATION: (344)..(344)
<223> OTHER INFORMATION: Met or Phe
<220> FEATURE:
<221> NAME/KEY: MOD_RES
<222> LOCATION: (350)..(350)
<223> OTHER INFORMATION: Gln or Glu
<220> FEATURE:
<221> NAME/KEY: MOD_RES
```

```
<222> LOCATION: (351)..(351)
<223> OTHER INFORMATION: Gln or Lys
<220> FEATURE:
<221> NAME/KEY: MOD_RES
<222> LOCATION: (353)..(353)
<223> OTHER INFORMATION: Phe or Tyr
<220> FEATURE:
<221> NAME/KEY: MOD_RES
<222> LOCATION: (357)..(357)
<223> OTHER INFORMATION: Ala or Met
<220> FEATURE:
<221> NAME/KEY: MOD_RES
<222> LOCATION: (361)..(361)
<223> OTHER INFORMATION: Asn or Ser
<220> FEATURE:
<221> NAME/KEY: MOD_RES
<222> LOCATION: (368)..(368)
<223> OTHER INFORMATION: Tyr or Leu
<220> FEATURE:
<221> NAME/KEY: MOD_RES
<222> LOCATION: (372)..(372)
<223> OTHER INFORMATION: Tyr or Asp
<220> FEATURE:
<221> NAME/KEY: MOD_RES
<222> LOCATION: (373)..(373)
<223> OTHER INFORMATION: Asn or Thr
<220> FEATURE:
<221> NAME/KEY: MOD_RES
<222> LOCATION: (376)..(376)
<223> OTHER INFORMATION: Ala or Leu
<220> FEATURE:
<221> NAME/KEY: MOD_RES
<222> LOCATION: (378)..(378)
<223> OTHER INFORMATION: Phe or Leu
<220> FEATURE:
<221> NAME/KEY: MOD_RES
<222> LOCATION: (380)..(380)
<223> OTHER INFORMATION: Ala or His
<220> FEATURE:
<221> NAME/KEY: MOD_RES
<222> LOCATION: (381)..(381)
<223> OTHER INFORMATION: Val or Ile
<220> FEATURE:
<221> NAME/KEY: MOD_RES
<222> LOCATION: (383)..(383)
<223> OTHER INFORMATION: Gly or Asp
<220> FEATURE:
<221> NAME/KEY: MOD_RES
<222> LOCATION: (384)..(386)
<223> OTHER INFORMATION: May or may not be present
<220> FEATURE:
<221> NAME/KEY: MOD_RES
<222> LOCATION: (387)..(387)
<223> OTHER INFORMATION: Thr or Ser
<220> FEATURE:
<221> NAME/KEY: MOD_RES
<222> LOCATION: (389)..(389)
<223> OTHER INFORMATION: Gln or Asp
<220> FEATURE:
<221> NAME/KEY: MOD_RES
<222> LOCATION: (391)..(391)
<223> OTHER INFORMATION: Leu or Pro
<220> FEATURE:
<221> NAME/KEY: MOD_RES
<222> LOCATION: (392)..(392)
<223> OTHER INFORMATION: Thr or His
<220> FEATURE:
<221> NAME/KEY: MOD_RES
<222> LOCATION: (393)..(393)
<223> OTHER INFORMATION: Gly or Ile
<220> FEATURE:
<221> NAME/KEY: MOD_RES
<222> LOCATION: (395)..(395)
<223> OTHER INFORMATION: Ser or Lys
<220> FEATURE:
<221> NAME/KEY: MOD_RES
<222> LOCATION: (401)..(401)
<223> OTHER INFORMATION: Phe or Tyr
<220> FEATURE:
```

-continued

```
<221> NAME/KEY: MOD_RES
<222> LOCATION: (404)..(404)
<223> OTHER INFORMATION: Pro or Gly
<220> FEATURE:
<221> NAME/KEY: MOD_RES
<222> LOCATION: (407)..(407)
<223> OTHER INFORMATION: Ser or Thr
<220> FEATURE:
<221> NAME/KEY: MOD_RES
<222> LOCATION: (409)..(409)
<223> OTHER INFORMATION: Pro or Gly
<220> FEATURE:
<221> NAME/KEY: MOD_RES
<222> LOCATION: (410)..(410)
<223> OTHER INFORMATION: Asp or Met
<220> FEATURE:
<221> NAME/KEY: MOD_RES
<222> LOCATION: (412)..(412)
<223> OTHER INFORMATION: Ser or Glu
<220> FEATURE:
<221> NAME/KEY: MOD_RES
<222> LOCATION: (413)..(413)
<223> OTHER INFORMATION: May or may not be present
<220> FEATURE:
<221> NAME/KEY: MOD_RES
<222> LOCATION: (415)..(415)
<223> OTHER INFORMATION: Thr or Glu
<220> FEATURE:
<221> NAME/KEY: MOD_RES
<222> LOCATION: (416)..(416)
<223> OTHER INFORMATION: Gln or Glu
<220> FEATURE:
<221> NAME/KEY: MOD_RES
<222> LOCATION: (417)..(417)
<223> OTHER INFORMATION: Ser or Pro
<220> FEATURE:
<221> NAME/KEY: MOD_RES
<222> LOCATION: (418)..(418)
<223> OTHER INFORMATION: Ala or Tyr
<220> FEATURE:
<221> NAME/KEY: MOD_RES
<222> LOCATION: (419)..(419)
<223> OTHER INFORMATION: Asn or Thr
<220> FEATURE:
<221> NAME/KEY: MOD_RES
<222> LOCATION: (420)..(420)
<223> OTHER INFORMATION: Ile or Ser
<220> FEATURE:
<221> NAME/KEY: MOD_RES
<222> LOCATION: (421)..(421)
<223> OTHER INFORMATION: Leu or Arg
<220> FEATURE:
<221> NAME/KEY: MOD_RES
<222> LOCATION: (422)..(422)
<223> OTHER INFORMATION: Asp or Ala
<220> FEATURE:
<221> NAME/KEY: MOD_RES
<222> LOCATION: (423)..(423)
<223> OTHER INFORMATION: Asp or Thr
<220> FEATURE:
<221> NAME/KEY: MOD_RES
<222> LOCATION: (424)..(424)
<223> OTHER INFORMATION: Val or Glu
<220> FEATURE:
<221> NAME/KEY: MOD_RES
<222> LOCATION: (425)..(425)
<223> OTHER INFORMATION: His or Cys
<220> FEATURE:
<221> NAME/KEY: MOD_RES
<222> LOCATION: (426)..(426)
<223> OTHER INFORMATION: Ile or Val
<220> FEATURE:
<221> NAME/KEY: MOD_RES
<222> LOCATION: (427)..(427)
<223> OTHER INFORMATION: Cys or Arg
<220> FEATURE:
<221> NAME/KEY: MOD_RES
<222> LOCATION: (428)..(428)
<223> OTHER INFORMATION: Phe or Leu
```

```
<220> FEATURE:
<221> NAME/KEY: MOD_RES
<222> LOCATION: (429)..(429)
<223> OTHER INFORMATION: Leu or Asp
<220> FEATURE:
<221> NAME/KEY: MOD_RES
<222> LOCATION: (430)..(430)
<223> OTHER INFORMATION: Pro or Asp
<220> FEATURE:
<221> NAME/KEY: MOD_RES
<222> LOCATION: (431)..(431)
<223> OTHER INFORMATION: Thr or Val
<220> FEATURE:
<221> NAME/KEY: MOD_RES
<222> LOCATION: (432)..(432)
<223> OTHER INFORMATION: Thr or Val
<220> FEATURE:
<221> NAME/KEY: MOD_RES
<222> LOCATION: (435)..(435)
<223> OTHER INFORMATION: Ala or Gly
<220> FEATURE:
<221> NAME/KEY: MOD_RES
<222> LOCATION: (436)..(436)
<223> OTHER INFORMATION: Ala or Asp
<220> FEATURE:
<221> NAME/KEY: MOD_RES
<222> LOCATION: (437)..(437)
<223> OTHER INFORMATION: Ala or Val
<220> FEATURE:
<221> NAME/KEY: MOD_RES
<222> LOCATION: (438)..(438)
<223> OTHER INFORMATION: Gly or Glu
<220> FEATURE:
<221> NAME/KEY: MOD_RES
<222> LOCATION: (441)..(441)
<223> OTHER INFORMATION: Ser or Gly
<220> FEATURE:
<221> NAME/KEY: MOD_RES
<222> LOCATION: (442)..(442)
<223> OTHER INFORMATION: Gly or Asp
<220> FEATURE:
<221> NAME/KEY: MOD_RES
<222> LOCATION: (443)..(443)
<223> OTHER INFORMATION: Ser or Thr
<220> FEATURE:
<221> NAME/KEY: MOD_RES
<222> LOCATION: (444)..(444)
<223> OTHER INFORMATION: Gly or Ala
<220> FEATURE:
<221> NAME/KEY: MOD_RES
<222> LOCATION: (445)..(445)
<223> OTHER INFORMATION: Gly or Thr
<220> FEATURE:
<221> NAME/KEY: MOD_RES
<222> LOCATION: (446)..(446)
<223> OTHER INFORMATION: Ser or Glu
<220> FEATURE:
<221> NAME/KEY: MOD_RES
<222> LOCATION: (447)..(447)
<223> OTHER INFORMATION: Ser or Val
<220> FEATURE:
<221> NAME/KEY: MOD_RES
<222> LOCATION: (448)..(448)
<223> OTHER INFORMATION: Ala or Pro
<220> FEATURE:
<221> NAME/KEY: MOD_RES
<222> LOCATION: (449)..(449)
<223> OTHER INFORMATION: Lys or Ala
<220> FEATURE:
<221> NAME/KEY: MOD_RES
<222> LOCATION: (451)..(451)
<223> OTHER INFORMATION: Ile or Ser
<220> FEATURE:
<221> NAME/KEY: MOD_RES
<222> LOCATION: (452)..(452)
<223> OTHER INFORMATION: Ala or Ser
<220> FEATURE:
<221> NAME/KEY: MOD_RES
<222> LOCATION: (453)..(453)
```

```
<223> OTHER INFORMATION: Val or Gly
<220> FEATURE:
<221> NAME/KEY: MOD_RES
<222> LOCATION: (454)..(454)
<223> OTHER INFORMATION: Gly or Ser
<220> FEATURE:
<221> NAME/KEY: MOD_RES
<222> LOCATION: (455)..(455)
<223> OTHER INFORMATION: Thr or Arg
<220> FEATURE:
<221> NAME/KEY: MOD_RES
<222> LOCATION: (456)..(456)
<223> OTHER INFORMATION: Ala or Leu
<220> FEATURE:
<221> NAME/KEY: MOD_RES
<222> LOCATION: (458)..(458)
<223> OTHER INFORMATION: Leu or Val
<220> FEATURE:
<221> NAME/KEY: MOD_RES
<222> LOCATION: (459)..(459)
<223> OTHER INFORMATION: Ala or Val
<220> FEATURE:
<221> NAME/KEY: MOD_RES
<222> LOCATION: (460)..(460)
<223> OTHER INFORMATION: Ala or Leu
<220> FEATURE:
<221> NAME/KEY: MOD_RES
<222> LOCATION: (462)..(462)
<223> OTHER INFORMATION: Leu or Ala
<220> FEATURE:
<221> NAME/KEY: MOD_RES
<222> LOCATION: (463)..(463)
<223> OTHER INFORMATION: Leu or Val
<220> FEATURE:
<221> NAME/KEY: MOD_RES
<222> LOCATION: (465)..(465)
<223> OTHER INFORMATION: Leu or Ile
<220> FEATURE:
<221> NAME/KEY: MOD_RES
<222> LOCATION: (466)..(466)
<223> OTHER INFORMATION: Ile or Leu
<220> FEATURE:
<221> NAME/KEY: MOD_RES
<222> LOCATION: (467)..(467)
<223> OTHER INFORMATION: His or Ser
<220> FEATURE:
<221> NAME/KEY: MOD_RES
<222> LOCATION: (469)..(469)
<223> OTHER INFORMATION: Leu or Val
<220> FEATURE:
<221> NAME/KEY: MOD_RES
<222> LOCATION: (470)..(470)
<223> OTHER INFORMATION: Leu or Ala
<220> FEATURE:
<221> NAME/KEY: MOD_RES
<222> LOCATION: (471)..(471)
<223> OTHER INFORMATION: Phe or Asn
<220> FEATURE:
<221> NAME/KEY: MOD_RES
<222> LOCATION: (472)..(601)
<223> OTHER INFORMATION: May or may not be present

<400> SEQUENCE: 20

Glu Tyr Thr Pro Pro Thr Thr Asn Tyr Asp Arg Cys Leu Thr Ala Asp
 1               5                  10                  15

Xaa Xaa Xaa Xaa Xaa Xaa Xaa Xaa Xaa Xaa Xaa Xaa Xaa Xaa Val Asp
                20                  25                  30

Xaa Phe Xaa Xaa Lys Val Xaa Xaa Xaa Xaa Ser Xaa Xaa Trp Xaa Xaa
            35                  40                  45

Xaa Tyr Xaa Xaa Thr Tyr Lys Ile Xaa Xaa Asn Xaa Xaa Asp Thr Val
        50                  55                  60

Asn Thr Thr Tyr Leu Leu Tyr Gln Cys Gly Xaa Xaa Xaa Pro Xaa Xaa
65                  70                  75                  80
```

```
Xaa Xaa Xaa Pro Glu Leu Glu Xaa Xaa Phe Xaa Xaa Val Xaa Xaa
             85                  90                  95

Xaa Pro Xaa Xaa Xaa Gly Xaa Xaa Xaa Xaa Thr Xaa Xaa Ile Xaa
        100                 105                 110

Xaa Xaa Glu Xaa Leu Xaa Xaa Xaa Xaa Xaa Xaa Ala Phe Xaa Xaa
        115                 120                 125

Xaa Xaa Xaa Xaa Xaa Ser Ser Pro Cys Xaa Xaa Xaa Ile Xaa Xaa
        130                 135                 140

Gly Asn Val Leu Thr Leu Val Glu Pro Ser Glu Gly Val Asp Ala Pro
145                 150                 155                 160

Ala Thr Gly Asn Xaa Xaa Xaa Xaa Gly Xaa Xaa Xaa Phe Xaa Xaa
                165                 170                 175

Xaa Xaa Xaa Xaa Xaa Xaa Xaa Xaa Xaa Val Xaa Xaa Xaa Xaa
        180                 185                 190

Xaa Xaa Xaa Xaa Xaa Gly Ala Trp Asp Thr Asp Xaa Xaa Xaa Xaa
        195                 200                 205

Xaa Val Xaa Xaa Xaa Xaa Val Xaa Xaa Xaa Xaa Glu Xaa Xaa Xaa Xaa
    210                 215                 220

Gln Xaa Xaa Xaa Xaa Xaa Glu Xaa Xaa Phe Xaa Xaa Xaa Xaa Xaa
225                 230                 235                 240

Xaa Xaa Xaa Xaa Xaa Xaa Xaa Xaa Xaa Gly Xaa Xaa Pro Val Val
            245                 250                 255

Leu Trp Ala Tyr Xaa Asn Xaa Asp Phe Xaa Gly Asn Asp Val Gly Trp
                260                 265                 270

Asp Val Xaa Glu Cys Pro Asn Tyr Tyr Cys Xaa Xaa Ala Xaa Xaa Cys
            275                 280                 285

Xaa Xaa Glu Xaa Xaa Xaa Ser Thr Glu Gly Xaa Xaa Xaa Xaa Gly
        290                 295                 300

Xaa Pro Xaa Met Thr Xaa Glu Glu Xaa Xaa Glu Xaa Gly Lys Xaa Ala
305                 310                 315                 320

Asp Xaa Trp Xaa Tyr Pro Ser Ser Xaa Trp Xaa Xaa Ser Xaa Xaa
        325                 330                 335

Xaa Xaa Xaa Xaa Leu Xaa Xaa Xaa Lys Ala Val Gln Asp Xaa Xaa Val
            340                 345                 350

Xaa Asp Tyr Gln Xaa Ser Gly Glu Xaa Ala Trp Phe Glu Gln Arg Xaa
        355                 360                 365

Ala Glu Tyr Xaa Xaa Val Leu Xaa Asp Xaa Cys Xaa Xaa Val Xaa Arg
        370                 375                 380

Ala Val Xaa Thr Xaa Pro Xaa Xaa Xaa Arg Xaa Trp Phe Arg Asn Val
385                 390                 395                 400

Xaa Thr Glu Xaa Val Gly Xaa Leu Xaa Xaa Cys Xaa Asp Pro Xaa Xaa
            405                 410                 415

Xaa Xaa Xaa Xaa Xaa Xaa Xaa Xaa Xaa Xaa Xaa Xaa Xaa Xaa Xaa
        420                 425                 430

Gly Gly Xaa Xaa Xaa Xaa Gly Gly Xaa Xaa Xaa Xaa Xaa Xaa Xaa
        435                 440                 445

Xaa Ala Xaa Xaa Xaa Xaa Xaa Ala Xaa Xaa Xaa Gly Xaa Xaa Ser
    450                 455                 460

Xaa Xaa Xaa Val Xaa Xaa Xaa Glu Val Phe Thr Ser Ala Arg Glu Leu
465                 470                 475                 480

Ser Phe Thr Lys Glu Met Ser Ile Asp Asp Val Ala Asn Val Leu Ser
                485                 490                 495

Asp Cys Arg Val Ile Phe Gly Ile His Gly Ala Gly His Met Asn Ala
```

```
                    500                 505                 510
Leu Phe Ala Arg Pro Asp Val Ala Val Ile Glu Ile Ile Gly Lys Asp
            515                 520                 525

Pro Ser Tyr His Ser Ser Asp Glu Asp Gln Lys Gly Tyr Pro Ala Tyr
        530                 535                 540

Phe Arg Asn Ile Asn Met Leu Leu Gly Gln Tyr Tyr Gln Ser Ile Ala
545                 550                 555                 560

Gly Asp Ser Thr Arg Gly Met Tyr Asp Asp Gly Tyr Val Ile Asp Leu
                565                 570                 575

Glu Glu Ala Arg Glu Ala Leu Val Arg Ala Arg His His Ser Thr Ser
            580                 585                 590

Trp Ile Glu Glu His Gly His Trp Arg
            595                 600

<210> SEQ ID NO 21
<211> LENGTH: 644
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (1)..(9)
<223> OTHER INFORMATION: May or may not be present
<220> FEATURE:
<221> NAME/KEY: MOD_RES
<222> LOCATION: (11)..(11)
<223> OTHER INFORMATION: Gln, Asp or not present
<220> FEATURE:
<221> NAME/KEY: MOD_RES
<222> LOCATION: (13)..(13)
<223> OTHER INFORMATION: Thr, Gly or not present
<220> FEATURE:
<221> NAME/KEY: MOD_RES
<222> LOCATION: (14)..(14)
<223> OTHER INFORMATION: Val, Ser or not present
<220> FEATURE:
<221> NAME/KEY: MOD_RES
<222> LOCATION: (16)..(16)
<223> OTHER INFORMATION: Gly, Leu or not present
<220> FEATURE:
<221> NAME/KEY: MOD_RES
<222> LOCATION: (18)..(18)
<223> OTHER INFORMATION: Asn, Glu or not present
<220> FEATURE:
<221> NAME/KEY: MOD_RES
<222> LOCATION: (21)..(21)
<223> OTHER INFORMATION: Ile, Val or not present
<220> FEATURE:
<221> NAME/KEY: MOD_RES
<222> LOCATION: (22)..(22)
<223> OTHER INFORMATION: Asn, Asp or not present
<220> FEATURE:
<221> NAME/KEY: MOD_RES
<222> LOCATION: (23)..(23)
<223> OTHER INFORMATION: Glu, Gly or not present
<220> FEATURE:
<221> NAME/KEY: MOD_RES
<222> LOCATION: (24)..(24)
<223> OTHER INFORMATION: Tyr, Ala, Arg or not present
<220> FEATURE:
<221> NAME/KEY: MOD_RES
<222> LOCATION: (26)..(26)
<223> OTHER INFORMATION: Pro, Ala, Val or not present
<220> FEATURE:
<221> NAME/KEY: MOD_RES
<222> LOCATION: (27)..(27)
<223> OTHER INFORMATION: Pro, Val, Ile or not present
<220> FEATURE:
<221> NAME/KEY: MOD_RES
<222> LOCATION: (32)..(32)
```

-continued

```
<223> OTHER INFORMATION: Asp, Asn or not present
<220> FEATURE:
<221> NAME/KEY: MOD_RES
<222> LOCATION: (33)..(33)
<223> OTHER INFORMATION: Arg, Asp or not present
<220> FEATURE:
<221> NAME/KEY: MOD_RES
<222> LOCATION: (34)..(34)
<223> OTHER INFORMATION: Cys, Asn, Asp or not present
<220> FEATURE:
<221> NAME/KEY: MOD_RES
<222> LOCATION: (40)..(40)
<223> OTHER INFORMATION: Glu, Ala, Ile or Val
<220> FEATURE:
<221> NAME/KEY: MOD_RES
<222> LOCATION: (43)..(43)
<223> OTHER INFORMATION: Ala, Ile, Arg or Gln
<220> FEATURE:
<221> NAME/KEY: MOD_RES
<222> LOCATION: (52)..(52)
<223> OTHER INFORMATION: Ser, Glu, Asn or Asp
<220> FEATURE:
<221> NAME/KEY: MOD_RES
<222> LOCATION: (53)..(53)
<223> OTHER INFORMATION: Val or Ile
<220> FEATURE:
<221> NAME/KEY: MOD_RES
<222> LOCATION: (60)..(60)
<223> OTHER INFORMATION: Val or Phe
<220> FEATURE:
<221> NAME/KEY: MOD_RES
<222> LOCATION: (64)..(64)
<223> OTHER INFORMATION: Phe, Gln, Glu or Asn
<220> FEATURE:
<221> NAME/KEY: MOD_RES
<222> LOCATION: (65)..(65)
<223> OTHER INFORMATION: Ser, Thr or not present
<220> FEATURE:
<221> NAME/KEY: MOD_RES
<222> LOCATION: (66)..(66)
<223> OTHER INFORMATION: Ser or Thr
<220> FEATURE:
<221> NAME/KEY: MOD_RES
<222> LOCATION: (69)..(69)
<223> OTHER INFORMATION: Trp or Leu
<220> FEATURE:
<221> NAME/KEY: MOD_RES
<222> LOCATION: (70)..(70)
<223> OTHER INFORMATION: Asn or Glu
<220> FEATURE:
<221> NAME/KEY: MOD_RES
<222> LOCATION: (75)..(75)
<223> OTHER INFORMATION: Asn, Ser, Asp or Lys
<220> FEATURE:
<221> NAME/KEY: MOD_RES
<222> LOCATION: (83)..(83)
<223> OTHER INFORMATION: Leu, Thr, Ser or Lys
<220> FEATURE:
<221> NAME/KEY: MOD_RES
<222> LOCATION: (85)..(85)
<223> OTHER INFORMATION: Asp or Gln
<220> FEATURE:
<221> NAME/KEY: MOD_RES
<222> LOCATION: (86)..(86)
<223> OTHER INFORMATION: Thr, Gln, Asp or not present
<220> FEATURE:
<221> NAME/KEY: MOD_RES
<222> LOCATION: (88)..(88)
<223> OTHER INFORMATION: Asn or Pro
<220> FEATURE:
<221> NAME/KEY: MOD_RES
<222> LOCATION: (100)..(100)
<223> OTHER INFORMATION: Pro, Glu, Ile or Lys
<220> FEATURE:
<221> NAME/KEY: MOD_RES
<222> LOCATION: (102)..(102)
<223> OTHER INFORMATION: Ala, Thr, Gln or not present
<220> FEATURE:
<221> NAME/KEY: MOD_RES
```

```
<222> LOCATION: (107)..(107)
<223> OTHER INFORMATION: Pro, Asn, Asp or not present
<220> FEATURE:
<221> NAME/KEY: MOD_RES
<222> LOCATION: (108)..(108)
<223> OTHER INFORMATION: Glu, Gly, Pro or not present
<220> FEATURE:
<221> NAME/KEY: MOD_RES
<222> LOCATION: (109)..(110)
<223> OTHER INFORMATION: May or may not be present
<220> FEATURE:
<221> NAME/KEY: MOD_RES
<222> LOCATION: (112)..(112)
<223> OTHER INFORMATION: Gly, Ile, Phe or Asn
<220> FEATURE:
<221> NAME/KEY: MOD_RES
<222> LOCATION: (113)..(113)
<223> OTHER INFORMATION: Asn, Thr, Ala or Lys
<220> FEATURE:
<221> NAME/KEY: MOD_RES
<222> LOCATION: (120)..(120)
<223> OTHER INFORMATION: Ile or Val
<220> FEATURE:
<221> NAME/KEY: MOD_RES
<222> LOCATION: (139)..(139)
<223> OTHER INFORMATION: Gln, Ile, Leu or Met
<220> FEATURE:
<221> NAME/KEY: MOD_RES
<222> LOCATION: (144)..(144)
<223> OTHER INFORMATION: Asp, Ser, Glu or Gly
<220> FEATURE:
<221> NAME/KEY: MOD_RES
<222> LOCATION: (146)..(146)
<223> OTHER INFORMATION: Ile or Val
<220> FEATURE:
<221> NAME/KEY: MOD_RES
<222> LOCATION: (150)..(150)
<223> OTHER INFORMATION: Leu, Ala, Val or Ile
<220> FEATURE:
<221> NAME/KEY: MOD_RES
<222> LOCATION: (154)..(154)
<223> OTHER INFORMATION: Asp, Asn, Gln or Ser
<220> FEATURE:
<221> NAME/KEY: MOD_RES
<222> LOCATION: (157)..(157)
<223> OTHER INFORMATION: Ser or Thr
<220> FEATURE:
<221> NAME/KEY: MOD_RES
<222> LOCATION: (163)..(163)
<223> OTHER INFORMATION: Asp, Gln, Tyr or Ser
<220> FEATURE:
<221> NAME/KEY: MOD_RES
<222> LOCATION: (164)..(164)
<223> OTHER INFORMATION: Glu, Gln, Met or Leu
<220> FEATURE:
<221> NAME/KEY: MOD_RES
<222> LOCATION: (166)..(166)
<223> OTHER INFORMATION: Ala, Ile, Thr or Asp
<220> FEATURE:
<221> NAME/KEY: MOD_RES
<222> LOCATION: (167)..(167)
<223> OTHER INFORMATION: Ala, Pro, Gly or not present
<220> FEATURE:
<221> NAME/KEY: MOD_RES
<222> LOCATION: (168)..(168)
<223> OTHER INFORMATION: Gly, Ala or not present
<220> FEATURE:
<221> NAME/KEY: MOD_RES
<222> LOCATION: (169)..(169)
<223> OTHER INFORMATION: Asn, Gly or not present
<220> FEATURE:
<221> NAME/KEY: MOD_RES
<222> LOCATION: (170)..(170)
<223> OTHER INFORMATION: Val, Asp or not present
<220> FEATURE:
<221> NAME/KEY: MOD_RES
<222> LOCATION: (172)..(172)
<223> OTHER INFORMATION: Thr, Asp, Gly or not present
<220> FEATURE:
```

```
<221> NAME/KEY: MOD_RES
<222> LOCATION: (173)..(173)
<223> OTHER INFORMATION: Leu, Gln, Ser or not present
<220> FEATURE:
<221> NAME/KEY: MOD_RES
<222> LOCATION: (185)..(185)
<223> OTHER INFORMATION: Thr, Glu, Met or Gln
<220> FEATURE:
<221> NAME/KEY: MOD_RES
<222> LOCATION: (186)..(186)
<223> OTHER INFORMATION: Gly, Asp, Glu or Arg
<220> FEATURE:
<221> NAME/KEY: MOD_RES
<222> LOCATION: (191)..(191)
<223> OTHER INFORMATION: Ser, Phe, Thr or Asp
<220> FEATURE:
<221> NAME/KEY: MOD_RES
<222> LOCATION: (192)..(192)
<223> OTHER INFORMATION: Ala, Leu, Phe or Tyr
<220> FEATURE:
<221> NAME/KEY: MOD_RES
<222> LOCATION: (193)..(193)
<223> OTHER INFORMATION: Gly, Pro, Arg or Ile
<220> FEATURE:
<221> NAME/KEY: MOD_RES
<222> LOCATION: (194)..(194)
<223> OTHER INFORMATION: Thr, Glu or not present
<220> FEATURE:
<221> NAME/KEY: MOD_RES
<222> LOCATION: (195)..(195)
<223> OTHER INFORMATION: Glu, Arg or not present
<220> FEATURE:
<221> NAME/KEY: MOD_RES
<222> LOCATION: (196)..(196)
<223> OTHER INFORMATION: His, Asn or not present
<220> FEATURE:
<221> NAME/KEY: MOD_RES
<222> LOCATION: (201)..(201)
<223> OTHER INFORMATION: Ala, Asn, Met or Ile
<220> FEATURE:
<221> NAME/KEY: MOD_RES
<222> LOCATION: (215)..(215)
<223> OTHER INFORMATION: Val, Thr, Ile or Met
<220> FEATURE:
<221> NAME/KEY: MOD_RES
<222> LOCATION: (235)..(235)
<223> OTHER INFORMATION: Phe, Ser, Tyr or Trp
<220> FEATURE:
<221> NAME/KEY: MOD_RES
<222> LOCATION: (247)..(247)
<223> OTHER INFORMATION: Gln or Arg
<220> FEATURE:
<221> NAME/KEY: MOD_RES
<222> LOCATION: (249)..(249)
<223> OTHER INFORMATION: Val, Arg, Ser or Thr
<220> FEATURE:
<221> NAME/KEY: MOD_RES
<222> LOCATION: (250)..(250)
<223> OTHER INFORMATION: Glu, Asp, Thr or Ser
<220> FEATURE:
<221> NAME/KEY: MOD_RES
<222> LOCATION: (251)..(251)
<223> OTHER INFORMATION: Ala, Val, Leu or Glu
<220> FEATURE:
<221> NAME/KEY: MOD_RES
<222> LOCATION: (253)..(253)
<223> OTHER INFORMATION: Glu or Gln
<220> FEATURE:
<221> NAME/KEY: MOD_RES
<222> LOCATION: (256)..(256)
<223> OTHER INFORMATION: Phe or Tyr
<220> FEATURE:
<221> NAME/KEY: MOD_RES
<222> LOCATION: (259)..(259)
<223> OTHER INFORMATION: Val, Leu, Ile or Ser
<220> FEATURE:
<221> NAME/KEY: MOD_RES
<222> LOCATION: (264)..(264)
<223> OTHER INFORMATION: Gly, Ser, Thr or Lys
```

-continued

```
<220> FEATURE:
<221> NAME/KEY: MOD_RES
<222> LOCATION: (267)..(267)
<223> OTHER INFORMATION: Gln, Asn, Val or Ala
<220> FEATURE:
<221> NAME/KEY: MOD_RES
<222> LOCATION: (272)..(272)
<223> OTHER INFORMATION: Pro, Ala, Asn or not present
<220> FEATURE:
<221> NAME/KEY: MOD_RES
<222> LOCATION: (273)..(273)
<223> OTHER INFORMATION: Gly, Leu or not present
<220> FEATURE:
<221> NAME/KEY: MOD_RES
<222> LOCATION: (274)..(274)
<223> OTHER INFORMATION: May or may not be present
<220> FEATURE:
<221> NAME/KEY: MOD_RES
<222> LOCATION: (275)..(275)
<223> OTHER INFORMATION: Asn, Glu or not present
<220> FEATURE:
<221> NAME/KEY: MOD_RES
<222> LOCATION: (276)..(276)
<223> OTHER INFORMATION: Val, Leu or not present
<220> FEATURE:
<221> NAME/KEY: MOD_RES
<222> LOCATION: (277)..(277)
<223> OTHER INFORMATION: Gly, Val or not present
<220> FEATURE:
<221> NAME/KEY: MOD_RES
<222> LOCATION: (278)..(278)
<223> OTHER INFORMATION: Glu, Pro or not present
<220> FEATURE:
<221> NAME/KEY: MOD_RES
<222> LOCATION: (280)..(280)
<223> OTHER INFORMATION: Tyr, Glu or not present
<220> FEATURE:
<221> NAME/KEY: MOD_RES
<222> LOCATION: (281)..(281)
<223> OTHER INFORMATION: Val, Gly, His or Lys
<220> FEATURE:
<221> NAME/KEY: MOD_RES
<222> LOCATION: (282)..(282)
<223> OTHER INFORMATION: Lys, Val, Thr or Gln
<220> FEATURE:
<221> NAME/KEY: MOD_RES
<222> LOCATION: (285)..(285)
<223> OTHER INFORMATION: Val or Ile
<220> FEATURE:
<221> NAME/KEY: MOD_RES
<222> LOCATION: (289)..(289)
<223> OTHER INFORMATION: Tyr or Asn
<220> FEATURE:
<221> NAME/KEY: MOD_RES
<222> LOCATION: (294)..(294)
<223> OTHER INFORMATION: Cys, Phe, Asp or Gln
<220> FEATURE:
<221> NAME/KEY: MOD_RES
<222> LOCATION: (295)..(295)
<223> OTHER INFORMATION: Gly, Glu, Asp or Asn
<220> FEATURE:
<221> NAME/KEY: MOD_RES
<222> LOCATION: (296)..(296)
<223> OTHER INFORMATION: Gly or Leu
<220> FEATURE:
<221> NAME/KEY: MOD_RES
<222> LOCATION: (298)..(300)
<223> OTHER INFORMATION: May or may not be present
<220> FEATURE:
<221> NAME/KEY: MOD_RES
<222> LOCATION: (302)..(302)
<223> OTHER INFORMATION: Asp or Ser
<220> FEATURE:
<221> NAME/KEY: MOD_RES
<222> LOCATION: (304)..(304)
<223> OTHER INFORMATION: Ala or Gly
<220> FEATURE:
<221> NAME/KEY: MOD_RES
<222> LOCATION: (311)..(311)
```

```
<223> OTHER INFORMATION: Ala, Ser or not present
<220> FEATURE:
<221> NAME/KEY: MOD_RES
<222> LOCATION: (324)..(324)
<223> OTHER INFORMATION: Glu or Thr
<220> FEATURE:
<221> NAME/KEY: MOD_RES
<222> LOCATION: (328)..(328)
<223> OTHER INFORMATION: Ser or Arg
<220> FEATURE:
<221> NAME/KEY: MOD_RES
<222> LOCATION: (329)..(329)
<223> OTHER INFORMATION: Thr or Pro
<220> FEATURE:
<221> NAME/KEY: MOD_RES
<222> LOCATION: (332)..(332)
<223> OTHER INFORMATION: Asn, Ser, Val or Ala
<220> FEATURE:
<221> NAME/KEY: MOD_RES
<222> LOCATION: (334)..(334)
<223> OTHER INFORMATION: Phe, Tyr or not present
<220> FEATURE:
<221> NAME/KEY: MOD_RES
<222> LOCATION: (336)..(336)
<223> OTHER INFORMATION: Thr, Ile, Arg or Lys
<220> FEATURE:
<221> NAME/KEY: MOD_RES
<222> LOCATION: (353)..(353)
<223> OTHER INFORMATION: Leu, Phe, Ala or not present
<220> FEATURE:
<221> NAME/KEY: MOD_RES
<222> LOCATION: (356)..(356)
<223> OTHER INFORMATION: Leu, Phe, Met or not present
<220> FEATURE:
<221> NAME/KEY: MOD_RES
<222> LOCATION: (362)..(362)
<223> OTHER INFORMATION: His, Val, Ile or not present
<220> FEATURE:
<221> NAME/KEY: MOD_RES
<222> LOCATION: (372)..(372)
<223> OTHER INFORMATION: Thr, Arg, Ser or not present
<220> FEATURE:
<221> NAME/KEY: MOD_RES
<222> LOCATION: (375)..(375)
<223> OTHER INFORMATION: Glu, Thr, Lys or not present
<220> FEATURE:
<221> NAME/KEY: MOD_RES
<222> LOCATION: (376)..(376)
<223> OTHER INFORMATION: Thr, Gln, Ser or not present
<220> FEATURE:
<221> NAME/KEY: MOD_RES
<222> LOCATION: (377)..(377)
<223> OTHER INFORMATION: Phe, Lys, His or not present
<220> FEATURE:
<221> NAME/KEY: MOD_RES
<222> LOCATION: (378)..(378)
<223> OTHER INFORMATION: Gly, Met, Ser or not present
<220> FEATURE:
<221> NAME/KEY: MOD_RES
<222> LOCATION: (379)..(379)
<223> OTHER INFORMATION: Glu, Phe, Ser or not present
<220> FEATURE:
<221> NAME/KEY: MOD_RES
<222> LOCATION: (380)..(380)
<223> OTHER INFORMATION: Gln, Tyr, Met or not present
<220> FEATURE:
<221> NAME/KEY: MOD_RES
<222> LOCATION: (382)..(382)
<223> OTHER INFORMATION: Gln, Ser, Asp or not present
<220> FEATURE:
<221> NAME/KEY: MOD_RES
<222> LOCATION: (390)..(390)
<223> OTHER INFORMATION: Gln, Glu, Lys or not present
<220> FEATURE:
<221> NAME/KEY: MOD_RES
<222> LOCATION: (398)..(398)
<223> OTHER INFORMATION: Ser or Gln
<220> FEATURE:
<221> NAME/KEY: MOD_RES
```

```
<222> LOCATION: (400)..(400)
<223> OTHER INFORMATION: Glu or Pro
<220> FEATURE:
<221> NAME/KEY: MOD_RES
<222> LOCATION: (415)..(415)
<223> OTHER INFORMATION: Leu or Gly
<220> FEATURE:
<221> NAME/KEY: MOD_RES
<222> LOCATION: (426)..(428)
<223> OTHER INFORMATION: May or may not be present
<220> FEATURE:
<221> NAME/KEY: MOD_RES
<222> LOCATION: (429)..(429)
<223> OTHER INFORMATION: Val, Thr, Ser or not present
<220> FEATURE:
<221> NAME/KEY: MOD_RES
<222> LOCATION: (434)..(434)
<223> OTHER INFORMATION: Leu, Pro, Asn or Gln
<220> FEATURE:
<221> NAME/KEY: MOD_RES
<222> LOCATION: (436)..(436)
<223> OTHER INFORMATION: Gly, Ile, Ala or Glu
<220> FEATURE:
<221> NAME/KEY: MOD_RES
<222> LOCATION: (444)..(444)
<223> OTHER INFORMATION: Phe or Tyr
<220> FEATURE:
<221> NAME/KEY: MOD_RES
<222> LOCATION: (448)..(448)
<223> OTHER INFORMATION: Val or Ile
<220> FEATURE:
<221> NAME/KEY: MOD_RES
<222> LOCATION: (453)..(453)
<223> OTHER INFORMATION: Asp, Met, Val or Thr
<220> FEATURE:
<221> NAME/KEY: MOD_RES
<222> LOCATION: (455)..(455)
<223> OTHER INFORMATION: Ser, Glu, Asp or Asn
<220> FEATURE:
<221> NAME/KEY: MOD_RES
<222> LOCATION: (458)..(458)
<223> OTHER INFORMATION: Thr, Glu, Gly or not present
<220> FEATURE:
<221> NAME/KEY: MOD_RES
<222> LOCATION: (459)..(459)
<223> OTHER INFORMATION: Gln, Glu, Gly or Asp
<220> FEATURE:
<221> NAME/KEY: MOD_RES
<222> LOCATION: (462)..(462)
<223> OTHER INFORMATION: Asn, Thr, Ser or Phe
<220> FEATURE:
<221> NAME/KEY: MOD_RES
<222> LOCATION: (469)..(469)
<223> OTHER INFORMATION: Ile, Val, Lys or Gly
<220> FEATURE:
<221> NAME/KEY: MOD_RES
<222> LOCATION: (470)..(470)
<223> OTHER INFORMATION: Cys, Arg, Val or Thr
<220> FEATURE:
<221> NAME/KEY: MOD_RES
<222> LOCATION: (471)..(471)
<223> OTHER INFORMATION: Phe, Leu, Asn or Glu
<220> FEATURE:
<221> NAME/KEY: MOD_RES
<222> LOCATION: (474)..(474)
<223> OTHER INFORMATION: Thr, Val, Gln or Ser
<220> FEATURE:
<221> NAME/KEY: MOD_RES
<222> LOCATION: (475)..(475)
<223> OTHER INFORMATION: Thr, Val, Pro or Ala
<220> FEATURE:
<221> NAME/KEY: MOD_RES
<222> LOCATION: (477)..(477)
<223> OTHER INFORMATION: Gly or Glu
<220> FEATURE:
<221> NAME/KEY: MOD_RES
<222> LOCATION: (479)..(479)
<223> OTHER INFORMATION: Ala, Asp, Gly or not present
<220> FEATURE:
```

```
<221> NAME/KEY: MOD_RES
<222> LOCATION: (481)..(481)
<223> OTHER INFORMATION: Gly, Glu, Lys or not present
<220> FEATURE:
<221> NAME/KEY: MOD_RES
<222> LOCATION: (484)..(484)
<223> OTHER INFORMATION: Ser, Gly, Asn or Asp
<220> FEATURE:
<221> NAME/KEY: MOD_RES
<222> LOCATION: (485)..(485)
<223> OTHER INFORMATION: Gly, Asp, Arg or Thr
<220> FEATURE:
<221> NAME/KEY: MOD_RES
<222> LOCATION: (487)..(487)
<223> OTHER INFORMATION: Gly, Ala, Lys or Ser
<220> FEATURE:
<221> NAME/KEY: MOD_RES
<222> LOCATION: (494)..(494)
<223> OTHER INFORMATION: Ile, Ser, Gln or Glu
<220> FEATURE:
<221> NAME/KEY: MOD_RES
<222> LOCATION: (495)..(495)
<223> OTHER INFORMATION: Ala, Ser, Glu or Lys
<220> FEATURE:
<221> NAME/KEY: MOD_RES
<222> LOCATION: (496)..(496)
<223> OTHER INFORMATION: Val, Gly, Gln or not present
<220> FEATURE:
<221> NAME/KEY: MOD_RES
<222> LOCATION: (497)..(497)
<223> OTHER INFORMATION: Gly, Ser, Val or not present
<220> FEATURE:
<221> NAME/KEY: MOD_RES
<222> LOCATION: (498)..(498)
<223> OTHER INFORMATION: Thr, Arg, Glu or not present
<220> FEATURE:
<221> NAME/KEY: MOD_RES
<222> LOCATION: (499)..(499)
<223> OTHER INFORMATION: Ala, Leu, Asp or not present
<220> FEATURE:
<221> NAME/KEY: MOD_RES
<222> LOCATION: (501)..(501)
<223> OTHER INFORMATION: Leu, Val, Asp or not present
<220> FEATURE:
<221> NAME/KEY: MOD_RES
<222> LOCATION: (502)..(502)
<223> OTHER INFORMATION: Ala, Val, Ser or not present
<220> FEATURE:
<221> NAME/KEY: MOD_RES
<222> LOCATION: (508)..(508)
<223> OTHER INFORMATION: Leu, Ile, Cys or Ala
<220> FEATURE:
<221> NAME/KEY: MOD_RES
<222> LOCATION: (509)..(509)
<223> OTHER INFORMATION: Ile, Leu, Asn or Phe
<220> FEATURE:
<221> NAME/KEY: MOD_RES
<222> LOCATION: (512)..(512)
<223> OTHER INFORMATION: Leu, Val, Ser or Ala
<220> FEATURE:
<221> NAME/KEY: MOD_RES
<222> LOCATION: (513)..(513)
<223> OTHER INFORMATION: Leu, Ala, Tyr or Met
<220> FEATURE:
<221> NAME/KEY: MOD_RES
<222> LOCATION: (514)..(514)
<223> OTHER INFORMATION: Phe, Asn, Ser or Val
<220> FEATURE:
<221> NAME/KEY: MOD_RES
<222> LOCATION: (515)..(515)
<223> OTHER INFORMATION: Glu, Asn, Ala or not present
<220> FEATURE:
<221> NAME/KEY: MOD_RES
<222> LOCATION: (516)..(516)
<223> OTHER INFORMATION: Val, Leu, Phe or not present
<220> FEATURE:
<221> NAME/KEY: MOD_RES
<222> LOCATION: (517)..(517)
<223> OTHER INFORMATION: Phe, Met, Val or not present
```

```
<220> FEATURE:
<221> NAME/KEY: MOD_RES
<222> LOCATION: (520)..(520)
<223> OTHER INFORMATION: Ala, Ser, Val or not present
<220> FEATURE:
<221> NAME/KEY: MOD_RES
<222> LOCATION: (521)..(521)
<223> OTHER INFORMATION: Arg, Phe or not present
<220> FEATURE:
<221> NAME/KEY: MOD_RES
<222> LOCATION: (522)..(522)
<223> OTHER INFORMATION: Glu, Ala or not present
<220> FEATURE:
<221> NAME/KEY: MOD_RES
<222> LOCATION: (523)..(523)
<223> OTHER INFORMATION: Leu, Gly or not present
<220> FEATURE:
<221> NAME/KEY: MOD_RES
<222> LOCATION: (524)..(524)
<223> OTHER INFORMATION: Ser, Met or not present
<220> FEATURE:
<221> NAME/KEY: MOD_RES
<222> LOCATION: (525)..(525)
<223> OTHER INFORMATION: Phe, Val or not present
<220> FEATURE:
<221> NAME/KEY: MOD_RES
<222> LOCATION: (526)..(526)
<223> OTHER INFORMATION: Thr, Val or not present
<220> FEATURE:
<221> NAME/KEY: MOD_RES
<222> LOCATION: (527)..(527)
<223> OTHER INFORMATION: Lys, Ser or not present
<220> FEATURE:
<221> NAME/KEY: MOD_RES
<222> LOCATION: (528)..(528)
<223> OTHER INFORMATION: Glu, Gln or not present
<220> FEATURE:
<221> NAME/KEY: MOD_RES
<222> LOCATION: (530)..(644)
<223> OTHER INFORMATION: May or may not be present

<400> SEQUENCE: 21

Gln Asp Ile Asn Val Gly Gly Thr Thr Gln Xaa Glu Xaa Xaa Ile Xaa
1               5                   10                  15

Val Xaa Asn Leu Xaa Xaa Xaa Xaa Cys Xaa Xaa Asp Tyr Asp Pro Xaa
                20                  25                  30

Xaa Xaa Val Asp Tyr Phe Pro Xaa Lys Tyr Xaa Lys Pro Ser Ile Ser
        35                  40                  45

Ser Tyr Gly Xaa Xaa Asp Ile Phe Gly Glu Lys Xaa Glu Pro His Xaa
    50                  55                  60

Xaa Xaa Asp Phe Xaa Xaa Ile Thr Tyr His Xaa Thr Tyr Lys Ile Val
65                  70                  75                  80

Thr Asn Xaa His Xaa Xaa Pro Xaa Thr Thr Tyr Leu Leu Tyr Gln Cys
                85                  90                  95

Gly Thr Glu Xaa Pro Xaa Asp Val Val Asp Xaa Xaa Leu Glu Asp Xaa
                100                 105                 110

Xaa Phe Asp Leu Val Leu Ser Xaa Pro His Gln Gly Gly Leu Ala Leu
            115                 120                 125

Thr Gln Thr Pro Gln Ile Pro Tyr Ile Glu Xaa Leu Gly Leu Arg Xaa
130                 135                 140

Glu Xaa Ile Ala Phe Xaa Gly Asp Pro Xaa Tyr Val Xaa Ser Pro Cys
145                 150                 155                 160

Leu Ser Xaa Xaa Ile Xaa Xaa Xaa Xaa Asp Xaa Xaa Val Glu Val
                165                 170                 175

Val Tyr Asp Ser Asn Ala Thr Ile Xaa Xaa Gly Leu Ile Asp Xaa Xaa
            180                 185                 190
```

-continued

Xaa Xaa Xaa Xaa Pro Asn Thr Ile Xaa Phe Ser Gly Pro Thr Asn Asn
            195             200                 205

Val Val Gly Asp Arg Val Xaa Val Val Ser Ala Thr Gln Glu Arg Thr
210                 215                 220

Asn Val Ala Thr Phe Asp Trp Val Ala Phe Xaa Ala Val Phe Tyr Asn
225                 230                 235                 240

Leu Glu Gly Glu Ala Asn Xaa Ile Xaa Xaa Xaa Met Xaa Ala Ser Xaa
                245                 250                 255

Asp Cys Xaa Ser Asp Asn Ala Xaa Ala Val Xaa Ala Gln Gln Arg Xaa
            260                 265                 270

Xaa Glu Xaa Xaa Xaa Glu Xaa Xaa Xaa Pro Val Xaa Leu Trp Ala
            275                 280                 285

Xaa Tyr Phe Thr Tyr Xaa Xaa Xaa Gly Asp Val Gly Trp Xaa Val Xaa
            290                 295                 300

Glu Cys Pro Thr Trp Asp Xaa Asn Tyr Tyr Cys Glu Tyr Ala Ala His
305                 310                 315                 320

Cys Asp Ala Xaa Ile Leu Ser Xaa Xaa Glu Gly Xaa Gly Xaa Asn Xaa
            325                 330                 335

Thr Tyr Gly Gly Ser Pro Thr Val Tyr Trp Tyr Met Thr Asp Glu Glu
            340                 345                 350

Xaa Leu Glu Xaa Gly Lys Asn Ala Asp Xaa Trp Ile Tyr Pro Ser Ser
            355                 360                 365

Asp Trp Asp Xaa Val Ser Xaa Xaa Xaa Xaa Xaa Leu Xaa Gln Phe
            370                 375                 380

Lys Ala Val Gln Asp Xaa Gln Val Phe Asp Tyr Gln Gly Xaa Gly Xaa
385                 390                 395                 400

Ser Ala Trp Phe Glu Gln Arg Tyr Ala Glu Tyr Asp Thr Val Xaa Leu
            405                 410                 415

Asp Leu Cys Asp Ile Val Gly Arg Ser Ser Met Ala Xaa Thr Thr Gly
            420                 425                 430

Pro Xaa His Xaa Arg Arg Trp Phe Arg Asn Val Xaa Thr Glu Pro Xaa
            435                 440                 445

Gly Ser Leu Pro Xaa Cys Xaa Val Pro Xaa Xaa Glu Ile Xaa Gln Pro
450                 455                 460

Tyr Val Pro Pro Xaa Xaa Xaa Cys Asp Xaa Xaa Gly Xaa Glu Xaa Val
465                 470                 475                 480

Xaa Gly Gly Xaa Xaa Thr Xaa Glu Ser Ser Ala Ala Xaa Xaa Xaa
            485                 490                 495

Xaa Xaa Xaa Ala Xaa Xaa Ala Gly Ser Leu Ser Xaa Xaa Tyr Val Xaa
            500                 505                 510

Xaa Xaa Xaa Xaa Xaa Leu Val Xaa Xaa Xaa Xaa Xaa Xaa Xaa Xaa
            515                 520                 525

Met Ser Ile Asp Asp Val Ala Asn Val Leu Ser Asp Cys Arg Val Ile
530                 535                 540

Phe Gly Ile His Gly Ala Gly His Met Asn Ala Leu Phe Ala Arg Pro
545                 550                 555                 560

Asp Val Ala Val Ile Glu Ile Ile Gly Lys Asp Pro Ser Tyr His Ser
            565                 570                 575

Ser Asp Glu Asp Gln Lys Gly Tyr Pro Ala Tyr Phe Arg Asn Ile Asn
            580                 585                 590

Met Leu Leu Gly Gln Tyr Tyr Gln Ser Ile Ala Gly Asp Ser Thr Arg
            595                 600                 605

Gly Met Tyr Asp Asp Gly Tyr Val Ile Asp Leu Glu Glu Ala Arg Glu

-continued

```
            610                 615                 620
Ala Leu Val Arg Ala Arg His His Ser Thr Ser Trp Ile Glu Glu His
625                 630                 635                 640

Gly His Trp Arg

<210> SEQ ID NO 22
<211> LENGTH: 26
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (3)..(3)
<223> OTHER INFORMATION: Ile or Leu
<220> FEATURE:
<221> NAME/KEY: MOD_RES
<222> LOCATION: (5)..(5)
<223> OTHER INFORMATION: Thr or Pro
<220> FEATURE:
<221> NAME/KEY: MOD_RES
<222> LOCATION: (6)..(6)
<223> OTHER INFORMATION: Asp or Glu
<220> FEATURE:
<221> NAME/KEY: MOD_RES
<222> LOCATION: (9)..(9)
<223> OTHER INFORMATION: Glu or Ser
<220> FEATURE:
<221> NAME/KEY: MOD_RES
<222> LOCATION: (10)..(10)
<223> OTHER INFORMATION: Pro or Ser
<220> FEATURE:
<221> NAME/KEY: MOD_RES
<222> LOCATION: (11)..(11)
<223> OTHER INFORMATION: Leu or Asp
<220> FEATURE:
<221> NAME/KEY: MOD_RES
<222> LOCATION: (12)..(12)
<223> OTHER INFORMATION: Phe or Gln
<220> FEATURE:
<221> NAME/KEY: MOD_RES
<222> LOCATION: (14)..(14)
<223> OTHER INFORMATION: Gln or Val
<220> FEATURE:
<221> NAME/KEY: MOD_RES
<222> LOCATION: (15)..(15)
<223> OTHER INFORMATION: Gly or Tyr
<220> FEATURE:
<221> NAME/KEY: MOD_RES
<222> LOCATION: (17)..(17)
<223> OTHER INFORMATION: Asn or Glu
<220> FEATURE:
<221> NAME/KEY: MOD_RES
<222> LOCATION: (18)..(18)
<223> OTHER INFORMATION: Ile or Val
<220> FEATURE:
<221> NAME/KEY: MOD_RES
<222> LOCATION: (19)..(19)
<223> OTHER INFORMATION: Thr or Asp
<220> FEATURE:
<221> NAME/KEY: MOD_RES
<222> LOCATION: (21)..(21)
<223> OTHER INFORMATION: His or Arg
<220> FEATURE:
<221> NAME/KEY: MOD_RES
<222> LOCATION: (22)..(22)
<223> OTHER INFORMATION: Asn or Ser

<400> SEQUENCE: 22

Val Asp Xaa Phe Xaa Xaa Lys Val Xaa Xaa Xaa Ser Xaa Xaa Trp
1               5                   10                  15

Xaa Xaa Xaa Tyr Xaa Xaa Thr Tyr Lys Ile
                20                  25
```

```
<210> SEQ ID NO 23
<211> LENGTH: 14
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (11)..(11)
<223> OTHER INFORMATION: Ser or Leu
<220> FEATURE:
<221> NAME/KEY: MOD_RES
<222> LOCATION: (12)..(12)
<223> OTHER INFORMATION: Thr or Pro
<220> FEATURE:
<221> NAME/KEY: MOD_RES
<222> LOCATION: (13)..(13)
<223> OTHER INFORMATION: Pro or Glu

<400> SEQUENCE: 23

Asn Thr Thr Tyr Leu Leu Tyr Gln Cys Gly Xaa Xaa Xaa Pro
1               5                   10

<210> SEQ ID NO 24
<211> LENGTH: 10
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (1)..(1)
<223> OTHER INFORMATION: Ile or Val
<220> FEATURE:
<221> NAME/KEY: MOD_RES
<222> LOCATION: (6)..(6)
<223> OTHER INFORMATION: Phe or Leu
<220> FEATURE:
<221> NAME/KEY: MOD_RES
<222> LOCATION: (7)..(7)
<223> OTHER INFORMATION: Leu or Ser
<220> FEATURE:
<221> NAME/KEY: MOD_RES
<222> LOCATION: (8)..(8)
<223> OTHER INFORMATION: Asp or Gln
<220> FEATURE:
<221> NAME/KEY: MOD_RES
<222> LOCATION: (9)..(9)
<223> OTHER INFORMATION: Glu or Gln

<400> SEQUENCE: 24

Xaa Ser Ser Pro Cys Xaa Xaa Xaa Xaa Ile
1               5                   10

<210> SEQ ID NO 25
<211> LENGTH: 46
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (8)..(8)
<223> OTHER INFORMATION: Tyr or His
<220> FEATURE:
<221> NAME/KEY: MOD_RES
<222> LOCATION: (9)..(9)
<223> OTHER INFORMATION: May or may not be present
<220> FEATURE:
<221> NAME/KEY: MOD_RES
```

```
<222> LOCATION: (10)..(10)
<223> OTHER INFORMATION: Ser or Gln
<220> FEATURE:
<221> NAME/KEY: MOD_RES
<222> LOCATION: (13)..(13)
<223> OTHER INFORMATION: Cys or Glu
<220> FEATURE:
<221> NAME/KEY: MOD_RES
<222> LOCATION: (15)..(17)
<223> OTHER INFORMATION: May or may not be present
<220> FEATURE:
<221> NAME/KEY: MOD_RES
<222> LOCATION: (22)..(22)
<223> OTHER INFORMATION: Ala or Gly
<220> FEATURE:
<221> NAME/KEY: MOD_RES
<222> LOCATION: (30)..(30)
<223> OTHER INFORMATION: Glu or Thr
<220> FEATURE:
<221> NAME/KEY: MOD_RES
<222> LOCATION: (31)..(31)
<223> OTHER INFORMATION: Phe or Tyr
<220> FEATURE:
<221> NAME/KEY: MOD_RES
<222> LOCATION: (33)..(33)
<223> OTHER INFORMATION: Asn or Lys
<220> FEATURE:
<221> NAME/KEY: MOD_RES
<222> LOCATION: (34)..(34)
<223> OTHER INFORMATION: Ala or His
<220> FEATURE:
<221> NAME/KEY: MOD_RES
<222> LOCATION: (36)..(36)
<223> OTHER INFORMATION: Gly or His
<220> FEATURE:
<221> NAME/KEY: MOD_RES
<222> LOCATION: (37)..(37)
<223> OTHER INFORMATION: Ala or Val
<220> FEATURE:
<221> NAME/KEY: MOD_RES
<222> LOCATION: (39)..(39)
<223> OTHER INFORMATION: Ile or Met
<220> FEATURE:
<221> NAME/KEY: MOD_RES
<222> LOCATION: (40)..(40)
<223> OTHER INFORMATION: Ile or Leu
<220> FEATURE:
<221> NAME/KEY: MOD_RES
<222> LOCATION: (41)..(41)
<223> OTHER INFORMATION: Ser or Asn
<220> FEATURE:
<221> NAME/KEY: MOD_RES
<222> LOCATION: (46)..(46)
<223> OTHER INFORMATION: Asn or Ser

<400> SEQUENCE: 25

Pro Val Val Leu Trp Ala Tyr Xaa Asn Xaa Asp Phe Xaa Gly Asn Asp
1               5                   10                  15

Val Gly Trp Asp Val Xaa Glu Cys Pro Asn Tyr Tyr Cys Xaa Xaa Ala
            20                  25                  30

Xaa Xaa Cys Xaa Xaa Glu Xaa Xaa Xaa Ser Thr Glu Gly Xaa
        35                  40                  45

<210> SEQ ID NO 26
<211> LENGTH: 31
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (2)..(2)
<223> OTHER INFORMATION: Ala or Tyr
<220> FEATURE:
```

```
<221> NAME/KEY: MOD_RES
<222> LOCATION: (4)..(4)
<223> OTHER INFORMATION: Tyr or Arg
<220> FEATURE:
<221> NAME/KEY: MOD_RES
<222> LOCATION: (7)..(7)
<223> OTHER INFORMATION: Thr or Asp
<220> FEATURE:
<221> NAME/KEY: MOD_RES
<222> LOCATION: (10)..(10)
<223> OTHER INFORMATION: Leu or Phe
<220> FEATURE:
<221> NAME/KEY: MOD_RES
<222> LOCATION: (11)..(11)
<223> OTHER INFORMATION: Val or Leu
<220> FEATURE:
<221> NAME/KEY: MOD_RES
<222> LOCATION: (13)..(13)
<223> OTHER INFORMATION: Leu or Phe
<220> FEATURE:
<221> NAME/KEY: MOD_RES
<222> LOCATION: (16)..(16)
<223> OTHER INFORMATION: Asp or Asn
<220> FEATURE:
<221> NAME/KEY: MOD_RES
<222> LOCATION: (19)..(19)
<223> OTHER INFORMATION: His or Val
<220> FEATURE:
<221> NAME/KEY: MOD_RES
<222> LOCATION: (21)..(21)
<223> OTHER INFORMATION: Ile or Val
<220> FEATURE:
<221> NAME/KEY: MOD_RES
<222> LOCATION: (26)..(26)
<223> OTHER INFORMATION: Asn or Asp
<220> FEATURE:
<221> NAME/KEY: MOD_RES
<222> LOCATION: (28)..(28)
<223> OTHER INFORMATION: Asn or Asp
<220> FEATURE:
<221> NAME/KEY: MOD_RES
<222> LOCATION: (29)..(29)
<223> OTHER INFORMATION: Thr or Arg
<220> FEATURE:
<221> NAME/KEY: MOD_RES
<222> LOCATION: (30)..(30)
<223> OTHER INFORMATION: Ala or Val

<400> SEQUENCE: 26

Gly Xaa Pro Xaa Met Thr Xaa Glu Glu Xaa Xaa Glu Xaa Gly Lys Xaa
1               5                   10                  15

Ala Asp Xaa Trp Xaa Tyr Pro Ser Ser Xaa Trp Xaa Xaa Xaa Ser
            20                  25                  30

<210> SEQ ID NO 27
<211> LENGTH: 38
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (6)..(6)
<223> OTHER INFORMATION: Gln or Glu
<220> FEATURE:
<221> NAME/KEY: MOD_RES
<222> LOCATION: (7)..(7)
<223> OTHER INFORMATION: Gln or Lys
<220> FEATURE:
<221> NAME/KEY: MOD_RES
<222> LOCATION: (9)..(9)
<223> OTHER INFORMATION: Phe or Tyr
<220> FEATURE:
<221> NAME/KEY: MOD_RES
<222> LOCATION: (13)..(13)
```

```
<223> OTHER INFORMATION: Ala or Met
<220> FEATURE:
<221> NAME/KEY: MOD_RES
<222> LOCATION: (17)..(17)
<223> OTHER INFORMATION: Asn or Ser
<220> FEATURE:
<221> NAME/KEY: MOD_RES
<222> LOCATION: (24)..(24)
<223> OTHER INFORMATION: Tyr or Leu
<220> FEATURE:
<221> NAME/KEY: MOD_RES
<222> LOCATION: (28)..(28)
<223> OTHER INFORMATION: Tyr or Asp
<220> FEATURE:
<221> NAME/KEY: MOD_RES
<222> LOCATION: (29)..(29)
<223> OTHER INFORMATION: Asn or Thr
<220> FEATURE:
<221> NAME/KEY: MOD_RES
<222> LOCATION: (32)..(32)
<223> OTHER INFORMATION: Ala or Leu
<220> FEATURE:
<221> NAME/KEY: MOD_RES
<222> LOCATION: (34)..(34)
<223> OTHER INFORMATION: Phe or Leu
<220> FEATURE:
<221> NAME/KEY: MOD_RES
<222> LOCATION: (36)..(36)
<223> OTHER INFORMATION: Ala or His
<220> FEATURE:
<221> NAME/KEY: MOD_RES
<222> LOCATION: (37)..(37)
<223> OTHER INFORMATION: Val or Ile

<400> SEQUENCE: 27

Lys Ala Val Gln Asp Xaa Xaa Val Xaa Asp Tyr Gln Xaa Ser Gly Glu
1               5                   10                  15

Xaa Ala Trp Phe Glu Gln Arg Xaa Ala Glu Tyr Xaa Xaa Val Leu Xaa
                20                  25                  30

Asp Xaa Cys Xaa Xaa Val
        35

<210> SEQ ID NO 28
<211> LENGTH: 21
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (2)..(2)
<223> OTHER INFORMATION: Ser or Lys
<220> FEATURE:
<221> NAME/KEY: MOD_RES
<222> LOCATION: (8)..(8)
<223> OTHER INFORMATION: Phe or Tyr
<220> FEATURE:
<221> NAME/KEY: MOD_RES
<222> LOCATION: (11)..(11)
<223> OTHER INFORMATION: Pro or Gly
<220> FEATURE:
<221> NAME/KEY: MOD_RES
<222> LOCATION: (14)..(14)
<223> OTHER INFORMATION: Ser or Thr
<220> FEATURE:
<221> NAME/KEY: MOD_RES
<222> LOCATION: (16)..(16)
<223> OTHER INFORMATION: Pro or Gly
<220> FEATURE:
<221> NAME/KEY: MOD_RES
<222> LOCATION: (17)..(17)
<223> OTHER INFORMATION: Asp or Met
<220> FEATURE:
<221> NAME/KEY: MOD_RES
```

```
<222> LOCATION: (19)..(19)
<223> OTHER INFORMATION: Ser or Glu
<220> FEATURE:
<221> NAME/KEY: MOD_RES
<222> LOCATION: (20)..(20)
<223> OTHER INFORMATION: May or may not be present

<400> SEQUENCE: 28

Arg Xaa Trp Phe Arg Asn Val Xaa Thr Glu Xaa Val Gly Xaa Leu Xaa
1               5                   10                  15

Xaa Cys Xaa Asp Pro
            20

<210> SEQ ID NO 29
<211> LENGTH: 11
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (1)..(1)
<223> OTHER INFORMATION: Val or Ile
<220> FEATURE:
<221> NAME/KEY: MOD_RES
<222> LOCATION: (3)..(3)
<223> OTHER INFORMATION: Leu or Ile
<220> FEATURE:
<221> NAME/KEY: MOD_RES
<222> LOCATION: (5)..(5)
<223> OTHER INFORMATION: Thr, Pro or Gly
<220> FEATURE:
<221> NAME/KEY: MOD_RES
<222> LOCATION: (6)..(6)
<223> OTHER INFORMATION: Asp, Asn or Glu
<220> FEATURE:
<221> NAME/KEY: MOD_RES
<222> LOCATION: (8)..(8)
<223> OTHER INFORMATION: Val or Phe
<220> FEATURE:
<221> NAME/KEY: MOD_RES
<222> LOCATION: (9)..(9)
<223> OTHER INFORMATION: Glu, Ser or Val
<220> FEATURE:
<221> NAME/KEY: MOD_RES
<222> LOCATION: (10)..(10)
<223> OTHER INFORMATION: Pro or Ser
<220> FEATURE:
<221> NAME/KEY: MOD_RES
<222> LOCATION: (11)..(11)
<223> OTHER INFORMATION: Leu, Asp or His

<400> SEQUENCE: 29

Xaa Asp Xaa Phe Xaa Xaa Lys Xaa Xaa Xaa Xaa
1               5                   10

<210> SEQ ID NO 30
<211> LENGTH: 10
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (2)..(2)
<223> OTHER INFORMATION: His, Arg or Phe
<220> FEATURE:
<221> NAME/KEY: MOD_RES
<222> LOCATION: (3)..(3)
<223> OTHER INFORMATION: Asn, Ser, Asp or Lys
<220> FEATURE:
<221> NAME/KEY: MOD_RES
```

```
<222> LOCATION: (4)..(4)
<223> OTHER INFORMATION: Thr or Asn
<220> FEATURE:
<221> NAME/KEY: MOD_RES
<222> LOCATION: (8)..(8)
<223> OTHER INFORMATION: Ala, Leu or Val
<220> FEATURE:
<221> NAME/KEY: MOD_RES
<222> LOCATION: (9)..(9)
<223> OTHER INFORMATION: Asn, Lys or Thr

<400> SEQUENCE: 30

Tyr Xaa Xaa Xaa Tyr Lys Ile Xaa Xaa Asn
1               5                   10

<210> SEQ ID NO 31
<211> LENGTH: 13
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (1)..(1)
<223> OTHER INFORMATION: Asn or Pro
<220> FEATURE:
<221> NAME/KEY: MOD_RES
<222> LOCATION: (2)..(2)
<223> OTHER INFORMATION: Thr, Lys or Val
<220> FEATURE:
<221> NAME/KEY: MOD_RES
<222> LOCATION: (3)..(3)
<223> OTHER INFORMATION: Thr or Ser
<220> FEATURE:
<221> NAME/KEY: MOD_RES
<222> LOCATION: (11)..(11)
<223> OTHER INFORMATION: Ser, Leu or Thr
<220> FEATURE:
<221> NAME/KEY: MOD_RES
<222> LOCATION: (12)..(12)
<223> OTHER INFORMATION: Thr, Pro or Glu
<220> FEATURE:
<221> NAME/KEY: MOD_RES
<222> LOCATION: (13)..(13)
<223> OTHER INFORMATION: Pro, Glu, Ile or Lys

<400> SEQUENCE: 31

Xaa Xaa Xaa Tyr Leu Leu Tyr Gln Cys Gly Xaa Xaa Xaa
1               5                   10

<210> SEQ ID NO 32
<211> LENGTH: 47
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (2)..(2)
<223> OTHER INFORMATION: Asn or Asp
<220> FEATURE:
<221> NAME/KEY: MOD_RES
<222> LOCATION: (3)..(3)
<223> OTHER INFORMATION: Ala, Ser or Leu
<220> FEATURE:
<221> NAME/KEY: MOD_RES
<222> LOCATION: (5)..(5)
<223> OTHER INFORMATION: Val, Leu or Phe
<220> FEATURE:
<221> NAME/KEY: MOD_RES
<222> LOCATION: (6)..(6)
<223> OTHER INFORMATION: Glu, Ser or Pro
<220> FEATURE:
```

```
<221> NAME/KEY: MOD_RES
<222> LOCATION: (7)..(7)
<223> OTHER INFORMATION: Ile or Val
<220> FEATURE:
<221> NAME/KEY: MOD_RES
<222> LOCATION: (9)..(9)
<223> OTHER INFORMATION: Leu or His
<220> FEATURE:
<221> NAME/KEY: MOD_RES
<222> LOCATION: (10)..(10)
<223> OTHER INFORMATION: Ser, Thr or Gln
<220> FEATURE:
<221> NAME/KEY: MOD_RES
<222> LOCATION: (11)..(11)
<223> OTHER INFORMATION: Asn or Gly
<220> FEATURE:
<221> NAME/KEY: MOD_RES
<222> LOCATION: (12)..(12)
<223> OTHER INFORMATION: May or may not be present
<220> FEATURE:
<221> NAME/KEY: MOD_RES
<222> LOCATION: (13)..(13)
<223> OTHER INFORMATION: Val or Leu
<220> FEATURE:
<221> NAME/KEY: MOD_RES
<222> LOCATION: (14)..(14)
<223> OTHER INFORMATION: Gly, Leu or Ala
<220> FEATURE:
<221> NAME/KEY: MOD_RES
<222> LOCATION: (15)..(15)
<223> OTHER INFORMATION: Leu or Val
<220> FEATURE:
<221> NAME/KEY: MOD_RES
<222> LOCATION: (16)..(16)
<223> OTHER INFORMATION: Ser or Thr
<220> FEATURE:
<221> NAME/KEY: MOD_RES
<222> LOCATION: (17)..(17)
<223> OTHER INFORMATION: Gln or Ala
<220> FEATURE:
<221> NAME/KEY: MOD_RES
<222> LOCATION: (19)..(19)
<223> OTHER INFORMATION: Pro or Thr
<220> FEATURE:
<221> NAME/KEY: MOD_RES
<222> LOCATION: (20)..(20)
<223> OTHER INFORMATION: His or Gln
<220> FEATURE:
<221> NAME/KEY: MOD_RES
<222> LOCATION: (22)..(22)
<223> OTHER INFORMATION: Gly or Pro
<220> FEATURE:
<221> NAME/KEY: MOD_RES
<222> LOCATION: (23)..(23)
<223> OTHER INFORMATION: Phe, Tyr or Asn
<220> FEATURE:
<221> NAME/KEY: MOD_RES
<222> LOCATION: (24)..(24)
<223> OTHER INFORMATION: Met, Ile or Pro
<220> FEATURE:
<221> NAME/KEY: MOD_RES
<222> LOCATION: (26)..(26)
<223> OTHER INFORMATION: Gln, Ile, Leu or Met
<220> FEATURE:
<221> NAME/KEY: MOD_RES
<222> LOCATION: (28)..(28)
<223> OTHER INFORMATION: Glu, Asn or Gly
<220> FEATURE:
<221> NAME/KEY: MOD_RES
<222> LOCATION: (29)..(29)
<223> OTHER INFORMATION: Leu or Arg
<220> FEATURE:
<221> NAME/KEY: MOD_RES
<222> LOCATION: (30)..(30)
<223> OTHER INFORMATION: Val or Arg
<220> FEATURE:
<221> NAME/KEY: MOD_RES
<222> LOCATION: (31)..(31)
<223> OTHER INFORMATION: Asp, Ser, Glu or Gly
```

```
<220> FEATURE:
<221> NAME/KEY: MOD_RES
<222> LOCATION: (32)..(32)
<223> OTHER INFORMATION: Glu or Gln
<220> FEATURE:
<221> NAME/KEY: MOD_RES
<222> LOCATION: (33)..(33)
<223> OTHER INFORMATION: Ile or Val
<220> FEATURE:
<221> NAME/KEY: MOD_RES
<222> LOCATION: (34)..(34)
<223> OTHER INFORMATION: Ala, Ile or Val
<220> FEATURE:
<221> NAME/KEY: MOD_RES
<222> LOCATION: (35)..(35)
<223> OTHER INFORMATION: Ala or Gly
<220> FEATURE:
<221> NAME/KEY: MOD_RES
<222> LOCATION: (36)..(36)
<223> OTHER INFORMATION: Phe, Tyr or Leu
<220> FEATURE:
<221> NAME/KEY: MOD_RES
<222> LOCATION: (37)..(37)
<223> OTHER INFORMATION: Leu, Ala, Val or Ile
<220> FEATURE:
<221> NAME/KEY: MOD_RES
<222> LOCATION: (38)..(38)
<223> OTHER INFORMATION: Thr, Val or Gly
<220> FEATURE:
<221> NAME/KEY: MOD_RES
<222> LOCATION: (39)..(39)
<223> OTHER INFORMATION: Asp, Ser or Asn
<220> FEATURE:
<221> NAME/KEY: MOD_RES
<222> LOCATION: (40)..(40)
<223> OTHER INFORMATION: Thr, Glu or Pro
<220> FEATURE:
<221> NAME/KEY: MOD_RES
<222> LOCATION: (41)..(41)
<223> OTHER INFORMATION: Asp, Asn, Gln or Ser
<220> FEATURE:
<221> NAME/KEY: MOD_RES
<222> LOCATION: (42)..(42)
<223> OTHER INFORMATION: Phe, Leu or Tyr
<220> FEATURE:
<221> NAME/KEY: MOD_RES
<222> LOCATION: (43)..(43)
<223> OTHER INFORMATION: Ile or Val
<220> FEATURE:
<221> NAME/KEY: MOD_RES
<222> LOCATION: (44)..(44)
<223> OTHER INFORMATION: Ser or Thr

<400> SEQUENCE: 32

Phe Xaa Xaa Val Xaa Xaa Xaa Pro Xaa Xaa Xaa Gly Xaa Xaa Xaa Xaa
1               5                   10                  15

Xaa Thr Xaa Xaa Ile Xaa Xaa Xaa Glu Xaa Leu Xaa Xaa Xaa Xaa Xaa
            20                  25                  30

Xaa Xaa Xaa Xaa Xaa Xaa Xaa Xaa Xaa Xaa Xaa Xaa Ser Pro Cys
        35                  40                  45

<210> SEQ ID NO 33
<211> LENGTH: 19
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (2)..(2)
<223> OTHER INFORMATION: Asn or Asp
<220> FEATURE:
<221> NAME/KEY: MOD_RES
<222> LOCATION: (3)..(3)
```

```
<223> OTHER INFORMATION: Val or Leu
<220> FEATURE:
<221> NAME/KEY: MOD_RES
<222> LOCATION: (4)..(4)
<223> OTHER INFORMATION: Ala or Lys
<220> FEATURE:
<221> NAME/KEY: MOD_RES
<222> LOCATION: (5)..(5)
<223> OTHER INFORMATION: Val, Met or Thr
<220> FEATURE:
<221> NAME/KEY: MOD_RES
<222> LOCATION: (6)..(6)
<223> OTHER INFORMATION: Phe or Lys
<220> FEATURE:
<221> NAME/KEY: MOD_RES
<222> LOCATION: (7)..(7)
<223> OTHER INFORMATION: Glu, Asn or Asp
<220> FEATURE:
<221> NAME/KEY: MOD_RES
<222> LOCATION: (8)..(8)
<223> OTHER INFORMATION: Trp or Lys
<220> FEATURE:
<221> NAME/KEY: MOD_RES
<222> LOCATION: (9)..(9)
<223> OTHER INFORMATION: Val, Ile or Met
<220> FEATURE:
<221> NAME/KEY: MOD_RES
<222> LOCATION: (10)..(10)
<223> OTHER INFORMATION: Lys, Ile or Ala
<220> FEATURE:
<221> NAME/KEY: MOD_RES
<222> LOCATION: (11)..(11)
<223> OTHER INFORMATION: Phe or Ile
<220> FEATURE:
<221> NAME/KEY: MOD_RES
<222> LOCATION: (12)..(12)
<223> OTHER INFORMATION: Phe, Ser, Tyr or Trp
<220> FEATURE:
<221> NAME/KEY: MOD_RES
<222> LOCATION: (13)..(13)
<223> OTHER INFORMATION: Ser, Asp or Ala
<220> FEATURE:
<221> NAME/KEY: MOD_RES
<222> LOCATION: (14)..(14)
<223> OTHER INFORMATION: Val, Ser or Ala
<220> FEATURE:
<221> NAME/KEY: MOD_RES
<222> LOCATION: (15)..(15)
<223> OTHER INFORMATION: Phe, Gly or Leu
<220> FEATURE:
<221> NAME/KEY: MOD_RES
<222> LOCATION: (16)..(16)
<223> OTHER INFORMATION: Phe, Glu or Tyr
<220> FEATURE:
<221> NAME/KEY: MOD_RES
<222> LOCATION: (17)..(17)
<223> OTHER INFORMATION: Asn or Ser
<220> FEATURE:
<221> NAME/KEY: MOD_RES
<222> LOCATION: (18)..(18)
<223> OTHER INFORMATION: Lys, Pro or Leu

<400> SEQUENCE: 33

Thr Xaa Xaa Xaa Xaa Xaa Xaa Xaa Xaa Xaa Xaa Xaa Xaa Xaa Xaa Xaa
1               5                   10                  15

Xaa Xaa Glu

<210> SEQ ID NO 34
<211> LENGTH: 14
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
```

```
<222> LOCATION: (2)..(2)
<223> OTHER INFORMATION: Val or Thr
<220> FEATURE:
<221> NAME/KEY: MOD_RES
<222> LOCATION: (3)..(3)
<223> OTHER INFORMATION: Val or Ile
<220> FEATURE:
<221> NAME/KEY: MOD_RES
<222> LOCATION: (4)..(4)
<223> OTHER INFORMATION: Leu or Phe
<220> FEATURE:
<221> NAME/KEY: MOD_RES
<222> LOCATION: (7)..(7)
<223> OTHER INFORMATION: Tyr or Asn
<220> FEATURE:
<221> NAME/KEY: MOD_RES
<222> LOCATION: (8)..(8)
<223> OTHER INFORMATION: Tyr, His or Phe
<220> FEATURE:
<221> NAME/KEY: MOD_RES
<222> LOCATION: (9)..(9)
<223> OTHER INFORMATION: Ser, Asn or Phe
<220> FEATURE:
<221> NAME/KEY: MOD_RES
<222> LOCATION: (10)..(10)
<223> OTHER INFORMATION: Asp, Gln or Thr
<220> FEATURE:
<221> NAME/KEY: MOD_RES
<222> LOCATION: (11)..(11)
<223> OTHER INFORMATION: Phe, Asp or Tyr
<220> FEATURE:
<221> NAME/KEY: MOD_RES
<222> LOCATION: (12)..(12)
<223> OTHER INFORMATION: Cys, Phe, Asp or Gln
<220> FEATURE:
<221> NAME/KEY: MOD_RES
<222> LOCATION: (13)..(13)
<223> OTHER INFORMATION: Gly, Glu, Asp or Asn
<220> FEATURE:
<221> NAME/KEY: MOD_RES
<222> LOCATION: (14)..(14)
<223> OTHER INFORMATION: Gly or Leu

<400> SEQUENCE: 34

Pro Xaa Xaa Xaa Trp Ala Xaa Xaa Xaa Xaa Xaa Xaa Xaa Xaa
1               5                   10

<210> SEQ ID NO 35
<211> LENGTH: 7
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (2)..(2)
<223> OTHER INFORMATION: Asp or Ser
<220> FEATURE:
<221> NAME/KEY: MOD_RES
<222> LOCATION: (4)..(4)
<223> OTHER INFORMATION: Ala or Gly
<220> FEATURE:
<221> NAME/KEY: MOD_RES
<222> LOCATION: (5)..(5)
<223> OTHER INFORMATION: Glu or Asp

<400> SEQUENCE: 35

Trp Xaa Val Xaa Xaa Cys Pro
1               5

<210> SEQ ID NO 36
<211> LENGTH: 20
<212> TYPE: PRT
<213> ORGANISM: Artificial Sequence
```

```
<220> FEATURE:
<223> OTHER INFORMATION: Description of Artificial Sequence: Synthetic
      consensus sequence
<220> FEATURE:
<221> NAME/KEY: MOD_RES
<222> LOCATION: (1)..(1)
<223> OTHER INFORMATION: Asn or Ala
<220> FEATURE:
<221> NAME/KEY: MOD_RES
<222> LOCATION: (2)..(2)
<223> OTHER INFORMATION: Tyr or Phe
<220> FEATURE:
<221> NAME/KEY: MOD_RES
<222> LOCATION: (5)..(5)
<223> OTHER INFORMATION: Thr or Glu
<220> FEATURE:
<221> NAME/KEY: MOD_RES
<222> LOCATION: (6)..(6)
<223> OTHER INFORMATION: Phe or Tyr
<220> FEATURE:
<221> NAME/KEY: MOD_RES
<222> LOCATION: (8)..(8)
<223> OTHER INFORMATION: Asn, Lys or Ala
<220> FEATURE:
<221> NAME/KEY: MOD_RES
<222> LOCATION: (9)..(9)
<223> OTHER INFORMATION: His or Ala
<220> FEATURE:
<221> NAME/KEY: MOD_RES
<222> LOCATION: (11)..(11)
<223> OTHER INFORMATION: Gly, His or Asp
<220> FEATURE:
<221> NAME/KEY: MOD_RES
<222> LOCATION: (12)..(12)
<223> OTHER INFORMATION: Ala or Val
<220> FEATURE:
<221> NAME/KEY: MOD_RES
<222> LOCATION: (13)..(13)
<223> OTHER INFORMATION: Glu or Thr
<220> FEATURE:
<221> NAME/KEY: MOD_RES
<222> LOCATION: (14)..(14)
<223> OTHER INFORMATION: Ile or Met
<220> FEATURE:
<221> NAME/KEY: MOD_RES
<222> LOCATION: (15)..(15)
<223> OTHER INFORMATION: Ile or Leu
<220> FEATURE:
<221> NAME/KEY: MOD_RES
<222> LOCATION: (16)..(16)
<223> OTHER INFORMATION: Ser or Asn
<220> FEATURE:
<221> NAME/KEY: MOD_RES
<222> LOCATION: (17)..(17)
<223> OTHER INFORMATION: Ser or Arg
<220> FEATURE:
<221> NAME/KEY: MOD_RES
<222> LOCATION: (18)..(18)
<223> OTHER INFORMATION: Thr or Pro

<400> SEQUENCE: 36

Xaa Xaa Tyr Cys Xaa Xaa Ala Xaa Xaa Cys Xaa Xaa Xaa Xaa Xaa Xaa
1               5                   10                  15

Xaa Xaa Glu Gly
            20

<210> SEQ ID NO 37
<211> LENGTH: 25
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (1)..(1)
```

```
<223> OTHER INFORMATION: Ser or Gln
<220> FEATURE:
<221> NAME/KEY: MOD_RES
<222> LOCATION: (3)..(3)
<223> OTHER INFORMATION: Pro or Glu
<220> FEATURE:
<221> NAME/KEY: MOD_RES
<222> LOCATION: (4)..(4)
<223> OTHER INFORMATION: Asn or Ser
<220> FEATURE:
<221> NAME/KEY: MOD_RES
<222> LOCATION: (7)..(7)
<223> OTHER INFORMATION: Phe, Leu or Asn
<220> FEATURE:
<221> NAME/KEY: MOD_RES
<222> LOCATION: (11)..(11)
<223> OTHER INFORMATION: Tyr or Leu
<220> FEATURE:
<221> NAME/KEY: MOD_RES
<222> LOCATION: (15)..(15)
<223> OTHER INFORMATION: Tyr, Asp or Asn
<220> FEATURE:
<221> NAME/KEY: MOD_RES
<222> LOCATION: (16)..(16)
<223> OTHER INFORMATION: Asn, Thr or Val
<220> FEATURE:
<221> NAME/KEY: MOD_RES
<222> LOCATION: (18)..(18)
<223> OTHER INFORMATION: Leu or Gly
<220> FEATURE:
<221> NAME/KEY: MOD_RES
<222> LOCATION: (19)..(19)
<223> OTHER INFORMATION: Ala or Leu
<220> FEATURE:
<221> NAME/KEY: MOD_RES
<222> LOCATION: (21)..(21)
<223> OTHER INFORMATION: Phe, Leu or Met
<220> FEATURE:
<221> NAME/KEY: MOD_RES
<222> LOCATION: (23)..(23)
<223> OTHER INFORMATION: Ala, Asp or His
<220> FEATURE:
<221> NAME/KEY: MOD_RES
<222> LOCATION: (24)..(24)
<223> OTHER INFORMATION: Val or Ile

<400> SEQUENCE: 37

Xaa Gly Xaa Xaa Ala Trp Xaa Glu Gln Arg Xaa Ala Glu Tyr Xaa Xaa
1               5                   10                  15

Val Xaa Xaa Asp Xaa Cys Xaa Xaa Val
            20                  25

<210> SEQ ID NO 38
<211> LENGTH: 16
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (6)..(6)
<223> OTHER INFORMATION: Phe or Tyr
<220> FEATURE:
<221> NAME/KEY: MOD_RES
<222> LOCATION: (9)..(9)
<223> OTHER INFORMATION: Pro or Gly
<220> FEATURE:
<221> NAME/KEY: MOD_RES
<222> LOCATION: (10)..(10)
<223> OTHER INFORMATION: Val or Ile
<220> FEATURE:
<221> NAME/KEY: MOD_RES
<222> LOCATION: (12)..(12)
<223> OTHER INFORMATION: Ser, Thr or Ala
<220> FEATURE:
```

```
<221> NAME/KEY: MOD_RES
<222> LOCATION: (14)..(14)
<223> OTHER INFORMATION: Pro, Gly or Glu
<220> FEATURE:
<221> NAME/KEY: MOD_RES
<222> LOCATION: (15)..(15)
<223> OTHER INFORMATION: Asp, Met, Val or Thr

<400> SEQUENCE: 38

Trp Phe Arg Asn Val Xaa Thr Glu Xaa Xaa Gly Xaa Leu Xaa Xaa Cys
1               5                   10                  15

<210> SEQ ID NO 39
<211> LENGTH: 12
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (5)..(5)
<223> OTHER INFORMATION: Ala or Gly

<400> SEQUENCE: 39

Gly Trp Asp Val Xaa Glu Cys Pro Asn Tyr Tyr Cys
1               5                   10

<210> SEQ ID NO 40
<211> LENGTH: 8
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (1)..(1)
<223> OTHER INFORMATION: Thr or Ser

<400> SEQUENCE: 40

Xaa Tyr Leu Leu Tyr Gln Cys Gly
1               5

<210> SEQ ID NO 41
<211> LENGTH: 7
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (2)..(2)
<223> OTHER INFORMATION: Asp or Ser
<220> FEATURE:
<221> NAME/KEY: MOD_RES
<222> LOCATION: (4)..(4)
<223> OTHER INFORMATION: Ala or Gly
<220> FEATURE:
<221> NAME/KEY: MOD_RES
<222> LOCATION: (5)..(5)
<223> OTHER INFORMATION: Glu or Asp

<400> SEQUENCE: 41

Trp Xaa Val Xaa Xaa Cys Pro
1               5

<210> SEQ ID NO 42
<211> LENGTH: 11
<212> TYPE: PRT
```

```
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (1)..(1)
<223> OTHER INFORMATION: Ser or Asn
<220> FEATURE:
<221> NAME/KEY: MOD_RES
<222> LOCATION: (4)..(4)
<223> OTHER INFORMATION: Phe, Leu or Asn
<220> FEATURE:
<221> NAME/KEY: MOD_RES
<222> LOCATION: (8)..(8)
<223> OTHER INFORMATION: Tyr or Leu

<400> SEQUENCE: 42

Xaa Ala Trp Xaa Glu Gln Arg Xaa Ala Glu Tyr
1               5                   10

<210> SEQ ID NO 43
<211> LENGTH: 13
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (6)..(6)
<223> OTHER INFORMATION: Phe or Tyr
<220> FEATURE:
<221> NAME/KEY: MOD_RES
<222> LOCATION: (9)..(9)
<223> OTHER INFORMATION: Pro or Gly
<220> FEATURE:
<221> NAME/KEY: MOD_RES
<222> LOCATION: (10)..(10)
<223> OTHER INFORMATION: Ser, Thr or Ala
<220> FEATURE:
<221> NAME/KEY: MOD_RES
<222> LOCATION: (12)..(12)
<223> OTHER INFORMATION: Any amino acid

<400> SEQUENCE: 43

Trp Phe Arg Asn Val Xaa Thr Glu Xaa Xaa Gly Xaa Leu
1               5                   10

<210> SEQ ID NO 44
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Phe Phe Ser Val Phe Phe Asn Lys
1               5

<210> SEQ ID NO 45
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Glu His Thr Ala Asn Gln Val Val Glu Ala Ala Glu Ser Arg
1               5                   10
```

-continued

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
caccatgatg aagttttcgt                                              20

<210> SEQ ID NO 47
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
gaacaacaat acgtgtataa gact                                         24

<210> SEQ ID NO 48
<211> LENGTH: 456
<212> TYPE: PRT
<213> ORGANISM: Phaeodactylum tricornutum

<400> SEQUENCE: 48

Met Met Lys Phe Ser Phe Ala Ala Thr Thr Phe Leu Gly Val Val Ala
1               5                   10                  15

Val Ile Gly Thr Val His Ala Asp Glu Pro Pro Ala Cys Leu Thr Ser
            20                  25                  30

Thr Ala Asp Leu Ser Val Asp Ile Phe Thr Asp Lys Val Glu Pro Leu
        35                  40                  45

Phe Ser Gln Gly Trp Asn Val Thr Tyr His Asn Thr Tyr Lys Ile Ala
    50                  55                  60

Asn Asn Leu Phe Asp Asn Thr Thr Tyr Leu Leu Tyr Gln Cys Gly Ser
65                  70                  75                  80

Thr Pro Pro Ala Asp Val Val Asp Asn Gly Asn Phe Asn Ala Val Leu
                85                  90                  95

Glu Ile Pro Leu Ser Asn Val Gly Leu Ser Gln Thr Pro His Ile Gly
            100                 105                 110

Phe Met Glu Gln Leu Glu Leu Val Asp Glu Ile Ala Ala Phe Leu Thr
        115                 120                 125

Asp Thr Asp Phe Ile Ser Ser Pro Cys Phe Leu Asp Glu Ile Ala Ala
    130                 135                 140

Gly Asn Val Leu Thr Leu Val Glu Pro Ser Gly Val Asp Ala Pro
145                 150                 155                 160

Ala Thr Gly Asn Thr Ala Leu Ser Ala Gly Thr Val Ala Phe Val Ala
                165                 170                 175

Ser Phe Thr Gln Val Pro Phe Asp Asn Thr Val Asn Ile Gln Glu Tyr
            180                 185                 190

Ser Glu Leu Thr Asn Val Ala Val Phe Glu Trp Val Lys Phe Phe Ser
        195                 200                 205

Val Phe Phe Asn Lys Glu His Thr Ala Asn Gln Val Val Glu Ala Ala
    210                 215                 220

Glu Ser Arg Phe Asp Cys Val Ala Gln Asn Ala Gly Ala Val Gln Ala
225                 230                 235                 240

Asp Asn Met Pro Val Lys Pro Val Val Leu Trp Ala Tyr Tyr Ser Asp
            245                 250                 255

Phe Cys Gly Gly Trp Asp Val Ala Glu Cys Pro Asn Tyr Tyr Cys Glu
            260                 265                 270

Phe Ala Asn Ala Cys Gly Ala Glu Ile Ile Ser Ser Thr Glu Gly Asn
            275                 280                 285

Thr Thr Val Cys Gly Ala Pro Tyr Met Thr Thr Glu Glu Leu Val Glu
            290                 295                 300

Leu Gly Lys Asp Ala Asp His Trp Ile Tyr Pro Ser Ser Asn Trp Asp
305                 310                 315                 320

Thr Ala Ser Glu Thr Phe Gly Glu Gln Leu Gln Asn Met Lys Ala Val
            325                 330                 335

Gln Asp Gln Gln Val Phe Asp Tyr Gln Ala Ser Gly Glu Asn Ala Trp
            340                 345                 350

Phe Glu Gln Arg Tyr Ala Glu Tyr Tyr Asn Val Leu Ala Asp Phe Cys
            355                 360                 365

Ala Val Val Gly Thr Thr Gln Pro Leu Thr Gly Arg Ser Trp Phe Arg
            370                 375                 380

Asn Val Phe Thr Glu Pro Val Gly Ser Leu Pro Asp Cys Ser Pro Thr
385                 390                 395                 400

Gln Ser Ala Asn Ile Leu Asp Asp Val His Ile Cys Phe Leu Pro Thr
            405                 410                 415

Thr Gly Gly Ala Ala Ala Gly Gly Gly Ser Gly Ser Gly Gly Ser Ser
            420                 425                 430

Ala Lys Ala Ile Ala Val Gly Thr Ala Leu Ala Ala Gly Leu Leu
            435                 440                 445

Ser Leu Ile His Val Leu Leu Phe
450                 455

<210> SEQ ID NO 49
<211> LENGTH: 456
<212> TYPE: PRT
<213> ORGANISM: Phaeodactylum tricornutum

<400> SEQUENCE: 49

Met Met Lys Phe Ser Phe Ala Ala Thr Thr Phe Leu Gly Val Val Ala
1               5                   10                  15

Val Ile Gly Thr Val His Ala Asp Glu Pro Pro Ala Cys Leu Thr Ser
            20                  25                  30

Thr Ala Asp Leu Ser Val Asp Ile Phe Thr Asp Lys Val Glu Pro Leu
            35                  40                  45

Phe Ser Gln Gly Trp Asn Val Thr Tyr His Asn Thr Tyr Lys Ile Ala
            50                  55                  60

Asn Asn Leu Phe Asp Asn Thr Thr Tyr Leu Leu Tyr Gln Cys Gly Ser
65                  70                  75                  80

Thr Pro Pro Ala Asp Val Val Asp Asn Gly Asn Phe Asn Ala Val Leu
            85                  90                  95

Glu Ile Pro Leu Ser Asn Val Gly Leu Ser Gln Thr Pro His Ile Gly
            100                 105                 110

Phe Met Glu Gln Leu Glu Leu Val Asp Glu Ile Ala Ala Phe Leu Thr
            115                 120                 125

Asp Thr Asp Phe Ile Ser Ser Pro Cys Phe Leu Asp Glu Ile Ala Ala
            130                 135                 140

Gly Asn Val Leu Thr Leu Val Glu Pro Ser Glu Gly Val Asp Ala Pro

```
            145                 150                 155                 160
        Ala Thr Gly Asn Thr Ala Leu Ser Ala Gly Thr Val Ala Phe Val Ala
                        165                 170                 175

Ser Phe Thr Gln Val Pro Phe Asp Asn Thr Val Asn Ile Gln Glu Tyr
                    180                 185                 190

Ser Glu Leu Thr Asn Val Ala Val Phe Glu Trp Val Lys Phe Phe Ser
                195                 200                 205

Leu Phe Phe Asn Lys Glu His Thr Ala Asn Gln Val Val Glu Ala Ala
            210                 215                 220

Glu Ser Arg Phe Asp Cys Val Ala Gln Asn Ala Gly Ala Val Gln Ala
        225                 230                 235                 240

Asp Asn Met Pro Val Gln Pro Val Val Leu Trp Ala Tyr Tyr Ser Asp
                        245                 250                 255

Phe Cys Gly Gly Trp Asp Val Ala Glu Cys Pro Asn Tyr Tyr Cys Glu
                    260                 265                 270

Phe Ala Asn Ala Cys Gly Ala Glu Ile Ile Ser Ser Thr Glu Gly Asn
                275                 280                 285

Thr Thr Val Cys Gly Ala Pro Tyr Met Thr Thr Glu Glu Leu Val Glu
            290                 295                 300

Leu Gly Lys Asp Ala Asp His Trp Ile Tyr Pro Ser Asn Asn Trp Asp
        305                 310                 315                 320

Thr Ala Ser Glu Thr Phe Gly Glu Gln Leu Gln Asn Met Lys Ala Val
                        325                 330                 335

Gln Asp Gln Gln Val Phe Asp Tyr Gln Ala Ser Gly Glu Asn Ala Trp
                    340                 345                 350

Phe Glu Gln Arg Tyr Ala Glu Tyr Tyr Asn Val Leu Ala Asp Phe Cys
                355                 360                 365

Ala Val Val Gly Thr Thr Gln Pro Leu Thr Gly Arg Ser Trp Phe Arg
            370                 375                 380

Asn Val Phe Thr Glu Pro Val Gly Ser Leu Pro Asp Cys Ser Pro Thr
        385                 390                 395                 400

Gln Ser Ala Asn Ile Leu Asp Asp Val His Ile Cys Phe Leu Pro Thr
                        405                 410                 415

Thr Gly Gly Ala Ala Ala Gly Gly Gly Ser Gly Ser Gly Gly Ser Ser
                    420                 425                 430

Ala Lys Ala Ile Ala Val Gly Thr Ala Ala Leu Ala Ala Gly Leu Leu
                435                 440                 445

Ser Leu Ile His Val Leu Leu Phe
            450                 455

<210> SEQ ID NO 50
<211> LENGTH: 8
<212> TYPE: PRT
<213> ORGANISM: Phaeodactylum tricornutum

<400> SEQUENCE: 50

Phe Phe Ser Leu Phe Phe Asn Lys
1               5

<210> SEQ ID NO 51
<211> LENGTH: 22
<212> TYPE: PRT
<213> ORGANISM: Phaeodactylum tricornutum

<400> SEQUENCE: 51

Ala Val Gln Asp Gln Gln Val Phe Asp Tyr Gln Ala Ser Gly Glu Asn
```

```
1               5                  10                 15
Ala Trp Phe Glu Gln Arg
            20

<210> SEQ ID NO 52
<211> LENGTH: 4
<212> TYPE: PRT
<213> ORGANISM: Thassiosira pseudonana

<400> SEQUENCE: 52

Asp Glu Ala Asp
1

<210> SEQ ID NO 53
<211> LENGTH: 4
<212> TYPE: PRT
<213> ORGANISM: Thassiosira pseudonana

<400> SEQUENCE: 53

Asp Glu Ala His
1
```

COBALAMIN ACQUISITION PROTEIN AND USE THEREOF

CROSS-REFERENCE TO RELATED APPLICATIONS

This application is a divisional of U.S. patent application Ser. No. 13/874,437, filed Apr. 30, 2013, which claims priority to and the benefit of U.S. Provisional Patent Application No. 61/640,261, filed Apr. 30, 2012; the entire contents of each of which are incorporated by reference herein.

GOVERNMENT SUPPORT

This invention was made with support provided by the National Science Foundation (Grant No. OCE-0752291); therefore, the government has certain rights in the invention.

FIELD OF THE INVENTION

The present invention relates to cobalamin acquisition proteins, compositions containing the cobalamin acquisition proteins, and the use of such proteins and compositions.

BACKGROUND OF THE INVENTION

Diatoms are responsible for an estimated 40% of marine primary production and are therefore important players in global carbon cycling (Nelson et al. (1995) "Production and Dissolution of Biogenic Silica in the Oceans: Revised Global Estimates, Comparison with Regional Data and Relationship to Biogenic Sedimentation," *Global Biogeochem. Cycles* 9(3): 359-372; Falkowski et al. (2004) "The evolution of Modern Eukaryotic Phytoplankton," *Science* 305: 354-360). Though diatom growth in the oceans is thought to be controlled primarily by nitrogen and iron availability, recent studies support long standing hypotheses that cobalamin availability can impact marine phytoplankton growth and community composition (Boyd et al. (2007) "Mesoscale Iron Enrichment Experiments 1993-2005: Synthesis and Future Directions," *Science* 315: 612-618; Moore et al. (2004) "Upper Ocean Ecosystem Dynamics and Iron Cycling in a Global Three-dimensional Model," *Global Biogeochem. Cycles* 18: GB4028, doi:10.1029/2004GB002220; Panzeca et al. (2006) "B Vitamins as Regulators of Phytoplankton Dynamics," *Eos Trans. AGU*, 87(52): 593-596; Bertrand et al. (2007) "Vitamin $B_{12}$ and Iron Co-Limitation of Phytoplankton Growth in the Ross Sea," *Limnology and Oceanography* 52(3)1079-1093; Gobler et al. (2007) "Effect of B-Vitamins and Inorganic Nutrients on Algal Bloom Dynamics in a Coastal Ecosystem," *Aquat. Microb. Ecol.* 49: 181-194; Koch et al. (2011) "The Effect of Vitamin $B_{12}$ on Phytoplankton Growth and Community Structure in the Gulf of Alaska," *Limnol. and Oceanog.* 56: 1023-1034; Cowey C B (1956) "A Preliminary Investigation of the Variaton of Vitamin $B_{12}$ in Oceanic and Coastal Waters," *J. Mar. Biol. Ass. UK*, 35: 609-620; Droop (1957) "Vitamin $B_{12}$ in Marine Ecology" *Nature* 180: 1041-1042; Menzel et al. (1962) "Occurrence of Vitamin $B_{12}$ in the Sargasso Sea," *Limnol. Oceanogr.* 7: 151-154). In the open ocean, cobalamin is present in exceedingly low concentrations and is depleted in irradiated surface waters, largely due to biological utilization (See, Menzel et al., supra).

Because no eukaryotic organism is known to produce cobalamin (Rodionov et al. (2003) "Comparative Genomics of the Vitamin $B_{12}$ Metabolism and Regulation in Prokaryotes," *J. Biol. Chem.* 278: 41148-41159), marine bacteria and archaea must therefore supply auxotrophic (vitamin-requiring) phytoplankton with the vitamin, either through direct interaction (Croft et al. (2005) "Algae Acquire Vitamin $B_{12}$ Through a Symbiotic Relationship With Bacteria," *Nature* 438: 90-93) or through production and release into the water column upon death and cell lysis (Droop M R (2007) "Vitamins, Phytoplankton and Bacteria: Symbiosis or Scavenging?" *Journal of Plankton Res.* 29: 107-113; Karl D M (2002) "Nutrient Dynamics in the Deep Blue Sea," *Trends in Microbiol.* 10: 410-418). This chemical dependency is one of many that underlie interactions between marine microbial groups; assessing the role of these dependencies in oceanic processes is of considerable interest (Azam et al. (2007) "Microbial Structuring of Marine Ecosystems," *Nat. Rev. Microbiol.* 5: 782-791). Cobalamin availability may play a significant role in the climatically important Southern Ocean where it appears to periodically colimit the growth of diatom-dominated phytoplankton communities (Bertrand et al. (2007), (supra)) and is likely in short supply relative to other marine environments (Bertrand et al. (2011) "Vitamin $B_{12}$ Biosynthesis Gene Diversity in the Ross Sea: the Identification of a New Group of Putative Polar $B_{12}$-Biosynthesizers," *Environmental Microbiology* 13: 1285-1298).

The three available genome sequences of marine diatoms (*P. tricornutum, T. pseudonana*, and *F. cylindrus*) lack proteins homologous to known metazoan and bacterial cobalamin acquisition proteins (Koch et al. (2011) "The Effect of Vitamin $B_{12}$ on Phytoplankton Growth and Community Structure in the Gulf of Alaska," *Limnol. and Oceanog.* 56: 1023-1034). As a result, the mechanisms by which these phytoplankton acquire the vitamin from their environment remain unclear. Cobalamin requirements in eukaryotic algae, like diatoms, arise primarily from its use in the enzyme methionine synthase (Croft et al. (2005) (supra); Helliwell et al. (2011) "Insights into the Evolution of Vitamin $B_{12}$ Auxotrophy from Sequenced Algal Genomes" *Mol. Biol. Evol.* 28(10):2921-33). Methionine synthase is responsible for generating methionine and tetrahydrofolate from homocysteine and 5-methyltetrahydrofolate, thus playing an essential role in cellular one carbon metabolism (Banerjee et al. (1990) "Cobalamin-dependent Methionine Synthase," *FASEB Journal* 4: 1449-1459). Some eukaryotic algal genomes encode only one version of this enzyme, MetH, which uses methylcobalamin as an intermediate methyl group carrier (Goulding et al. (1997) "Cobalamin-dependent Methionine Synthase is a Modular Protein with Distinct Regions for Homocysteine, Methyltetrahydrofolate, Cobalamin and Adenosylmethionine," *Biochemistry* 36: 8082-8091). These algae thus have an absolute cobalamin requirement. In contrast, other algal strains encode both MetH as well as MetE, an enzyme that accomplishes the same reaction as MetH but without cobalamin and with much lower efficiency (Gonzalez et al. (1992) "Comparison of Cobalamin-independent and Cobalamin-dependent Methionine Synthases from *E. coli*: Two Solutions to the Same chemical Problem," *Biochemistry* 31: 6045-6056). Organisms with MetE and MetH thus have a flexible cobalamin demand and use cobalamin when available but do not absolutely require it. The maintenance of the much lower efficiency MetE enzyme in phytoplankton genomes presumably allows for ecological flexibility in environments with scarce or variable cobalamin availability (Helliwell et al. (2011) (supra)).

Once methionine is produced, it has several known fates within algal cells, including incorporation into proteins.

Methionine also serves as the precursor to S-adenosyl methionine (AdoMet, SAM), an important methylating agent, propylamine donor, and radical source that participates in a wide range of cellular functions. Methionine can be used to produce another sulfur-containing metabolite dimethylsulfonium propionate (DMSP), which is only made by some diatoms, possibly as a cryoprotectant, osmolyte (Stefels J P (2000) "Physiological Aspects of the Production and Conversion of DMSP in Marine Algae and Higher Plants," *J. Sea Res*. 43: 183-197) or antioxidant (Sunda et al. (2002) "An Antioxidant Function for DMSP and DMS in Marine Algae" *Nature* 418: 317-320), and is the precursor to the climatically important gas dimethylsulfide (DMS), and is the precursor to the climatically important gas dimethylsulfide (DMS) (Lovelock (1972) "Gala as Seen Through the Atmosphere," *Atmos. Environ*. 6:579-580). In addition, impaired methionine synthase activity causes 'methyl folate trapping' whereby folate compounds can build up inside the cell in a form only usable by methionine synthase, thus preventing efficient folate recycling for use in its other essential functions such as nucleic acid biosynthesis. This phenomenon has been described in humans (Scott et al. (1981) "The Methyl Folate Trap: A Physiological Response in Man to Prevent Methyl Group Deficiency in Kwashiorkor (Methionine Deficiency) and an Explanation for Folic-Acid-Induced Exacerbation of Subacute Combined Degeneration in Pernicious Anaemia," *The Lancet* 318: 337-340) and may also occur in algae (Croft et al. (2005) (supra)). The effects of cobalamin starvation on phytoplankton therefore potentially impact a wide range of cellular and ecological functions.

SUMMARY

The present invention is based, in part, upon the discovery of the function of certain protein sequences encoded by nucleic acid sequences present in the genomes of various marine diatoms, including *Thassiosira pseudonana* and *Phaeodactylum tricornutum*. As discussed herein below and in Examples 1 and 2, certain of the sequences have now been discovered to encode the protein sequence of a cobalamin acquisition protein (CBA1). As will be discussed in more detail below, CBA1, given that it can sequester vitamin $B_{12}$, has antimicrobial properties, and therefore can be used in a pharmaceutical preparation. In addition, organisms of interest can be genetically modified to express or over express CBA1 (for example, Example 3 describes a recombinant organism that overexpresses CBA1). The resulting organisms, which, for example, can be used in biofuel production or the production of various products (for example carbon products), can be grown under conditions and in environments where the presence and/or amount of vitamin $B_{12}$ is limiting. Furthermore, the CBA1 can be used in a variety of purification or separation technologies to purify, separate, and quantitate vitamin $B_{12}$.

In one aspect, the invention provides a recombinant microorganism comprising a nucleic acid encoding a CBA1 protein comprising an amino acid sequence selected from the group consisting of SEQ ID NO: 2, an amino acid sequence at least 90% identical to SEQ ID NO: 2, SEQ ID NO: 4, an amino acid sequence at least 90% identical to SEQ ID NO: 4, SEQ ID NO: 6, an amino acid sequence at least 90% identical to SEQ ID NO: 6, SEQ ID NO: 8, an amino acid sequence at least 90% identical to SEQ ID NO: 8, SEQ ID NO: 10, an amino acid sequence at least 90% identical to SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20 SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30 SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40 SEQ ID NO: 41, SEQ ID NO: 42, SEQ ID NO: 43, SEQ ID NO: 48, SEQ ID NO: 49, SEQ ID NO: 50. The nucleic acid is expressed in the organism to produce a protein that binds and/or sequesters vitamin $B_{12}$.

The nucleic acid can be disposed within an expression vector, or can be integrated into the genome of the microorganism. The nucleic acid typically is operatively associated with an inducible promoter or with a constitutive promoter.

The microorganism is characterized such that, under the same environmental conditions, it (i) is capable of binding more vitamin $B_{12}$ over a preselected period of time than an organism without the nucleic acid, (ii) is capable of taking up more vitamin $B_{12}$ over a preselected period of time than an organism without the nucleic acid, (iii) is capable of growing faster over a preselected period of time than an organism without the nucleic acid, or a combination thereof.

In certain embodiments, the microorganism is an algae. Furthermore, the organism can be used to create a viable culture, such that the microorganisms can be propagated under the appropriate culture conditions, for example, in an indoor bioreactor or in an outdoor facility such as a pond or lake.

In another aspect, the invention provides a solid support having immobilized thereon a CBA1 protein comprising an amino acid sequence selected from the group consisting of SEQ ID NO: 2, an amino acid sequence at least 90% identical to SEQ ID NO: 2, SEQ ID NO: 4, an amino acid sequence at least 90% identical to SEQ ID NO: 4, SEQ ID NO: 6, an amino acid sequence at least 90% identical to SEQ ID NO: 6, SEQ ID NO: 8, an amino acid sequence at least 90% identical to SEQ ID NO: 8, SEQ ID NO: 10, an amino acid sequence at least 90% identical to SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20 SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30 SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40 SEQ ID NO: 41, SEQ ID NO: 42, SEQ ID NO: 43, SEQ ID NO: 48, SEQ ID NO: 49, and SEQ ID NO: 50.

The CBA1 protein preferably binds vitamin $B_{12}$ with an affinity less than $10^{-5}$ M. The solid support can be a planar support, bead, or a particle.

Vitamin $B_{12}$ can be purified or separated from a sample, for example, a liquid sample, by combining such a solid support with the sample under conditions to permit vitamin $B_{12}$ in the sample to bind to the solid support. The solid support can then be washed to remove molecules in the liquid sample that have not bound to the solid support. Thereafter, and if appropriate, the vitamin $B_{12}$ can be eluted from the solid support.

In addition, the methods and compositions described herein can be used to determine the presence and/or amount of vitamin $B_{12}$ in a sample. The method comprises: (a) combining a sample to be tested with a solid support having CBA1 immobilized thereon under conditions to permit vitamin $B_{12}$, if present in the sample, to bind to the solid support; and (b) determining the presence and/or amount of vitamin $B_{12}$ bound to the solid support. HPLC, HPLC-MS, triple quadrupole mass spectrometry, or ELISA can be used to determine the presence and/or amount of vitamin $B_{12}$.

In another aspect, the invention provides a pharmaceutical composition comprising a CBA1 protein comprising an amino acid sequence selected from the group consisting of SEQ ID NO: 2, an amino acid sequence at least 90% identical to SEQ ID NO: 2, SEQ ID NO: 4, an amino acid sequence at least 90% identical to SEQ ID NO: 4, SEQ ID NO: 6, an amino acid sequence at least 90% identical to SEQ ID NO: 6, SEQ ID NO: 8, an amino acid sequence at least 90% identical to SEQ ID NO: 8, SEQ ID NO: 10, an amino acid sequence at least 90% identical to SEQ ID NO:10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20 SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30 SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40 SEQ ID NO: 41, SEQ ID NO: 42, SEQ ID NO: 43, SEQ ID NO: 48, SEQ ID NO: 49, and SEQ ID NO: 50, and a pharmaceutically acceptable excipient.

The CBA1 protein may bind vitamin $B_{12}$, and optionally binds vitamin $B_{12}$ with an affinity less than $10^{-5}$ M. In some embodiments, the CBA1 protein binds vitamin $B_{12}$ with an affinity from about $10^{-5}$ M to about $10^{-12}$ M. In other embodiments, the CBA1 protein binds vitamin $B_{12}$ with an affinity from about $10^{-5}$ M to about $10^{-11}$ M, from about $10^{-5}$ M to about $10^{-10}$ M, from about $10^{-5}$ M to about $10^{-9}$ M, from about $10^{-56}$ M to about $10^{-8}$ M, or from about $10^{-5}$ M to about $10^{-7}$ M. In some embodiments, the protein binds vitamin $B_{12}$ with an affinity from about $10^{-7}$ M to about $10^{-12}$ M, from about $10^{-8}$ M to about $10^{-12}$ M, from about $10^{-9}$ M to about $10^{-12}$ M, from about $10^{-10}$ M to about $10^{-12}$ M, from about $10^{-11}$ M to about $10^{-12}$ M, from about $10^{-7}$ M to about $10^{-11}$ M, or from about $10^{-8}$ M to about $10^{-10}$ M. The pharmaceutical composition can be a liquid, solid, cream or paste.

In yet another aspect, the invention provides a method of treating a subject comprising administering to a subject in need thereof a therapeutically effective amount of such a pharmaceutical composition. The composition can be administered topically to the subject.

The pharmaceutical composition may also be used in the manufacture of a medicament to treat, prevent, or ameliorate a bacterial infection.

These aspects and feature of the invention will be discussed in more detail below.

BRIEF DESCRIPTION OF FIGURES

FIGS. 7A-7C depict three independent quantitative analyses of the effect of low $B_{12}$ availability on CBA1. FIG. 7A: Bars are means of spectral counting abundance scores for protein CBA1 in four treatments in both diatoms as measured via shotgun ion trap mass spectrometry. Error bars represent one standard deviation about the mean of technical triplicate measurements. FIG. 7B: Bars are means of transcript RPKM abundance scores for CBA1 sequences in four treatments in both diatoms in RNA seq transcriptomic analyses. Error bars represent one standard deviation about the mean of biological duplicate measurements. FIG. 7C Bars are the absolute abundance of two peptides from CBA1 in *P. tricornutum* measured via SRM mass spectrometry in two low $B_{12}$ and two replete cultures. Error bars are one standard deviaton about the mean of technical triplicate measurements.

FIG. 9C depicts fragmentation tables for both peptides, showing the masses of the product ions predicted to be generated from these peptides. Product ions highlighted were detected via LTQ-MS (spectra shown in B); those in gray are different between these two peptides, while those in black boxes are conserved. Fifteen unique ions were identified for peptide FFSVFFNK (SEQ ID NO: 18) and fourteen were identified for FFSLFFNK (SEQ ID NO: 50). FIG. 9D depicts the number of times these allelic peptides were found in *P. tricornututm* cultures under four different culturing conditions.

FIGS. 12B-12E depict abundance patterns for select proteins included in the schematic of FIG. 12A are displayed.

DETAILED DESCRIPTION OF THE INVENTION

Figure 1A:
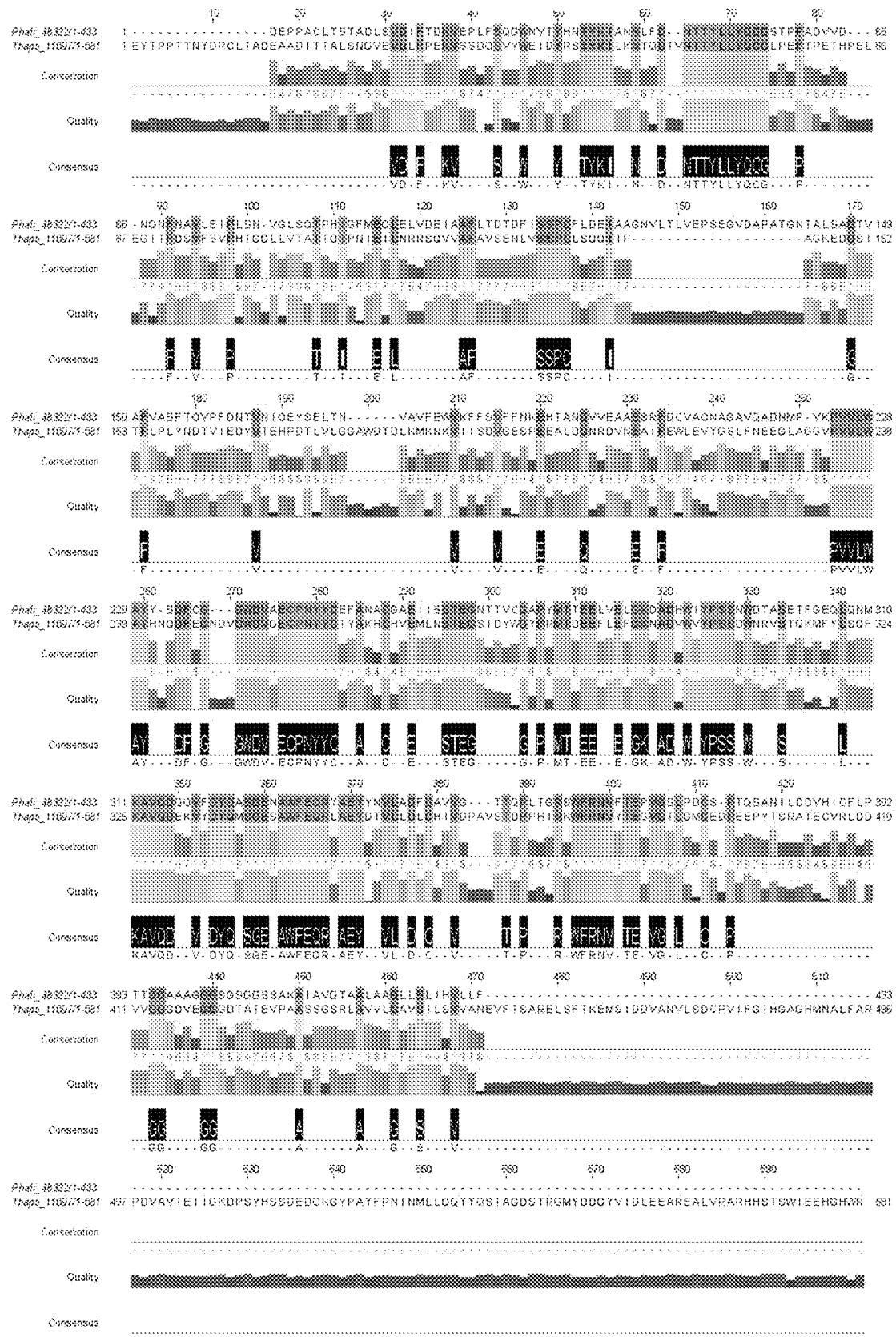
FIG. 1A depicts alignment of two CBA1 sequences from the diatoms *Phaeodactylum tricornutum* and *Thassiosira pseudonana* (Phatr_48322 (SEQ ID NO: 2) and Thaps_11697 (SEQ ID NO: 6), respectively) and the consensus sequence (SEQ ID NO: 20)

The present invention is based, in part, upon the discovery of the function of certain protein sequences encoded by nucleic acid sequences present in the genomes of various marine diatoms, including *Thassiosira pseudonana* and *Phaeodactylum tricornutum*. Armbrust et al. (Science (2004), 306:79-86) report the sequencing of the 34 million-base pair nuclear genome of the marine diatom *Thalassiosira pseudonana*, its 129 thousand-base pair plastid and its 44-thousand-base pair mitochondrial genome. Bowler et al. (*Nature* (2008) 456:239-244) report the sequencing of the complete genome of the diatom *Phaeodactylum tricornutum*. Although many nucleic acid sequences were reported, the function of many of the putative proteins encoded by the genomic, plastid and mitochondrial sequences remains unknown. As discussed herein below and in Examples 1 and 2, certain of the sequences have now been discovered to encode the protein sequence of cobalamin acquisition proteins (CBA1), or also known as a vitamin $B_{12}$ binding protein.

Because the function of these sequences has now been elucidated, the cobalamin acquisition proteins ("CBA proteins") described herein can be used in a number of applications, for example, in therapeutic compositions, for example, therapeutic compositions with antibiotic activity, the creation of recombinant organisms (e.g., unicellular eukaryotic organisms or prokaryotic organisms such as algae, bacteria, yeast, etc.) which can grow faster in view of the expression of exogenous cobalamin acquisition protein, and in separation and analytical technologies.

The practice of the present invention employs, unless otherwise indicated, conventional techniques of molecular biology (including recombinant techniques), cell biology, biochemistry, organic chemistry, pharmacology, analytics and separation technologies, which are within the skill of the art. Such techniques are explained fully in the literature, such as "Comprehensive Organic Synthesis" (B. M. Trost & I. Fleming, eds., 1991-1992); "Molecular Cloning: a Laboratory Manual" Second Edition (Sambrook et al., 1989); "Oligonucleotide synthesis" (M. J. Gait, ed., 1984); "Animal cell culture" (R. I. Freshney, ed., 1987); the series "Methods in Enzymology" (Academic Press, Inc.); "Handbook of Experimental Immunology" (D. M. Weir & C. C. Blackwell, eds.); "Gene Transfer Vectors for Mammalian Cells" (J. M. Miller & M. P. Calos, eds., 1987); "Current Protocols in Molecular Biology" (F. M. Ausubel et al., eds., 1987, and periodic updates); "PCR: the Polymerase Chain Reaction" (Mullis et al., eds., 1994); and "Current Protocols in Immunology" (J. E. Coligan et al., eds., 1991), each of which is herein incorporated by reference in its entirety. Various aspects of the invention are set forth below in sections; however, aspects of the invention described in one particular section are not to be limited to any particular section. Further, when a variable is not accompanied by a definition, the previous definition of the variable controls.

Definitions

To facilitate an understanding of the present invention, a number of terms and phrases are defined below.

The terms "a," "an" and "the" as used herein mean "one or more" and include the plural unless the context is inappropriate.

As used herein, the term "subject" refers to organisms to be treated by the methods of the present invention. Such organisms preferably include, but are not limited to, mammals (e.g., murines, simians, equines, bovines, porcines, canines, felines, and the like), and most preferably includes humans. In the context of the invention, the term "subject" generally refers to an individual who will receive or who has received treatment (e.g., administration of a compound of the present invention and optionally one or more other agents) for a condition characterized by microbial growth or infection.

As used herein, the term "effective amount" refers to the amount of a compound (e.g., a compound of the present invention) sufficient to effect beneficial or desired results. An effective amount can be administered in one or more administrations, applications or dosages and is not intended to be limited to a particular formulation or administration route. As used herein, the term "treating" includes any effect, e.g., lessening, reducing, modulating, ameliorating or eliminating, that results in the improvement of the condition, disease, disorder, and the like, or ameliorating a symptom thereof. The term "therapeutically-effective amount" as used herein means that amount of a compound, material, or composition comprising a protein of the present invention that is effective for producing some desired therapeutic effect in at least a sub-population of cells in a subject at a reasonable benefit/risk ratio applicable to any medical treatment.

As used herein, the term "pharmaceutical composition" refers to the combination of an active agent with a carrier, inert or active, making the composition especially suitable for diagnostic or therapeutic use in vivo or ex vivo.

The term "pharmaceutically acceptable" is employed herein to refer to those compounds, materials, compositions, and/or dosage forms which are, within the scope of sound medical judgment, suitable for use in contact with the tissues of a subject (for example, human beings and animals)

without excessive toxicity, irritation, allergic response, or other problem or complication, commensurate with a reasonable benefit/risk ratio.

The term "pharmaceutically-acceptable excipient" as used herein means a pharmaceutically-acceptable material, carrier or vehicle, such as a liquid or solid filler, diluent, manufacturing aid (e.g., lubricant, talc, magnesium, calcium or zinc stearate, or steric acid), or solvent encapsulating material, involved in carrying or transporting the protein or a fragment thereof from one organ, or portion of the body, to another organ, or portion of the body. Each excipient must be "acceptable" in the sense of being compatible with the other ingredients of the formulation and not injurious to the intended recipient. Some examples of materials which can serve as pharmaceutically-acceptable excipients include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) oils, such as peanut oil, cottonseed oil, safflower oil, sesame oil, olive oil, corn oil and soybean oil; (9) glycols, such as propylene glycol; (10) polyols, such as glycerin, sorbitol, mannitol and polyethylene glycol; (11) esters, such as ethyl oleate and ethyl laurate; (12) agar; (13) buffering agents, such as magnesium hydroxide and aluminum hydroxide; (14) alginic acid; (15) pyrogen-free water; (16) isotonic saline; (17) Ringer's solution; (18) ethyl alcohol; (19) pH buffered solutions; (20) polyesters, polycarbonates and/or polyanhydrides; and (21) other non-toxic compatible substances employed in pharmaceutical formulations. For exemplary excipients, see, for example, Martin, Remington's Pharmaceutical Sciences, 15th Ed., Mack Publ. Co., Easton, Pa. (1975)).

Throughout the description, where compositions are described as having, including, or comprising specific components, or where processes and methods are described as having, including, or comprising specific steps, it is contemplated that, additionally, there are compositions of the present invention that consist essentially of, or consist of, the recited components, and that there are processes and methods according to the present invention that consist essentially of, or consist of, the recited processing steps.

I. Cobalamin Acquisition Protein (CBA Protein)

As discussed in more detail below and in Examples 1 and 2, certain protein sequences encoded by the genomes of various marine diatoms have now been identified as cobalamin acquisition proteins. The following section discusses the full length sequences (both the predicted protein sequences and the corresponding nucleic acid sequences that encode the predicted protein sequences) of the cobalamin acquisition proteins of various diatoms, proteins containing one or more peptide fragments, consensus sequences of diatom cobalamin acquisition proteins, and putative vitamin $B_{12}$ binding sites within the cobalamin acquisition protein, which are referred to collectively as "CBA proteins."

In the following full length sequences the signal sequences and the nucleic acids encoding the signal sequences have not been included.

A. Cobalamin Acquisition Protein in the Diatom *Phaeodactylum tricornutum* (Phatr_48322)
(i) Nucleic Acid-SEQ ID NO: 1
(SEQ ID NO: 1)
GACGAACCTCCGGCTTGCCTGACATCGACTGCGGACCTTTCGGTGGATAT

CTTCACCGACAAGGTAGAACCGCTCTTCTCCCAAGGATGGAATGTGACTT

ACCATAACACCTACAAGATTGCCAACAATCTCTTCGACAACACGACCTAC

CTCCTCTACCAGTGTGGTAGCACGCCTCCGGCCGATGTCGTCGACAACGG

CAACTTCAACGCCGTCCTCGAGATTCCCCTGTCCAACGTGGGTCTCTCGC

AAACGCCGCACATTGGCTTTATGGAGCAACTCGAACTCGTCGACGAAATT

GCGGCCTTTTTGACCGACACGGACTTTATTTCGTCGCCTTGCTTCTTGGA

CGAGATCGCCGCCGGTAACGTCCTCACACTGGTGGAACCCAGTGAAGGGG

TAGACGCACCCGCCACTGGCAACACTGCACTCAGTGCTGGCACGGTAGCC

TTTGTAGCGTCCTTCACCCAAGTCCCCTTTGACAATACGGTCAACATCCA

AGAGTACAGCGAACTCACCAACGTGGCCGTCTTTGAATGGGTCAAGTTCT

TTTCCGTCTTCTTCAACAAGGAGCACACCGCCAACCAAGTCGTCGAGGCC

GCGGAATCGCGCTTTGATTGCGTCGCGCAAAACGCCGGAGCCGTCCAGGC

CGACAATATGCCGGTCAAACCCGTCGTCTTGTGGGCCTACTACAGTGATT

TCTGTGGCGGATGGGATGTCGCCGAATGCCCCAACTACTACTGCGAATTC

GCCAACGCGTGCGGGCCGAAATTATTAGCAGTACCGAAGGCAACACCAC

CGTCTGCGGTGCACCCTACATGACCACGGAAGAATTGGTGGAACTCGGAA

AGGATGCCGATCACTGGATCTATCCGTCCAGTAACTGGGATACGGCATCG

GAAACCTTCGGCGAGCAGCTTCAGAACATGAAGGCCGTGCAGGACCAACA

AGTCTTCGATTACCAGGCATCCGGAGAAAATGCTTGGTTTGAGCAGCGCT

ATGCGGAATACTACAACGTCTTGGCCGACTTTTGTGCCGTTGTTGGTACC

ACCCAGCCCTTGACCGGTCGTTCCTGGTTCCGCAACGTATTTACCGAACC

CGTCGGTAGTCTCCCTGATTGCTCGCCCACTCAGTCGGCCAACATTTTGG

ACGATGTCCACATTTGCTTCCTTCCCACGACCGGCGGTGCTGCGGCTGGT

GGTGGCAGTGGTAGTGGCGGTAGCAGCGCCAAGGCGATCGCGGTCGGGAC

CGCTGCGCTGGCGGCGGGACTACTCAGTCTTATACACGTATTGTTGTTCT

AA (ii) Protein Sequence-SEQ ID. NO: 2
(SEQ ID NO: 2)
DEPPACLTSTADLSVDIFTDKVEPLFSQGWNVTYHNTYKIANNLFDNTTY

LLYQCGSTPPADVVDNGNFNAVLEIPLSNVGLSQTPHIGFMEQLELVDEI

AAFLTDTDFISSPCFLDEIAAGNVLTLVEPSEGVDAPATGNTALSAGTVA

FVASFTQVPFDNTVNIQEYSELTNVAVFEWVKFFSVFFNKEHTANQVVEA

AESRFDCVAQNAGAVQADNMPVKPVVLWAYYSDFCGGWDVAECPNYYCEF

ANACGAEIISSTEGNTTVCGAPYMTTEELVELGKDADHWIYPSSNWDTAS

ETFGEQLQNMKAVQDQQVFDYQASGENAWFEQRYAEYYNVLADFCAVVGT

TQPLTGRSWFRNVFTEPVGSLPDCSPTQSANILDDVHICFLPTTGGAAAG

GGSGSGGSSAKAIAVGTAALAAGLLSLIHVLLF (ii) Nucleic Acid-Allelic Variant 1 (SEQ ID NO: 3)
(SEQ ID NO: 3)
GACGAACCTCCGGCTTGCCTGACATCGACTGCGGACCTTTCGGTGGATAT

CTTCACCGACAAGGTAGAACCGCTCTTCTCCCAAGGATGGAATGTGACTT

ACCACAACACCTACAAGATTGCCAACAATCTCTTCGACAACACGACCTAC

CTCCTCTACCAGTGTGGTAGCACGCCTCCGGCCGATGTCGTCGACAACGG

```
-continued
CAACTTCAACGCCGTCCTCGAGATTCCCCTGTCCAACGTGGGTCTCTCGC
AAACGCCGCACATTGGCTTTATGGAGCAACTCGAACTCGTCGACGAAATC
GCGGCCTTTTTGACCGACACGGACTTTATTTCGTCGCCTTGCTTCTTGGA
CGAGATCGCCGCCGGCAACGTCCTCACACTGGTGGAACCCAGTGAAGGGG
TAGACGCACCCGCCACTGGCAACACTGCACTCAGTGCTGGCACGGTAGCC
TTTGTAGCGTCCTTCACCCAAGTCCCCTTTGACAATACGGTCAACATCCA
AGAGTACAGCGAACTCACCAACGTGGCCGTCTTTGAATGGGTCAAGTTCT
TTTCCCTCTTCTTCAACAAGGAGCACACCGCCAACCAAGTCGTCGAGGCC
GCGGAATCGCGCTTTGATTGCGTCGCGCAAAACGCCGGAGCCGTCCAGGC
CGACAATATGCCGGTCCAACCCGTCGTCTTGTGGGCCTACTACAGTGATT
TCTGTGGCGGATGGGATGTCGCCGAATGCCCCAACTACTACTGCGAATTC
GCCAACGCGTGCGGGGCCGAAATTATTAGCAGTACCGAAGGCAACACCAC
CGTCTGTGGCGCACCCTACATGACCACGGAAGAATTGGTGGAACTCGGAA
AGGATGCCGATCACTGGATCTACCCGTCCAATAACTGGGATACGGCATCG
GAAACCTTCGGCGAGCAGCTTCAGAACATGAAGGCCGTGCAGGACCAACA
AGTCTTCGATTACCAGGCATCCGGAGAAAATGCTTGGTTTGAGCAGCGCT
ATGCGGAATACTACAACGTCTTGGCCGACTTTTGTGCCGTTGTTGGTACC
ACCCAGCCCTTGACCGGTCGTTCCTGGTTCCGCAACGTATTTACCGAACC
CGTCGGTAGTCTCCCTGATTGCTCGCCCACTCAGTCGGCCAACATTTTGG
ACGATGTCCACATTTGCTTCCTTCCCACGACCGGCGGTGCTGCGGCTGGT
GGTGGCAGTGGTAGTGGCGGTAGCAGCGCCAAGGCGATCGCGGTCGGGAC
CGCTGCGCTGGCGGCGGGACTACTCAGTCTTATACACGTATTGTTGTTCT
AA (iv.) Protein Sequence-Allelic Variant 1
(SEQ ID NO: 4)
                                        (SEQ ID NO: 4)
DEPPACLTSTADLSVDIFTDKVEPLFSQGWNVTYHNTYKIANNLFDNTTY
LLYQCGSTPPADVVDNGNFNAVLEIPLSNVGLSQTPHIGFMEQLELVDEI
AAFLTDTDFISSPCFLDEIAAGNVLTLVEPSEGVDAPATGNTALSAGTVA
FVASFTQVPFDNTVNIQEYSELTNVAVFEWVKFFSLFFNKEHTANQVVEA
AESRFDCVAQNAGAVQADNMPVQPVVLWAYYSDFCGGWDVAECPNYYCEF
ANACGAEIISSTEGNTTVCGAPYMTTEELVELGKDADHWIYPSNNWDTAS
ETFGEQLQNMKAVQDQQVFDYQASGENAWFEQRYAEYYNVLADFCAVVGT
TQPLTGRSWFRNVFTEPVGSLPDCSPTQSANILDDVHICFLPTTGGAAAG
GGSGSGGSSAKAIAVGTAALAAGLLSLIHVLLF B. Cobalamin Acquisition Protein in the diatom
Thassiosira pseudonana (Thaps_11697)
(i) Nucleic Acid-SEQ ID NO: 5
                                        (SEQ ID NO: 5)
GAGTACACCCCTCCAACCACAAACTACGACCGATGCCTCACCGCCGACGA
AGCAGCCGACATCACCACCGCCCTCTCCAACGGTGTCGAGGTTGATCTCT
TCCCTGAGAAGGTATCCAGCGATCAATCCGTTTACTGGGAGATTGACTAT
CGTTCCACCTACAAGATCCTCAAGAATACACAAGATACAGTCAACACCAC
CTACCTTTTGTACCAATGTGGTCTCCCCGAACCTACTCCCGAGACACACC
```

```
-continued
CTGAACTCGAAGGAATCACATTTGATAGCGTCTTTAGTGTCCCTCACACT
GGAGGACTGCTTGTTACTGCTACTACTCAGATCCCAAACATCGAGATACT
TAACCGTCGTAGTCAAGTTGTTGCGTTTGCAGTATCTGAGAACTTGGTTT
CCAGTCCTTGTTTGTCTCAGCAGATCATCCCTGCCGGGAAAGAAGATGGG
AGTATCACCTTCTTGCCATTGTATAATGATACAGTGATTGAGGACTACGT
AACGGAACACCCTGACACTTTAGTGTTGGGTGGAGCGTGGGATACCGATC
TCAAGATGAAGAACAAGGTCATCATCTCGGACGTGGGTGAGTCGCCCGA
AGAGGCACTGGACCAAAATCGTGATGTGAACGAAGCCATCTTTGAATGG
TTGGAAGTGTATGGGTCTTTGTTTAACGAGGAGGGATTGGCGGGAGGAGT
TCCCGTGGTACTTTGGGCATACCACAACCAGGACTTTGAAGGAAACGACG
TTGGATGGGACGTTGGTGAATGTCCCAACTACTACTGCACCTATGCCAAG
CATTGCCATGTTGAGATGTTGAACTCTACGGAAGGAAGTATTGATTATTG
GGGATATCCTCGCATGACGGATGAGGAGTTTTTGGAGTTTGGAAAGAATG
CCGATGTATGGGTTTACCCCTCTTCTGATTGGAACAGGGTATCAACCCAA
AAGATGTTCTACCTCAGTCAGTTCAAGGCTGTTCAGGATGAGAAGGTCTA
TGACTACCAGATGAGTGGAGAGAGTGCTTGGTTTGAGCAGCGTCTTGCCG
AGTACGATACTGTCCTCCTTGACCTCTGTCACATCGTTGATCGTGCCGTA
TCCACCGACCCACCCCACATTCGTAAGTGGTTTCGCAACGTCTACACCGA
AGGAGTAGGAACGTTGGGAATGTGTGAAGACCCTGAAGAGCCATACACCT
CTCGTGCTACTGAGTGTGTAAGGCTTGATGATGTTGTTGGCGGTGGTGAT
GTTGAGGGGGAGGTGATACTGCTACTGAAGTTCCCGCTGCTTCTTCTGG
AAGTCGTTTGGCCGTTGTGTTGGGAGCTGTCTCTATCTTGTCCGTGGTTG
CGAATGAGGTGTTTACCAGCGCCCGAGAGCTTAGCTTCACGAAAGAAATG
TCCATCGATGATGTAGCGAATGTTCTGAGCGACTGCAGAGTTATCTTTGG
GATACACGGAGCTGGACATATGAATGCCTTGTTTGCAAGACCTGATGTTG
CCGTCATTGAAATCATTGGAAAAGATCCTTCTTATCACAGCTCTGATGAA
GATCAGAAAGGATATCCTGCATACTTTCGGAATATAAACATGTTGCTTGG
ACAGTACTATCAA (ii) Protein Sequence-SEQ ID NO: 6
                                        (SEQ ID NO: 6)
EYTPPTTNYDRCLTADEAADITTALSNGVEVDLFPEKVSSDQSVYWEIDY
RSTYKILKNTQDTVNTTYLLYQCGLPEPTPETHPELEGITFDSVFSVPHT
GGLLVTATTQIPNIEILNRRSQVVAFAVSENLVSSPCLSQQIIPAGKEDG
SITFLPLYNDTVIEDYVTEHPDTLVLGGAWDTDLKMKNKVIISDVGESPE
EALDQNRDVNEAIFEWLEVYGSLFNEEGLAGGVPVVLWAYHNQDFEGNDV
GWDVGECPNYYCTYAKHCHVEMLNSTEGSIDYWGYPRMTDEEFLEFGKNA
DVWVYPSSDWNRVSTQKMFYLSQFKAVQDEKVYDYQMSGESAWFEQRLAE
YDTVLLDLCHIVDRAVSTDPPHIRKWFRNVYTEGVGTLGMCEDPEEPYTS
RATECVRLDDVVGGGDVEGGGDTATEVPAASSGSRLAVVLGAVSILSVVA
NEVFTSARELSFTKEMSIDDVANVLSDCRVIFGIHGAGHMNALFARPDVA
VIEIIGKDPSYHSSDEDQKGYPAYFRNINMLLGQYYQSIAGDSTRGMYDD
GYVIDLEEAREALVRARHHSTSWIEEHGHWR
```

C. Cobalamin Acquisition Protein in the Diatom *Fragilariopsis cylindrus* (Fracyl_241429)
(i) Nucleic Acid-SEQ ID NO: 7

(SEQ ID NO: 7)
CAACAAGAGACAGTGATTGGAGTGAATAATCTCATCAATGGTGCTTGTGC

CGTGGACTATGATCCGAATGATAATGTGGATTACTTTCCTATCAAGTATC

GGAAACCAAGCATCGAATCGTACGGCAACATTGATATTTTCGGTAACAAG

TTTGTACCACACGAATCGACTGACTTTTTAAACATCGAATATCACGACAA

CTACAAAATTGTTACAAACTCTCACCAACAACCACCGAAAACATACCTGT

TGTATCAATGTGGTACCGAAATTCCTGACATCGTCACTAATGGAGACTTT

GCATTTGACTTAGTCGTATCGGTTCCTCATCAGGGGGGATTGGCACTCAC

ACAAACTCCACAAATCCCATATATCGAATTACTAGGATTGCGGGAAGAGG

TGATTGCCTACGTAGGTGATCCACAGTATGTGACAAGTCCCTGTATGAGT

TACATGATGACGGGCGCCGAGATGATGATCAAATCCAAGTCGTCTATGA

TAGCAACATTACCATAATGGAAGGACTCACCGATACATTTCGCACCGAGC

ATCCTAATACTATCATGGTGAGTGGTCCCACCAACAATGTTGTGGGGGAT

CGAGTTATTGTGGCATCGGCCACACAAGAAAGGACCAATGTTGCAACTTT

TGATTGGATTGCTTTTTATGCATCATTCTATAACTTGGAAGGTGAATCTA

ATCGTATCTCGACATTGATGCAGGAGAGCTATGATTGCATCAGCGACGTT

TCCACTAACATTGTGAAACAGCAACGGAACCTGGAAAACGTAGGAGAAGA

GTACCACACCCCCACCATCTTTTGGGCCAATTTTTTCACCTATGATGATT

TGGGATGGAGTGTTGGCGACTGTCCCACGTGGGATGCAAATTTCTATTGT

GAATACGCCGCCCATTGTGACGCAACCATCCTATCACGACCGGAAGGTGT

TGGCTTCAACCGAACGTACGGAGGATCACCAACTGTGTATTGGTATATTA

GCGACGAAGAAGCGTTAGAGATGGGCAAGAATGCCGATATTTTTATTTAC

ACCGGAGGTGATTGGGACTCGGTGTATAAATCACACAGTTCGATGCTGGA

TCAATTCCAAGCCGTTCAAAACAAACAAGTATTTGATACATTGGGACAGG

GACCATCGGCATGGCTCGAACAACGGTATGCGGAATACAATACAGTAGGA

TTGGACTTGTGTGACATCGTTGGTCATTCATCAATGGCGACAGTAAATGG

TGGTAATAACGCGAATCGTTGGTTTCGAAATGTGTATACCGAACCTATTG

GTGCATTGCCGGTGTGTGATGTAGCAGGAGGTGAAATCAGCCAACCCTAT

GTTCCCCCAAAAGTGAACTGTGTCCAACCACCAGAGGAAGGTGTAAAAAT

TGTGAACAGACCAAAAGAAATCTCATCACCATCCCAAGAGCAAGTAGAAG

ATGGTGATTCGGCTGCTTCCGGGTTTTGTAATTACTTCTCCTACTCGAAC

TTAATGTTGGTATCGTTTGCTGGTATGGTTGTTTCTCAAATGTAG (ii) Protein Sequence-SEQ ID NO: 8

(SEQ ID NO: 8)
QQETVIGVNNLINGACAVDYDPNDNVDYFPIKYRKPSIESYGNIDIFGNK

FVPHESTDFLNIEYHDNYKIVTNSHQQPPKTYLLYQCGTEIPDIVTNGDF

AFDLVVSVPHQGGLALTQTPQIPYIELLGLREEVIAYVGDPQYVTSPCMS

YMMTGAGDDDQIQVVYDSNITIMEGLTDTFRTEHPNTIMVSGPTNNVVGD

RVIVASATQERTNVATFDWIAFYASFYNLEGESNRISTLMQESYDCISDV

STNIVKQQRNLENVGEEYHTPTIFWANFFTYDDLGWSVGDCPTWDANFYC

EYAAHCDATILSRPEGVGFNRTYGGSPTVYWYISDEEALEMGKNADIFIY

TGGDWDSVYKSHSSMLDQFQAVQNKQVFDTLGQGPSAWLEQRYAEYNTVG

LDLCDIVGHSSMATVNGGNNANRWFRNVYTEPIGALPVCDVAGGEISQPY

VPPKVNCVQPPEEGVKIVNRPKEISSPSQEQVEDGDSAASGFCNYFSYSN

LMLVSFAGMVVSQM

D. Cobalamin Acquisition Protein in the Diatom *Fragilariopsis cylindrus* (Fracyl_246327)
(i) Nucleic Acid-SEQ ID NO: 9

(SEQ ID NO: 9)
CAGGACATCAACGTAGGCGGAACAACTCAAGATGAAGGTTCTATCTTGGT

GGAAAATCTCGTCGATCGATGCGTAATCGACTATGATCCGGACGTTGATT

ACTTTCCTGTGAAGTATCAAAAACCATCGATTTCTTCCTATGGTGACATT

GATATCTTCGGAGAGAAATTTGAACCACACAATACAACCGATTTTTTAGA

AATCACATACTTCAAAACATACAAGATCGTTACGAACAAACATCAAGATC

CACCAGTCAGTTACTTACTGTACCAATGTGGTACGGAAAAACCACAAGAT

GTGATCGATGATCCCGATAACAAGTTTGATTTAGTTTTACCAATTCCTCA

TCAAGGAGGTCTTGCGTTGACTCAAACCCCACAAATCCCGTACCCTGAAA

TGTTAGGATTACGTGGAGAAATTATTGGATTAATTGGAAACCCGTCGTAC

GTGACAAGTCCTTGTCTCAGCTCCTTGTTAGATGATGGATCAGTCGAAGT

TGTATATGATTCCAATTCTACTATACAAAGAGAGCTTATTGATGATTACA

TTGAACGTAATCCAAATGTTATTATCTTTAGTGGACCAACGAACAACGTT

GTTGGTGATCGTGTCATGGTTGTTTCTGCTACTCAAGAACGAACAAATGT

TGCTACATTTGATTGGATGGCATTTTGGGCGGCCTTATACAACCTAGAGG

GAGAAGCATCAAGAATTACAAGTGAAATGCAAGCATCGTATGATTGTTCA

AGTGATAATGCCAAGGCTGTTGCTGCACAACAACGTGAACTTGTTCCCGA

AGAAAACAACCAGTAATTCTATGGGCAAATTACTTCACCTATCAAAATC

TTGGCTGGTCCGTTGCCGAGTGCCCCACTTGGGACTCGGCATACTATTGT

GAGTACGCAGCGCATTGTGATGCGACCATCTTATCTCGTCCTGAAGGAGC

TGGTTATAACAAGACATATGGCGGTTCGCCAACAGTTTACTGGTATTTGA

TACACTCTGGACAGGGTCCATCAGCATGGAATGAACAACGGTATGCTGAA

TATGACGTTGTTGGATTAGACATGTGTGATATTGTTGGACGTTCCAGTAC

GACAGGTGTTCAGCACGAACGTCGTTGGTTCCGTAATGTATTCACTGAAC

CAATCGGTTCCTTAGAAACGTGCAACGTTCCCGATGAAATCTTTCAACCG

TACGTACCACCAGGAACAGAATGCGATTCAGCAGGAGAAGAAGATACTAC

CTCGGAGTCGTCTTCTGCACCGGAAAAATCATCTTTGTTAGCATTTTATC

TTGCTATGGTTGCATTTGTTTTGGTCGTCTAA (ii) Protein Sequence-SEQ ID NO: 10

(SEQ ID NO: 10)
QDINVGGTTQDEGSILVENLVDRCVIDYDPDVDYFPVKYQKPSISSYGDI

DIFGEKFEPHNTTDFLEITYFKTYKIVTNKHQDPPVSYLLYQCGTEKPQD

VIDDPDNKFDLVLPIPHQGGLALTQTPQIPYPEMLGLREGEIIGLIGNPSY

VTSPCLSSLLDDGSVEVVYDSNSTIQRELIDDYIERNPNVIIFSGPTNNV

VGDRVMVVSATQERTNVATFDWMAFWAALYNLEGEASRITSEMQASYDCS

SDNAKAVAAQQRELVPEEKQPVILWANYFTYQNLGWSVAECPTWDSAYYC

-continued

EYAAHCDATILSRPEGAGYNKTYGGSPTVYWYLIHSGQGPSAWNEQRYAE

YDVVGLDMCDIVGRSSTTGVQHERRWFRNVFTEPIGSLETCNVPDEIFQP

YVPPGTECDSAGEEDTTSESSSAPEKSSLLAFYLAMVAFVLVV

Based upon sequences alignment analysis using the default parameters of BLASTP 2.2.26+(Altschul et al. (1997), "Gapped BLAST and PSI-BLAST: A New Generation of Protein Database Search Programs," *Nucleic Acids Res.* 25:3389-3402; Altschul et al. (2005) "Protein Database Searches Using Compositionally Adjusted Substitution Matrices," FEBS J. 272:5101-5109), the percent identities between the various sequences are set forth in Table 1.

TABLE 1

|  | SEQ ID NO: 2 | SEQ ID NO: 6 | SEQ ID NO: 8 | SEQ ID NO: 10 |
|---|---|---|---|---|
| SEQ ID NO: 2 | 100% | 37% | 34% | 31% |
| SEQ ID NO: 6 | — | 100% | 35% | 35% |
| SEQ ID NO: 8 | — | — | 100% | 58% |
| SEQ ID NO: 10 | — | — | — | 100% |

As a result, the invention provides cobalamin acquisition proteins that are at least 30%, 35%, 40%, 45%, 50%, 55%, 60%, 65%, 70%, 75%, 80%, 85%, 90%, 95%, or 98% identical to SEQ ID NO: 2, or fragments thereof that are capable of binding vitamin $B_{12}$ with at least 70%, 80%, 90%, or 95% of the binding affinity of the vitamin $B_{12}$ binding protein of SEQ ID NO: 2. In addition, the invention provides cobalamin acquisition proteins that are at least 30%, 35%, 40%, 45%, 50%, 55%, 60%, 65%, 70%, 75%, 80%, 85%, 90%, 95%, or 98% identical to SEQ ID NO: 4, or fragments thereof that are capable of binding vitamin $B_{12}$ with at least 70%, 80%, 90%, or 95% of the binding affinity of the vitamin $B_{12}$ binding protein of SEQ ID NO: 4. In addition, the invention provides cobalamin acquisition proteins that are at least 30%, 35%, 40%, 45%, 50%, 55%, 60%, 65%, 70%, 75%, 80%, 85%, 90%, 95%, or 98% identical to SEQ ID NO: 6, or fragments thereof that are capable of binding vitamin $B_{12}$ with at least 70%, 80%, 90%, or 95% of the binding affinity of the vitamin $B_{12}$ binding protein of SEQ ID NO: 6. In addition, In addition, the invention provides cobalamin acquisition proteins that are at least 30%, 35%, 40%, 45%, 50%, 55%, 60%, 65%, 70%, 75%, 80%, 85%, 90%, 95%, or 98% identical to SEQ ID NO: 8, or fragments thereof that are capable of binding vitamin $B_{12}$ with at least 70%, 80%, 90%, or 95% of the binding affinity of the vitamin $B_{12}$ binding protein of SEQ ID NO: 8. In addition, In addition, the invention provides cobalamin acquisition proteins that are at least 30%, 35%, 40%, 45%, 50%, 55%, 60%, 65%, 70%, 75%, 80%, 85%, 90%, 95%, or 98% identical to SEQ ID NO: 10, or fragments thereof that are capable of binding vitamin $B_{12}$ with at least 70%, 80%, 90%, or 95% of the binding affinity of the vitamin $B_{12}$ binding protein of SEQ ID NO: 10.

The fragments of the cobalamin acquisition proteins can include, as appropriate, peptides corresponding, as appropriate, to the consecutive amino acids 1-25, 25-50, 50-75, 75-100, 100-125, 125-150, 150-175, 175-200, 200-225, 225-250, 250-275, 275-300, 300-325, 325-350, 350-375, 375-400, 400-425, 425-450, 450-475, 475-500, 500-525, 525-550, 550-575, and 575-581 of SEQ ID NOs 2, 4, 6, 8, or 10.

In addition, the CBA proteins of the invention can include a protein comprising one, two, three, four, five, six or more of the following peptide sequences that preferably total 15, 20, 25 or 30 amino acids present in the following sequences:

```
                                        (SEQ ID NO: 11)
YLLYQCG (SEQ ID NO: 12)
NTTYLLYQCG (SEQ ID NO: 13)
ECPNYYC (SEQ ID NO: 14)
PVVLWAY (SEQ ID NO: 15)
AWFEQR (SEQ ID NO: 16)
WFRNV (SEQ ID NO: 17)
VIISDVGESPEEALDQNR (SEQ ID NO: 18)
FFSVFFNK (SEQ ID NO: 19)
EHTANQVVEAAESR
```

For example, SEQ ID NOs 11 and 12, when combined have a total of 17 amino acids that may be present in a CBA protein or SEQ ID NOs 11, 12 and 16, when combined have a total of 22 amino acids that may be present in a CBA protein, etc.

For example, a CBA protein of the invention may include the amino acid sequences of SEQ ID NOS: 11 and 12, or SEQ ID NOS: 11 and 13, or SEQ ID NOS: 11 and 14, or SEQ ID NOS: 11 and 15, or SEQ ID NOS: 11 and 16, or SEQ ID NOS: 11 and 17, or SEQ ID NOS: 11 and 18, or SEQ ID NOS: 11 and 19.

For example, a CBA protein of the invention may include the amino acid sequences of SEQ ID NOS: 12 and 13, or SEQ ID NOS: 12 and 14, or SEQ ID NOS: 12 and 15, or SEQ ID NOS: 12 and 16, or SEQ ID NOS: 12 and 17, or SEQ ID NOS: 12 and 18, or SEQ ID NOS: 12 and 19.

For example, a CBA protein of the invention may include the amino acid sequences of SEQ ID NOS: 13 and 14, or SEQ ID NOS: 13 and 15, or SEQ ID NOS: 13 and 16, or SEQ ID NOS: 13 and 17, or SEQ ID NOS: 13 and 18, or SEQ ID NOS: 13 and 19.

For example, a CBA protein of the invention may include the amino acid sequences of SEQ ID NOS: 14 and 15, or SEQ ID NOS: 14 and 16, or SEQ ID NOS: 14 and 17, or SEQ ID NOS: 14 and 18, or SEQ ID NOS: 14 and 19.

For example, a CBA protein of the invention may include the amino acid sequences of SEQ ID NOS: 15 and 16, or SEQ ID NOS: 15 and 17, or SEQ ID NOS: 15 and 18, or SEQ ID NOS: 15 and 19.

For example, a CBA protein of the invention may include the amino acid sequences of SEQ ID NOS: 16 and 17, or SEQ ID NOS: 16 and 18, or SEQ ID NOS: 16 and 19.

For example, a CBA protein of the invention may include the amino acid sequences of SEQ ID NOS: 17 and 18, or SEQ ID NOS: 17 and 19, or SEQ ID NOS: 18 and 19.

For example, a CBA protein of the invention may include two or more of amino acid sequences SEQ ID NOS: 11, 12, 13, 14, 15, 16, 17, 18 or 19.

For example, a CBA protein of the invention may include three or more of amino acid sequences SEQ ID NOS: 11, 12, 13, 14, 15, 16, 17, 18 or 19.

For example, a CBA protein of the invention may include four or more of amino acid sequences SEQ ID NOS: 11, 12, 13, 14, 15, 16, 17, 18 or 19.

For example, a CBA protein of the invention may include five or more of amino acid sequences SEQ ID NOS: 11, 12, 13, 14, 15, 16, 17, 18 or 19.

For example, a CBA protein of the invention may include six or more of amino acid sequences SEQ ID NOS: 11, 12, 13, 14, 15, 16, 17, 18 or 19.

For example, a CBA protein of the invention may include seven or more of amino acid sequences SEQ ID NOS: 11, 12, 13, 14, 15, 16, 17, 18 or 19.

For example, a CBA protein of the invention may include eight or more of amino acid sequences SEQ ID NOS: 11, 12, 13, 14, 15, 16, 17, 18 or 19.

For example, a CBA protein of the invention may include the amino acid sequences of SEQ ID NOS: 11, 12, 13, 14, 15, 16, 17, 18 and 19.

E. Consensus Sequences (i) Full Length Consensus Sequences a. Consensus Sequence based upon SEQ ID NOs. 2 and 6

The full length consensus sequence (SEQ ID NO: 20) of SEQ ID NOs. 2 and 6 is set forth in FIG. 1A, where the residues that are identical at each position are identified in the line titled "consensus" and all of the amino acid variants at a given position can be identified as each amino acid at that position on each of lines denoted "Phatr_48322/1-433" and "Thaps_11697/1-581".

b. Consensus Sequence based upon SEQ ID NOs. 2, 6, 8 and 10

Figure 1B:
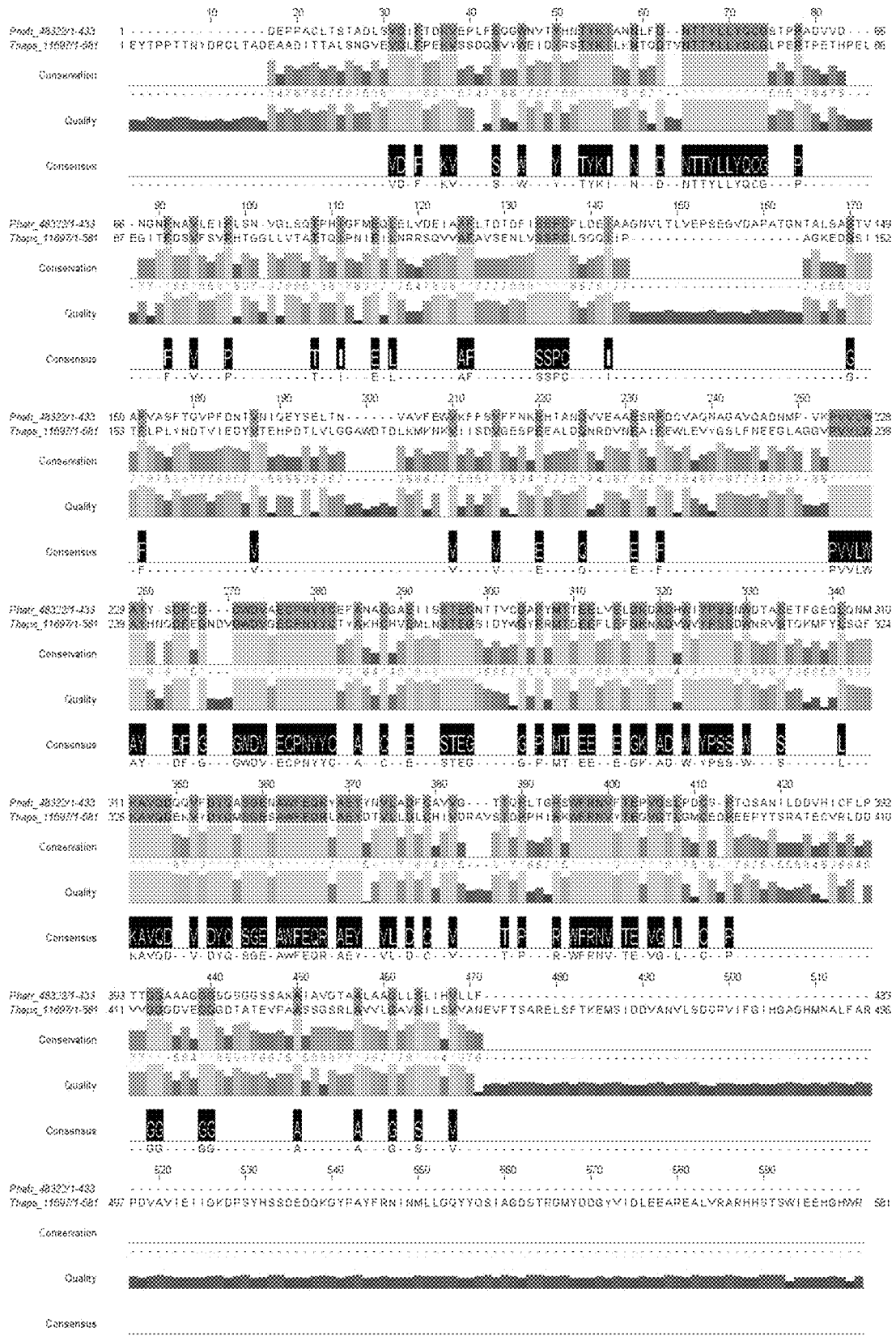
FIG. 1B depicts alignment of four CBA1 sequences from the three diatoms *P. tricornutum, T. pseudonana*, and *Fragilariopsis cylindrus* (Phatr_48322 (SEQ ID NO: 2), Thaps_11697 (SEQ ID NO: 6), Fracyl_241429 (SEQ ID NO: 8) and Fracyl_246327 (SEQ ID NO: 10)) and the consensus sequence (SEQ ID NO: 21).

The full length consensus sequence (SEQ ID NO: 21) of SEQ ID NOs. 2, 6, 8 and 10 can be seen in FIG. 1B, where the residues that are identical at each position are identified in the line titled "consensus" and all of the amino acid variants at a given position can be identified as each amino acid at that position on each of the lines denoted "Phatr_48322/1-433," "Thaps_11697/1-581," "Fracyl_241429/1-514," and "Fracyl_246327/1-443."

(ii) Consensus Sequences of Putative Vitamin $B_{12}$ Binding Sites

The putative vitamin $B_{12}$ binding sites were identified by aligning the various sequences being interrogated, and then determining the regions of sequence conservation. The consensus sequences of the putative vitamin $B_{12}$ binding sites are set forth below.

a. Putative Vitamin $B_{12}$ binding sites based upon SEQ ID NOs. 2 and 6:

$VDX_1FX_2X_3KVX_4I_5X_6X_7SX_8X_9WX_{10}X_{11}X_{12}YX_{13}$-$X_{14}TYKI$ (SEQ ID NO: 22), wherein $X_1$ is I or L; $X_2$ is T or P; $X_3$ is D or E; $X_4$ is E or S; $X_5$ is P or S; $X_6$ is L or D; $X_7$ is F or Q; $X_8$ is Q or V; $X_9$ is G or Y; $X_{10}$ is N or E; $X_{11}$ is I or V; $X_{12}$ is T or D; $X_{13}$ is H or R; and $X_{14}$ is N or S;

$NTTYLLYQCGX_1X_2X_3P$ (SEQ ID NO: 23), wherein $X_1$ is S or L; $X_2$ is T or P; and $X_3$ is P or E;

$X_1SSPCX_2X_3X_4X_5I$ (SEQ ID NO: 24), wherein $X_1$ is I or V; $X_2$ is F or L; $X_3$ is L or S; $X_4$ is D or Q; and $X_5$ is E or Q;

$PVVLWAYX_1X_2X_3DFX_4GX_5X_6X_7GWDVX_8ECPNY$-$YCX_9X_{10}AX_{11}X_{12}CX_{13}X_{14}EX_{15}X_{16}X_{17}STEGX_{18}$ (SEQ ID NO: 25), wherein $X_1$ is Y or H; $X_2$ is N or a bond; $X_3$ is S or Q; $X_4$ is C or E; $X_5$ is N or a bond; $X_6$ is D or a bond; $X_7$ is V or a bond $X_8$ is A or G; $X_9$ is E or T; $X_{10}$ is F or Y; $X_{11}$ is N or K; $X_{12}$ is A or H; $X_{13}$ is G or H; $X_{14}$ is A or V; $X_{15}$ is I or M; $X_{16}$ is I or L; $X_{17}$ is S or N; and $X_{18}$ is N or S;

$GX_1PX_2MTX_3EEX_4X_5EX_6GKX_7ADX_8WX_9YPSSX_{10}$-$WX_{11}X_{12}X_{13}S$ (SEQ ID NO: 26), wherein $X_1$ is A or Y; $X_2$ is Y or R; $X_3$ is T or D; $X_4$ is L or F; $X_5$ is V or L; $X_6$ is L or F; $X_7$ is D or N; $X_8$ is H or V; $X_9$ is I or V; $X_{10}$ is N or D; $X_{11}$ is N or D; $X_{12}$ is T or R; and $X_{13}$ is A or V;

$KAVQDX_1X_2VX_3DYQX_4SGEX_5AWFEQRX_6AEYX_7$-$X_8VLX_9DX_{10}CX_{11}X_{12}V$ (SEQ ID NO: 27), wherein $X_1$ is Q or E; $X_2$ is Q or K; $X_3$ is F or Y; $X_4$ is A or M; $X_5$ is N or S; $X_6$ is Y or L; $X_7$ is Y or D; $X_8$ is N or T; $X_9$ is A or L; $X_{10}$ is F or L; $X_{11}$ is A or H; and $X_{12}$ is V or I;

$RX_1WFRNVX_2TEX_3VGX_4LX_5X_6CX_7X_8P$ (SEQ ID NO: 28), wherein $X_1$ is S or K; $X_2$ is F or Y; $X_3$ is P or G; $X_4$ is S or T; $X_5$ is P or G; $X_6$ is D or M; $X_7$ is S or E; and $X_8$ is D or a bond;

b. Putative Vitamin $B_{12}$ binding sites based upon SEQ ID NOs. 2, 6, 8 and 10:

$X_1DX_2FX_3X_4KX_5X_6X_7X_8$ (SEQ ID NO: 29), wherein $X_1$ is V or I, $X_2$ is L or I, $X_3$ is T, P, or G, $X_4$ is D, N, or E; $X_5$ is V or F; $X_6$ is E, S, or V; $X_7$ is P or S, and $X_8$ is L, D, or H;

$YX_1X_2X_3YKIX_4X_5N$ (SEQ ID NO: 30), wherein $X_1$ is H, R or F; $X_2$ is N, S, D, or K; $X_3$ is T or N; $X_4$ is A, L, or V; and $X_5$ is N, K, or T;

$X_1X_2X_3YLLYQCGX_4X_5X_6$ (SEQ ID NO: 31), wherein $X_1$ is N or P; $X_2$ is T, K, or V; $X_3$ is T or S; $X_4$ is S, L, or T; $X_5$ is T, P, or E; and $X_6$ is P, E, I, or K;

$FX_1X_2VX_3X_4X_5PX_6X_7X_8X_9X_{10}X_{11}X_{12}X_{13}X_{14}TX_{15}$-$X_{16}I$ $X_{17}X_{18}X_{19}EX_{20}LX_{21}X_{22}X_{23}X_{24}X_{25}X_{26}X_{27}X_{28}X_{29}X_{30}$-$X_{31}X_{32}X_{33}X_{34}X_{35}X_{36}X_{37}SPC$ (SEQ ID NO: 32), wherein $X_1$ is N or D; $X_2$ is A, S, or L; $X_3$ is V, L, or F; $X_4$ is E, S, or P; $X_5$ is I or V; $X_6$ is L or H; $X_7$ is S, T, or Q; $X_8$ is N or G; $X_9$ is G or a bond; $X_{10}$ is V or L; $X_{11}$ is G, L, or A; $X_{12}$ is L or V; $X_{13}$ is S or T; $X_{14}$ is Q or A; $X_{15}$ is P or T; $X_{16}$ is H or Q; $X_{17}$ is G or P; $X_{18}$ is F, Y, or N; $X_{19}$ is M, I, or P; $X_{20}$ is Q, I, L, or M; $X_{21}$ is E, N, or G; $X_{22}$ is L or R; $X_{23}$ is V or R; $X_{24}$ is D, S, E, or G; $X_{25}$ is E or Q; $X_{26}$ is I or V; $X_{27}$ is A, I, or V; $X_{28}$ is A or G; $X_{29}$ is F, Y, or L; $X_{30}$ is L, A, V, or I; $X_{31}$ is T, V, or G; $X_{32}$ is D, S, or N; $X_{33}$ is T, E, or P; $X_{34}$ is D, N, Q, or S; $X_{35}$ is F, L, or Y; $X_{36}$ is I or V; and $X_{37}$ is S or T;

$TX_1X_2X_3X_4X_5X_6X_7X_8X_9X_{10}X_{11}X_{12}X_{13}X_{14}X_{15}X_{16}$-$X_{17}E$ (SEQ ID NO: 33), wherein $X_1$ is N or D; $X_2$ is V or L; $X_3$ is A or K; $X_4$ is V, M, or T; $X_5$ is F or K; $X_6$ is E, N, or D; $X_7$ is W or K; $X_8$ is V, I, or M; $X_9$ is K, I, or A; $X_{10}$ is F or I; $X_{11}$ is F, S, Y, or W; $X_{12}$ is S, D, or A; $X_{13}$ is V, S, or A; $X_{14}$ is F, G, or L; $X_{15}$ is F, E, or Y; $X_{16}$ is N or S; and $X_{17}$ is K, P, or L;

$PX_1X_2X_3WAX_4X_5X_6X_7X_8X_9X_{10}X_{11}$ (SEQ ID NO: 34), wherein $X_1$ is V or T; $X_2$ is V or I; $X_3$ is L or F; $X_4$ is Y or N; $X_5$ is Y, H, or F; $X_6$ is S, N, or F; $X_7$ is D, Q, or T; $X_8$ is F, D, or Y; $X_9$ is C, F, D, or Q; $X_{10}$ is G, E, D, or N; and $X_{11}$ is G or L;

$WX_1VX_2X_3CP$ (SEQ ID NO: 35), wherein $X_1$ is D or S; $X_2$ is A or G; and $X_3$ is E or D;

$X_1X_2YCX_3X_4AX_5X_6CX_7X_8X_9X_{10}X_{11}X_{12}X_{13}X_{14}EG$ (SEQ ID NO: 36), wherein $X_1$ is N or A; $X_2$ is Y or F; $X_3$ is T or E; $X_4$ is F or Y; $X_5$ is N, K, or A; $X_6$ is H or A; $X_7$ is G, H, or D; $X_8$ is A or V; $X_9$ is E or T; $X_{10}$ is I or M; $X_{11}$ is I or L; $X_{12}$ is S or N; $X_{13}$ is S or R; and $X_{14}$ is T or P;

$X_1GX_2X_3AWX_4EQRX_5AEYX_6X_7VX_8X_9DX_{10}CX_{11}$-$X_{12}V$ (SEQ ID NO: 37), wherein $X_1$ is S or Q; $X_2$ is P or E; $X_3$ is N or S; $X_4$ is F, L, or N; $X_5$ is Y or L; $X_6$ is Y, D, or N; $X_7$ is N, T, or V; $X_8$ is L or G; $X_9$ is A or L; $X_{10}$ is F, L, or M; $X_{11}$ is A, D, or H; and $X_{12}$ is V or I;

WFRNVX$_1$TEX$_2$X$_3$GX$_4$LX$_5$X$_6$C (SEQ ID NO: 38), wherein X$_1$ is F or Y; X$_2$ is P or G; X$_3$ is V or I; X$_4$ is S, T, or A; X$_5$ is P, G, or E; and X$_6$ is D, M, V, or T;

GWDVX$_1$ECPNYYC (SEQ ID NO: 39), wherein X$_1$ can be A or G;

X$_1$YLLYQCG (SEQ ID NO: 40), wherein X$_1$ is T or S;

WX$_1$VX$_2$X$_3$CP (SEQ ID NO: 41), wherein X$_1$ is D or S; X$_2$ is A or G; and X$_3$ is E or D;

X$_1$AWX$_2$EQRX$_3$AEY (SEQ ID NO: 42), wherein X$_1$ is S or N, X$_2$ is F, L, or N, X$_3$ is Y or L; or WFRNVX$_1$TEX$_2$X$_3$GX$_4$L (SEQ ID NO: 43), wherein X$_1$ is F or Y, X$_2$ is P or G, X$_3$ is S, T, or A.

It is understood that the proteins or peptides described herein above can be produced using conventional techniques, for example, via purification from natural sources, via conventional synthetic peptide chemistries followed by conventional purification protocols, or via recombinant techniques (for example, expression in a suitable expression system and then using a purification protocol). It is also understood that each of the CBA proteins described herein above have a variety of applications, some of which are discussed herein below.

II. Recombinant Organisms and Use Thereof

A. General Methods for Engineering Microorganisms that Express or Over Express a CBA Protein It is understood that nucleic acid sequences encoding the CBA proteins described herein can be transformed into microorganisms, for example, photoautotrophic organisms, to improve growth potential especially under conditions and in environments where the amount of vitamin B$_{12}$ may limit the growth of the organism. As a result, it may be possible to grow organisms in environments where the presence of vitamin B$_{12}$ may be limiting so as to improve the growth of biomass under those conditions, which in turn can enhance the production of products of interest, e.g., carbon-based products, during biomass and/or biofuel production (see, e.g. U.S. Patent Publication No. 2011/0262975). Principles of metabolic engineering and their uses are known in the art. For example, engineered pathways as described in, e.g., WO 2007/136762 and WO 2007/139925 can be used make products from energy captured by photoautotrophic organisms. Generally, improved organisms that are useful in creating products of interest (for example, biofuels (for example, biodiesel), carbon products (for example, dicarboxylic acids, for example, succinic acid), etc.) can be produced by expressing one or more of the CBA proteins described herein in a microorganism, for example, a photoautotrophic microorganism, e.g., algae, cyanobacteria, etc.

The genes can be introduced into the host organism to reside in a plasmid, for example, an expression plasmid, or be introduced into the genome of the host organism via recombination, for example, homologous recombination. Expression or integration plasmids can be constructed using standard molecular biology methodologies to express one or more of the protein sequences (see, e.g., SEQ ID NOs: 2, 4, 6, 8, or 10) described herein. The nucleic acid encoding the protein sequence of interest preferably is operatively linked to a suitable promoter (for example, a constitutive promoter or an inducible promoter). The resulting expression or integration plasmids containing the genes of interest and an optional selection marker (for example, an antibiotic resistance gene) then are transformed into the host and the resulting transformants are selected under appropriate selection conditions. For example, transformants carrying a gene encoding the cobalamin acquisition protein and an antibiotic resistance may be selected on culture media supplemented with an antibiotic such as spectinomycin, carbenicillin, etc.

Cells in which a nucleic acid molecule has been introduced are transformed to express or over-express desired genes while other nucleic acid molecules can be attenuated or functionally deleted. Nucleic acids can be introduced in the host cell via a number of standard techniques including, for example, transformation (for example, transformation with plasmid vectors), transfection (for example, transfection with viral vectors), conjugation, or the introduction of naked DNA by electroporation, lipofection, and/or particle gun acceleration.

The resulting transformants, when selected, are inoculated into a suitable medium and propagated under the appropriate growth conditions until they reach an appropriate end point, for example, cell density, as can be measured by optical density or other suitable approaches. The resulting cells can then be harvested, for example, via centrifugation, and, if desired, products of interest can then be purified from the resulting biomass using standard techniques.

B. Selected or Engineered Microorganisms

The methods and compositions can be used to enhance the growth of organisms that produce products of interest (for example, carbon products, for example, dicarboxylic acids, for example, succinic acid (see, for example, U.S. Pat. Nos. 5,770,435, 5,869,301, and 6,743,610, which describe the production of certain dicarboxylic acids using certain genetically modified strains of *E. coli*, and butanediol (see, for example, U.S. Publication No. 2011/0245515)).

The term microorganism includes prokaryotic and eukaryotic microbial species, for example, prokaryotic and eukaryotic species from the domains Archaea, Bacteria and Eucarya, the latter including yeast and filamentous fungi, protozoa, algae, or higher Protista. The terms "microbial cells" and "microbes" are used interchangeably with the term microorganism.

A variety of host organisms can be transformed with a gene expressing a CBA protein. Photoautotrophic organisms include eukaryotic plants and algae, as well as prokaryotic cyanobacteria, green-sulfur bacteria, green non-sulfur bacteria, purple sulfur bacteria, and purple non-sulfur bacteria.

Suitable organisms include, for example, extremophiles that withstand various environmental parameters such as temperature, radiation, pressure, gravity, vacuum, desiccation, salinity, pH, oxygen tension, and chemicals. They include hyperthermophiles, which grow at or above 80° C. such as *Pyrolobus fumarii*; thermophiles, which grow between 60-80° C. such as *Synechococcus lividis*; mesophiles, which grow between 15-60° C. and psychrophiles, which grow at or below 15° C. such as *Psychrobacter* and some insects. Radiation tolerant organisms include *Deinococcus radiodurans*. Pressure tolerant organisms include piezophiles or barophiles which tolerate pressure of 130 MPa. Hypergravity (e.g., >1 g) hypogravity (e.g., <1 g) tolerant organisms are also contemplated. Vacuum tolerant organisms include tardigrades, insects, microbes and seeds. Desiccant tolerant and anhydrobiotic organisms include xerophiles such as *Anemia salina*; nematodes, microbes, fungi and lichens. Salt tolerant organisms include halophiles (e.g., 2-5 M NaCl) Halobacteriacea and *Dunaliella salina*. pH tolerant organisms include alkaliphiles such as *Natronobacterium, Bacillus firmus* OF4, *Spirulina* spp. (e.g., pH>9) and acidophiles such as *Cyanidium caldarium, Ferroplasma* sp. (e.g., low pH). Anaerobes, which cannot tolerate O$_2$ such as *Methanococcus jannaschii*; microaerophils, which tolerate some O$_2$ such as *Clostridium* and aerobes, which require O$_2$ are also contemplated. Gas tolerant organisms, which tolerate pure CO$_2$ include *Cyanidium caldarium* and metal tolerant organisms include metalotolerants such as *Ferro-*

*plasma acidarmanus* (e.g., Cu, As, Cd, Zn), *Ralstonia* sp. CH34 (e.g., Zn, Co, Cd, Hg, Pb). (See, for example, Seckbach, J. (1997) "Search for Life in the Universe with Terrestrial Microbes Which Thrive Under Extreme Conditions, in Cosmovici et al. eds. Astronomical and Biochemical Origins and the Search for Life in the Universe. Bologna, Italy, pp. 511-523).

Plants include but are not limited to the following genera: *Arabidopsis, Beta, Glycine, Jatropha, Miscanthus, Panicum, Phalaris, Populus, Saccharum, Salix, Simmondsia* and *Zea.*

Algae and cyanobacteria include but are not limited to the following genera: *Acanthoceras, Acanthococcus, Acaryochloris, Achnanthes, Achnanthidium, Actinastrum, Actinochloris, Actinocyclus, Actinotaenium, Amphichrysis, Amphidinium, Amphikrikos, Amphipleura, Amphiprora, Amphithrix, Amphora, Anabaena, Anabaenopsis, Aneumastus, Ankistrodesmus, Ankyra, Anomoeoneis, Apatococcus, Aphanizomenon, Aphanocapsa, Aphanochaete, Aphanothece, Apiocystis, Apistonema, Arthrodesmus, Artherospira, Ascochloris, Asterionella, Asterococcus, Audouinella, Aulacoseira, Bacillaria, Balbiania, Bambusina, Bangia, Basichlamys, Batrachospermum, Binuclearia, Bitrichia, Blidingia, Botrdiopsis, Botrydium, Botryococcus, Botryosphaerella, Brachiomonas, Brachysira, Brachytrichia, Brebissonia, Bulbochaete, Bumilleria, Bumilleriopsis, Caloneis, Calothrix, Campylodiscus, Capsosiphon, Carteria, Catena, Cavinula, Centritractus, Centronella, Ceratium, Chaetoceros, Chaetochloris, Chaetomorpha, Chaetonella, Chaetonema, Chaetopeltis, Chaetophora, Chaetosphaeridium, Chamaesiphon, Chara, Characiochloris, Characiopsis, Characium, Charales, Chilomonas, Chlainomonas, Chlamydoblepharis, Chlamydocapsa, Chlamydomonas, Chlamydomonopsis, Chlamydomyxa, Chlamydonephris, Chlorangiella, Chlorangiopsis, Chlorella, Chlorobotrys, Chlorobrachis, Chlorochytrium, Chlorococcum, Chlorogloea, Chlorogloeopsis, Chlorogonium, Chlorolobion, Chloromonas, Chlorophysema, Chlorophyta, Chlorosaccus, Chlorosarcina, Choricystis, Chromophyton, Chromulina, Chroococcidiopsis, Chroococcus, Chroodactylon, Chroomonas, Chroothece, Chrysamoeba, Chrysapsis, Chrysidiastrum, Chrysocapsa, Chrysocapsella, Chrysochaete, Chrysochromulina, Chrysococcus, Chrysocrinus, Chrysolepidomonas, Chrysolykos, Chrysonebula, Chrysophyta, Chrysopyxis, Chrysosaccus, Chrysophaerella, Chrysostephanosphaera, Clodophora, Clastidium, Closteriopsis, Closterium, Coccomyxa, Cocconeis, Coelastrella, Coelastrum, Coelosphaerium, Coenochloris, Coenococcus, Coenocystis, Colacium, Coleochaete, Collodictyon, Compsogonopsis, Compsopogon, Conjugatophyta, Conochaete, Coronastrum, Cosmarium, Cosmioneis, Cosmocladium, Crateriportula, Craticula, Crinalium, Crucigenia, Crucigeniella, Cryptoaulax, Cryptomonas, Cryptophyta, Ctenophora, Cyanodictyon, Cyanonephron, Cyanophora, Cyanophyta, Cyanothece, Cyanothomonas, Cyclonexis, Cyclostephanos, Cyclotella, Cylindrocapsa, Cylindrocystis, Cylindrospermum, Cylindrotheca, Cymatopleura, Cymbella, Cymbellonitzschia, Cystodinium Dactylococcopsis, Debarya, Denticula, Dermatochrysis, Dermocarpa, Dermocarpella, Desmatractum, Desmidium, Desmococcus, Desmonema, Desmosiphon, Diacanthos, Diacronema, Diadesmis, Diatoma, Diatomella, Dicellula, Dichothrix, Dichotomococcus, Dicranochaete, Dictyochloris, Dictyococcus, Dictyosphaerium, Didymocystis, Didymogenes, Didymosphenia, Dilabifilum, Dimorphococcus, Dinobryon, Dinococcus, Diplochloris, Diploneis, Diplostauron, Distrionella, Docidium, Draparnaldia, Dunaliella, Dysmorphoccus, Ecballocystis, Elakatothrix, Ellerbeckia, Encyonema, Enteromorpha, Entocladia, Entomoneis, Entophysalis, Epichrysis, Epipyxis, Epithemia, Eremosphaera, Euastropsis, Euastrum, Eucapsis, Eucocconeis, Eudorina, Euglena, Euglenophyta, Eunotia, Eustigmatophyta, Eutreptia, Fallacia, Fischerella, Fragilaria, Fragilariforma, Franceia, Frustulia, Curcilla, Geminella, Genicularia, Glaucocystis, Glaucophyta, Glenodiniopsis, Glenodinium, Gloeocapsa, Gloeochaete, Gloeochrysis, Gloeococcus, Gloeocystis, Gloeodendron, Gloeomonas, Gloeoplax, Gloeothece, Gloeotila, Gloeotrichia, Gloiodictyon, Golenkinia, Golenkiniopsis, Gomontia, Gomphocymbella, Gomphonema, Gomphosphaeria, Gonatozygon, Gongrosia, Gongrosira, Goniochloris, Gonium, Gonyostomum, Granulochloris, Granulocystopsis, Groenbladia, Gymnodinium, Gymnozyga, Gyrosigma, Haematococcus, Hafniomonas, Hallassia, Hammatoidea, Hannaea, Hantzschia, Hapalosiphon, Haplotaenium, Haptophyta, Haslea, Hemidinium, Hemitoma, Heribaudiella, Heteromastix, Heterothrix, Hibberdia, Hildenbrandia, Hillea, Holopedium, Homoeothrix, Hormanthonema, Hormotila, Hyalobrachion, Hyalocardium, Hyalodiscus, Hyalogonium, Hyalotheca, Hydrianum, Hydrococcus, Hydrocoleum, Hydrocoryne, Hydrodictyon, Hydrosera, Hydrurus, Hyella, Hymenomonas, Isthmochloron, Johannesbaptistia, Juranyiella, Karayevia, Kathablepharis, Katodinium, Kephyrion, Keratococcus, Kirchneriella, Klebsormidium, Kolbesia, Koliella, Komarekia, Korshikoviella, Kraskella, Lagerheimia, Lagynion, Lamprothamnium, Lemanea, Lepocinclis, Leptosira, Lobococcus, Lobocystis, Lobomonas, Luticola, Lyngbya, Malleochloris, Mallomonas, Mantoniella, Marssoniella, Martyana, Mastigocoleus, Gastogloia, Melosira, Merismopedia, Mesostigma, Mesotaenium, Micractinium, Micrasterias, Microchaete, Microcoleus, Microcystis, Microglena, Micromonas, Microspora, Microthamnion, Mischococcus, Monochrysis, Monodus, Monomastix, Monoraphidium, Monostroma, Mougeotia, Mougeotiopsis, Myochloris, Myromecia, Myxosarcina, Naegeliella, Nannochloris, Nautococcus, Navicula, Neglectella, Neidium, Nephroclamys, Nephrocytium, Nephrodiella, Nephroselmis, Netrium, Nitella, Nitellopsis, Nitzschia, Nodularia, Nostoc, Ochromonas, Oedogonium, Oligochaetophora, Onychonema, Oocardium, Oocystis, Opephora, Ophiocytium, Orthoseira, Oscillatoria, Oxyneis, Pachycladella, Palmella, Palmodictyon, Pnadorina, Pannus, Paralia, Pascherina, Paulschulzia, Pediastrum, Pedinella, Pedinomonas, Pedinopera, Pelagodictyon, Penium, Peranema, Peridiniopsis, Peridinium, Peronia, Petroneis, Phacotus, Phacus, Phaeaster, Phaeodermatium, Phaeophyta, Phaeosphaera, Phaeothamnion, Phormidium, Phycopeltis, Phyllariochloris, Phyllocardium, Phyllomitas, Pinnularia, Pitophora, Placoneis, Planctonema, Planktosphaeria, Planothidium, Plectonema, Pleodorina, Pleurastrum, Pleurocapsa, Pleurocladia, Pleurodiscus, Pleurosigma, Pleurosira, Pleurotaenium, Pocillomonas, Podohedra, Polyblepharides, Polychaetophora, Polyedriella, Polyedriopsis, Polygoniochloris, Polyepidomonas, Polytaenia, Polytoma, Polytomella, Porphyridium, Posteriochromonas, Prasinochloris, Prasinocladus, Prasinophyta, Prasiola, Prochlorphyta, Prochlorothrix, Protoderma, Protosiphon, Provasoliella, Prymnesium, Psammodictyon, Psammothidium, Pseudanabaena, Pseudenoclonium, Psuedocarteria, Pseudochate, Pseudocharacium, Pseudococcomyxa, Pseudodictyosphaerium, Pseudokephyrion, Pseudoncobyrsa, Pseudoquadrigula, Pseudosphaerocystis, Pseudostaurastrum, Pseudostaurosira, Pseudotetrastrum, Pteromonas, Punctastruata, Pyramichlamys, Pyramimonas, Pyrrophyta, Quadrichloris,*

*Quadricoccus, Quadrigula, Radiococcus, Radiofilum, Raphidiopsis, Raphidocelis, Raphidonema, Raphidophyta, Peimeria, Rhabdoderma, Rhabdomonas, Rhizoclonium, Rhodomonas, Rhodophyta, Rhoicosphenia, Rhopalodia, Rivularia, Rosenvingiella, Rossithidium, Roya, Scenedesmus, Scherffelia, Schizochlamydella, Schizochlamys, Schizomeris, Schizothrix, Schroederia, Scolioneis, Scotiella, Scotiellopsis, Scourfieldia, Scytonema, Selenastrum, Selenochloris, Sellaphora, Semiorbis, Siderocelis, Diderocystopsis, Dimonsenia, Siphononema, Sirocladium, Sirogonium, Skeletonema, Sorastrum, Spermatozopsis, Sphaerellocystis, Sphaerellopsis, Sphaerodinium, Sphaeroplea, Sphaerozosma, Spiniferomonas, Spirogyra, Spirotaenia, Spirulina, Spondylomorum, Spondylosium, Sporotetras, Spumella, Staurastrum, Stauerodesmus, Stauroneis, Staurosira, Staurosirella, Stenopterobia, Stephanocostis, Stephanodiscus, Stephanoporos, Stephanosphaera, Stichococcus, Stichogloea, Stigeoclonium, Stigonema, Stipitococcus, Stokesiella, Strombomonas, Stylochrysalis, Stylodinium, Styloyxis, Stylosphaeridium, Surirella, Sykidion, Symploca, Synechococcus, Synechocystis, Synedra, Synochromonas, Synura, Tabellaria, Tabularia, Teilingia, Temnogametum, Tetmemorus, Tetrachlorella, Tetracyclus, Tetradesmus, Tetraedriella, Tetraedron, Tetraselmis, Tetraspora, Tetrastrum, Thalassiosira, Thamniochaete, Thorakochloris, Thorea, Tolypella, Tolypothrix, Trachelomonas, Trachydiscus, Trebouxia, Trentepholia, Treubaria, Tribonema, Trichodesmium, Trichodiscus, Trochiscia, Tryblionella, Ulothrix, Uroglena, Uronema, Urosolenia, Urospora, Uva, Vacuolaria, Vaucheria, Volvox, Volvulina, Westella, Woloszynskia, Xanthidium, Xanthophyta, Xenococcus, Zygnema, Zygnemopsis*, and *Zygonium*.

Green non-sulfur bacteria include but are not limited to the following genera: *Chloroflexus, Chloronema, Oscillochloris, Heliothrix, Herpetosiphon, Roseiflexus*, and *Thermomicrobium*.

Green sulfur bacteria include but are not limited to the following genera: *Chlorobium, Clathrochloris*, and *Prosthecochloris*.

Purple sulfur bacteria include but are not limited to the following genera: *Allochromatium, Chromatium, Halochromatium, Isochromatium, Marichromatium, Rhodovulum, Thermochromatium, Thiocapsa, Thiorhodococcus*, and *Thiocystis*.

Purple non-sulfur bacteria include but are not limited to the following genera: *Phaeospirillum, Rhodobaca, Rhodobacter, Rhodomicrobium, Rhodopila, Rhodopseudomonas, Rhodothalassium, Rhodospirillum, Rodovibrio*, and *Roseospira*.

Aerobic chemolithotrophic bacteria include but are not limited to nitrifying bacteria such as *Nitrobacteraceae* sp., *Nitrobacter* sp., *Nitrospira* sp., *Nitrococcus* sp., *Nitrospira* sp., *Nitrosomonas* sp., *Nitrosococcus* sp., *Nitrosospira* sp., *Nitrosolobus* sp., *Nitrosovibrio* sp.; colorless sulfur bacteria such as, *Thiovulum* sp., *Thiobacillus* sp., *Thiomicrospira* sp., *Thiosphaera* sp., *Thermothrix* sp.; obligately chemolithotrophic hydrogen bacteria such as *Hydrogenobacter* sp., iron and manganese-oxidizing and/or depositing bacteria such as *Siderococcus* sp., and magnetotactic bacteria such as *Aquaspirillum* sp.

Archaeobacteria include but are not limited to methanogenic archaeobacteria such as *Methanobacterium* sp., *Methanobrevibacter* sp., *Methanothermus* sp., *Methanococcus* sp., *Methanomicrobium* sp., *Methanospirillum* sp., *Methanogenium* sp., *Methanosarcina* sp., *Methanolobus* sp., *Methanothrix* sp., *Methanococcoides* sp., *Methanoplanus* sp.; extremely thermophilic Sulfur-Metabolizers such as *Thermoproteus* sp., *Pyrodictium* sp., *Sulfolobus* sp., *Acidianus* sp. and other microorganisms such as, *Bacillus subtilis, Saccharomyces cerevisiae, Streptomyces* sp., *Ralstonia* sp., *Rhodococcus* sp., *Corynebacteria* sp., *Brevibacteria* sp., *Mycobacteria* sp., and oleaginous yeast.

Still, other suitable organisms include microorganisms that can be engineered to fix carbon dioxide bacteria such as *Escherichia coli, Acetobacter aceti, Bacillus subtilis*, yeast and fungi such as *Clostridium ljungdahlii, Clostridium thermocellum, Penicillium chrysogenum, Pichia pastoris, Saccharomyces cerevisiae, Schizosaccharomyces pombe, Pseudomonas fluorescens*, or *Zymomonas mobilis*.

A common theme in selecting or engineering a suitable organism is autotrophic fixation of carbon, such as $CO_2$, to products via photosynthesis and/or methanogenesis. The capability to use carbon dioxide as the sole source of cell carbon (autotrophy) is found in almost all major groups of prokaryotes. $CO_2$ fixation pathways differ between groups, and there is no clear distribution pattern of the four presently-known autotrophic pathways. The reductive pentose phosphate cycle (Calvin-Bassham-Benson cycle) represents a $CO_2$ fixation pathway present in almost all aerobic autotrophic bacteria, for example, the cyanobacteria.

C. Transformation of Selected Microorganisms

It is contemplated that the microbial cells can be transformed and/or transfected with the appropriate vectors and/or genes using standard transformation and/or transfection techniques known in the art.

*E. coli* can be transformed using standard techniques known to those skilled in the art, including heat shock of chemically competent cells and electroporation (Berger and Kimmel, Guide to Molecular Cloning Techniques, Methods in Enzymology, Volume 152, Academic Press, Inc., San Diego, Calif.; Sambrook et al. (1989) Molecular Cloning—A Laboratory Manual (2nd ed.) Vol. 1-3, Cold Spring Harbor Laboratory, Cold Spring Harbor Press, N.Y.; and Current Protocols in Molecular Biology, F. M. Ausubel et al., eds.). Each gene or engineered nucleic acid is optimized individually, or alternately, in parallel. Functional promoter and gene sequences are subsequently integrated into the *E. coli* chromosome to enable stable propagation in the absence of selective pressure (i.e., inclusion of antibiotics) using standard techniques known to those skilled in the art.

*Synechococcus* sp. PCC 7002 cells can be transformed according to the optimized protocol previously described (Essich E S, Stevens Jr E, Porter R D "Chromosomal Transformation in the Cyanobacterium Agmenellum quadruplicatum," *J. Bacteriol.* (1990), 172(4):1916-1922). Cells are grown in Medium A (18 g/L NaCl, 5 g/L $MgSO_4 \cdot 7H_2O$, 30 mg/L $Na_2EDTA$, 600 mg/L KCl, 370 mg/L $CaCl_2 \cdot 2H_2O$, 1 g/L $NaNO_3$, 50 mg/L $KH_2PO_4$, 1 g/L Trizma base pH 8.2, 4 µg/L Vitamin $B_{12}$, 3.89 mg/L $FeCl_3$ $6H_2O$, 34.3 mg/L $H_3BO_3$, 4.3 mg/L $MnCl_2 \cdot 4H_2O$, 315 µg/L $ZnCl_2$, 30 µg/L $MoO_3$, 3 µg/L $CuSO_4 \cdot 5H_2O$, 12.2 µg/L $CoCl_2$ $6H_2O$) (Stevens S E, Patterson C O P, and Myers J. "The production of hydrogen peroxide by green algae: a survey." *J. Phycology* (1973), 9:427-430) plus 5 g/L of $NaNO_3$ to approximately 108 cells/mL. Nine volumes of cells are mixed with 1 volume of 1-10 µg/mL DNA in 0.15 M NaCl/0.015 M $Na_3$citrate and incubated at 27-30° C. for 3 hours before addition of 1 volume of DNaseI to a final concentration of 10 µg/mL. The cells are plated in 2.5 mL of 0.6% medium A overlay agar at 45° C. and incubated. Cells can be challenged with antibiotic by under-laying 2.0 mL of 0.6% medium A agar containing appropriate concentration of antibiotic with a sterile Pasteur pipette. Transformants can be picked 3-4 days later. Selections can typically be performed by including 200 μg/mL kanamycin, 8 μg/mL chloramphenicol, 10 μg/ml spectinomycin on solid media.

D. Propagation of Selected Microorganisms

The microorganisms, once transfected and/or transformed with a vector encoding a CBA protein, can be cultured under standard growth conditions.

Methods for propagating photosynthetic organisms in liquid media and on agarose-containing plates are well known to those skilled in the art (see, e.g., websites associated with ATCC, and with the Institute Pasteur). For example, *Synechococcus* sp. PCC 7002 cells (available from the Pasteur Culture Collection of Cyanobacteria) can be cultured in BG-11 medium (17.65 mM $NaNO_3$, 0.18 mM $K_2HPO_4$, 0.3 mM $MgSO_4$, 0.25 mM $CaCl_2$, 0.03 mM citric acid, 0.03 mM ferric ammonium citrate, 0.003 mM EDTA, 0.19 mM $Na_2CO_3$, 2.86 mg/L $H_3BO_3$, 1.81 mg/L $MnCl_2$, 0.222 mg/L $ZnSO_4$, 0.390 mg/L $Na_2MoO_4$, 0.079 mg/L $CuSO_4$, and 0.049 mg/L $Co(NO_3)_2$, pH 7.4) supplemented with 16 μg/L biotin, 20 mM $MgSO_4$, 8 mM KCl, and 300 mM NaCl (see, e.g., Price et al. "Identification of a SulP-type Bicarbonate Transporter in Marine Cyanobacteria," *Proc Natl. Acad. Sci. USA* (2004), 101(52):18228-33).

By way of example, cultures may be propagated in the temperature range of 20° C. to 40° C. (for example, 28° C.) and bubbled continuously with 5% $CO_2$ under a light intensity of 120 μmol photons/$m^2$/s. Alternatively, *Synechococcus* sp. PCC 7002 cells can be cultured in $A^+$ medium as previously described (Frigaard N U et al. (2004) "Gene Inactivation in the Cyanobacterium *Synechococcus* sp. PCC 7002 and the Green Sulfur Bacterium *Chlorobium tepidum* Using in vitro-made DNA Constructs and Natural Transformation," *Methods Mol. Biol.*, 274:325-340).

Depending upon the circumstances, the organisms are propagated using alternate media or gas compositions, alternate temperatures (5-75° C.), and/or light fluxes (0-5500 μmol photons/$m^2$/s).

Where appropriate, light can be delivered through a variety of mechanisms, including natural illumination (sunlight), standard incandescent, fluorescent, or halogen bulbs, or via propagation in specially-designed illuminated growth chambers (for example Model LI15 Illuminated Growth Chamber (Sheldon Manufacturing, Inc. Cornelius, Oreg.). For experiments requiring specific wavelengths and/or intensities, light is distributed via light emitting diodes (LEDs), in which wavelength spectra and intensity can be carefully controlled (Philips).

Carbon dioxide can be supplied via inclusion of solid media supplements (i.e., sodium bicarbonate) or as a gas via its distribution into the growth incubator or media. Most experiments are performed using concentrated carbon dioxide gas, at concentrations between 1 and 30%, which is directly bubbled into the growth media at velocities sufficient to provide mixing for the organisms. When concentrated carbon dioxide gas is utilized, the gas originates in pure form from commercially-available cylinders, or preferentially from concentrated sources including off-gas or flue gas from coal plants, refineries, cement production facilities, natural gas facilities, breweries, and the like.

In addition, it is contemplated that the propagation can be conducted using an indoor bioreactor (for example, commercial fermenters) or in an outdoor facility such as in one or more ponds or lakes.

E. Downstream Processing

Once propagated, the cells can be harvested using standard techniques known in the art, for example, via centrifugation and/or filtration. The resulting cells, once harvested, can then be used as is or frozen and stored for future processing. A desired compound, for example, a carbon-based product, e.g., an oil, can be extracted and optionally purified using standard purification techniques. (See, for example, U.S. Patent Publication No. 2011/0269219.) Furthermore, the purification of dicarboxylic acids from fermentation cultures is described in U.S. Pat. Nos. 5,770,435, 5,869,301 and 6,743,610, and U.S. Patent Publication No. 2011/0237831 and International Application Publication No. WO2011/123268.

III. Pharmaceutical Compositions and Dosing Considerations

In another aspect, the invention provides pharmaceutically acceptable compositions which comprise a therapeutically-effective amount of one or more of the CBA proteins described hereinabove, formulated together with one or more pharmaceutically acceptable excipients (e.g., carriers and/or diluents). As described in detail below, the pharmaceutical compositions may be specially formulated for administration in solid or liquid form, including those adapted for the following: (1) topical application, for example, as a cream, ointment, or a controlled-release patch or spray applied to the skin; (2) oral administration, for example, drenches (aqueous or non-aqueous solutions or suspensions), tablets, e.g., those targeted for buccal, sublingual, and systemic absorption, boluses, powders, granules, pastes for application to the tongue; (3) non-parenteral administration, for example, by subcutaneous, intramuscular, intravenous or epidural injection as, for example, a sterile solution or suspension, or sustained-release formulation; (4) intravaginally or intrarectally, for example, as a pessary, cream or foam; (5) sublingually; (6) ocularly; (7) transdermally; or (8) nasally.

It is understood that the CBA proteins can have antibiotic properties and can be used in pharmaceutical compositions, for example, as antibiotics. Because vitamin $B_{12}$ is required for growth and/or proliferation of a number of microorganisms, for example, certain pathogenic microorganisms, it is understood that the cobalamin acquisition protein may sequester or scavenge vitamin $B_{12}$ from the organism or its surrounding environment thereby slowing or stopping the growth or the proliferation of the pathogenic organism. As a result, it is contemplated that the cobalamin acquisition protein can be included in pharmaceutical compositions, for example, pastes and ointments, for topical administration and/or compositions for non-parenteral administration.

It is contemplated that the CBA protein may comprise from about 0.1% (w/w) to about 90% (w/w) of the pharmaceutical composition (for example, a tablet or ointment), from about 0.1% (w/w) to about 80% (w/w) of the pharmaceutical composition, from about 0.1% (w/w) to about 70% (w/w) of the pharmaceutical composition, from about 0.1% (w/w) to about 60% (w/w) of the pharmaceutical composition, from about 0.1% (w/w) to about 50% (w/w) of the pharmaceutical composition, from about 0.1% (w/w) to about 40% (w/w) of the pharmaceutical composition, from 0.1% (w/w) to about 30% (w/w) of the pharmaceutical composition, from about 0.5% (w/w) to about 90% (w/w) of the pharmaceutical composition, from about 0.5% (w/w) to about 80% (w/w) of the pharmaceutical composition, from about 0.5% (w/w) to about 70% (w/w) of the pharmaceutical composition, from about 0.5% (w/w) to about 60% (w/w) of the pharmaceutical composition, from about 0.5% (w/w) to about 50% (w/w) of the pharmaceutical composition, from about 0.5% (w/w) to about 40% (w/w) of the pharmaceutical composition, from 0.5% (w/w) to about 30% (w/w) of the pharmaceutical composition, from about 1% (w/w) to about 90% (w/w) of the pharmaceutical composition, from about 1% (w/w) to about 80% (w/w) of the pharmaceutical composition, from about 1% (w/w) to about 70% (w/w) of the pharmaceutical composition, from about 1% (w/w) to about 60% (w/w) of the pharmaceutical composition, from about 1% (w/w) to about 50% (w/w) of the pharmaceutical composition, from about 1% (w/w) to about 40% (w/w) of the pharmaceutical composition, or from 1% (w/w) to about 30% (w/w) of the pharmaceutical composition.

It is also understood that the CBA proteins of the invention can be co-formulated with other active ingredients, for example, iron-binding siderophore molecules or siderophore binding proteins (siderocalins). It is contemplated that the combined active ingredients (the combination of the cobalamin acquisition protein and the other pharmaceutically active agents in the pharmaceutical composition) may comprise from about 0.1% (w/w) to about 90% (w/w) of the pharmaceutical composition, from about 0.1% (w/w) to about 80% (w/w) of the pharmaceutical composition, from about 0.1% (w/w) to about 70% (w/w) of the pharmaceutical composition, from about 0.1% (w/w) to about 60% (w/w) of the pharmaceutical composition, from about 0.1% (w/w) to about 50% (w/w) of the pharmaceutical composition, from about 0.1% (w/w) to about 40% (w/w) of the pharmaceutical composition, from 0.1% (w/w) to about 30% (w/w) of the pharmaceutical composition, from about 0.5% (w/w) to about 90% (w/w) of the pharmaceutical composition, from about 0.5% (w/w) to about 80% (w/w) of the pharmaceutical composition, from about 0.5% (w/w) to about 70% (w/w) of the pharmaceutical composition, from about 0.5% (w/w) to about 60% (w/w) of the pharmaceutical composition, from about 0.5% (w/w) to about 50% (w/w) of the pharmaceutical composition, from about 0.5% (w/w) to about 40% (w/w) of the pharmaceutical composition, from 0.5% (w/w) to about 30% (w/w) of the pharmaceutical composition, from about 1% (w/w) to about 90% (w/w) of the pharmaceutical composition, from about 1% (w/w) to about 80% (w/w) of the pharmaceutical composition, from about 1% (w/w) to about 70% (w/w) of the pharmaceutical composition, from about 1% (w/w) to about 60% (w/w) of the pharmaceutical composition, from about 1% (w/w) to about 50% (w/w) of the pharmaceutical composition, from about 1% (w/w) to about 40% (w/w) of the pharmaceutical composition, or from 1% (w/w) to about 30% (w/w) of the pharmaceutical composition.

It is contemplated that the pharmaceutical compositions can be formulated (for example, the determination of the dosage form and/or the determination of optimal excipients for a particular route of administration) using formulation methodologies known in the formulary arts.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

The formulations may conveniently be presented in unit dosage form and may be prepared by any methods well known in the art of pharmacy. The amount of active ingredient which can be combined with an excipient to produce a single dosage form will vary depending upon the host being treated, the particular mode of administration. The amount of active ingredient which can be combined with a carrier material to produce a single dosage form will generally be that amount of the compound which produces a therapeutic effect.

In certain embodiments, a formulation of the present invention comprises an excipient selected from the group consisting of cyclodextrins, celluloses, liposomes, micelle forming agents, e.g., bile acids, nanoparticles, and polymeric carriers, e.g., polyesters and polyanhydrides; and a compound of the present invention. In certain embodiments, an aforementioned formulation renders orally bioavailable a compound of the present invention.

Methods of preparing these formulations or compositions include the step of bringing into association a compound of the present invention with the excipient and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable excipients, and with any preservatives, buffers, or propellants which may be required. The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. If desired, the effective daily dose of the active compound may be administered as two, three, four, five, six or more sub-doses administered separately at appropriate intervals throughout the day, optionally, in unit dosage forms. Preferred dosing is one administration per day.

Suitable dosage formulations and methods of administering the agents are readily determined by those of skill in the art. Preferably, the compounds are administered at about 0.01 mg/kg to about 200 mg/kg, more preferably at about 0.1 mg/kg to about 100 mg/kg, even more preferably at about 0.5 mg/kg to about 50 mg/kg. When the compounds described herein are co-administered with another agent (e.g., as sensitizing agents), the effective amount may be less than when the agent is used alone.

IV. Analytical and Separation Technologies

In addition, it is contemplated that the CBA proteins may be used in a variety of analytical and separation technologies. For example, it is contemplated that the binding proteins described herein can be used to selectively bind vitamin $B_{12}$, and can be used in the types of assays that use and separation technologies that utilize antibodies and other binding proteins.

For example, it is contemplated that the CBA proteins can be immobilized on or in a solid support (for example, on the surface of an inert bead or particle, or on the surface of a microtiter plate, slide, membrane, etc.) The solid supports can also vary in the materials that they are composed of including plastic, glass, silicon, nylon, polystyrene, silica gel, latex and the like.

The CBA proteins can be immobilized on the surface of the solid support using conventional immobilization techniques (for example, via adsorption or via a covalent linkage) provided that the immobilization does not destroy the ability of the cobalamin acquisition protein from binding vitamin $B_{12}$. For example, a cobalamin binding protein may be coupled directly (through a covalent linkage) to commercially available pre-activated resin as described in Formosa et al., *Methods in Enzymology* (1991), 208: 24-45; Sopta et al., *J. Biol. Chem.* (1985), 260: 10353-60; and Archambault et al., *Proc. Natl. Acad. Sci. USA* (1997), 94: 14300-5. Alternatively, the polypeptide may be immobilized on the solid support via high affinity binding interaction. For example, if the cobalamin acquisition protein is expressed fused to a tag, such as GST, the fusion tag can be used to anchor the polypeptide to the matrix support, for example Sepharose beads containing immobilized glutathione. Solid supports that take advantage of these tags are commercially available.

The binding activity of the cobalamin acquisition protein, before and after immobilization, can be determined by titration of the resin using radiolabeled vitamin $B_{12}$ molecules and a gamma detector counting system. Alternatively, a rapid charcoal assay for $B_{12}$-binding affinity can be used (see, Gottlieb et al. (1965) "Rapid Charcoal Assay for Intrinsic Factor (IF), Gastric Juice Unsaturated $B_{12}$-binding Capacity, Antibody to IF, and Serum Unsaturated $B_{12}$-binding Capacity," *Blood*, 25:875-884) or an isothermal titration calorimetry assay, also known as microcal titration, can be used to determine binding activity (see, Cadieux et al. (2002) "Identification of the Periplasmic Cobalamin-Binding Protein BtuF of *Escherichia coli*," *J. Bacteriol.* 184(3): 706-717).

By way of example, beads having a CBA protein immobilized therein or thereon can be packed in a column. A test sample of interest, for example, a biological fluid, can be passed through the column for a time and under conditions to permit the CBA protein to bind vitamin $B_{12}$ present in the sample to be tested. Once the sample has been passed through the column, the column, if desired, can be washed with an appropriate solution (for example, a buffer) to remove unbound material. Thereafter, the vitamin $B_{12}$ can be eluted from the column using the appropriate elution buffer (for example, a buffer having the appropriate salt concentration, pH, detergent, chelating agent, etc) under the appropriate conditions. The presence and/or amount of vitamin $B_{12}$ present in the eluate can be detected and/or measured using conventional techniques in the art, for example, by high pressure liquid chromatography spectrophotometric detection or high pressure liquid chromatography mass spectrometry analytical systems, where vitamin $B_{12}$ elutes at a known elution time, based on comparisons to a vitamin $B_{12}$ standard, and its concentration calculated by measurement of peak area detected by visible light absorption (spectrophotometric detection) or by detection of vitamin $B_{12}$ parent ion mass and fragment masses (mass spectrometry).

EXAMPLES

The invention now being generally described, will be more readily understood by reference to the following examples, which are included merely for purposes of illustration of certain aspects and embodiments of the present invention, and are not intended to limit the scope of the invention in any way.

With regard to the following examples, axenic cultures of *Thalassiosira pseudonana* CCMP 1335 and *Phaeodactylum tricornutum* CCMP 632 were obtained from the Provasoli-Guillard National Center for Culture of Marine Phytoplankton and maintained using sterile and trace metal clean techniques. All culturing was conducted at 16° C. under a constant light level of 150 µE/m²/sec. Media was prepared in a 0.2 µm filtered oligotrophic seawater base collected in a trace metal clean manner, microwave sterilized, and supplemented with macronutrients at f/2 concentrations and vitamins with EDTA-buffered trace metals (EDTA$_{total}$=10$^{-4}$ M) as described in Sunda et al. (1995) *Limnol. Oceanogr.* 40: 1404-1417. All culturing was conducted in polycarbonate bottles and manipulations were conducted in a class 100 clean room facility. Fe' concentrations (the summation of all inorganic iron species) were calculated according to previously described relationships (See, Sunda et al. (2003) *Marine Chemistry* 84: 35-47) interpolated to 16° C. and assuming that pH remained constant at 8.2 (Fe'/Fe$_{total}$=2.6 e$^{-3}$).

Example 1

Colimitation Experiment to Identify Proteins that Become More Abundant Upon Iron and Vitamin $B_{12}$ Deprivation This example describes the effect of vitamin $B_{12}$ and iron starvation upon the growth, proteomes and transcriptomes of various diatoms, and identifies certain proteins that become more abundant upon vitamin $B_{12}$ deprivation.

*T. pseudonana* Colimitation: *T. pseudonana* cells were acclimated for the experiment under conditions described above except with 1 pM added vitamin $B_{12}$ and 65 nM added total Fe (10$^{-9.88}$ M Fe') for four transfers allowing at least three doublings per transfer. The vitamin $B_{12}$ and iron concentrations used were chosen based on previous work (Allen et al. (2008) "Whole-cell Response of the Pennate Diatom *Phaeodactylum tricornutum* to Iron Starvation," *Proc. Natl. Acad. Sci. USA*, 105: 10438-10443; Kustka et al. (2007) "Sequence Analysis and Transcriptional Regulation of Iron Aquisition Genes in Two Marine Diatoms" *J. Phycol.* 43: 715-729; Swift et al. (1972) "Growth of Vitamin $B_{12}$-limited Cultures: *Thalassiosira pseudonana, Monochyrsis lutheri*, and *Isochrysis galbana*," *J. Phycol.* 10: 385-391). Cells were then inoculated (3.2% vol/vol) into twelve, 2.2 L bottles, containing 1.8 L of media (twelve bottles were for the four treatments in biological triplicates). The media was as described above except for variable iron and vitamin $B_{12}$ concentrations (Allen et al. (2008) supra; Kustka et al. (2007) supra; Swift et al. (1972) supra).

Four sets of conditions were tested: 1) low iron treatment, having 50 nM Fe total (10$^{-10.0}$ M Fe') and 100 pM added vitamin $B_{12}$; 2) low $B_{12}$ treatment, having 0.3 pM added vitamin $B_{12}$ and 400 nM Fe total (10$^{-9.09}$ M Fe'); 3) low $B_{12}$/low iron treatment, having 0.3 pM added vitamin $B_{12}$ and 50 nM Fe$_{total}$ (10$^{-10.0}$ M Fe');) and 4) replete treatment, having 100 pM added vitamin $B_{12}$ and 400 nM Fe$_{total}$ (10$^{-9.09}$ M Fe'). Samples were taken daily for fluorescence and cell counts. Cells were counted using a Palmer Maloney nanoplankton counting chamber counting at least 10 fields of view or 200 individuals at 400× magnification with light microscopy (Carl Zeiss, Inc., Thornwood, N.Y.). In vivo fluorescence was monitored using a Turner Designs TD 700 Fluorometer, referenced daily to a solid standard. After 6 days for the replete and low $B_{12}$ treatment, and 9 days for the low iron (FIG. 2A, arrow locations indicate protein harvest time points), samples were harvested for protein analysis. Protein samples (200-300 mL) were filtered onto 0.4 µm polyethersulfone filters, flash frozen in liquid nitrogen, and stored at −80° C.

*P. tricornutum* Colimitation: This experiment was conducted as with the *T. pseudonana* experiment except with different vitamin $B_{12}$ and iron concentrations due to known differences in $B_{12}$ and iron requirements for these diatoms (see Allen et al. (2008) supra; Kustka et al. (2007) supra). Acclimation cultures contained 5 nM added total iron (10$^{-11}$ M Fe') and 0.5 pM added vitamin $B_{12}$ for four transfers allowing at least three doublings per transfer. *P. tricornutum* cells were then inoculated (3.2% vol/vol) into twelve, 2.2 L bottles containing 1.8 L of media (twelve bottles were for the four treatments in biological triplicates). Similar to the experiment above, four sets of conditions were tested: 1) low iron treatment, having 2.5 nM Fe total ($10^{-11.3}$ M Fe') and 100 pM added vitamin $B_{12}$; 2) low $B_{12}$ treatment, having no added vitamin $B_{12}$ and 100 nM $Fe_{total}$ ($10^{-9.69}$ M Fe'); 3) low $B_{12}$/low iron treatment, having no added vitamin $B_{12}$ and 2.5 nM $Fe_{total}$ ($10^{-11.3}$ mol L Fe'); and 4) replete treatment, having 100 pM added vitamin $B_{12}$ and 100 nM $Fe_{total}$ ($10^{-9.69}$ M Fe').

Figure 2A:
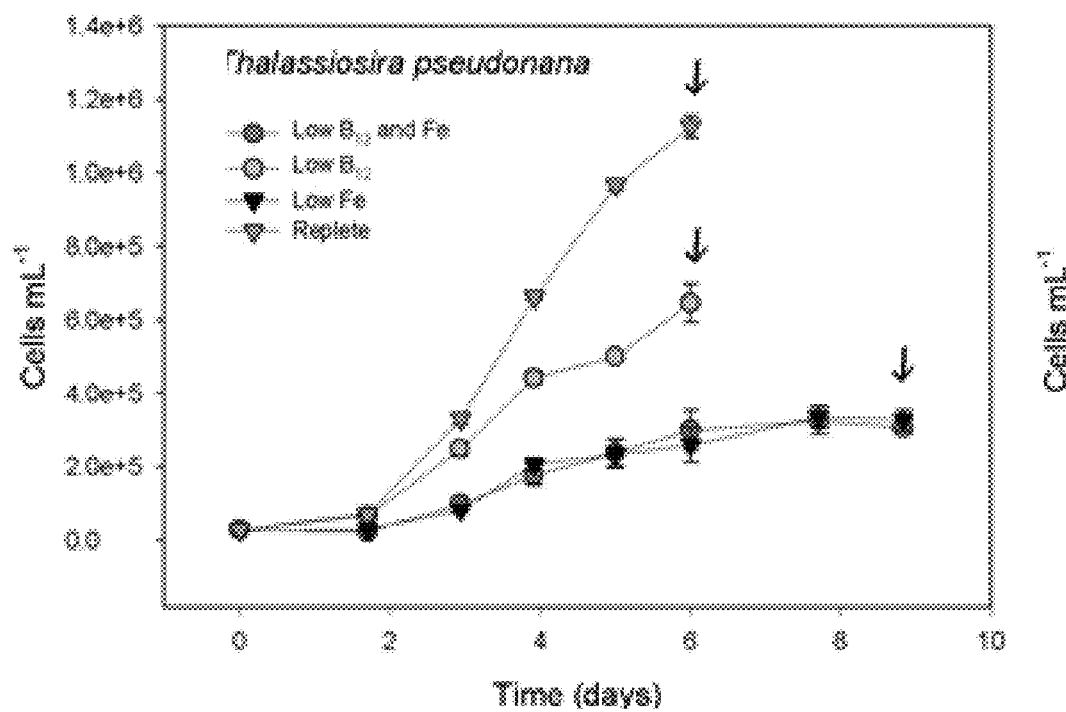
FIGS. 2A and 2B depict the effect of vitamin $B_{12}$ and iron (Fe) starvation on growth and protein expression in *T. pseudonana* (A) and *P. tricornutum* (B).
Figure 2B:
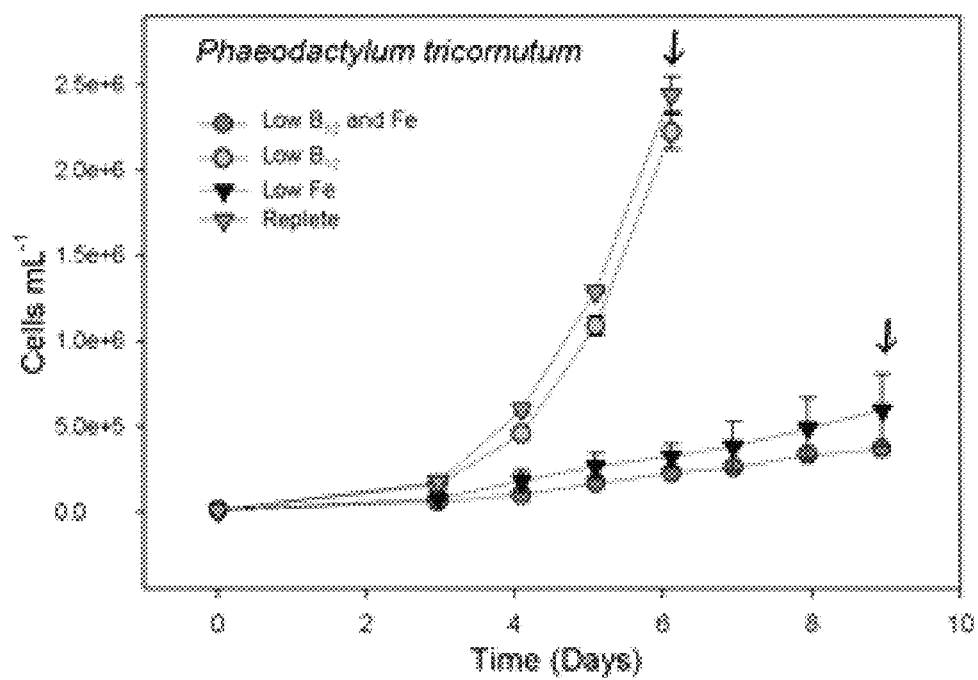

FIGS. 2A and 2B depict the four different treatments: (1) low vitamin $B_{12}$ (grey circles), (2) low Fe (black triangles), (3) low vitamin $B_{12}$ and low Fe (black circles), and (4) replete (grey triangles). The arrows indicate where samples for proteomic and transcriptomic analyses were taken for each treatment group. Low cobalamin availability had a much larger impact on T. pseudonana growth than on the growth of P. tricornutum, likely due to P. tricornutum's use of MetE as an alternative to the $B_{12}$-requiring MetH. Low iron had a more severe impact on growth than low $B_{12}$ in both diatoms, as expected given the extreme low iron availability in the experiment.

Figure 3:
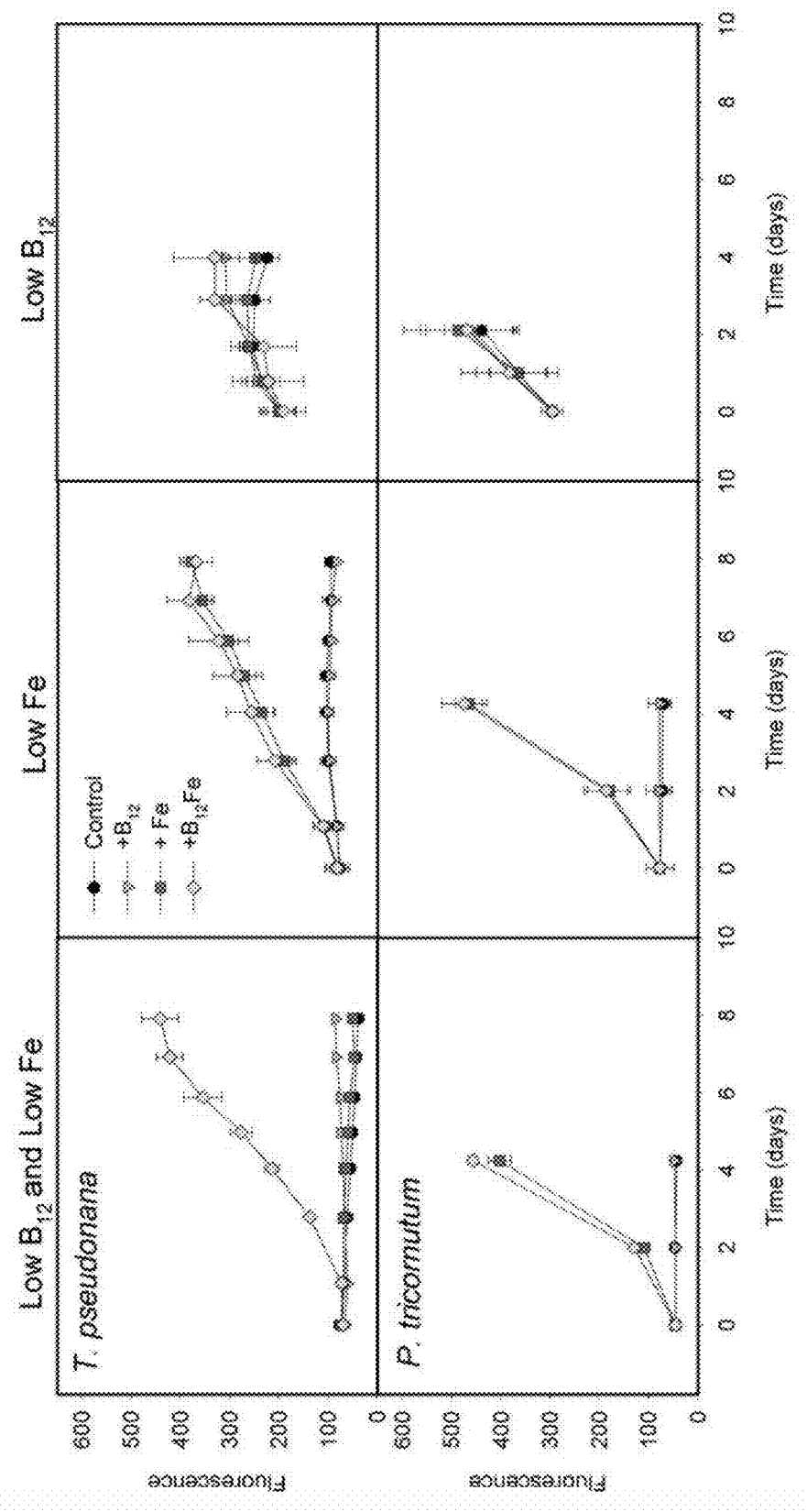
FIG. 3 depicts the effect of re-supplying starved *T. pseudonana* and *P. tricornutum* cultures with cobalamin ($B_{12}$) and iron (Fe).

A. Re-supply Experiment: For both colimitation experiments (T. pseudonana and P. tricornutum), each remaining culture was split in four just after the protein harvest time point. For the T. pseudonana study, the cultures were re-supplied with either 1) nothing, 2) 100 pM $B_{12}$, 3) 400 nM $Fe_{total}$, or 4) both 100 pM $B_{12}$ and 400 nM Fe. For the P. tricornutum study, the cultures were re-supplied with either 1) nothing, 2) 100 pM $B_{12}$, 3) 100 nM $Fe_{total}$, or 4) both 100 pM $B_{12}$ and 100 nM Fe. As shown in FIG. 3, these four different treatments are depicted as follows: 1) control (circles), 2) added vitamin $B_{12}$ (+$B_{12}$, triangles), 3) added iron (+Fe, squares), and 4) added vitamin $B_{12}$ and iron (+$B_{12}$Fe, diamonds).

For both studies, each culture was monitored for growth via in vivo fluorescence.

As expected, the cobalamin and iron re-supply experiments confirmed that the diatom cultures were starved for nutrients as intended by the colimitation experiments.

To this end, iron rescued the growth of both low iron cultures, and cobalamin rescued the growth only in the low cobalamin culture of the cobalamin requiring diatom, T. pseudonana (see, FIG. 3). Growth in the low cobalamin/low iron T. pseudonana culture was only restored upon the addition of both cobalamin and iron together, demonstrating that this culture was simultaneously limited by the availability of both nutrients (co-limited). In contrast, growth in low cobalamin/low Fe P. tricornutum cultures was rescued by iron addition alone and was further enhanced by the co-addition of cobalamin and iron (see, FIG. 3). This difference in the responses was expected because T. pseudonana has an absolute requirement for cobalamin while P. tricornutum does not. These results indicate that all cultures used for the proteomic analyses in this study were limited or colimited as expected.

B. Protein Extraction, Digestion and Analysis: The cells from the colimitation experiments were scraped from the filters and resuspended in 600 mL B-PER reagent (Thermo Scientific, Rockford, Ill.) supplemented with 5 mM EDTA and 1 mM phenylmethanesulfonyl fluoride (a serine protease inhibitor). Samples were incubated at room temperature for 20 min with occasional gentle vortexing. The cells were then sonicated with a microtip (Branson digital sonifier) on ice, twice for 1 min at constant duty cycle with a 5 min pause on ice between sonication steps. Samples were centrifuged for 30 min at 14,100 RCF and 4° C., and supernatants were precipitated overnight in 50% acetone/50% methanol/0.5 mM HCl at −20° C. Precipitated protein was collected by centrifugation at 14,100 RCF for 30 min at 4° C. and dried by speed vacuum at room temperature. Protein was resuspended in 100 µL of the extraction buffer for 30 min at room temperature. Aliquots were taken for protein determination by DC assay using bovine serum albumin as a protein standard (BioRad Inc., Hercules Calif.). Proteins were stored at −80° C. until digestion.

Protein was digested following the tube gel digestion procedure with minor modifications. Briefly, samples were immobilized in 15% acrylamide in pH 7.5 Tris buffer, fixed with 10% acetic acid and 50% ethanol, and washed successively with 10% acetic acid and 50% methanol, then acetonitrile and 25 mM ammonium bicarbonate to remove detergents and protease inhibitors. Samples were then cut into 1 $mm^2$ pieces. Reduction of the samples was done with 10 mM dithiothreitol (DTT) at 56° C. for 1 hour. The samples were alkyated with 30 mM iodoacetamide for 1 hour, and then washed in 25 mM ammonium bicarbonate and digested with trypsin in 25 mM ammonium bicarbonate for 16 hours at 37° C. (1:20 ratio trypsin to total protein, Promega Gold Mass Spectrometry Grade, Promega Inc., Madison Wis.). The peptides were extracted by successive additions of a peptide extraction buffer, containing 50% acetonitrile and 5% formic acid. The extracted peptides were combined and concentrated by speed vacuum for about three hours to less than 20 µL, diluted with 2% acetonitrile and 0.1% formic acid and stored at −80° C.

The protein digestions were analyzed (4 µg total protein per analysis) using a peptide Cap Trap in-line with a reversed phase Magic C18 AQ column (0.2×150 mm, 3 µm particle size, 200 Å pore size, Michrom Bioresources Inc. Auburn Calif.) on a Paradigm MS4 HPLC system (Michrom Bioresources Inc.). An ADVANCE nanocapillary electrospray source (Michrom Bioresources Inc.) introduced the sample into a LTQ (linear ion trap) mass spectrometer (Thermo Scientific Inc. San Jose Calif.). The chromatography consisted of a hyperbolic gradient from 5% buffer A to 95% buffer B for 300 min, where A was 0.1% formic acid (Michrom Ultra Pure) in water (Fisher Optima) and B was 0.1% formic acid in acetonitrile (Fisher Optima) at a flow rate of 2 µL $min^{-1}$. The mass spectrometer was set to perform MS/MS on the top 7 ions using data-dependent settings and a dynamic exclusion window of 30 s and parent ions were monitored over the range of 400-2000 m/z. Three technical replicate mass spectrometry experiments were processed for each of the 8 biological samples (4 treatments per diatom, 2 diatoms).

The mass spectra were searched using SEQUEST (Bioworks version 3.3, Thermo Inc., San Jose Calif.) with a fragment tolerance of 1 Da, parent tolerance of 2 Da, +57 on cysteine for carbamidomethylation by iodoacetamide as a static modification and +16 for methionine oxidation as a dynamic modification, trypsin fully enzymatic peptide cleavage, and a maximum of 2 missed cleavage sites. An amino acid database for Thalassiosira pseudonana was compiled by combining data from the Joint Genome Institute (JGI) and the National Center for Biotechnology Information (NCBI) and contained the files Thaps3_chromosomes_geneModels_FilteredModels2_aa.fasta and Thaps3_bd_unmapped_GeneModels_FilteredModels1_aa.fasta from JGI as well as the mitochondrial and plastid genomes from NCBI (Plastid-Project ID: 20561; Mitochondrial-Project ID: 15818), all of which contributed to the complete genome sequencing project (Armbrust et al. (2004) supra). Common contaminants as well as a reversed decoy version of these databases for false positive rate analysis were also included. The *Phaeodactylum tricornutum* database was similarly constructed from the following files: Phatr2_chromosomes_geneModels_FilteredModels2_aa.fasta and Phatr2_bd_unmapped_GeneModels_FilteredModels1_aa.fasta and the plastid genome (Project ID: 18283) all of which contributed to the complete genome sequencing project (Bowler et al. (2008) supra). Database search results were further processed using the PeptideProphet statistical model (Keller et al. (2002) "Empirical Statistical Model to Estimate the Accuracy of Peptide Identifications Made by MS/MS and Database Search," *Analytical Chemistry* 74: 5383-92) within Scaffold 3.0 (Proteome Software Inc., Portland Oreg.). Proteins were identified if their peptide identification probability was >95%, protein identification probability was >99%, and two or more peptides from its sequence were detected.

In this analysis, 764 *T. pseudonana* proteins were detected from a total of 4955 unique peptides with a 0.19% peptide false discovery rate. In addition, 859 *P. tricornutum* proteins were detected from 5172 unique peptides with a 0.22% peptide false discovery rate. 52% of *P. tricornutum* spectra were assigned to peptides found in the genomic databases, while 46% of spectra acquired for *T. pseudonana* were assigned.

Figure 4:
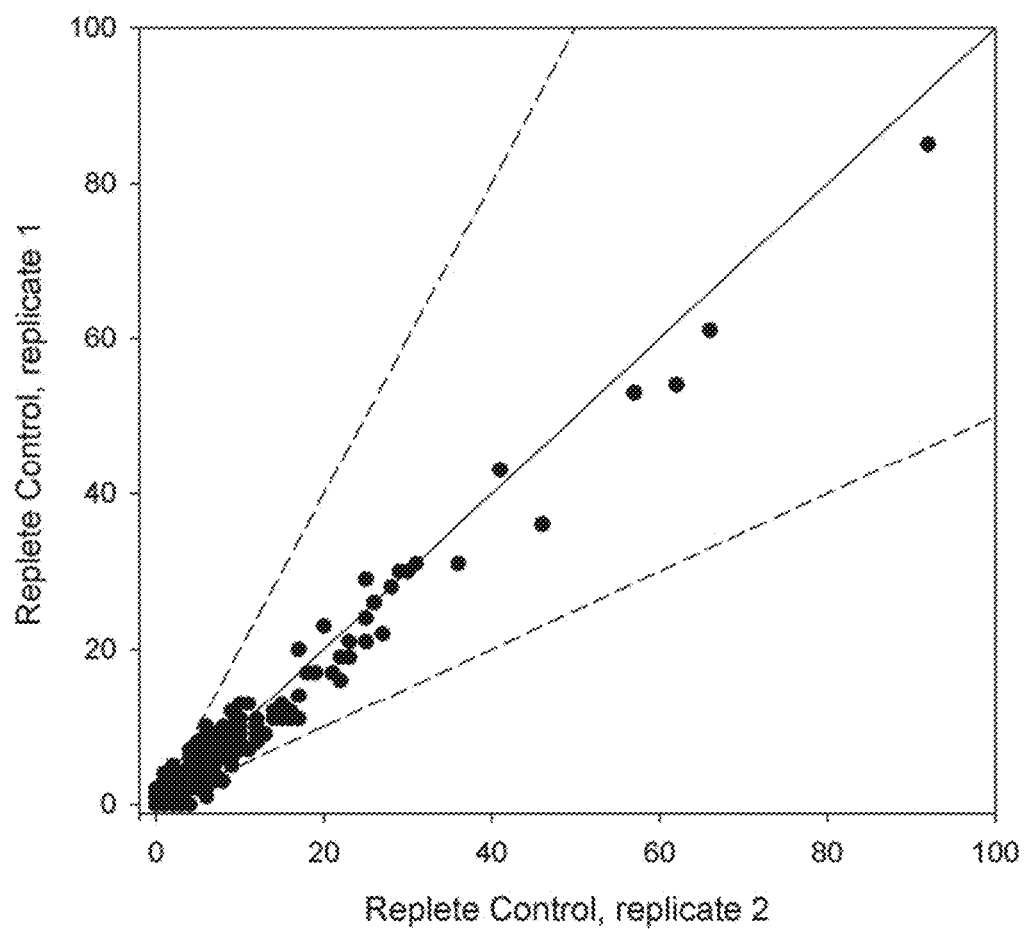
FIG. 4 depicts the technical replicate shotgun proteomic analysis of the *P. tricornutum* replete culture.

Relative protein abundance was determined via calculating a spectral counting score in Scaffold 3.0. Spectral counts were normalized across all mass spectrometry samples in each experiment, including three technical replicates for each of four treatments, to allow comparison of relative protein abundance. Technical replicates of spectral count data from the replete control conditions were plotted against each other to demonstrate the precision of the method (see, FIG. 4). As seen in FIG. 4, all proteins were plotted as black circles and were not significantly differentially abundant. The solid line is 1:1 protein abundance, and the dashed lines are 2:1. Proteins discussed as 'differentially expressed' were determined by the Fisher exact test (p<0.01) as described in Zhang et al. (2006) "Detecting Differential and Correlated Protein Expression in Label-Free Shotgun Proteomics," *J. Proteome Res.* 5: 2909-2918. False positive identification rate was estimated as described by Peng et al. (2003) "Evaluation of Multidimensional Chromatography Coupled with Tandem Mass Spectrometry (LC/LC-MS/MS) for Large-Scale Protein Analysis: The Yeast Proteome," *J. Proteome Res.* 2: 43-50.

Figure 5A:
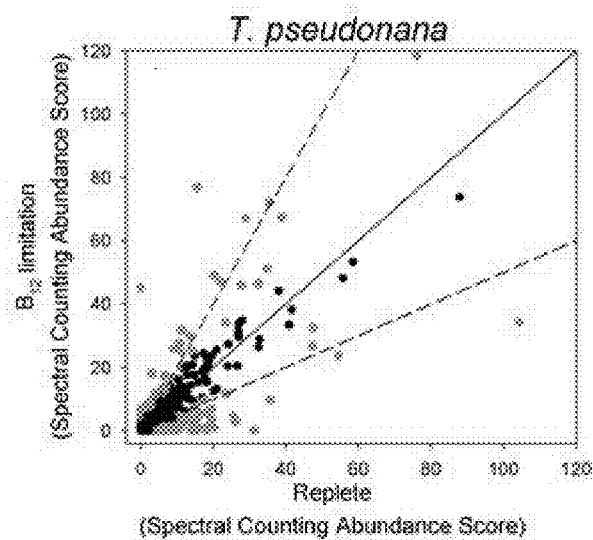
FIGS. 5A-5H depict pairwise comparisons of detected *T. pseudonana* and *P. tricornutum* proteomes for the different treatment groups.
Figure 5B:
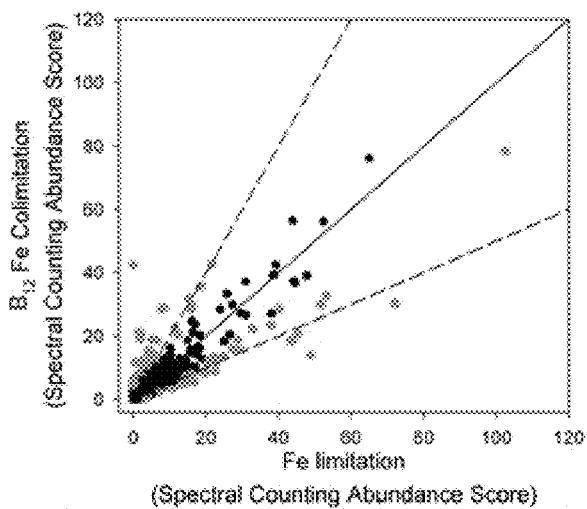
Figure 5C:
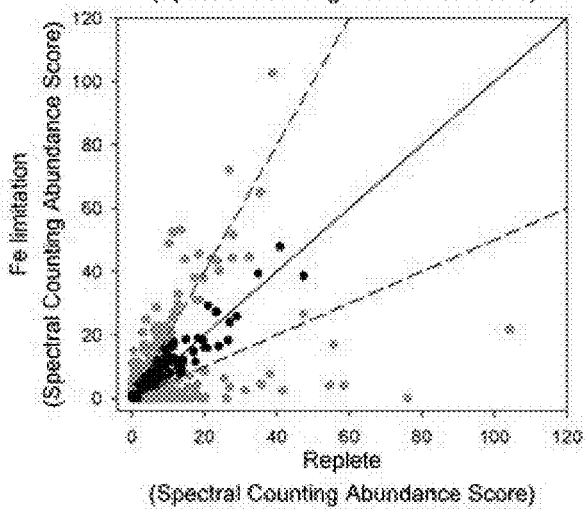
Figure 5D:
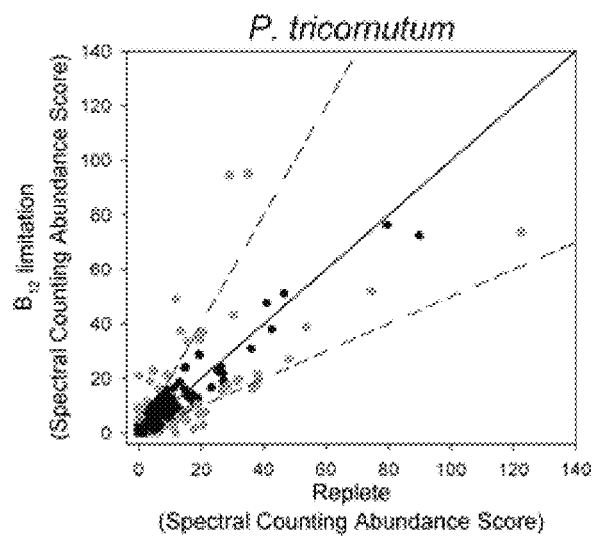
Figure 5E:
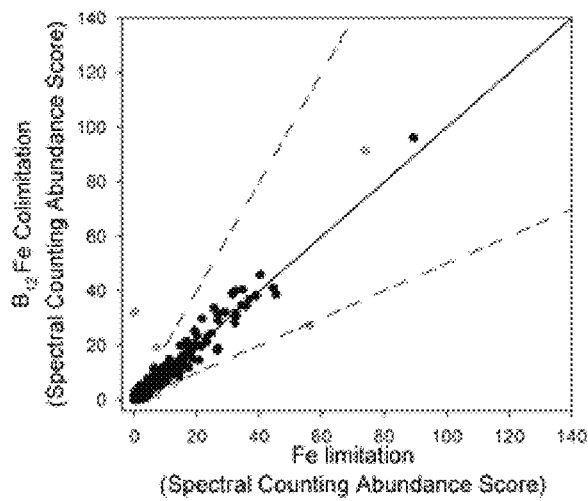
Figure 5F:
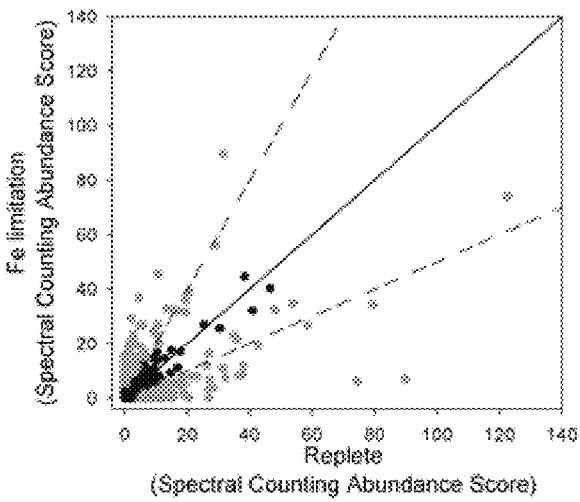
Figure 5G:
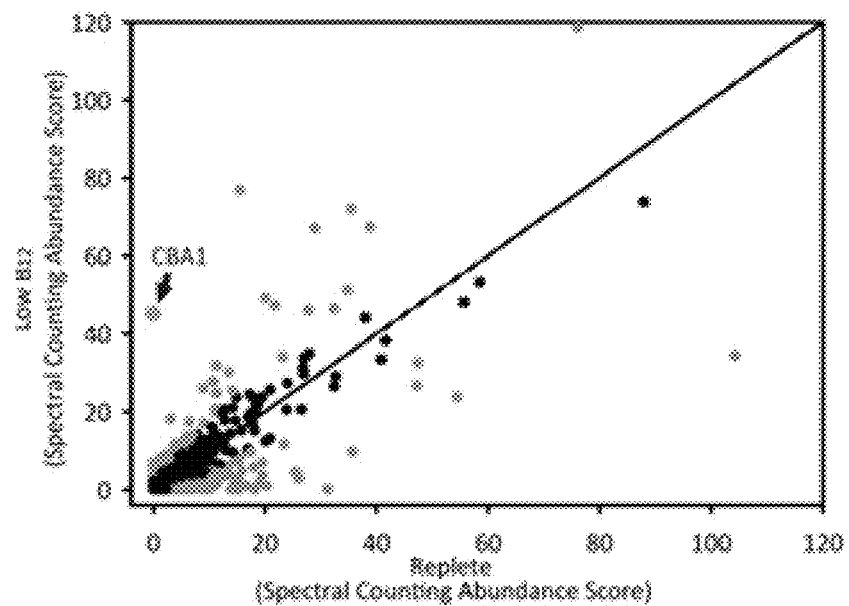
Figure 5H:
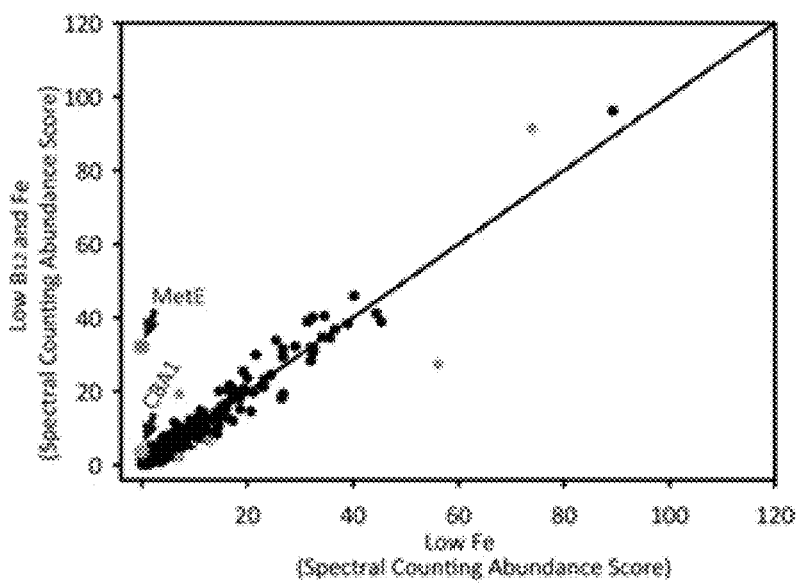

As shown in FIGS. 5A-5H, each point is an identified protein with the mean of its technical triplicate abundance scores in one treatment plotted against the mean of the abundance scores in another treatment. The solid line is 1:1 abundance and the dashed lines denote 2:1 and 1:2 abundance. Proteins plotted as black circles are not significantly differentially abundant (Fisher Exact Test p<0.01) and those plotted as grey circles are differentially abundant. FIGS. 5A and 5G show the same comparison, low $B_{12}$ versus replete treatment in *T. pseudonana*, except FIG. 5G identifies the CBA1 protein. FIGS. 5E and 5H show the same comparison, low $B_{12}$/Fe versus low Fe treatment in *P. tricornutum*, except FIG. 5H identifies the CBA1, Tp11697 and Pt 48322 proteins and MetE protein. In the cobalamin-requiring diatom *T. pseudonana*, 19% of detected proteins were significantly differentially abundant under cobalamin starvation compared to the replete control (Table 2, FIG. 5A, 5G). This suggests that the diatom conducts a significant rearrangement of cellular function when grown under cobalamin limitation. Though some of these changing proteins are likely responding to the accompanying growth rate depression, there are many that display different behavior under cobalamin versus iron limitation and have putative functions suggesting they are directly related to $B_{12}$ metabolism (Table 3 and Table 4). Even though iron limitation induced in this study had a much more severe impact on growth rate than cobalamin limitation did, changes induced in the *T. pseudonana* proteome by cobalamin starvation were nearly as large as those induced by iron limitation (Table 2, FIG. 5A-5H). In contrast, *P. tricornutum*, which can accomplish methionine synthesis without the use of the vitamin and therefore had a flexible cobalamin demand, displayed a relatively minor proteome change in response to cobalamin scarcity (see, Table 2, FIG. 5A-5H). Protein abundance changes under the combined low $B_{12}$ and low iron treatment versus low iron alone showed a similar pattern. *T. pseudonana*, even under severe iron limitation, rearranged its protein complement significantly to manage cobalamin starvation while *P. tricornutum* changed the abundance of less than 1% of the proteins in its detected proteome (see, Table 2, FIGS. 5E and 5H). The small change detected between these two treatments in *P. tricornutum* reflects both the minimal metabolic rearrangement induced in these cells as well as the efficacy of the proteomic analyses applied here.

TABLE 2

Impact of $B_{12}$ and Fe Starvation on Diatom Growth, Proteomes, and Transcriptomes

| % proteins differentially abundant | Low $B_{12}$ vs Replete | Low $B_{12}$Fe vs Low Fe | Low Fe vs Replete |
|---|---|---|---|
| *T. pseudonana* | 19 | 18 | 30 |
| *P. tricornutum* | 5 | 1 | 20 |
| % transcripts differentially abundant | Low $B_{12}$ vs Replete | Low $B_{12}$Fe vs Low Fe | Low Fe vs Replete |
| *T. pseudonana* | 26 | 5 | 25 |
| *P. tricornutum* | 6 | 2 | 16 |
| fold cell yield decrease | Low $B_{12}$ vs Replete | Low $B_{12}$Fe vs Low Fe | Low Fe vs Replete |
| *T. pseudonana* | 1.8 +/− 0.1 | 1.0 +/− 0.1 | 3.4 +/− 0.1 |
| *P. tricornutum* | 1.1 +/− 0.1 | 1.6 +/− 0.2 | 4.1 +/− 0.4 |
| fold growth rate decrease | Low $B_{12}$ vs Replete | Low $B_{12}$Fe vs Low Fe | Low Fe vs Replete |
| *T. pseudonana* | 1.2 +/− 0.1 | 1.2 +/− 0.1 | 2.0 +/− 0.1 |
| *P. tricornutum* | 1.0 +/− 0.1 | 1.3 +/− 0.1 | 2.8 +/− 0.3 |

Table 2 shows pair wise comparisons of growth rate, cell yield, protein abundance changes and transcript abundance changes between low cobalamin versus replete growth, low cobalamin with low iron versus low iron growth, and low iron versus replete growth in two diatoms. The percentage of proteins changing in abundance was calculated from the total number of identified proteins and those that had significantly different abundance between the two treatments compared (Fisher Exact test p<0.01). The percentage of differentially abundant transcripts was calculated from the number of transcripts mapped to genomic locations that had log 2 fold change RPKM values greater than 1 or less than −1 between the two treatments. Fold cell yield and growth rate decreases were calculated by determining the fold change between the maximum cell density or cell-specific growth rate in each treatment and are given as means of biological triplicates±one standard deviation. Growth rates are cell specific and were calculated from the following time periods: *T. pseudonana* high iron: days 2-4 and low iron: days 3-5; *P. tricornutum* high iron: days 3-6 and low iron: days 5-7.

TABLE 3

Proteins More Abundant Under Two Types of Cobalamin Limitation

| JGI Protein ID | Description | Low B$_{12}$Fe | Low Fe | Low B$_{12}$ | Replete | JGI Protein ID | Low B$_{12}$Fe | Low Fe | Low B$_{12}$ | Replete |
|---|---|---|---|---|---|---|---|---|---|---|
| *T. pseudonana* | | | | | | Homolog in *P. tricornutum* | | | | |
| 270138 | possible glutamine synthetase | 4.0 | 0.0 | 118.5 | 76.1 | 22357 | 91.3 | 74.0 | 73.5 | 122.5 |
| 269942 | serine hydroxymethyltransferase, SHMT2, mitochondrial | 29.5 | 16.1 | 49.1 | 20.2 | 54015 | 8.3 | 7.6 | 19.7 | 32.4 |
| 22483 | unknown, conserved protein | 31.8 | 15.2 | 25.9 | 9.1 | 54686 | 31.0 | 22.0 | 0.7 | 2.0 |
| 11697 | unknown, conserved protein (like Pt 48322), CBA1 | 42.4 | 0.0 | 45.1 | 0.0 | 48322 | 1.9 | 0.0 | 8.5 | 0.0 |
| 24346 | unknown protein | 22.5 | 11.4 | 25.2 | 14.2 | N/A | | | | |
| 26031 | serine hydroxymethyltransferase, SHMT1, cytosolic | 19.0 | 1.9 | 27.6 | 10.8 | 18665 | 19.2 | 7.2 | 21.0 | 0.0 |
| 42612 | pyridoxal 5'-phosphate (PLP) synthase | 18.9 | 5.0 | 18.0 | 3.1 | 29885 | 0.3 | 0.0 | 2.5 | 0.5 |
| 23556 | unknown protein | 12.7 | 5.8 | 14.0 | 7.1 | N/A | | | | |
| 23657 | Globin-like protein | 6.6 | 2.2 | 7.2 | 1.1 | 46237 | 0.0 | 0.0 | 0.0 | 0.0 |
| 24639 | unknown protein, conserved domains | 5.4 | 1.3 | 8.0 | 1.4 | 42442 | 1.6 | 1.6 | 1.1 | 0.9 |
| 22096 | unknown protein with heme binding domain | 3.2 | 0.0 | 8.0 | 2.8 | bd1699 | 0.0 | 0.0 | 0.0 | 0.0 |
| 1896 | unknown protein | 5.5 | 1.3 | 6.0 | 1.4 | N/A | | | | |
| 41733 | Thiamine biosynthesis protein ThiC | 3.3 | 0.0 | 5.2 | 0.0 | 38085 | 0.0 | 0.0 | 5.5 | 0.4 |
| 1738 | Clp-like protease | 2.2 | 0.0 | 2.4 | 0.0 | 44382 | 1.6 | 1.3 | 0.0 | 0.0 |
| *P. tricornutum* | | | | | | Homolog in *T. pseudonana* | | | | |
| 18665 | serine hydroxymethyltransferase, SHMT1, cytosolic | 19.2 | 7.2 | 21.0 | 0.0 | 26031 | 19.0 | 1.9 | 27.6 | 10.8 |
| 28056 | MetE, Methionine synthase, cobalamin independent | 32.0 | 0.0 | 9.6 | 0.0 | N/A | | | | |
| 48322 | unknown, conserved protein (like Tp11697), CBA1 | 1.9 | 0.0 | 8.5 | 0.0 | 11697 | 42.4 | 0.0 | 45.1 | 0.0 |

Table 3 shows proteins present at higher concentrations and significantly differentially abundant (p<0.01) in both low B$_{12}$ compared to replete and low B$_{12}$ with low Fe compared to low Fe alone in the proteomic dataset, shown with a putative functional description and average spectral counting scores for each treatment. The average spectral counting scores for the homologous protein in the other diatom are also given. The two proteins highlighted in bold have protein abundances that appear to be driven by B$_{12}$-availability in both diatoms. N/A denotes the absence of a homologous protein encoded in the genome.

TABLE 4

Proteins More Abundant Under Cobalamin Limitation and Not Iron Limitation

| Protein ID | Description | Low B$_{12}$Fe | Low Fe | Low B$_{12}$ | Replete | JGI Protein ID | Low B$_{12}$Fe | Low Fe | Low B$_{12}$ | Replete |
|---|---|---|---|---|---|---|---|---|---|---|
| *T. pseudonana* | | | | | | Homolog in *P. tricornutum* | | | | |
| 21815 | methionine S-adenosyl transferase (MetK) | 33 | 26 | 67 | 29 | bd 913 | 21 | 23 | 95 | 35 |
| YP_874528.1 | ATP synthase, beta chain, thylakoid | 42 | 39 | 51 | 35 | YP_874407.1 | 34 | 26 | 43 | 30 |
| 40771 | enolase | 30 | 27 | 34 | 23 | bd1572 | 12 | 11 | 19 | 31 |
| 27997 | dihydroxyacid dehydratase | 25 | 16 | 20 | 11 | 20547 | 4 | 5 | 5 | 5 |
| 39299 | ADP-ribosylation factor GTPase | 16 | 18 | 20 | 12 | 43251 | 11 | 15 | 19 | 13 |
| 1093 | conserved unknown protein | 13 | 13 | 25 | 11 | 43233 | 4 | 3 | 6 | 10 |
| 37032 | ribosomal protein 6, 60S large ribosomal subunit | 15 | 15 | 17 | 9 | 34146 | 9 | 9 | 2 | 3 |
| 4875 | Pyruvate kinase | 10 | 9 | 14 | 6 | 22404 | 2 | 2 | 5 | 2 |
| 30193 | Urease | 10 | 8 | 11 | 5 | 29702 | 4 | 4 | 2 | 1 |
| 16169 | Pyruvate dehydrogenase E1, alpha subunit | 10 | 5 | 11 | 4 | 55035 | 2 | 1 | 0 | 0 |
| 3018 | Phosphoserine aminotransferase | 10 | 5 | 10 | 4 | 42458 | 37 | 37 | 23 | 5 |
| 4462 | unknown protein | 7 | 5 | 8 | 2 | 46709 | 1 | 0 | 0 | 2 |
| 4439 | unknown protein | 1 | 0 | 13 | 6 | 42494 | 1 | 2 | 3 | 3 |

TABLE 4-continued

Proteins More Abundant Under Cobalamin Limitation and Not Iron Limitation

| Protein ID | Description | Low $B_{12}$Fe | Low Fe | Low $B_{12}$ | Replete | JGI Protein ID | Low $B_{12}$Fe | Low Fe | Low $B_{12}$ | Replete |
|---|---|---|---|---|---|---|---|---|---|---|
| 21306 | conserved unknown protein | | 4 | 8 | 1 | N/A | | | | |
| 5026 | ATPase, gamma subunit | 1 | 0 | 12 | 5 | 18398 | 10 | 7 | 6 | 0 |
| 21887 | unknown protein | 5 | 2 | 6 | 2 | N/A | | | | |
| 517 | 20S proteasome subunit alpha type 1 | 3 | 0 | 6 | 2 | 45998 | 2 | 1 | 4 | 4 |
| 9947 | conserved unknown protein | 4 | 2 | 5 | 1 | N/A | | | | |
| 21965 | conserved unknown, similar to disulfide isomerase | 5 | 2 | 4 | 1 | 47306 | 1 | 0 | 2 | 4 |
| 20923 | conserved unknown protein | 4 | 1 | 4 | 1 | 6606 | 0 | 0 | 0 | 0 |
| 24738 | unknown protein | 1 | 0 | 6 | 0 | N/A | | | | |
| 22127 | unknown protein | 4 | 1 | 4 | 1 | N/A | | | | |
| 24708 | unknown protein, multicopy | 2 | 2 | 3 | 0 | 44663 | 0 | 0 | 0 | 0 |
| 21260 | unknown protein, multicopy | 3 | 2 | 2 | 0 | 47664 | 0 | 0 | 0 | 0 |
| 11175 | conserved unknown protein | 1 | 0 | 4 | 0 | N/A | | | | |
| 22442 | unknown protein | 1 | 0 | 2 | 0 | 43378 | 0 | 0 | 0 | 0 |
| 23511 | unknown protein | 1 | 0 | 3 | 0 | N/A | | | | |
| *P. tricornutum* | | | | | | Homolog in *T. pseudonana* | | | | |
| 54465 | ISIP2A, iron stress induced protein | 78 | 144 | 268 | 142 | N/A | | | | |
| 23658 | Flavodoxin, plastid targeted | 18 | 27 | 152 | 59 | 19141 | 3 | 1 | 4 | 2 |
| bd 913 | methionine S-adenosyl transferase (MetK) | 21 | 23 | 95 | 35 | 21815 | 33 | 26 | 67 | 29 |
| 46547 | multicopy hypothetical protein | 0 | 0 | 49 | 12 | N/A | | | | |
| 51242 | adenosine kinase-like protein | 8 | 5 | 19 | 4 | 644 | 20 | 2 | 20 | 13 |
| 44603 | ATP synthase | 4 | 4 | 7 | 1 | 29359 | 11 | 5 | 3 | 7 |
| 47395 | ascorbate peroxidase | 1 | 2 | 9 | 1 | 262753 | 15 | 4 | 15 | 18 |
| 38085 | Thiamin biosynthesis protein | 0 | 0 | 5 | 0 | 41733 | 3 | 0 | 5 | 0 |

Table 4 shows proteins in higher concentration and significantly differentially abundant ($p<0.01$) in low $B_{12}$ compared to replete and not in higher concentration and significantly differentially abundant in low Fe compared to replete are shown with a description and average spectral counting scores for each treatment. The average spectral counting scores for the homologous protein in the other diatom are also given. The proteins highlighted in gray are driven by $B_{12}$-availability in both diatoms. N/A denotes the absence of a homologous protein encoded in the genome.

C. RNA Extraction, Sequence Data Acquisition and Analysis: RNA was purified using the Trizol reagent (Life Technologies; Carlsbad, Calif.) according to the manufacturer's instructions, treated with DNase, and run through RNeasy spin columns (Qiagen; Valencia, Calif.) for additional purification. RNA quantity and quality was evaluated with a Quibit fluorometer (Life Technologies) and 2100 Bioanalyzer (Agilent Technologies; Santa Clara, Calif.). 50 ng of total RNA was amplified using the MessageAmp II aRNA Amplification Kit (Life Technologies). Amplified aRNA was then used to prepare SOLiD Total RNA-Seq Kit (Life Technologies) libraries, according the instructions of the manufacturer. Briefly, PolyA selected RNA was fragmented and quantified, followed by adapter ligation and cDNA synthesis. cDNA was amplified and purified. Libraries with unique barcodes (arising from the adapters) were pooled prior to dilution and sequencing. Computational analyses were performed with the *Phaeodactylum tricornutum* genome, version 2.0 ([http://genome.jgi-psf.org/Phatr2/Phatr2.home.html]), and the *Thalassiosira pseudonana* genome, version 3.0 ([http://genome.jgi-psf.org/Thaps3/Thaps3.home.html]). Unmasked versions of the genomes were used in this study. The filtered gene models for the chromosomes and the unmapped transcripts were concatenated for use as a reference during RNA-Seq analysis. Functional annotations of the filtered gene models were obtained from a database created and maintained at JCVI (PhyloDB). The raw SOLiD sequence data was mapped to the unmasked reference genome into BAM format files using LifeScope Genomic Analysis Software (LifeTechnologies). The reads from the replicate samples for each condition were merged, and then aligned against the reference genome for visualization of the read coverage with the Integrated Genomics Viewer, version 2.0 (http://www.broadinstitute.org/igv). The RNA-Seq Analysis pipeline in CLCbio Genomics Workbench, version 4.7.2, was utilized to generate the RPKM values for each sample. CLCbio Genomics Workbench was first used to extract the nucleotides sequences from the BAM format sequence files before input into the CLC RNA-Seq Analysis pipeline. The RNA-Seq analysis was run with default settings, except for the use of 0.8 as the minimum length fraction, and 0.8 as the minimum similarity fraction. The RPKM values of the RNA-Seq analysis were output as an Excel spreadsheet, which was manually manipulated. In particular, the fold change for the sets of conditions was calculated by dividing the median RPKM values of the replicates, followed by a log 2 transformation. The resulting values were sorted by the fold change for low cobalamin compared to replete conditions. Approximately 60 genes with the highest fold change were plotted as a heatmap in MATLAB.

Figure 6A:
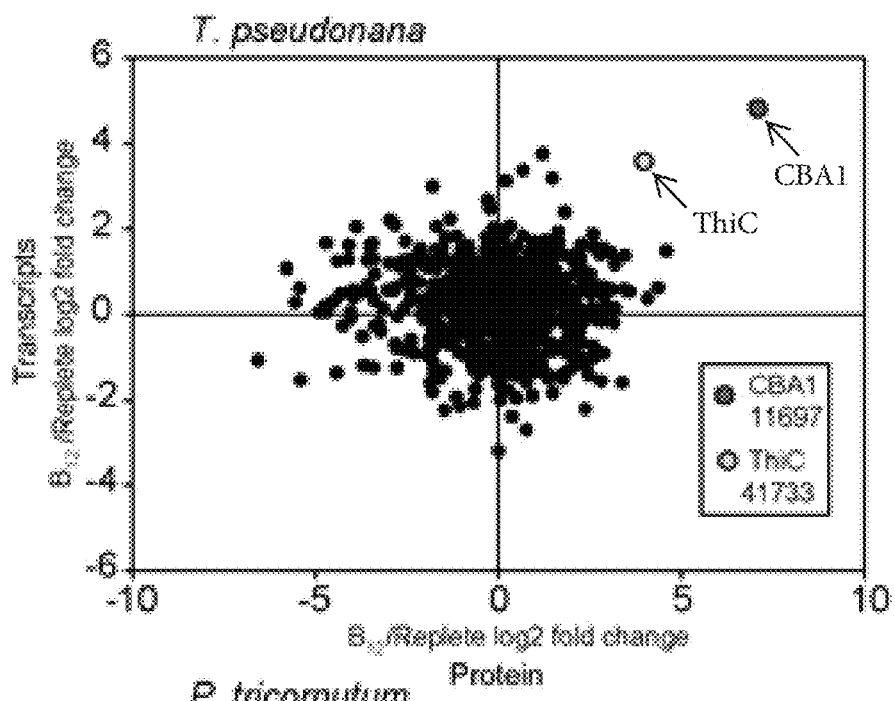
FIGS. 6A and 6B depict comparative proteome and transcriptome responses to cobalamin deprivation for *T. pseudonana* and *P. tricornutum*.
Figure 6B:
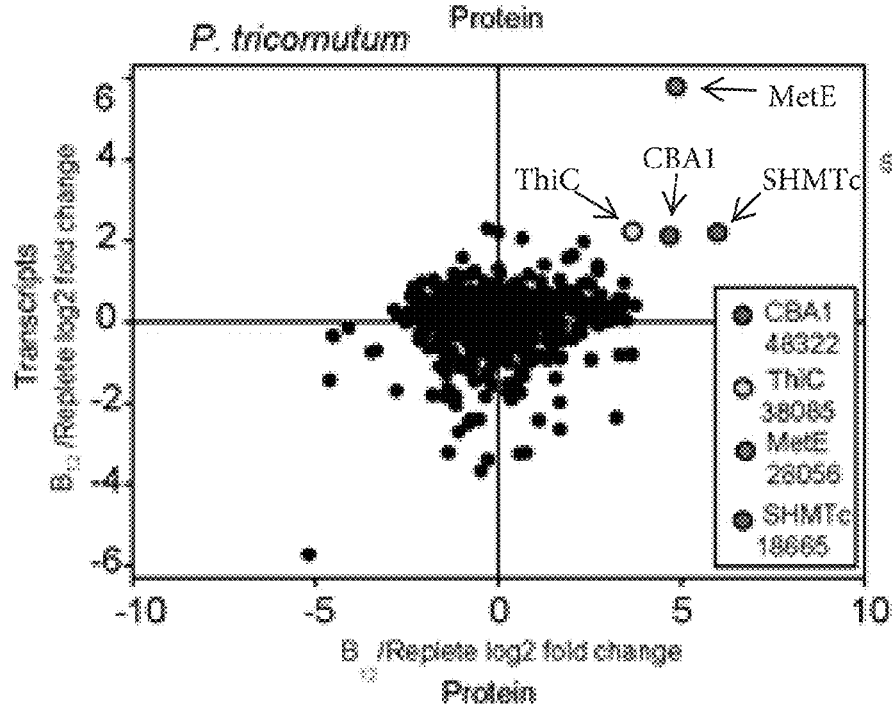
Figure 6C:
FIG. 6C is a heat map display of select *T. pseudonana* transcript responses to cobalamin and iron starvation.

FIGS. 6A and 6B depict the fold change ($log_2$) between the transcript abundance (RPKM value) in the cobalamin starved and replete treatments on the y-axis and the fold change ($log_2$) between the protein abundance (spectral counting score) in the cobalamin starved and replete treatments on the x-axis. For the protein data, any null values were replaced with a spectral counting score of 0.33, the lowest measurable value in the experiments, to facilitate the computation. Generally, coherence between the proteome and transcriptome responses is limited to specific proteins that display enhanced abundance under cobalamin starvation in both the transcript and protein pool. These include CBA1, MetE, ThiC, and cytosolic serine hydroxymethyltransferase (SHMTc) which are labeled in FIG. 6B. FIG. 6C is a heat map displaying select *T. pseudonana* transcript responses to cobalamin and iron starvation. Fold change RPKM (reads per kilobase of transcript per million mapped) values are shown for the low iron versus replete, low $B_{12}$ with low Fe versus low Fe, low $B_{12}$ with low Fe versus replete and low $B_{12}$ versus replete treatments, with up-regulation to down-regulation denoted on the scale from 4 to −1. The genes were selected by high-to-low ordering of the $log_2$ transformed fold change RPKM values and sorted by the comparison between low $B_{12}$ versus replete treatments. Gene products highlighted in FIG. 6A (ThiC, CBA1) are also highlighted in FIG. 6C. FIG. 6C shows that CBA1 expression is highly upregulated when vitamin $B_{12}$ is provided in low concentrations.

RNA-seq transcriptomic analyses revealed trends in diatom molecular physiology that were broadly coherent with those observed via proteomics; a similar percentage of the measured transcriptome and proteome changed as a result of each starvation scenario (Table 2). Given the deep coverage of the diatom genomes obtained via these RNA-seq analyses (10,404 genes with mapped transcripts in *P. tricornutum*, 11,778 in *T. pseudonana*) and the coherence in the proteome and transcriptome datasets, these data suggest that the cobalamin-requiring diatom *T. pseudonana* conducts a significant rearrangement of its molecular physiology under cobalamin starvation. The diatom with a flexible cobalamin demand, *P. tricornutum*, changed a much smaller proportion of transcript abundances in response to cobalamin starvation than the cobalamin-requiring *T. pseudonana*, also consistent with changes observed in the proteome.

Example 2

Identification of a Cobalamin Acquisition Protein

A. Cobalamin Acquisition Protein 1: In the shotgun proteomic analysis of Example 1, the protein that showed the largest response to cobalamin starvation in *T. pseudonana* was a previously uncharacterized hypothetical protein. The protein was identified as a cobalamin acquisition protein, as described below, and called CBA1 (cobalamin acquisition protein 1; FIG. 5G, FIG. 7A). A protein homologous to the *T. pseudonana* CBA1 was detected in the *P. tricornutum* global proteome, also only under cobalamin deprivation, suggesting that this protein may play a similar role in both diatoms and that it is likely involved in cobalamin metabolism (FIG. 5H, FIG. 7A).

Selected reaction monitoring (SRM) was conducted as previously described (Saito et al. (2011) "Iron Conservation by Reduction of Metalloenzyme Inventories in the Marine Diazotroph Crocosphaera watsonii," *Proc. Natl. Acad. Sci. USA* 108: 2184-2189) for two tryptic peptides found to be unique to CBA1 in *P. tricornutum*; FFSVFFNK (SEQ ID NO: 18), Pt48322_1; EHTANQVVEAAESR (SEQ ID NO: 19), Pt48322_2. Isotopically-labeled versions of each tryptic peptide (Sigma-Aldrich) (Stemmann et al. (2001) "Dual Inhibition of Sister Chromatid Separation at Metaphase," *Cell* 107: 715-726) were used as internal standards (FFS[V_C13N15]FFNK (SEQ ID NO: 44), EHTANQ[V_C13N15]VEAAESR (SEQ ID NO: 45)). Standard curves displaying the linear behavior of each peptide are given in FIGS. 8A-B.

Figure 8A:
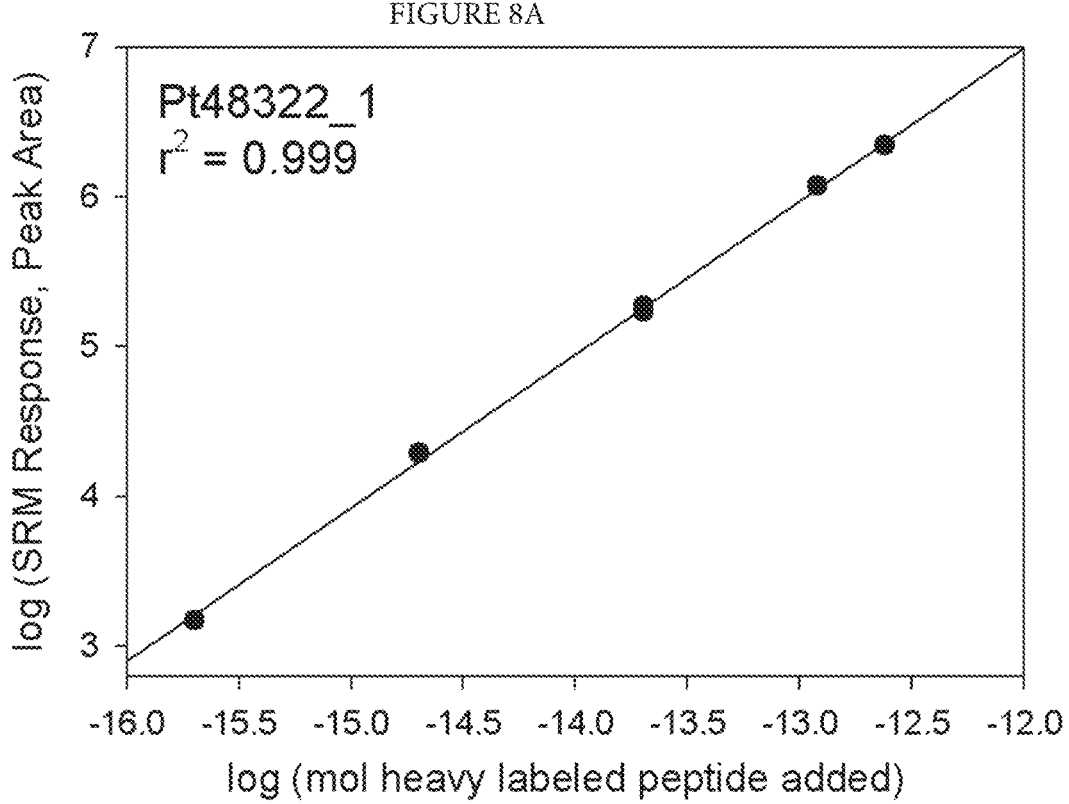
FIGS. 8A and 8B depict calibration curves for selected reaction monitoring detection of CBA1 peptides (Pt48322_1 and Pt48322_2).
Figure 8B:
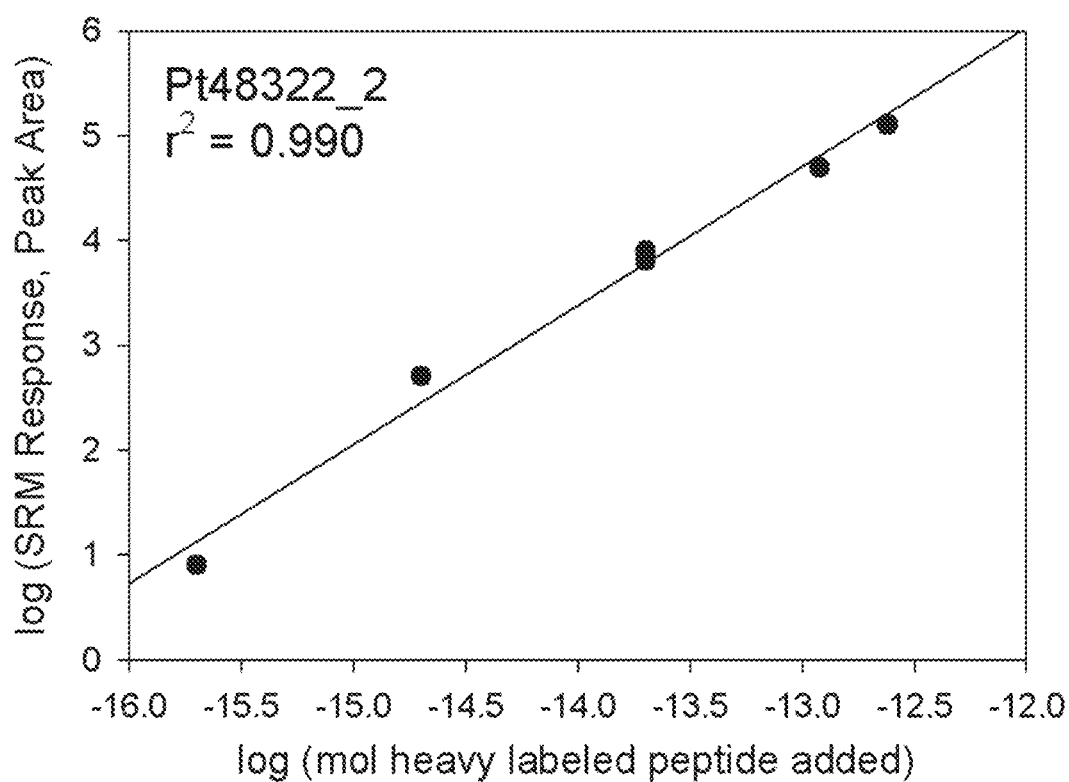

Briefly, 20 fmol of heavy isotope labeled versions of each peptide were added to diatom peptide extracts (1 μg total protein) and analyzed via SRM using a Thermo Vantage TSQ Triple Quadrapole Mass Spectrometer with the HPLC and ion source as described above for shotgun mass spectrometry. FIGS. 8A-B show the SRM response (peak area, sum of product ion intensities) plotted against moles of stable isotope-labeled (heavy) version of each CBA1 peptide added. Linear regressions are shown in the solid line and the coefficients of variance for each are given. For both peptides, the response is linear over four orders of magnitude, and the lowest concentrations detected were 0.2 fmol.

Figure 7C:
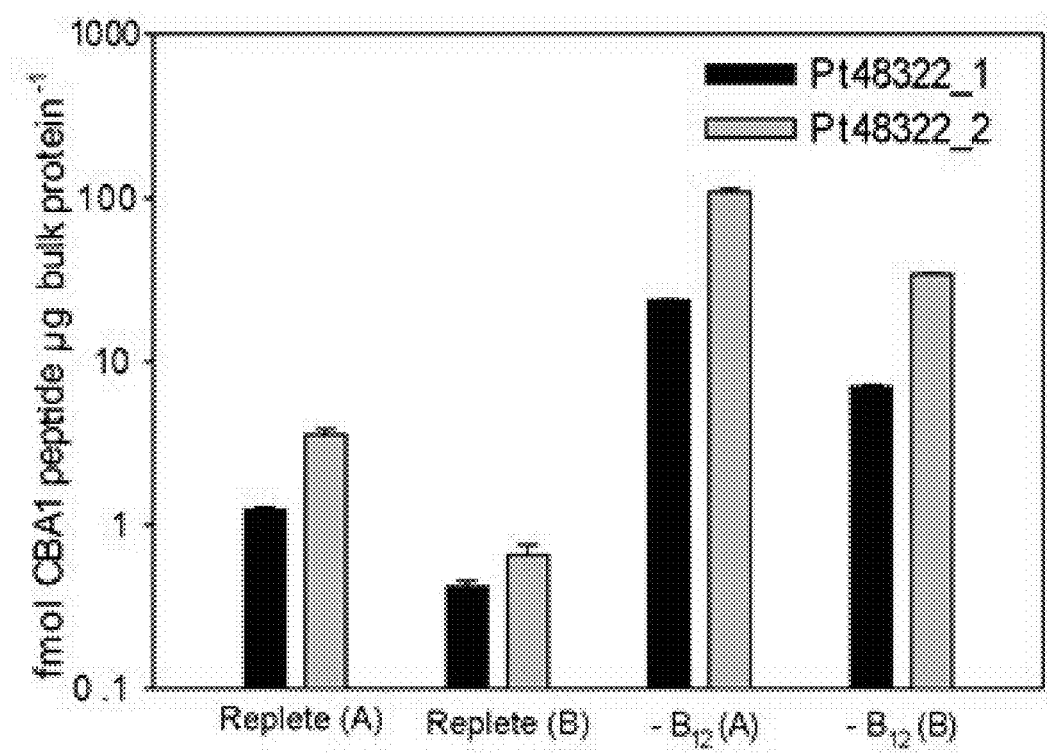

SRM mass spectrometry confirmed the shotgun proteomic results through absolute protein quantification via the more sensitive and quantitative technique, revealing that the concentration of CBA1 protein was between 10 and 160-fold higher under low $B_{12}$ availability in *P. tricornutum* (FIG. 7C). These SRM assays were developed by choosing tryptic peptides diagnostic for (indicative of) CBA1 and designing specific mass spectrometry detection assays for each diagnostic peptide, as previously described (Saito et al. (2011) supra) (Table 5). This method involves the use of stable isotopically labeled versions of two diagnostic tryptic peptides (Pt48322_1 and Pt48322_2) that were employed as internal standards. Table 5 shows the parent to product ion transitions monitored, collision energies applied, the chromatographic retention times over which the peptides were monitored, as well as the S-lens values employed for peptide measurements.

TABLE 5

Selected Reaction Monitoring Conditions for Absolute Quantification of CBA1

| Protein | Peptide | Peptide name | Parent ion + charge | Parent (m/z) | Product (m/z) | Collision Energy | Start time (min) | Stop time (min) | S-lens value |
|---|---|---|---|---|---|---|---|---|---|
| Pt48322 | FFS[V_C13N15]FFNK (SEQ ID NO: 44) | Pt48322_1heavy | 2 | 521.2686 | 747.3930 | 15 | 16.80 | 18.80 | 110 |
| | | | 2 | 521.2686 | 660.3610 | 15 | 16.80 | 18.80 | 110 |
| | | | 2 | 521.2686 | 555.2900 | 16 | 16.80 | 18.80 | 110 |
| Pt48322 | FFSVFFNK (SEQ ID NO: 18) | Pt48322_1native | 2 | 518.2682 | 741.3930 | 15 | 16.80 | 18.80 | 110 |
| | | | 2 | 518.2682 | 654.3610 | 15 | 16.80 | 18.80 | 110 |
| | | | 2 | 518.2682 | 555.2900 | 16 | 16.80 | 18.80 | 110 |
| Pt48322 | EHTANQ[V_C13N15]VEAAESR (SEQ ID NO: 45) | Pt48322_2heavy | 2 | 773.8712 | 1280.6335 | 21 | 10.10 | 12.10 | 136 |
| | | | 2 | 773.8712 | 1179.5858 | 24 | 10.10 | 12.10 | 136 |
| | | | 2 | 773.8712 | 866.4472 | 25 | 10.10 | 12.10 | 136 |
| | | | 2 | 773.8712 | 761.3788 | 25 | 10.10 | 12.10 | 136 |
| Pt48322 | EHTANQVVEAAESR (SEQ ID NO: 19) | Pt48322_2native | 2 | 770.8712 | 1274.6335 | 21 | 10.10 | 12.10 | 136 |
| | | | 2 | 770.8712 | 1173.5858 | 24 | 10.10 | 12.10 | 136 |
| | | | 2 | 770.8712 | 860.3788 | 25 | 10.10 | 12.10 | 136 |
| | | | 2 | 770.8712 | 761.3788 | 25 | 10.10 | 12.10 | 136 |

Figure 9A:
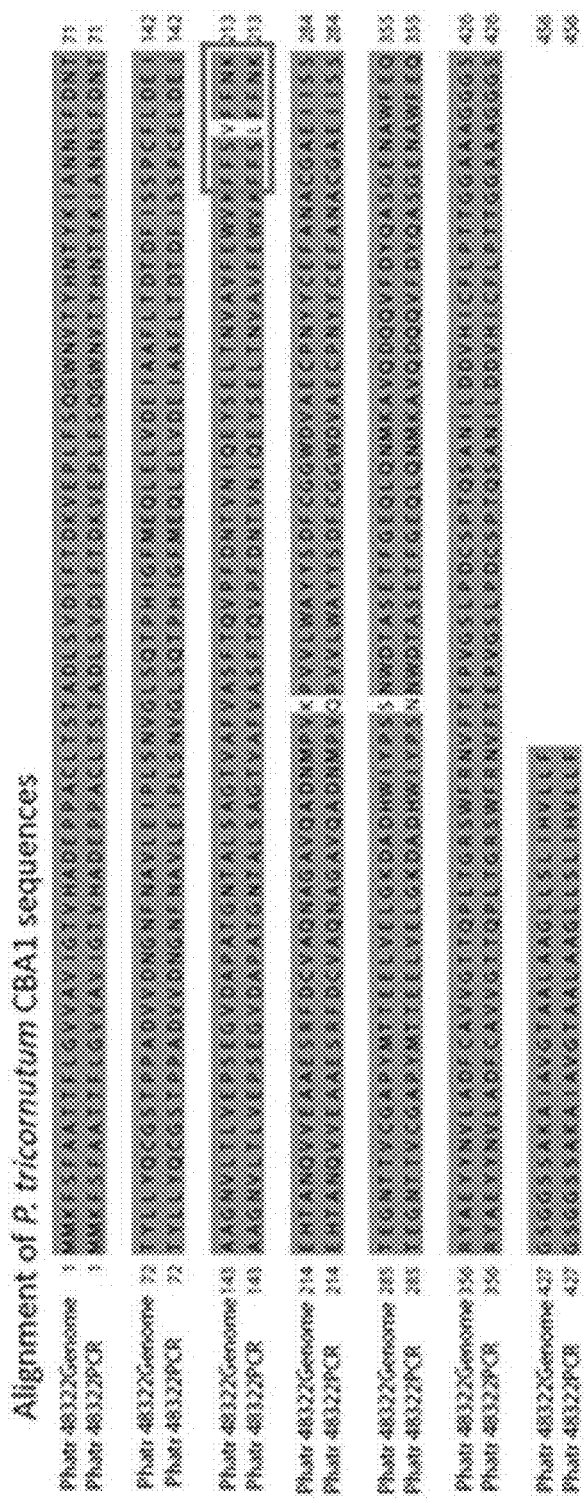
FIG. 9A depicts two allelic versions of a *P. tricornutum* CBA1 protein: (1) from the genome sequencing project, protein 48322 (SEQ ID NO: 48), and (2) the other translated from nucleic acid sequences amplified from cobalamin starved *P. tricornutum* cDNA (SEQ ID NO: 49).
Figure 9B:
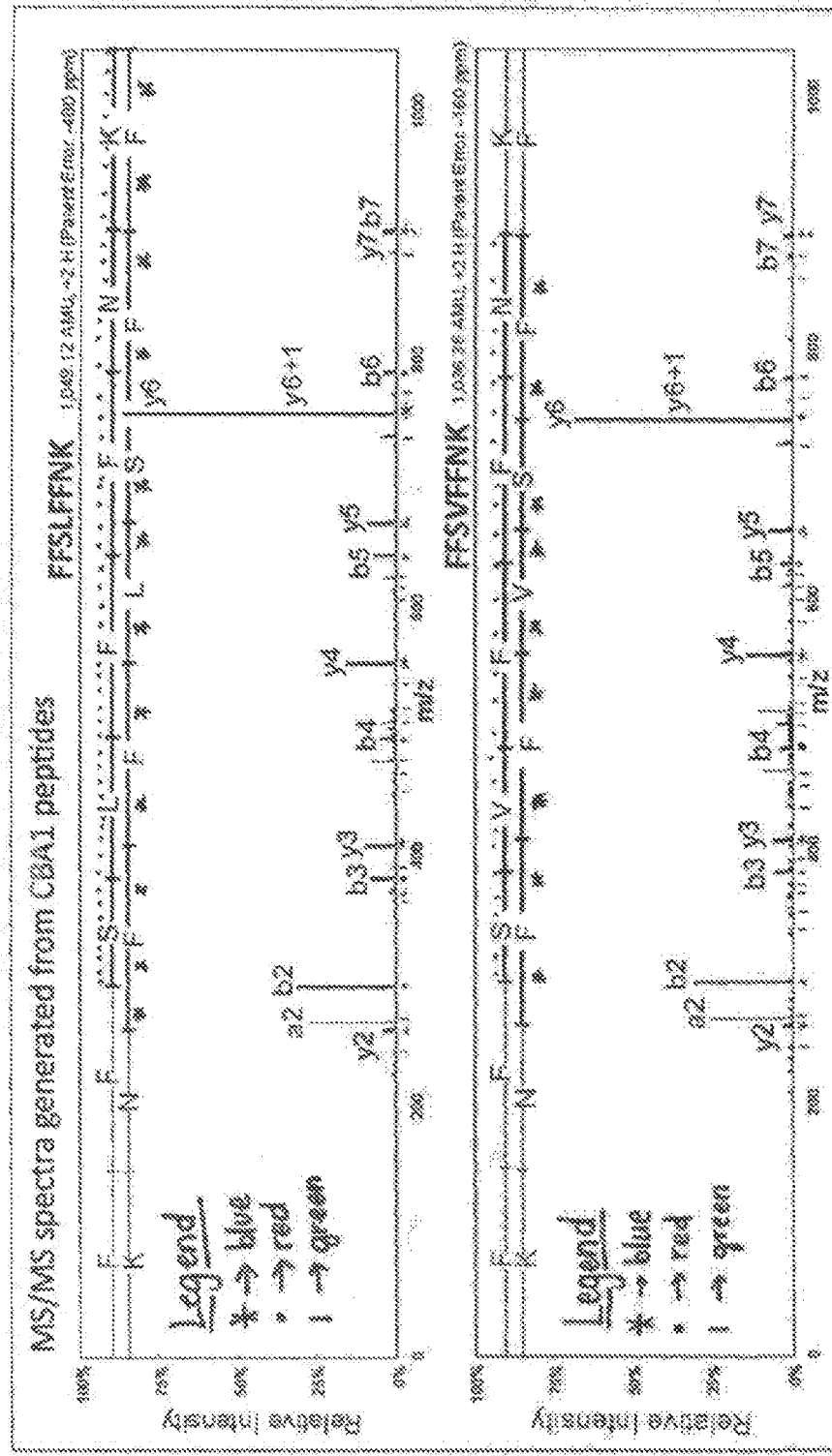
FIG. 9B depicts the product ion (MS/MS) mass spectra generated via LTQ-MS from peptides indicative of each form of CBA1, with y ions represented by lines labeled with (*) (blue); b ions represented by lines labeled with (•) (red); and other associated ions represented by lines labeled with (|) (green).

Each diagnostic tryptic peptide behaved linearly over four orders of magnitude (FIGS. 8A-B) and allowed for absolute quantification of each of these peptides, both generated from the CBA1 amino acid sequence, in *P. tricornutum* peptide samples. However, one peptide, Pt48322_2, was measured at consistently higher abundance in *P. tricornutum* than the other diagnostic peptide, Pt48322_1 (FIG. 7C). Careful examination of nucleic acid sequences amplified from cobalamin-limited *P. tricornutum* RNA extracts revealed that this variability was attributable to single nucleotide polymorphisms (SNPs) within allelic copies of the CBA1 coding sequences (CDS) of this diploid diatom genome. Diatoms possess two copies of each chromosome and sequence analysis revealed that there are minutely different versions of the gene encoding CBA1 on each of these copies. These slightly different genes produce CBA1 protein with amino acid sequences that differ by three amino acid residues. The diagnostic tryptic peptide target Pt48322_1 contains one of these variable amino acid residues and hence is encoded by one of the two chromosomal copies, while the other peptide target, Pt48322_2, does not contain a variable site and is encoded by both copies (see FIGS. 9A, 9B, 9C, and 9D for details). As shown in FIG. 9A, the amino acid differences in these sequences, which resulted from eight single nucleotide polymorphisms between the coding sequences for these proteins (not shown), are shown in white. The peptides highlighted by the box have one amino acid difference and were both detected via shotgun LTQ MS in this proteome study, suggesting that both allelic copies of the protein are expressed. One of these peptides, FFSVFFNK (SEQ ID NO: 18), was measured via SRM analyses and called Pt48322_1. The abundance of these peptides was consistent with their allelic variation; their abundance was linearly correlated across all samples ($r^2$=0.999 FIG. 10), and Pt48322_2, the peptide encoded by both allelic copies, was more abundant (FIG. 7C). This is therefore an example of canonical gene expression in a diploid genome where allelic copies display similar expression patterns.

Figure 10:
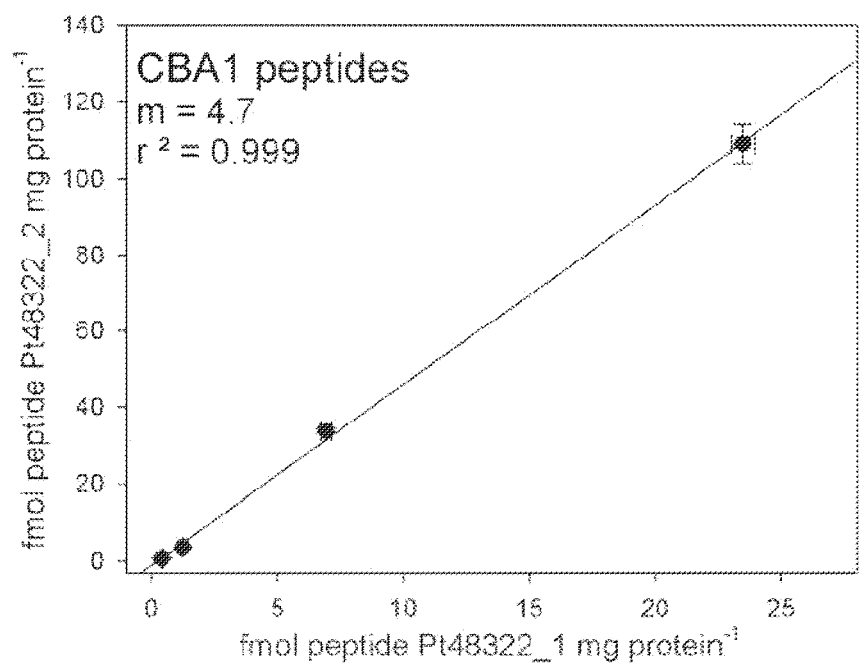
FIG. 10 depicts a comparison of abundance patterns of CBA1-diagnostic peptides in *P. tricornutum*. The peptides were plotted against each other as means of technical triplicate measurements, with error bars representing one standard deviation. Linear regression is shown in the solid line and the coefficients of variance ($r^2$) and the slope (m) are given.

Although the abundance of peptides measuring CBA1 are linearly correlated, the slopes of the lines are not (FIG. 10). This can be partially explained by the fact that peptide Pt48322_2 is encoded by both allelic copies of CBA1 while Pt48322_1 is encoded by only one copy.

In addition to the cobalamin-responsive behavior of CBA1 observed via these two proteomic approaches, RNA sequence analysis revealed that CBA1 transcript abundance patterns were similar to those observed for the corresponding proteins, with much higher CBA1 transcript abundance observed under low cobalamin availability in both *T. pseudonana* and *P. tricornutum* (FIG. 7B). Together, these analyses reveal that CBA1 protein and transcripts display coordinated behavior under cobalamin deprivation (FIGS. 7A-C).

CBA1 has a clear N-terminal signal peptide sequence for secretion (Cello and SignalP-predicted; Nielsen et al. (1997) "Identification of Prokaryotic and Eukaryotic Signal Peptides and Prediction of their Cleavage Sites" *Protein Engineering* 10: 1-6; Yu et al. (2006) "Prediction of Protein Subcellular Localization," *Proteins: Structure, Function and Bioinformatics* 64: 643-651) and no transmembrane domains. It contains a partial conserved domain that is weakly similar to the periplasmic component of a bacterial iron hydroxamate ABC transport system (FepB; N-terminal end is truncated, Pt48322 blastp search E-value 1.33e-4), but the protein otherwise lacks characterized domains. There appear to be homologous versions of CBA1 encoded in all currently sequenced diatom genomes as well as those from other members of the stramenopile lineage, *Ectocarpus siliculosus* and *Aureococcus anophageferens* (Table 6).

TABLE 6

Presence of Proteins Similar to CBA1 in Other Algal and Eukaryotic Genomes from NCBI or the Joint Genome Institute: Blastp vs *P. tricornutum* 48322 with an E-value cutoff of 1e−5

| Genome | Protein ID | E-value | % coverage |
|---|---|---|---|
| *Thalassiosira pseudonana* | 11697 | 4e−57 | 82 |
| *Fragilariopsis cylindrus* | 241429 | 5e−47 | 83 |
| *Fragilariopsis cylindrus* | 246327 | 9e−37 | 71 |
| *Fragilariopsis cylindrus* | 273295 | 8e−27 | 30 |
| *Fragilariopsis cylindrus* | 269995 | 3e−24 | 27 |
| *Aureococcus anophageferens* | 63075 | 2e−31 | 78 |
| *Ectocarpus siliculosus* | CBN74732 | 2e−28 | 80 |
| *Chlamydomonas reinhardtii* | 196738 | 5e−12 | 47 |
| *Chlorella* sp. NC64A | 57728 | 4e−12 | 25 |
| *Volvox carteri f. nagariensis* | 106040 | 1e−11 | 48 |
| *Micromonas pusilla* CCMP1545 | 46842 | 6e−9 | 51 |
| *Micromonas* sp. RCC299 | NONE | | |

TABLE 6-continued

Presence of Proteins Similar to CBA1 in Other Algal and Eukaryotic Genomes from NCBI or the Joint Genome Institute: Blastp vs P. tricornutum 48322 with an E-value cutoff of 1e−5

| Genome | Protein ID | E-value | % coverage |
|---|---|---|---|
| Ostreococcus lucimarinus | 27076 | 1e−9 | 50 |
| Ostreococcus sp. RCC809 | NONE | | |
| Ostreococcus tauri | NONE | | |
| Emiliania huxleyi | NONE | | |
| Phytophthora capsici | NONE | | |
| Phytophthora ramorum | NONE | | |
| Phytophthora sojae | NONE | | |

B. Other Cobalamin-Responsive Proteins: Identification of CBA1 and its abundance patterns in culture suggests that diatoms adjust their molecular physiology to increase capacity for cobalamin acquisition in the face of cobalamin deprivation. Other cobalamin-sensitive transcripts and proteins can be considered in order to identify additional molecular responses to vitamin starvation.

Figure 11:
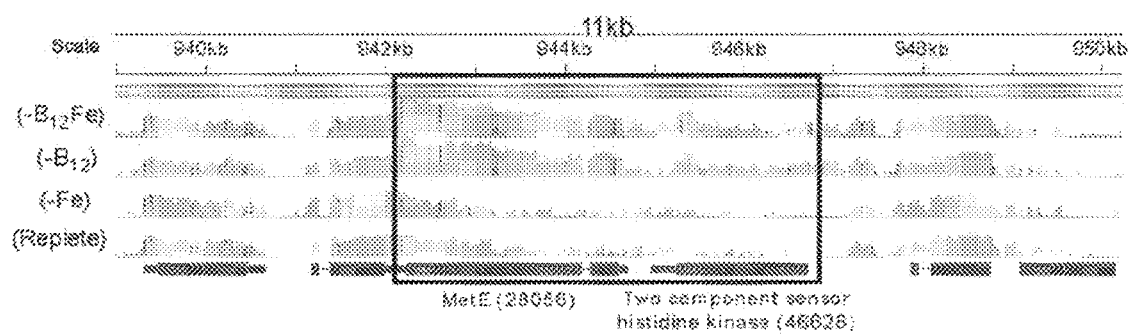
FIG. 11 depicts the RNA-seq coverage for an 11 kb region of the *P. tricornutum* genome. Individual tracks are shown for each treatment, cobalamin and iron starvation, cobalamin starvation, iron starvation, and the replete control. The x-axis shows the position in the genome and the y-axis (gray shading) shows the relative coverage of transcript data. Vertical black lines represent areas in the coverage mapping where there were mismatches of the reads to the reference genome. The bottom track shows the gene models from the JGI 2.0 genome project.

Included in the small pool of P. tricornutum gene products changing under cobalamin starvation was the cobalamin-independent methionine synthase MetE (28056), which was much more abundant under the low cobalamin or combined low cobalamin and low iron treatment in the proteome as well as the transcriptome (FIG. 5E, FIG. 6B, Table 3). This suggests that P. tricornutum expresses MetE to replace MetH (cobalamin-dependent methionine synthase) when cobalamin is scarce, which is consistent with transcript abundance patterns observed previously in this diatom (Helliwell et al. (2011) supra). These data imply that P. tricornutum reduces its cobalamin demand through utilizing MetE as a replacement enzyme when faced with cobalamin starvation. RNA seq results also revealed that an adjacent two component histidine kinase sensor appears to be co-regulated with metE and thus may play a role in the P. tricornutum response to cobalamin starvation (FIG. 11). The cobalamin dependent methionine synthase MetH was not detected in the proteome study, possibly due to low abundance. Lower concentrations of MetH are expected since this protein has much higher catalytic activity compared to MetE (Gonzalez et al. (1992) supra). MetH (Pt 23399, Tp 693) transcripts were detected here via RNA-seq and did not show significant changes in abundance as a function of cobalamin availability in P. tricornutum, but were more abundant under both types of cobalamin starvation in T. pseudonana (FIG. 6C).

Additionally, other proteins displayed abundance patterns suggesting that they may be involved in the cellular response to cobalamin starvation. While some of these proteins have predicted cellular functions, more than half of them play unknown roles (Table 3, 4). Three proteins of unknown function in T. pseudonana (24346, 23556, 1896, Table 3) do not have homologs in P. tricornutum, and were more abundant under low cobalamin alone and low cobalamin with low iron and did not increase in abundance under low iron alone. These unknown proteins may be involved in the T. pseudonana response to cobalamin starvation and warrant further study, particularly if they are present exclusively in genomes of $B_{12}$-requiring diatoms. In addition, there are several proteins of unknown function that are more abundant under low cobalamin and low cobalamin with low iron in T. pseudonana and were either not detected in P. tricornutum or display different abundance patterns (22483, 23657, 24639, 22096, 1869-Table 3). These proteins may play a part in the cellular response to severe methionine deprivation in T. pseudonana since they do not display the same patterns of abundance in P. tricornutum, which would likely not experience such severe methionine deprivation because it can utilize MetE in place of MetH.

Another potential use for cobalamin in diatom cells is as a cofactor for methylmalonyl coA mutase (MmcM; Pt 51830, Tp 33685). The enzyme's function remains unclear in diatoms, though it may be related to propionate metabolism or fatty acid synthesis (Croft et al. (2006) "Algae Need Their Vitamins," Eukaryotic Cell 5: 1175-1184). MmcM uses adenosylcobalamin as a cofactor, which could be produced via an adenosylcobalamin transferase enzyme encoded in these diatom genomes (Cb1B; Pt 45992, Tp 263198). A protein, Cb1A, is known to be involved in adenosylcobalamin transport for use by MmcM in humans (Dobson et al. (2002) "Identification of the Gene Responsible for the cb1B Complementation Group of Vitamin $B_{12}$-dependent Methylalonic Aciduria," Hum. Mol. Genet. 11: 3361-3369). Diatom genomes encode Cb1A homologs (Pt 12878, Tp 39110). None of these three proteins (MmcM, Cb1A, Cb1B) were detected in this study via mass spectrometry, but the transcripts encoding each were quantified via RNA sequencing Neither MmcM or Cb1A-encoding transcripts responded to cobalamin starvation, suggesting that, under the conditions studied here, MmcM does not appear to be regulated based on cobalamin availability. However, transcripts encoding Cb1B, the adenosyltransferase, appear to be more abundant under cobalamin starvation in both diatoms (FIGS. 6A, 6B, and 6C). It remains unclear, however, why the adenosyltransferase enzyme would respond to cobalamin deprivation since the form of cobalamin in use by diatoms appears to be methylcobalamin as a cofactor in methionine synthase, thus leaving open the possibility for additional, unrecognized cobalamin-dependent metabolism in diatoms.

C: Study of Cobalamin, Folate and Pyridoxal 5'Phosphate Relationship: Connections between cobalamin and folate metabolism are well-known in metazoans (Selhub (2002) "Folate, Vitamin $B_{12}$ and Vitamin $B_6$ and One Carbon Metabolism" J. Nutr. Health Aging 6: 39-42), and appear to exist in algae as well, since combined folic acid and methionine addition to $B_{12}$ starved green algal cultures was shown to partially rescue growth (Croft et al. (2005) supra). The mechanism for this is thought to be 'methyl folate trapping' whereby 5-methyltetrahydrofolate is produced by an irreversible reaction and then, under conditions of reduced methionine synthase activity, is trapped in this form rather than being recycled for further use in the active folate cycle (Scott et al. (1981) supra). Both of the diatoms displayed evidence for this phenomenon, as summarized in FIGS. 12A-E.

Figure 12A:
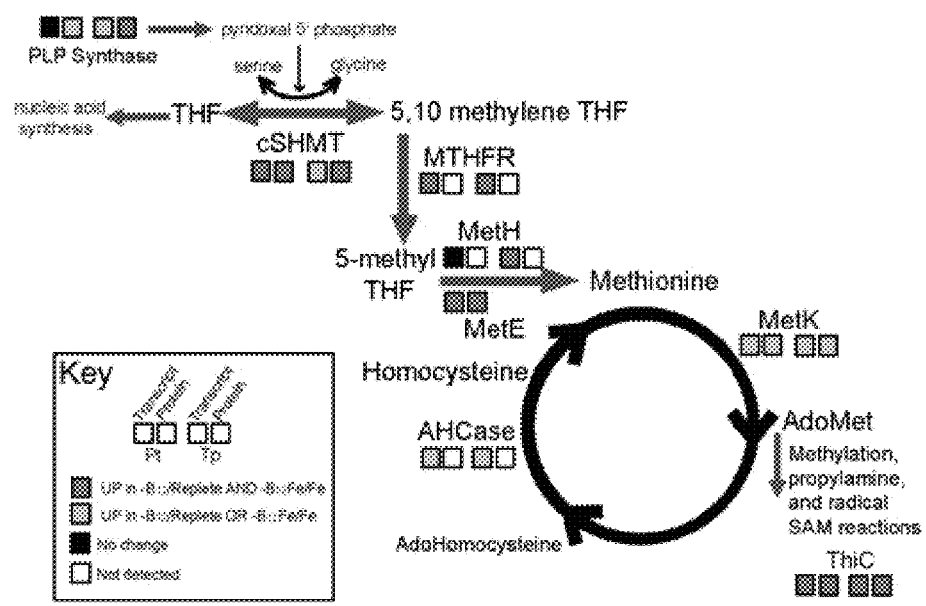
FIG. 12A is a schematic diagram displaying the connections between pyridoxal 5'phosphate (PLP), folate (tetrahydrofolate, THF), methionine, and thiamine metabolism in *T. pseudonana* and *P. tricornutum*, displayed with supporting protein abundance data.

FIG. 12A is a schematic diagram displaying the connections between pyridoxal 5'phosphate (PLP), folate (tetrahydrofolate, THF), methionine, and thiamine metabolism in T. pseudonana and P. tricornutum, displayed with supporting protein abundance data. The gene products involved in these pathways and their responses to cobalamin starvation are shown for each diatom, as denoted in the key. The behavior of both transcripts and proteins are shown, with Pt indicating P. tricornutum (left) and Tp indicating T. pseudonana (right). A black box with an X indicates that the gene product is more abundant under low $B_{12}$ versus replete and low $B_{12}$ with low Fe versus low Fe alone and a grey box indicates that the gene product was more abundant under one of those conditions. Black denotes that there was no change observed between these conditions, and white indicates that the product was not detected. FIGS. 12B-E depict abundance patterns for select proteins included in the schematic of FIG. 12A are displayed. Bar graphs of spectral counting abundance scores for proteins of interest are given for each of four treatments in both diatoms, where bars are means of technical triplicate measurements and error bars are one standard deviation about the mean. Overall, these patterns suggest that these diatoms employ coordinated responses reflecting interconnections between methionine, folate, PLP, and thiamine metabolism and cobalamin availability.

A protein involved in folate one carbon metabolism, cytosolic serine hydroxymethyltransferase (SHMT), is more abundant under both types of vitamin limitation in the two diatoms (FIGS. 6A, 6B, 6C, 12D). This is consistent with results from *E. coli* showing that SHMT activity increases under cobalamin starvation (Dev et al. (1984) "Regulation of Synthesis of Serine Hydroxymethyltransferase in Chemostat Cultures of *E. coli*," *J. Biol. Chem*. 259: 8394-8401).

SHMT is pyridoxal 5' phosphate (PLP, vitamin B6) dependent and catalyzes the reversible conversion of serine to glycine and tetrahydrofolate (THF) to 5,10-methylene tetrahydrofolate (5,10 MTHF; (Snell et al. (2000) "The Genetic Organization and Protein Crystallographic Structure of Human Serine Hydroxomethyltransferase," *Adv. Enzyme Regul*. 40: 353-403)). 5,10 MTHF can then be converted irreversibly to 5-methyltetrahydrofolate by methylenetetrahydrofolate reductase (MTHFR; Pt 30471, Tp 13444: transcripts more abundant under $B_{12}$ starvation (FIGS. 6A, 6B, 6C, 12A)). MeTHF, along with homocystine, is then used for methionine production by methionine synthase. Under cobalamin limitation, MeTHF accumulates at this step and leads to folate trapping. The increase in cytosolic SHMT abundance under cobalamin starvation suggests that diatoms may increase their capacity for THF and 5,10 MTHF interconversion under low vitamin conditions. This may be in an effort to prevent the folate trapping induced via impaired methionine synthase activity through reducing the pool of 5,10 MTHF that is irreversibly converted to MeTHF. This is consistent with suggestions that in humans SHMT mediates the partitioning of one carbon units between DNA synthesis and methionine cycling (Herbig et al. (2002) "Cytoplasmic Serine Hydroxymethyltransferase Mediates Competition Between Folate-dependent Deoxyribonucleotide and S-adenosylmethionine Biosyntheses," *J. Biol. Chem*. 277: 38381-38389).

In humans, low folate, vitamin $B_{12}$, and PLP (vitamin $B_6$) concentrations are correlated with elevated blood homocysteine levels, suggesting that utilization of these four compounds are linked (Selhub et al. (1993) "Vitamin Status and Intake as Primary Determinants of Homocysteinemia in an Elderly Population," *JAMA* 270: 2693-2698). Here, an enzyme putatively involved in PLP synthesis is much more abundant under both types of vitamin limitation in *T. pseudonana* (FIGS. 6A, 6B, and 6C, and FIG. 12C). This increase is consistent with higher demand for PLP under low $B_{12}$, potentially for use by the PLP-dependent SHMT enzymes. Taken together, these data suggest that folate, vitamin $B_{12}$ and PLP metabolism are linked in diatoms, as observed in humans (Selhub et al. (1993) supra).

D: Study of Cobalamin and S-Adenosyl Methionine Relationship: S-adenosyl methionine synthase (MetK) was also more abundant under vitamin limitation in both diatoms (FIG. 12B, Table 4).

MetK is responsible for the conversion of methionine to S-adenosyl methionine (AdoMet, SAM). In addition to many other cellular functions, AdoMet is also responsible, along with flavodoxin, for reductive methylation of cobalamin in methionine synthase when the active cofactor becomes periodically oxidized during its catalytic cycle (Drennan et al. (1994) "Cobalamin-dependent Methionine Synthase: the Structure of a Methylcobalamin-binding Fragment and Implications for Other $B_{12}$-dependent Enzymes," *Curr. Opin. Struct. Biol*. 4: 919-929). It is possible that increased MetK levels enhance AdoMet production, leading to more efficient repair of oxidized cobalamin in MetH. It is also possible that MetK is more abundant under vitamin limitation to increase encounter rates between methionine and the enzyme in an attempt to meet cellular AdoMet demand despite methionine scarcity. There was no increase in MetK abundance under vitamin and iron colimitation relative to iron limitation; it is possible that the cellular rearrangements diatoms employ to cope with iron limitation or generally slow growth rates alter cellular AdoMet requirements, negating the need for additional MetK. Elevation of MetK under low cobalamin availability suggests that AdoMet starvation may be an important consequence of $B_{12}$ deprivation in diatoms (FIG. 12B).

ThiC is responsible for the formation of the non-sulfur containing branch of thiamine, 4-amino-5-hydroxymethyl-2-methylpyrimidine, which is later combined with the sulfur-containing thiazole phosphate to form thiamine. ThiC has been shown to conduct this chemistry using a radical SAM reaction, which is S-adenosyl methionine dependent (Chatterjee et al. (2008) "Reconstitution of ThiC in Thiamine Pyrimidine Biosynthesis Expands the Radical SAM Superfamily," *Nat. Chem. Biol*. 4: 758-765). ThiC was more abundant in both diatoms in both the proteome and transcriptome analyses under vitamin starvation (FIGS. 6A, 6B, 6C, 12A). Since the other proteins involved in thiamine biosynthesis in algae were not observed to be more abundant under $B_{12}$ starvation, it may be that ThiC is up-regulated in response to AdoMet deprivation (FIG. 12A).

Example 3

Overexpression and Sub-cellular Localization of CBA1

Full length *P. tricornutum* 48322 cDNA was PCR amplified and cloned into a TOPO pENTR, subjected to Gateway (Invitrogen) recombination with a diatom C-terminal YFP pDONR vector (Siaut et al. (2007) Gene 406: 23-35), which was transformed into *P. tricornutum* via particle bombardment (Falciatore et al. (1999) *Marine Biotechnology* 1: 239-251). Transformants were screened via PCR and epifluorescence microscopy. Primers used for Pt48322 cDNA amplification were: sense 5'-C ACC ATG ATG AAG TTT TCG T-3'(SEQ ID NO: 46) and antisense 5'-GAA CAA CAA TAC GTG TAT AAG ACT-3' (SEQ ID NO: 47).

Epifluorescent microscopy was performed on a Zeiss Axioscope with the manufacturer filter cubes for yellow fluorescence protein and chlorophyll a. Confocal microscopy was performed on a Leica TCS SP5 spectral system.

$B_{12}$ Uptake Rate Assessments: Inorganic $^{57}$Co was removed from a carrier-free $^{57}$Co-$B_{12}$ stock solution (MP Biomedicals) via Chelex-100 (Price et al. (1988/1989) "Preparation and Chemistry of the Artificial Algal Culture Medium Aquil," *Biol Oceanogr* 6: 443-461) and the remaining solution was used as a radiotracer in cultures of *P. tricornutum*. Strains (wild type, two cell lines overexpressing CBA1_48322 and one line overexpressing urease) were grown through three successive transfers into media as described above, with 100 pM $B_{12}$ and 80 µg/mL zeocin added (zeocin not added to wild type). When the cells were in mid-exponential growth in the third transfer, each strain was used to inoculate (3%) three 28 mL polycarbonate tubes containing 20 mL of growth media with 100 pM $B_{12}$ and 80 μg/mL zeocin and allowed to acclimate for 3 hours. 0.5 pmol $^{57}Co$ $B_{12}$ was added to cultures and 24 hours later, the samples were each gently filtered onto 1 μm polycarbonate filters and rinsed with 4 mL filtered seawater. $B_{12}$ uptake was measured by assessing the percentage of added tracer that was taken up into the particulate fraction via gamma counting as previously described (Bertrand et al. (2007) supra) and assuming that total $B_{12}$ concentrations were 100 pM for the period of uptake. Cell growth was monitored by fluorescence and then translated to cell number via calibration curves created during growth of the $3^{rd}$ transfer.

Figure 13A:
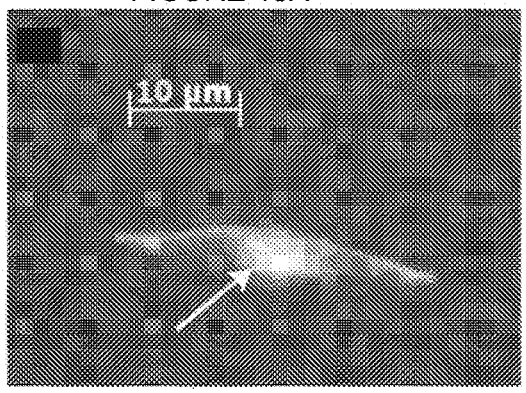
FIG. 13A depicts epifluorescent micrographs and FIG. 13B depicts confocal micrographs of protein CBA1 fused to yellow fluorescent protein (YFP) and overexpressed in *P. tricornutum*.
Figure 13B:
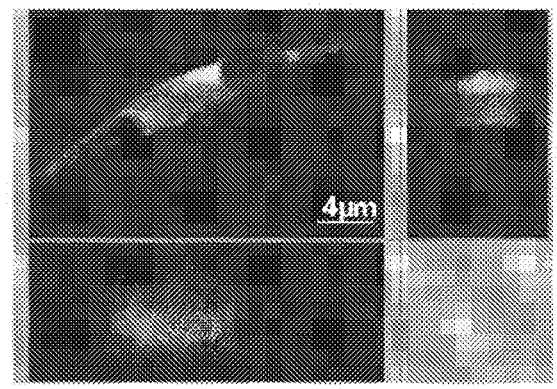

The sub-cellular localization of CBA1 was examined through overexpression of the *P. tricornutum* isoform (Pt48322) in the native host as a yellow fluorescent protein (YFP) fusion construct. Epifluorescent microscopy experiments are shown in FIGS. 13A and 13B. YFP fluorescence is false colored green, while chlorophyll a fluorescence is false colored red. The side panels of the confocal image show the fluorescence distribution in the cross sections of the central image indicated by the light yellow lines. Epifluorescent microscopy showed that the YFP signal was localized to the outer axis of the cell and also in close association with the chloroplast (white arrow in FIG. 13A). The intracellular localization around, but not within, the chloroplast was verified using confocal microscopy (FIG. 13B) and is similar to other proteins localized to the diatom endoplasmic reticulum (ER), which envelopes the chloroplast in red lineage algae (Apt et al. (2002) "In vivo Characterization of Diatom Multipartite Plastid Targeting Signals," *J. Cell Sci.* 115: 4061-4069). Since one of the primary pathways for protein export and secretion is through the ER, the likely ER processing detected here for CBA1 is consistent with the predicted signal peptide and outer axis localization.

Figure 13C:
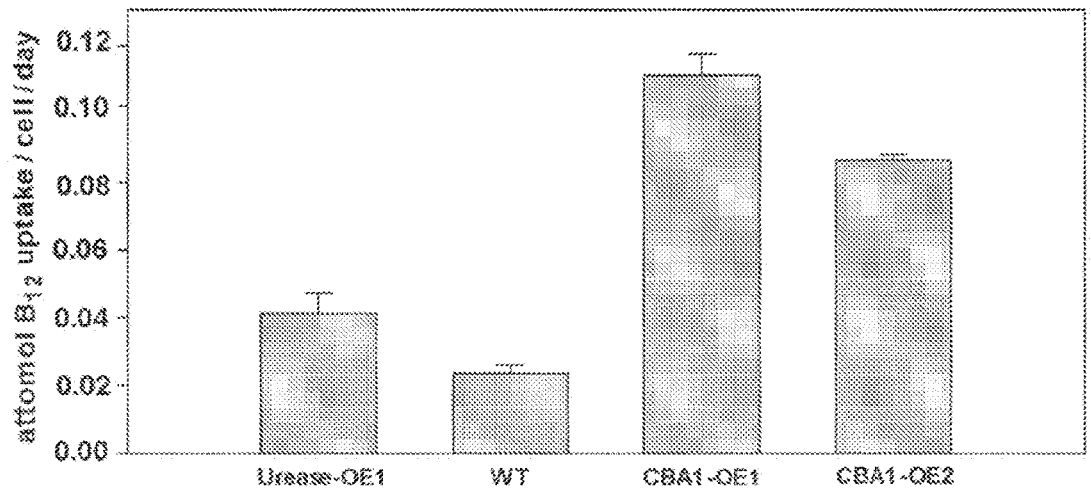
FIG. 13C depicts cobalamin uptake rates by wild-type *P. tricornutum* and transgenic *P. tricornutum* cell lines overexpressing CBA1 (CBA1-OE1, CBA1-OE2) or Urease (Urease-OE1) measured over 24 hours in exponential growth phase under $B_{12}$-replete conditions.

The phenotypic response of this overexpression in *P. tricornutum* was characterized by measuring cobalamin uptake rates in two cell lines overexpressing this protein (CBA1-OE1 and CBA1-OE2) and comparing them to uptake rates in the wild type (wt) and a line overexpressing an unrelated protein, urease (Urease-OE1). To repress native CBA1 expression, uptake rates were measured in cultures grown in cobalamin-replete conditions. In the transgenic diatoms, CBA1 overexpression is controlled by the promoter for a light harvesting complex protein (FcpB), which is highly expressed during exponential growth. As shown in FIG. 13C, growth rate over the 24 hour experiment for the wild type was 0.72±0.07, for Urease-OE1: 1.01±0.02, CBA1-OE2: 1.10±0.03, CBA1-OE1: 1.08±0.03, given as mean of measurements on biological triplicate cultures±one standard deviation. Thus, overexpression of CBA1 enhanced cell specific radiolabeled cobalamin uptake rates in exponentially growing *P. tricornutum* cells 2 to 3-fold (FIG. 13C). This enhanced uptake rate directly implicates CBA1 in cobalamin acquisition and, along with its outer axis localization, suggests that CBA1 may bind cobalamin and aid in shuttling the vitamin into the cell. This finding is significant in that CBA1 is, to our knowledge, the first identified protein in any marine eukaryotic microbe to be directly linked to vitamin $B_{12}$ acquisition.

Example 4

Metatranscriptomic Analyses

Multiple Ross Sea samples (77° S, 165° W) were collected through a hole drilled in sea ice or just over the ice edge. Around 250 L of surface (~3 m) seawater was pumped into a carboy and then onto 293 mm diameter 3 μm pore size polyethersulfone filters (Versapore, Pall). Pumping and filtration occurred over a period of approximately 30 min. Multiple Puget Sound samples (48° N, 122° W) were collected in a similar fashion onto 293 mm diameter 3 μm pore size filters. Monterey Bay samples were collected from a single location (36° 50.80° N, 121° 55.78) from surface waters (~3 m) and around 70 m on 0.22 Sterivex filters. Filters were frozen in liquid nitrogen, kept on dry ice for shipping and stored in the laboratory at −80° C. RNA was purified from filters using the Trizol reagent (Life Technologies; Carlsbad, Calif.). Total RNA was amplified linearly, cDNA was synthesized and material between 300 and 500 bp was purified from agarose gels. cDNA was prepared for sequencing on the 454 platform (Roche Diagnostics; Indianapolis, Ind.) according to manufacturer protocols. Orthologs to CBA1 were retrieved from the cDNA sequence data by TBLASTN.

Figure 14:
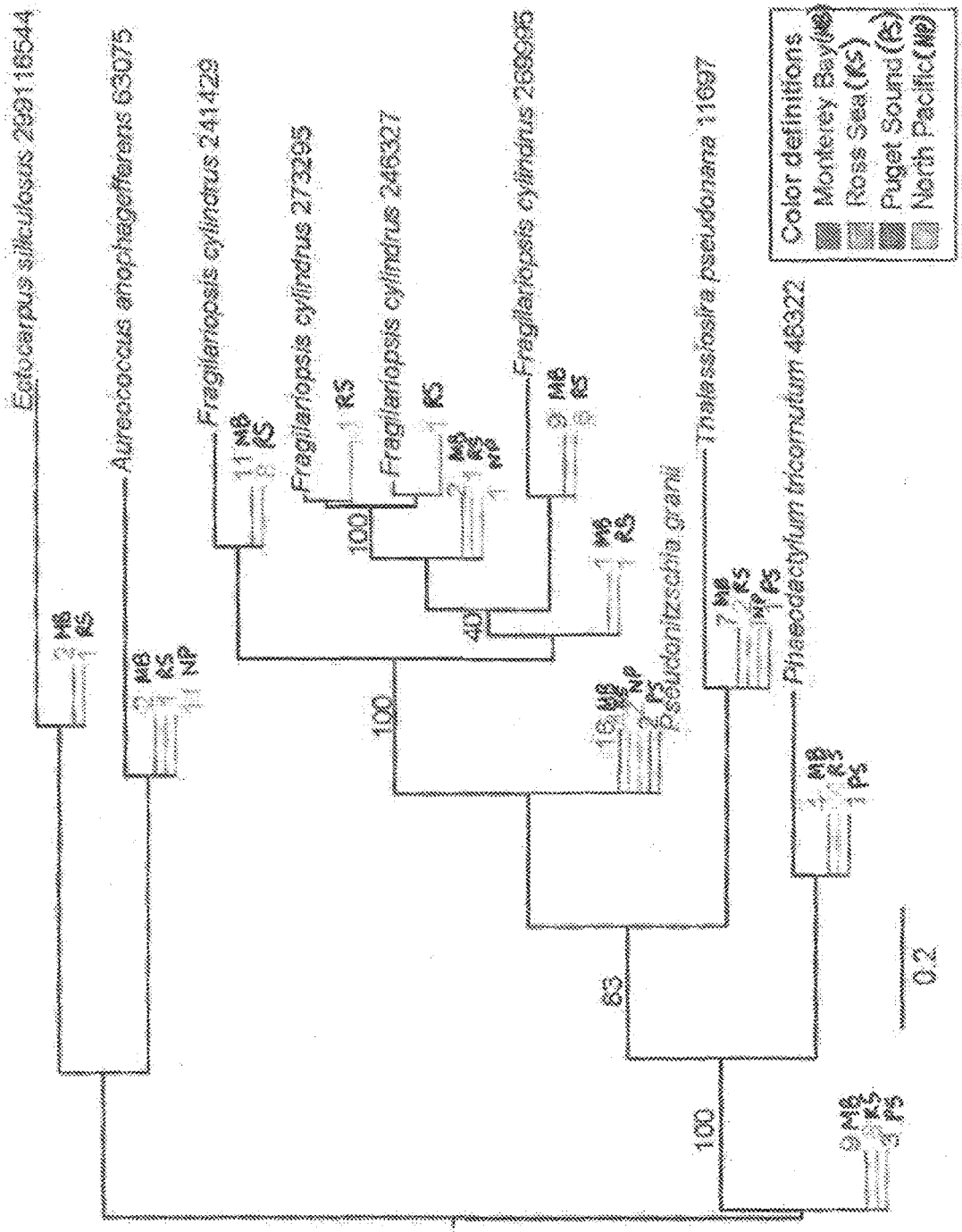
FIG. 14 depicts a phylogenetic tree with CBA1 sequences from metatranscriptomic (cDNA) libraries from the Ross Sea (RS) of the Southern Ocean, Monterey Bay (MB), Puget Sound (PS), and the North Pacific (NP). Reference sequences from *Phaeodactylum tricornutum, Fragilariopsis cylindrus, Thalassiosira pseudonana, Aureococcus anophagefferenas*, and *Ectocarpus siliculosus* genomes were used to construct these trees and are shown in black. CBA1-like sequences from environmental samples are labeled MB, RS, PS, and NP, as described in the key.

The transcripts that likely encode CBA1 were identified in these cDNA libraries generated from natural phytoplankton communities. As described above, these communities were from diverse marine locations including sea ice and water column samples. The corresponding nucleic acid sequences are displayed as a phylogenetic tree that uses CBA1 sequences from available genomes to construct a reference tree onto which these metatranscriptomic sequences are placed (Matsen et al. (2010) "Pplacer: Linear Time Maximum-Likelihood and Bayesian Phylogenetic Placement of Sequences Onto a Fixed Reference Tree," *BMC Bioinformatics* 11:538) (see FIG. 14). In metagenomic data, DNA sequences most similar to CBA1 were detected only in large size fraction (>3 μm) samples, suggesting that this protein is restricted to larger phytoplankton. This result may reflect that larger phytoplankton have more difficulty acquiring $B_{12}$ because they are large relative to their surface area that is in contact with seawater. However, it is contemplated that any organism that has a $B_{12}$ requirement can benefit from the expression or overexpression of CBA1.

A majority of the detected cDNA sequences from the Ross Sea were most similar to putative CBA1 sequences from *Fragilariopsis cylindrus*, which was expected since *F. cylindrus* is an Antarctic diatom and is known to be present in these locations. The detection of CBA1 genes and transcripts in these diverse marine locations suggests that this protein is of use to field populations and thus that cobalamin acquisition is an important part of the molecular physiology of these natural phytoplankton communities.

Example 5

Cobalamin Biochemistry and Marine Biogeochemistry

Figure 15:
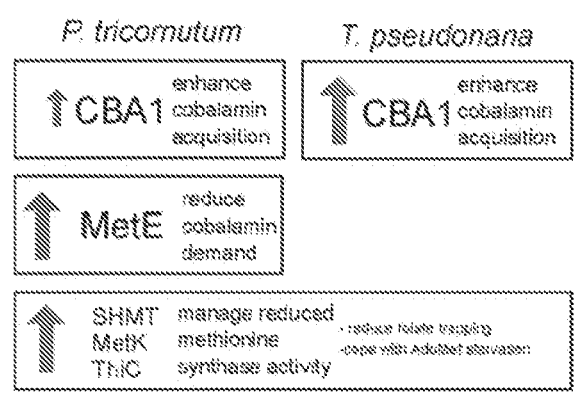
FIG. 15 is a schematic representation of the three primary responses to cobalamin starvation in two diatoms.

It is possible that diatoms can employ at least three strategies in response to cobalamin-deprivation including efforts to 1) increase cobalamin acquisition machinery, 2) reduce cobalamin demand, and 3) to mitigate damage induced by reduced methionine synthase activity (see FIG. 15). As shown in FIG. 15, both diatoms enhanced CBA1 production, likely in an effort to enhance cobalamin acquisition. The magnitude of the increase in CBA1 protein and transcripts was larger for *T. pseudonana*, likely because it has an absolute cobalamin requirement. *P. tricornutum* enhanced MetE production in order to reduce cobalamin demand; MetE is not encoded in the *T. pseudonana* genome, thus preventing this diatom from decreasing its $B_{12}$ demand in this way. Both diatoms also appeared conduct cellular rearrangements to cope with reduced methionine synthase activity including enhanced cytosolic serine hydroxymethyltransferase, methionine adenosyltransferase (MetK) and radical SAM enzyme ThiC abundance under low cobalamin availability. The results implicate enhanced CBA1 (Example 1D), MetE (Example 1E), and SHMT (Example 1F) abundance and altered folate and PLP metabolism (Example 1F) in the acclimation of diatom cells to low cobalamin availability and suggest that AdoMet (Example 1G) starvation is an important consequence of cobalamin deprivation in diatoms.

Detection of CBA1 transcripts in existing marine environmental datasets (see FIG. 14) implies that this protein is abundant and utilized by natural phytoplankton populations and therefore that cobalamin acquisition is an important component of diatom molecular physiology in the natural environment.

Example 6

Separation of Vitamin $B_{12}$ with CBA1

CBA1 can be used to separate vitamin $B_{12}$ from a mixture according to the following method. CBA1, or a CBA1 fragment capable of binding to vitamin $B_{12}$, can be labeled with an N-terminal GST tag and overexpressed in *E. coli* with an N-terminal GST tag and purified using affinity chromatography. The protein can be conjugated to a solid support using methods known in the art, e.g., sortase mediated-ligation (Chan et al. (2007) PLoS One 2(11) e164). CBA1 protein bound to a solid support can then be used in affinity chromatography to remove $B_{12}$ from dilute solutions.

Vitamin $B_{12}$ can be extracted from the solid matrix by changing the pH to alter CBA1 conformation. Vitamin $B_{12}$ can then be measured in a concentrated sample by mass methodologies known in the art (e.g. high performance liquid chromatography (HPLC), HPLC-MS, triple quadrupole mass spectrometry; Lu et al. (2008) *J. Chrom. Sci.* 46(3):225-32) or by commercially available ELISA (e.g, USCN ELISA kit for mouse Vitamin $B_{12}$, USCN Life Science and Technology Company, Missouri City, Tex.).

Example 7

Expression of CBA1 in *E. coli*

The CBA1 protein was heterologously expressed in *E. coli* using one of two overexpression plasmids, one being the Invitrogen GATEWAY® pDEST-17 vector having a cleavable histidine tag and another with the Invitrogen GATEWAY® pDEST-15 vector having a cleavable GST tag, to allow for preconcentration. This was performed by ligating the full length *P. tricornutum* (JGI ID No. 48322) nucleic acid sequence of SEQ ID NO: 1 into each plasmid. The resulting plasmids were then transformed into *E. coli* BL21 strain and the proteins expressed by the standard protocol for the vectors using L-arabinose induction with sampling at 2 hours, 4 hours, and overnight. The resulting CBA1 protein was then concentrated by centrifugation and extracted for proteomic analysis.

Confirmation of the CBA1 protein in *E. coli* protein extracts was conducted by proteomic analysis using shot gun mass spectrometry as described in Bertrand et al. (2012), *Proc. Natl. Acad. Sci. USA*, 109(26):E1762-71. Protein digestions were prepared and analyzed (4 µg total protein per analysis) using a peptide Cap Trap in line with a reversed phase Magic C18 AQ column (0.2×150 mm, 3 µm particle size, 200 Å pore size, (Michrom Bioresources Inc. Auburn Calif.) on a Paradigm MS4 HPLC system (Michrom Bioresources Inc.). An ADVANCE nanocapillary electrospray source (Michrom Bioresources Inc.) introduced the sample into a LTQ (linear ion trap) mass spectrometer (Thermo Scientific Inc. San Jose Calif.). The chromatography consisted of a hyperbolic gradient from 5% buffer A to 95% buffer B for 300 min, where A was 0.1% formic acid (Michrom Ultra Pure) in water (Fisher Optima) and B was 0.1% formic acid in acetonitrile (Fisher Optima) at a flow rate of 2 µl min$^{-1}$.

The resulting *E. coli* mass spectra data were searched against the entire *Phaeodactylum tricornutum* genome. (See FIGS. 16A and 16B). The protein identification of highest confidence was the CBA1 protein with multiple peptides identified including AVQDQQVFDYQASGENAWFEQR (SEQ ID NO: 51) and EHTANQVVEAAESR (SEQ ID NO:19), with only a small number of other *Phaeodactylum tricornutum* proteins identified (~6) and with much lower statistical confidence. Together these results demonstrate the successful overexpression of the CBA1 protein in *E coli.*

Example 8

CBA1 Binding Activity

The binding activity of CBA1 proteins of the invention can be ascertained using, for example, a rapid charcoal assay described in Gottlieb et al. ((1965) supra) or an isothermal calorimetry assay as described by Cadieux et al. ((2002) supra).

According to one method, for example, a charcoal suspension can be prepared by mixing equal volumes of 1% bovine serum albumin and 5% neutralized charcoal. Aliquots of 800 µL are then introduced into centrifuge filter tubes to provide 20 mg layers of charcoal on the filters.

Mixtures of 0.8 µm of CBA1 with varying amounts of radiolabeled vitamin $B_{12}$ are then prepared in 100 mM potassium phosphate at pH 6.6 and are allowed to incubate at room temperature for 5 minutes after which the samples can be transferred to the charcoal-containing centrifuge tubes. The tubes can be centrifuged at 8000 rpm for 15 seconds. Free Vitamin $B_{12}$ binds to the charcoal layer and CBA1 bound vitamin $B_{12}$ will be found in the filtrate. The vitamin $B_{12}$ in the filtrate can then be measured by counting the radioactivity using a liquid scintillation counter. The presence of radioactivity in the filtrate indicates that the CBA1 protein tested binds vitamin $B_{12}$. The binding affinity of the CBA1 protein can be ascertained by comparing the level of radioactivity in each tube's filtrate to the amount of vitamin B12 added to the sample.

Example 9

CBA1 Pharmaceutical Composition

The CBA1 protein can be expressed according to methods described herein, for example, as described above in Example 7. The protein is then collected and purified according to standard methods to ensure purity and to remove any contaminants. The protein can then be admixed with a suitable pharmaceutical excipient to create an ointment. The protein content is provided in the range of 0.5% (w/w) to about 30% (w/w).

The ointment can be applied to the skin of a subject, for example, to act as an antibiotic to prevent or mitigate infection at the site of application.

Incorporation by Reference

The entire disclosure of each of the patent documents and scientific articles referred to herein is incorporated by reference for all purposes.

Equivalents

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

What is claimed is:

1. A pharmaceutical composition comprising a protein that binds Vitamin $B_{12}$, said protein comprising an amino acid sequence having at least 90% identity with SEQ ID NO: 2, and a pharmaceutically acceptable excipient.

2. The composition of claim 1, wherein the protein binds Vitamin $B_{12}$ with an affinity less than $10^{-5}$ M.

3. The composition of claim 1, wherein the composition is a liquid, solid, cream, or paste.

4. The composition of claim 1, wherein the protein binds Vitamin $B_{12}$ with an affinity from about $10^{-5}$ M to about $10^{-12}$ M.

5. The composition of claim 1, wherein the composition, when administered to a subject, is capable of reducing the growth and/or proliferation of a microorganism in or on the subject.

6. The composition of claim 1, wherein the protein comprises from about 0.1% (w/w) to about 90% (w/w) of the pharmaceutical composition.

7. The composition of claim 6, wherein the protein comprises from about 0.5% (w/w) to about 30% (w/w) of the pharmaceutical composition.

8. A method of treating a bacterial infection in a subject in need thereof, the method comprising administering to the subject a therapeutically effective amount of the composition of claim 1.

9. The method of claim 8, wherein the composition is administered topically or orally to the subject.

10. The method of claim 8, wherein the composition is administered non-parenterally to the subject.

* * * * *